US008367697B2

(12) United States Patent
Jimenez et al.

(10) Patent No.: US 8,367,697 B2
(45) Date of Patent: Feb. 5, 2013

(54) KINASE INHIBITORS

(75) Inventors: Juan-Miguel Jimenez, Abingdon (GB); Michael Mortimore, Burford (GB); Andrew Miller, Upton (GB); Philip Collier, Abingdon (GB); Stephen Young, Oxford (GB); Guy Brenchley, Wantage (GB); Chris Davis, Salisbury (GB); Heather Twin, Denchworth (GB); Chau Mak, Abingdon (GB); Dean Boyall, Abingdon (GB); Shazia Keily, Oxford (GB); Luca Settimo, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/275,551

(22) Filed: Oct. 18, 2011

(65) Prior Publication Data

US 2012/0149680 A1    Jun. 14, 2012

Related U.S. Application Data

(63) Continuation of application No. 12/262,459, filed on Oct. 31, 2008, now Pat. No. 8,173,635.

(60) Provisional application No. 61/100,808, filed on Sep. 29, 2008, provisional application No. 61/044,575, filed on Apr. 14, 2008, provisional application No. 60/984,875, filed on Nov. 2, 2007.

(30) Foreign Application Priority Data

Oct. 31, 2008    (WO) ............... PCT/US2008/081933

(51) Int. Cl.
*C07D 513/02* (2006.01)
*C07D 515/02* (2006.01)
*A01N 43/42* (2006.01)
*A01K 31/44* (2006.01)

(52) U.S. Cl. ...................................... 514/303; 546/118
(58) Field of Classification Search ................. 546/118; 514/303

See application file for complete search history.

(56) References Cited

U.S. PATENT DOCUMENTS

| 3,314,941 A | 4/1967 | Littell et al. |
| 5,100,768 A | 3/1992 | Niki et al. |
| 5,202,224 A | 4/1993 | Yamakawa et al. |
| 5,338,740 A | 8/1994 | Carpino et al. |
| 5,439,916 A | 8/1995 | Ganguly et al. |
| 5,646,330 A | 7/1997 | Shieh et al. |
| 6,194,581 B1 | 2/2001 | Cosford et al. |
| 6,303,659 B2 | 10/2001 | Baxter et al. |
| 6,452,008 B2 | 9/2002 | Muraoka et al. |
| 6,638,935 B2 | 10/2003 | Emig et al. |
| 6,673,789 B2 | 1/2004 | Dickinson et al. |
| 6,770,662 B2 | 8/2004 | Nishide et al. |
| 6,831,175 B2 | 12/2004 | Li et al. |
| 7,135,474 B2 | 11/2006 | Weigand et al. |
| 8,173,635 B2 | 5/2012 | Jimenez et al. |
| 2002/0165218 A1 | 11/2002 | Halbrook et al. |
| 2005/0049274 A1 | 3/2005 | Wall et al. |
| 2005/0203067 A1 | 9/2005 | Hresco et al. |
| 2006/0148844 A1 | 7/2006 | Nakede et al. |
| 2006/0178378 A1 | 8/2006 | Dai et al. |
| 2006/0205739 A1 | 9/2006 | Eberle et al. |
| 2007/0208053 A1 | 9/2007 | Arnold et al. |
| 2009/0099213 A1 | 4/2009 | Berdini et al. |
| 2009/0291937 A1 | 11/2009 | Jimenez et al. |

FOREIGN PATENT DOCUMENTS

| FR | 2005-555 | 1/2005 |
| JP | 03271289 | 12/1991 |
| JP | 0220386 | 1/2002 |
| Wo | 8910365 A1 | 11/1989 |
| WO | 0102369 A2 | 11/2001 |
| WO | 2004014368 | 2/2004 |
| WO | 2004080463 | 9/2004 |
| WO | 2005044181 | 5/2005 |
| WO | 2006046023 A1 | 5/2006 |
| WO | 2006050076 | 5/2006 |
| WO | 2006050109 | 5/2006 |
| WO | 2006052568 A2 | 5/2006 |
| WO | 2007013896 A1 | 5/2006 |
| WO | 2006101456 | 9/2006 |
| WO | 03045949 A2 | 2/2007 |
| WO | 2007042178 A1 | 4/2007 |
| WO | 2007076423 | 5/2007 |
| WO | 2007084667 A2 | 7/2007 |
| WO | 2007012531 | 8/2007 |
| WO | 2007041379 | 12/2007 |
| WO | 2007144204 A1 | 12/2007 |
| WO | 2008079292 | 3/2008 |
| WO | 2008051493 A2 | 5/2008 |
| WO | 2008132121 | * 11/2008 |

OTHER PUBLICATIONS

Hohn, et al., "Potential Antidiabetic Agents. Pyrazolo [3, 4-b] pyridines", Journal of Medicinal Chemistry. (1973), vol. 16. No. 12; pp. 1340-1346.
Badgujar et al., "Reactions of 5-aminopyrazole with Active Methylene Compounds: Synthesis of Pyrazolo [3,4-b] pyridine Derivatives" Proceedings of ECSOC-9, Internatinal Electronic Conference on Synthetic Organic Chemistry, 9th Nov. 1-30, 2005, Postgraduate Department of Chemistry, www.usc.es/congresos/ecsoc/9/GOS/a005/index.htm.
Khadijah Mohamed Al-Zaydi et al., Enaminonitriles in heterocyclic synthesis: new routes for the synthesis of some novel azolo [1, 5-a]pyrimdo [1,2-a]benzimidazole, pyrazole and pyrimidine derivatives, J. Chem. Research (S), 200, pp. 13-15.
International Search Report Received in the corresponding PCT Application No. PCT/US2008/081933.

* cited by examiner

*Primary Examiner* — Niloofar Rahmani
(74) *Attorney, Agent, or Firm* — Min Lin

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

17 Claims, No Drawings

KINASE INHIBITORS

CROSS-REFERENCE TO RELATED APPLICATIONS

The present application is a continuation of U.S. application Ser. No. 12/262,459, filed Oct. 31, 2008, which claims the benefit, under 35 U.S.C. §119, of U.S. provisional patent application Ser. No. 61/100,808, filed on Sep. 29, 2008, and provisional patent application Ser. No. 61/044,575, filed on Apr. 14, 2008, and provisional application Ser. No. 60/984,875, filed on Nov. 2, 2007 the entire contents of each of above applications is incorporated herein by reference.

BACKGROUND OF THE INVENTION

Protein kinases constitute a large family of structurally related enzymes that are responsible for the control of a variety of signal transduction processes within the cell (see Hardie, G. and Hanks, S. *The Protein Kinase Facts Book, I and II*, Academic Press, San Diego, Calif.: 1995).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g. shock, heat shock, ultraviolet radiation, bacterial endotoxin, and $H_2O_2$), cytokines (e.g. interleukin-1 (IL-1) and tumor necrosis factor alpha (TNF-a), and growth factors (e.g. granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Kinases may be categorized into families by the substrates they phosphorylate (e.g. protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J.* 1994, 13, 2352-2361).

A serine/threonine kinase, protein kinase C-theta (PKC-theta), is a member of the novel, calcium independent PKC subfamily that is selectively expressed in T cells and skeletal muscle. Several lines of evidence indicate that PKC-theta has an essential role in T cell activation. Upon antigen stimulation of T cells, PKC-theta, but not other PKC isoforms, rapidly translocates from the cytoplasm to the site of cell contact between the T cell and antigen-presenting cell (APC), where it localizes with the T cell receptor (TCR) in a region termed the central supramolecular activation cluster (cSMAC) (Monks et al., 1997, Nature, 385: 83-86; Monks et al., 1998, Nature, 395: 82-86).

It has been reported that PKC-theta selectively activates the transcription factors AP-1 and NF-κB and integrates TCR and CD28 co-stimulatory signals leading to the activation of the CD28 response element (CD28RE) in the IL-2 promotor (Baier-Bitterlich et al., 1996, Mol. Cell. Biol., 16: 1842-1850; Coudronniere et al., 2000, PNAS, 97: 3394-3399). The specific role for PKC-theta in CD3/CD28 co-stimulation of T cells is highlighted in a study where expression of a kinase-dead PKC-theta mutant, or anti-sense PKC-theta dose-dependently inhibited CD3/CD28 co-stimulated NF-κB activation, but not TNF-alpha-stimulated NF-κB activation. This was not seen with other PKC isoforms (Lin et al., 2000, Mol. Cell. Biol., 20: 2933-2940). Recruitment of PKC-theta to the SMAC is reported to be mediated by its N-terminal regulatory domain and is necessary for T cell activation, as an over-expressed PKC-theta catalytic fragment did not translocate and was unable to activate NF-κB, whereas a PKC-theta catalytic domain-Lck membrane-binding domain chimera was able to reconstitute signaling (Bi et al., 2001, Nat. Immunol., 2:556-563).

Translocation of PKC-theta to the SMAC appears to be mediated by a largely PLC-gamma/DAG-independent mechanism, involving Vav and PI3-kinase (Villalba et al., 2002, JCB 157: 253-263), whilst activation of PKC-theta requires input from several signaling components including Lck, ZAP-70, SLP-76, PLC-gamma, Vav and PI3-kinase (Liu et al., 2000, JBC, 275: 3606-3609; Herndon et al., 2001, J. Immunol., 166: 5654-5664; Dienz et al., 2002, J. Immunol., 169: 365-372; Bauer et al., 2001 JBC., 276: 31627-31634). These biochemical studies in human T cells have gained credence from studies in PKC-theta knockout mice, which have confirmed a crucial role for this enzyme in T cell function. PKC-theta–/– mice are healthy and fertile, have a normally developed immune system, but exhibit profound defects in mature T cell activation (Sun et al., 200, Nature, 404:402-407). Proliferative responses to TCR and TCR/CD28 co-stimulation were inhibited (>90%) as were in vivo responses to antigen. In agreement with studies on human T cells, activation of the transcription factors AP-1 and NF-κB was abrogated, resulting in a severe deficit in IL-2 production and IL-2 R upregulation (Baier-Bitterlich et al., 1996, MBC, 16, 1842; Lin et al., 2000, MCB, 20, 2933; Courdonniere, 2000, 97, 3394). More recently, studies in PKC-theta-deficient mice have indicated a role for PKC-theta in the development of mouse models of autoimmune diseases, including multiple sclerosis (MS), rheumatoid arthritis (RA) and irritable bowel disease (IBD) (Salek-Ardakani et al., 2006; Tan et al., 2006; Healy et al., 2006; Anderson et al., 2006). In these models, PKC-theta-deficient mice exhibited a marked reduction in disease severity that was associated with a profound defect in the development and effector function of autoreactive T cells.

In addition to its role in T cell activation, PKC-theta is reported to mediate the phorbol ester-triggered survival signal that protects T cells from Fas- and UV-induced apoptosis (Villalba et al., 2001, J. Immunol. 166: 5955-5963; Bertto-lotto et al., 2000, 275: 37246-37250). This pro-survival role is of interest because the human PKC-theta gene has been mapped to chromosome 10 (10p15), a region associated with mutations leading to T cell leukaemias and lymphomas (Erdel et al., 1995, Genomics 25: 295-297; Verma et al., 1987, J. Cancer Res. Clin. Oncol., 113: 192-196).

In vivo, the role for PKC-theta in immune responses to infection is dependent on the type of pathogen encountered. PKC-theta deficient mice elicit normal Th1 and cytotoxic T cell-mediated responses to several viral infections and the protozoan parasite, *Leishmania major* and effectively clear these infections (Marsland et al., 2004; Berg-Brown et al., 2004; Marsland et al., 2005; Giannoni et al., 2005). However, PKC-theta deficient mice are unable to wage normal Th2 T cell responses against the parasite *Nippostrongylus brasiliensis* and certain allergens (Marsland et al., 2004; Salek-Ardakani et al., 2004) and are unable to clear *Listeria monocyto-* genes infection (Sakowicz-Burkiewicz et al., 2008). Clearly in some circumstances, the requirement for PKC-theta in T cell activation can be bypassed and this is likely to involve the provision of additional signals to T cells, either from cells of the innate immune system, or directly from the pathogen in the form of pathogen associated molecular patterns (PAMPs) (Marsland et al., 2007).

More recently, studies in PKC-theta-deficient mice have indicated a role for PKC-theta in the development of mouse models of autoimmune diseases, including multiple sclerosis, rheumatoid arthritis and inflammatory bowel disease. In all cases where examined, PKC-theta-deficient mice exhibited a marked reduction in disease severity that was associated with a profound defect in the development of a newly discovered class of T cells, Th17 cells (Salek-Ardakani et al., 2006; Tan et al., 2006; Healy et al., 2006; Anderson et al., 2006; Nagahama et al., 2008). PKC-theta therefore appears to be essential for the development of pathogenic auto-reactive Th17 cells in the context of autoimmunity. These observations support the notion that targeting PKC-theta will provide a way to target autoimmune T cell responses, leaving many T cell responses (e.g., to viral infections) intact.

In addition to its role in T cell activation, PKC-theta mediates the phorbol ester-triggered survival signal that protects T cells from Fas- and UV-induced apoptosis (Villalba et al., 2001, J. Immunol. 166: 5955-5963; Berttolotto et al., 2000, 275: 37246-37250). This pro-survival role is of interest because the human PKC-theta gene has been mapped to chromosome 10 (10p15), a region associated with mutations leading to T cell leukaemias and lymphomas (Erdel et al., 1995, Genomics 25: 295-297; Verma et al., 1987, J. Cancer Res. Clin. Oncol., 113: 192-196).

Together, these data indicate that PKC-theta is an attractive target for therapeutic intervention in inflammatory disorders, immune disorders, lymphomas and T cell leukaemias.

Accordingly, there is a great need to develop compounds useful as inhibitors of protein kinases. In particular, it would be desirable to develop compounds that are useful as inhibitors of kinases such as PKC-theta, particularly given the inadequate treatments currently available for the majority of the disorders implicated in their activation.

SUMMARY OF THE INVENTION

This invention provides, in general, compounds that are useful as kinase inhibitors.

In one embodiment the compounds of the present invention are represented by a structural formula selected from the group consisting of I or IA:

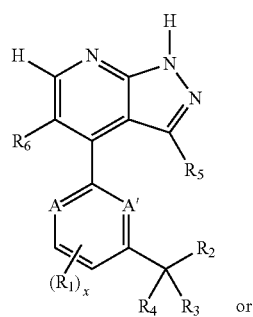

I

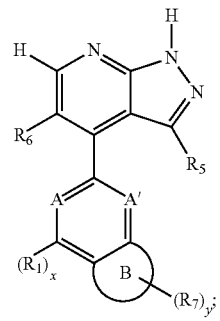

IA or a pharmaceutically acceptable salt thereof.

A and A' are independently —N— or —C($R^+$)—.

Ring B is five- or six-membered saturated carbocyclic or heterocyclic ring.

$R_1$ is halogen, —CN, —$NO_2$, or -T1-Q1.

T1 is absent or a C1-10 aliphatic wherein one or more methylene units of T1 are optionally and independently replaced by G wherein G is —O—, —S(O)$_p$—, —N(R')—, or —C(O)—; and T1 is optionally and independently substituted with one or more $J_{T1}$.

Q1 is absent or a 3-8 membered saturated, partially saturated, or fully unsaturated monocyclic ring having 0-3 heteroatoms independently selected from the groups consisting of O, N, and S, or an 8-12 membered saturated, partially saturated, or fully unsaturated bicyclic ring having 0-5 heteroatoms independently selected from the group consisting of O, N, and S, wherein Q1 is optionally and independently substituted with one or more $J_{Q1}$; wherein when $R_1$ is T1-Q1, then TI and Q1 are not both absent.

$R_2$ is —H, —(CR$^{++}_2$)$_n$CN, —(CR$^{++}_2$)$_n$N(R)$_2$, —(CR$^{++}_2$)$_n$OR, —(CR$^{++}_2$)$_n$C(O)N(R)$_2$, or C1-10 aliphatic optionally substituted with one or more halogen, phenyl, OR*, or N(R*)$_2$.

Each $R_3$ and $R_4$ independently are —H, halogen, C1-10 aliphatic, heterocyclyl, heterocyclylalkyl, aryl, aralkyl, wherein $R_3$ and $R_4$ are optionally and independently substituted with one or more selected from the group consisting of C1-10 alkyl, halogen, —CN, —$NO_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*; or $R_3$ and $R_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of =O, =S, =N—R*, C1-10 aliphatic, C1-10 haloaliphatic, halogen, —CN, —$NO_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*.

Each $R_5$ and $R_6$ are independently —H, halogen, C1-10 haloaliphatic, or C1-10 aliphatic.

Each $R_7$ is independently C1-10 haloaliphatic, C1-10 aliphatic, halogen, —$NO_2$, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R**)$_2$, or two $R_7$ groups together with the carbon to which they are attached form C=O.

Each $J_{T1}$ is independently halogen, —OR^, —N(R^)$_2$, or —CN.

Each $J_{Q1}$ is independently halogen, C1-10 alkyl, C1-10 haloalkyl, —OR'', —N(R'')$_2$, —CN, —NO$_2$, —S(O)$_p$R'', —S(O)$_p$NR'', acyl, carbalkoxyalkyl, or acetoxyalkyl.

Each $R^+$ is independently —H, halogen, or C1-C10 alkyl optionally and independently substituted with up to five halogen groups.

Each $R^{++}$ is independently —H or halogen.

Each R' is independently —H or C1-C10 alkyl optionally and independently substituted with up to five halogen groups.

Each R^ is independently —H, C1-C10 alkyl, or aralkyl wherein each R^ is optionally and independently substituted with up to five halogen groups.

Each R'' is independently —H or C1-C10 alkyl optionally and independently substituted with up to five halogen groups.

Each R is independently —H or C1-10 alkyl optionally and independently substituted with up to five halogen groups.

Each R* is independently —H or C1-10 alkyl optionally and independently substituted with up to five halogen groups.

Each R** is independently —H or C1-10 alkyl optionally and independently substituted with up to five halogen groups.

x is 0 or 1.

y is 0, 1 or 2.

Each n is independently 0, 1, 2, or 3.

Each p is independently 0, 1, or 2.

In one embodiment, the present invention is a method of treating or preventing protein kinase-mediated condition in a subject, comprising administering to the subject an effective amount of a compound or composition of the present invention.

In one embodiment the present invention is the manufacture of a compound or composition of the present invention for use in treating or preventing a protein kinase mediated condition in a subject.

In another embodiment, the compounds and compositions of the present invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention relates to compounds and compositions (such as, pharmaceutical compositions) useful as protein kinase inhibitors.

In one embodiment, the compounds and compositions of the present invention are effective as inhibitors of PKCtheta.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

In one embodiment the compounds of the present invention are represented by a structural formula selected from the group consisting of I or IA:

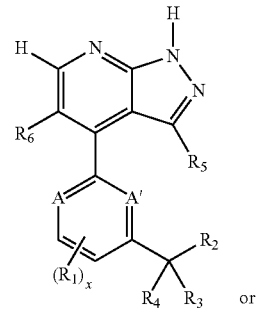

I

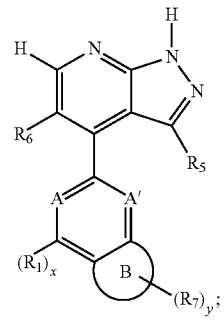

IA or a pharmaceutically acceptable salt thereof.

A and A' are independently —N— or —C(R$^+$)—.

Ring B is five- or six-membered saturated carbocyclic or heterocyclic ring.

$R_1$ is halogen, —CN, —NO$_2$, or -T1-Q1.

T1 is absent or a C1-10 aliphatic wherein one or more methylene units of T1 are optionally and independently replaced by G wherein G is —O—, —S(O)$_p$—, —N(R')—, or —C(O)—; and T1 is optionally and independently substituted with one or more $J_{T1}$.

Q1 is absent or a 3-8 membered saturated, partially saturated, or fully unsaturated monocyclic ring having 0-3 heteroatoms independently selected from the groups consisting of O, N, and S, or an 8-12 membered saturated, partially saturated, or fully unsaturated bicyclic ring having 0-5 heteroatoms independently selected from the group consisting of O, N, and S, wherein Q1 is optionally and independently substituted with one or more $J_{Q1}$; wherein when $R_1$ is T1-Q1, then T1 and Q1 are not both absent.

$R_2$ is —H, —(CR$^{++}{}_2$)$_n$CN, —(CR$^{++}{}_2$)$_n$N(R)$_2$, —(CR$^{++}{}_2$)$_n$OR, —(CR$^{++}{}_2$)$_n$C(O)N(R)$_2$, or C1-10 aliphatic optionally substituted with one or more halogen, OR*, or N(R*)$_2$.

Each $R_3$ and $R_4$ independently are —H, halogen, C1-10 aliphatic, heterocyclyl, heterocyclylalkyl, aryl, aralkyl, wherein $R_3$ and $R_4$ are optionally and independently substituted with one or more selected from the group consisting of C1-10 alkyl, halogen, —CN, —NO$_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*; or R$_3$ and R$_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of =O, =S, =N—R*, C1-10 aliphatic, C1-10 haloaliphatic, halogen, —CN, —NO$_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*.

Each R$_5$ and R$_6$ are independently —H, halogen, C1-10 haloaliphatic, or C1-10 aliphatic.

Each R$_7$ is independently C1-10 haloaliphatic, C1-10 aliphatic, halogen, —NO$_2$, —(CR$^{++}_2$)$_n$CN, —(CR$^{++}_2$)$_n$N(R)$_2$, —(CR$^{++}_2$)$_n$OR, or —(CR$^{++}_2$)$_n$C(O)R**)$_2$, or two R$_7$ groups together with the carbon to which they are attached form C=O.

Each J$_{T1}$ is independently halogen, —OR^, —N(R^)$_2$, or —CN.

Each J$_{Q1}$ is independently halogen, C1-10 alkyl, C1-10 haloalkyl, —OR", —N(R")$_2$, —CN, —NO$_2$, —S(O)$_p$R", —S(O)$_p$NR", acyl, carbalkoxyalkyl, or acetoxyalkyl.

Each R$^+$ is independently —H, halogen, or C1-10 alkyl optionally and independently substituted with up to five halogen groups.

Each R$^{++}$ is independently —H or halogen.

Each R' is independently —H or C1-10 alkyl optionally and independently substituted with up to five halogen groups.

Each R^ is independently —H, C1-10 alkyl, or aralkyl wherein each R^ is optionally and independently substituted with up to five halogen groups.

Each R" is independently —H or C1-10 alkyl optionally and independently substituted with up to five halogen groups.

Each R is independently —H or C1-10 alkyl optionally and independently substituted with up to five halogen groups.

Each R* is independently —H or C-10 alkyl optionally and independently substituted with up to five halogen groups.

Each R** is independently —H or C1-10 alkyl optionally and independently substituted with up to five halogen groups.

x is 0 or 1.

y is 0, 1 or 2.

Each n is independently 0, 1, 2, or 3.

Each p is independently 0, 1, or 2.

In one embodiment the compounds of the present invention are represented by a structural formula selected from the group consisting of I or IA:

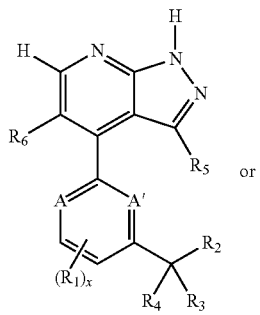

I

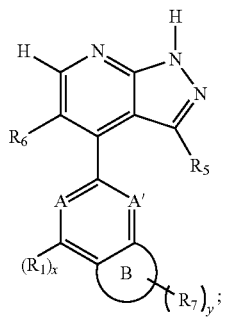

IA or a pharmaceutically acceptable salt thereof.

A and A' are independently —N— or —C(R$^+$)—.

Ring B is five- or six-membered saturated carbocyclic or heterocyclic ring.

R$_1$ is halogen, —CN, —NO$_2$, or -T1-Q1.

T1 is absent or a C1-10 aliphatic wherein up to three methylene units of T1 are optionally and independently replaced by G wherein G is —O—, —S(O)$_p$—, —N(R')—, or —C(O)—; and T1 is optionally and independently substituted with one or more J$_{T1}$.

Q1 is absent or a 3-8 membered saturated, partially saturated, or fully unsaturated monocyclic ring having 0-3 heteroatoms independently selected from the groups consisting of O, N, and S, or an 8-12 membered saturated, partially saturated, or fully unsaturated bicyclic ring having 0-5 heteroatoms independently selected from the group consisting of O, N, and S, wherein Q1 is optionally and independently substituted with one or more J$_{Q1}$; wherein when R$_1$ is T1-Q1, then T1 and Q1 are not both absent.

R$_2$ is —H, C1-10 aliphatic, —(CR$^{++}_2$)$_n$CN, —(CR$^{++}_2$)$_n$N(R*)$_2$, —(CR$^{++}_2$)$_n$OR, or —(CR$^{++}_2$)$_n$C(O)N(R*)$_2$.

Each R$_3$ and R$_4$ independently are —H, halogen, C1-10 aliphatic, heterocyclyl, heterocyclylalkyl, aryl, aralkyl, wherein R$_3$ and R$_4$ are optionally and independently substituted with one or more selected from the group consisting of C1-10 alkyl, halogen, —CN, —NO$_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*; or R$_3$ and R$_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of C1-10 aliphatic, C1-10 haloaliphatic, halogen, —CN, —NO$_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*.

Each R$_5$ and R$_6$ are independently —H, halogen, C1-10 haloaliphatic, or C1-10 aliphatic.

Each R$_7$ is independently C1-10 haloaliphatic, C1-10 aliphatic, halogen, —NO$_2$, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R**)$_2$, or two R$_7$ groups together with the carbon to which they are attached form C=O.

Each J$_{T1}$ is independently halogen, —OR^, —N(R^)$_2$, or —CN.

Each J$_{Q1}$ is independently halogen, C1-10 alkyl, C1-10 haloalkyl, —OR", —N(R")$_2$, —CN, —NO$_2$, —S(O)$_p$R", —S(O)$_p$NR", acyl, carbalkoxyalkyl, or acetoxyalkyl.

Each R$^+$ is independently —H, halogen, or C1-10 alkyl optionally and independently substituted with up to five halogen groups.

Each R$^{++}$ is independently —H or halogen.

Each R' is independently —H or C1-10 alkyl, optionally and independently substituted with up to five halogen groups.

Each R^ is independently —H or C1-10 alkyl, optionally and independently substituted with up to five halogen groups.

Each R" is independently —H or C1-10 alkyl, optionally and independently substituted with up to five halogen groups.

Each R is independently —H or C1-10 alkyl, optionally and independently substituted with up to five halogen groups.

Each R* is independently —H or C-10 alkyl, optionally and independently substituted with up to five halogen groups.

Each R** is independently —H or C1-10 alkyl, optionally and independently substituted with up to five halogen groups.

x is 0 or 1.

y is 0, 1 or 2.

Each n is independently 0, 1, 2, or 3.

Each p is independently 0, 1, or 2.

In one embodiment the present invention for a compound represented by structural formula I or IA, or a pharmaceutically acceptable salt thereof:

A and A' are independently —N— or —C(R$^+$)—. In one embodiment A is —N— or —C(R$^+$)—; and A' is —C(R$^+$)—. In another embodiment, both A and A' are —C(R$^+$)—.

Ring B is five- or six-membered saturated carbocyclic or heterocyclic ring. In one embodiment ring B is five- or six-membered saturated carbocyclic ring. In another embodiment ring B is five-membered saturated carbocyclic ring. Ring B is five- or six-membered non-aromatic carbocyclic or heterocyclic ring. In one embodiment ring B is five- or six-membered non-aromatic carbocyclic ring. In another embodiment ring B is five-membered non-aromatic carbocyclic ring. Ring B is non-aromatic, that is ring B and the ring to which it is fused are not, for example, indolyl or indazolyl.

R$_1$ is halogen, —CN, —NO$_2$, or -T1-Q1. In one embodiment, R$_1$ is halogen, or -T1-Q1.

T1 is absent or a C1-10 aliphatic wherein up to three methylene units of T1 are optionally and independently replaced by G wherein G is —O—, —S(O)$_p$—, —N(R')—, or —C(O)—; and T1 is optionally and independently substituted with one or more hi. In one embodiment, T1 is absent or a C1-10 aliphatic wherein up to three methylene units of T1 are optionally and independently replaced by G wherein G is —O—, —N(R')—, or —C(O)—; and T1 is optionally and independently substituted with one or more J$_{T1}$.

Q1 is absent or a 3-8 membered saturated, partially saturated, or fully unsaturated monocyclic ring having 0-3 heteroatoms independently selected from the groups consisting of O, N, and S, or an 8-12 membered saturated, partially saturated, or fully unsaturated bicyclic ring having 0-5 heteroatoms independently selected from the group consisting of O, N, and S, wherein Q1 is optionally and independently substituted with one or more J$_{Q1}$; wherein when R$_1$ is T1-Q1, then T1 and Q1 are not both absent. In one embodiment, Q1 is absent or a 3-8 membered saturated, partially saturated, or fully unsaturated monocyclic ring having 0-3 heteroatoms independently selected from the groups consisting of O, N, and S, wherein Q1 is optionally and independently substituted with one or more J$_{Q1}$.

R$_2$ is —H, C1-10 aliphatic, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R)$_2$. In one embodiment, R$_2$ is C1-10 aliphatic, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R)$_2$.

Each R$_3$ and R$_4$ independently are —H, halogen, C1-10 aliphatic, heterocyclyl, heterocyclylalkyl, aryl, aralkyl, wherein R$_3$ and R$_4$ are optionally and independently substituted with one or more selected from the group consisting of C1-10 alkyl, halogen, —CN, —NO$_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*; or R$_3$ and R$_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of C1-10 aliphatic, C1-10 haloaliphatic, halogen, —CN, —NO$_2$, —N(R*)$_2$, —S(O)$_p$R*, —S(O)$_p$NR*, —C(O)N(R*)$_2$, —NR*C(O), —OC(O)N(R*)$_2$, —N(R*)C(O)OR*, —N(R*)C(O)N(R*)$_2$ and —OR*. In one embodiment, each R$_3$ and R$_4$ independently is —H, C1-10 aliphatic, cycloalkylalkyl, wherein R$_3$ and R$_4$ are optionally and independently substituted with one or more selected from the group consisting of halogen, —CN, —NO$_2$, —N(R*)$_2$, and —OR*; or R$_3$ and R$_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of C1-10 aliphatic, C1-10 haloaliphatic, halogen, —CN, —N(R*)$_2$, and —OR*.

Each R$_5$ and R$_6$ are independently —H, halogen, C1-10 haloaliphatic, or C1-10 aliphatic.

Each R$_7$ is independently C1-10 haloaliphatic, C1-10 aliphatic, halogen, —NO$_2$, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R)$_2$, or two R$_7$ groups together with the carbon to which they are attached form C=O. In one embodiment, each R$_7$ is independently C1-10 alkyl, halogen, —CN, —N(R)$_2$, or —OR; or two R$_7$ groups together with the carbon to which they are attached form C=O. In another embodiment, each R$_7$ is independently C1-10 alkyl, halogen, or —OR; or two R$_7$ groups together with the carbon to which they are attached form C=O.

Each J$_{T1}$ is independently halogen, —OR^, —N(R^)$_2$, or —CN. In one embodiment, each J$_{T1}$ is independently —OR^, —N(R^)$_2$, or —CN.

Each J$_{Q1}$ is independently halogen, C1-10 alkyl, C1-10 haloalkyl, —OR", —N(R")$_2$, —CN, —NO$_2$, —S(O)$_p$R", —S(O)$_p$NR", acyl, carbalkoxyalkyl, or acetoxyalkyl. In one embodiment, each J$_{Q1}$ is independently C1-10 alkyl, —OR", —N(R")$_2$, or acyl.

Each R$^+$ is independently —H, halogen, or C1-10 alkyl optionally and independently substituted with up to five halogen groups. In one embodiment, each R$^+$ is —H.

Each R$^{++}$ is independently —H or halogen.

Each R' is independently —H or C1-10 alkyl, optionally and independently substituted with up to five halogen groups.

Each Rˆ is independently —H or C1-10 alkyl, optionally and independently substituted with up to five halogen groups.

Each R" is independently —H or C1-10 alkyl, optionally and independently substituted with up to five halogen groups.

Each R is independently —H or C1-10 alkyl, optionally and independently substituted with up to five halogen groups.

Each R* is independently —H or C-10 alkyl, optionally and independently substituted with up to five halogen groups.

Each R** is independently —H or C1-10 alkyl, optionally and independently substituted with up to five halogen groups.

x is 0 or 1.

y is 0, 1 or 2.

Each n is independently 0, 1, 2, or 3.

Each p is independently 0, 1, or 2.

In a first embodiment of the present invention the compound of the present invention is represented by Formula I, and the remainder of the variables are as described above. Alternatively, the compound of the present invention is represented by Formula IA, and the remainder of the variables are as described above.

In a second embodiment for compounds of the present invention represented by Formula I or IA, A is —N— or —C(R$^+$)—; and A' is —C(R$^+$)—, and the remainder of the variables are as described above for the first embodiment.

In a third embodiment for compounds of the present invention represented by Formula I or IA, R$^+$ is —H and the remainder of the variables are as described above for the second embodiment.

In a fourth embodiment for compounds of the present invention represented by Formula I or IA, R$_1$ is halogen, or -T1-Q1 and the remainder of the variables are as described above for the third embodiment.

In a fifth embodiment for compounds of the present invention represented by Formula I or IA, T1 is absent or a C1-10 aliphatic wherein up to three methylene units of T1 are optionally and independently replaced by G wherein G is —O—, —N(R')—, or —C(O)—; and T1 is optionally and independently substituted with one or more J$_{T1}$ and the remainder of the variables are as described above for the fourth embodiment.

In a sixth embodiment for compounds of the present invention represented by Formula I or IA, Q1 is absent or a 3-8 membered saturated, partially saturated, or fully unsaturated monocyclic ring having 0-3 heteroatoms independently selected from the groups consisting of O, N, and S, wherein Q1 is optionally and independently substituted with one or more J$_{Q1}$ and the remainder of the variables are as described above for the fifth embodiment.

In a seventh embodiment for compounds of the present invention represented by Formula I or IA, each J$_{T1}$ is independently —OR", —N(Rˆ)$_2$, or —CN and the remainder of the variables are as described above for the sixth embodiment.

In an eighth embodiment for compounds of the present invention represented by Formula I or IA, each J$_{Q1}$ is independently C1-10 alkyl, —OR", —N(R")$_2$, acyl, or aralkyl and the remainder of the variables are as described above for the seventh embodiment.

In a ninth embodiment for compounds of the present invention represented by Formula I, R$_2$ is C1-10 aliphatic, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R)$_2$ and the remainder of the variables are as described above for the eighth embodiment. Alternatively, R$_2$ is —H, C1-10 aliphatic, —(CR$^{++}_2$)$_n$CN, —(CR$^{++}_2$)$_n$N(R)$_2$, or —(CR$^{++}_2$)$_n$OR and the remainder of the variables are as described above for the eighth embodiment.

In a tenth embodiment for compounds of the present invention represented by Formula I, each R$_3$ and R$_4$ independently is —H, C1-10 aliphatic, cycloalkylalkyl, wherein R$_3$ and R$_4$ are optionally and independently substituted with one or more selected from the group consisting of halogen, —CN, —NO$_2$, —N(R*)$_2$, and —OR*; or R$_3$ and R$_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of C1-10 aliphatic, C1-10 haloaliphatic, halogen, —CN, —N(R*)$_2$, and —OR* and the remainder of the variables are as described above for the ninth embodiment. Alternatively, each R$_3$ and R$_4$ independently is —H, C1-10 aliphatic, cycloalkylalkyl, heterocyclyl, heterocyclylalkyl, aryl, or aralkyl wherein R$_3$ and R$_4$ are optionally and independently substituted with one or more selected from the group consisting of halogen, —CN, —NO$_2$, —N(R*)$_2$, and —OR*; or R$_3$ and R$_4$ taken together with the carbon to which they are attached form C=O, or a 3-8 membered saturated, partially saturated, or fully unsaturated monocyclic ring having 0-3 heteroatoms independently selected from the groups consisting of O, N, and S, wherein the ring is optionally and independently substituted with one or more selected from the group consisting of =O, =S, C1-10 aliphatic, C1-10 haloaliphatic, halogen, —CN, —N(R*)$_2$, and —OR*. In an eleventh embodiment for compounds of the present invention represented by Formula I, A is —C(R$^+$)— and the remainder of the variables are as described above for the tenth embodiment.

In a twelfth embodiment for compounds of the present invention represented by Formula I, J$_{T1}$ is —ORˆ and the remainder of the variables are as described above for the eleventh embodiment.

In a thirteenth embodiment for compounds of the present invention represented by Formula I each J$_{Q1}$ is independently C1-10 alkyl, —OR", —N(R")$_2$, or acyl and the remainder of the variables are as described above for the twelfth embodiment.

In a fourteenth embodiment for compounds of the present invention represented by Formula I, R$_2$ is —H, C1-10 aliphatic, —(CR$^{++}_2$)$_n$CN, —(CR$^{++}_2$)$_n$N(R)$_2$, or —(CR$^{++}_2$)$_n$OR and the remainder of the variables are as described above for the thirteenth embodiment.

In a fifteenth embodiment the present invention is a compound represented by Formula IB:

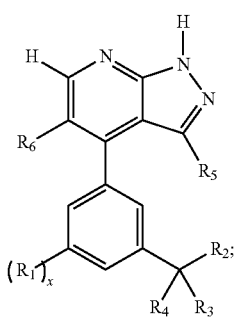

IB or a pharmaceutically acceptable salt thereof and the remainder of the variables are as described above for the fourteenth embodiment. In Formula IB if x is 0 then it is understood that $(R1)_x$ is replaced by —H.

In a sixteenth embodiment for compounds of the present invention represented by Formula I or IB, $R_3$ and $R_4$ taken together with the carbon to which they are attached form a 3-8 membered saturated, or partially saturated monocyclic ring having 0-3 heteroatoms independently selected from the groups consisting of O, N, and S, wherein the ring is optionally and independently substituted with one or more selected from the group consisting of =O, =S, C1-10 aliphatic, C1-10 haloaliphatic, halogen, —CN, —N(R*)$_2$, and —OR* and the remainder of the variables are as described above for the fifteenth embodiment.

In a seventeenth embodiment for compounds of the present invention represented by Formula I or IB, $R_3$ and $R_4$ taken together with the carbon to which they are attached form a monocyclic ring selected from the group consisting of cyclopropyl, cyclobutyl, cyclohexyl, cyclopentyl, azetidinyl, pyrrolidinyl, piperidinyl, piperazinyl, azepanyl, diazepanyl, tetrahydrofuranyl, tetrahydropyranyl, oxetanyl, imidazolinyl, thiazolidinyl, or oxazolidinyl, wherein the ring is optionally and independently substituted with one or more selected from the group consisting of =O, =S, C1-10 aliphatic, C1-10 haloaliphatic, halogen, —CN, —N(R*)$_2$, and —OR* and the remainder of the variables are as described above for the sixteenth embodiment.

In an eighthteenth embodiment for compounds of the present invention represented by Formula I or IIB, $R_2$ is —H, or C1-10 aliphatic; and $R_3$ and $R_4$ taken together with the carbon to which they are attached form a monocyclic ring selected from the group consisting of azetidinyl, pyrrolidinyl, piperidinyl, piperazinyl, azepanyl, diazepanyl, tetrahydrofuranyl, tetrahydropyranyl, oxetanyl, imidazolinyl, thiazolidinyl, or oxazolidinyl, wherein the ring is optionally and independently substituted with one or more selected from the group consisting of =O, =S, C1-10 aliphatic, C1-10 haloaliphatic, halogen, —CN, —N(R*)$_2$, and —OR* and the remainder of the variables are as described above for the seventeenth embodiment. Alternatively, $R_2$ is —(CR$^{++}_2$)$_n$CN, —(CR$^{++}_2$)$_n$N(R)$_2$, or —(CR$^{++}_2$)$_n$OR. $R_3$ and $R_4$ taken together with the carbon to which they are attached form a monocyclic ring selected from the group consisting of cyclopropyl, cyclobutyl, cyclohexyl, or cyclopentyl, wherein the ring is optionally and independently substituted with one or more selected from the group consisting of =O, =S, C1-10 aliphatic, C1-10 haloaliphatic, halogen, —CN, —N(R*)$_2$, and —OR* and the remainder of the variables are as described above for the seventeenth embodiment. Alternatively, $R_2$ is —H, C1-10 aliphatic, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R)$_2$; and each $R_3$ and $R_4$ independently is —H, C1-10 aliphatic, cycloalkylalkyl, heterocyclyl, heterocyclylalkyl, aryl, or aralkyl wherein $R_3$ and $R_4$ are optionally and independently substituted with one or more selected from the group consisting of halogen, —CN, —NO$_2$, —N(R*)$_2$, and —OR* and the remainder of the variables are as described above for the seventeenth embodiment.

In an nineteenth embodiment for compounds of the present invention represented by Formula I or IB $R_5$ is —H, Cl, C1-4 haloalkyl, or C1-4 alkyl; and $R_6$ is —H or C1-4 alkyl and the remainder of the variables are as described above for the eighteenth embodiment. In certain embodiments, $R_5$ is —H, Cl, trifluoromethyl, methyl, ethyl, or cyclopropyl; and $R_6$ is —H and the remainder of the variables are as described above for the eighteenth embodiment.

In a twentieth embodiment the present invention is a compound represented by Formula IC:

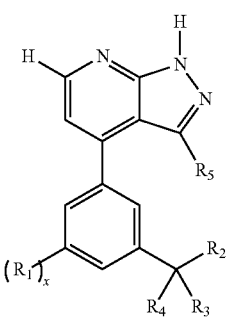

IC or a pharmaceutically acceptable salt thereof. In Formula IC if x is 0 then it is understood that $(R1)_x$ is replaced by —H.

In a twenty first embodiment for compounds of the present invention represented by Formula IA ring B is five- or six-membered saturated carbocyclic ring and the remainder of the variables are as described above for the eighth embodiment.

In a twenty second embodiment for compounds of the present invention represented by Formula IA each $R_7$ is independently C1-10 aliphatic, C1-10 haloaliphatic, halogen, —CN, —N(R)$_2$, or —OR; or two $R_7$ groups together with the carbon to which they are attached form C=O and the remainder of the variables are as described above for the twenty first embodiment.

In a twenty third embodiment for compounds of the present invention represented by Formula IA A is —C(R$^+$)— and the remainder of the variables are as described above for the second embodiment.

In a twenty fourth embodiment for compounds of the present invention represented by Formula IA $J_{T1}$ is —OR^ and the remainder of the variables are as described above for the twenty third embodiment.

In a twenty fifth embodiment for compounds of the present invention represented by Formula IA each $J_{Q1}$ is independently C1-10 alkyl, —OR", —N(R")$_2$, or acyl and the remainder of the variables are as described above for the twenty-fourth embodiment.

In a twenty sixth embodiment for compounds of the present invention represented by Formula IA ring B is five-membered saturated carbocyclic ring and the remainder of the variables are as described above for the twenty fifth embodiment.

In a twenty seventh embodiment of the present invention each $R_7$ is independently C1-10 aliphatic, C1-10 haloaliphatic, halogen, —CN, —N(R)$_2$, or —OR ; or two R$_7$ groups together with the carbon to which they are attached form C=O and the remainder of the variables are as described above for the twenty sixth embodiment.

As used herein "one or more" means, for example, that all substitutable carbon atoms can be substituted, for example, up to 6 carbons atoms, up to 5 carbon atoms, up to 3 carbon atoms, up to 2 carbon atoms, or one carbon atom can be substituted.

As described herein, a specified number range of atoms includes any integer therein. For example, a group having from 1-4 atoms could have 1, 2, 3, or 4 atoms.

As used here the terms "absent" and "a bond" can be used interchangeably to mean the variable does not exits in that embodiment, that is the variable does not represent an atom or groups of atoms.

The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In certain embodiments, aliphatic groups may be linear or branched. Unless indicated aliphatic groups include, but are not limited to, alkyl, alkenyl, or alkynyl groups. Specific examples include, but are not limited to, methyl, ethyl, isopropyl, n-propyl, sec-butyl, vinyl, methenyl (=CH$_2$), ethenyl, n-butenyl, ethynyl, and tert-butyl. Specifically examples, include but are not limited to, for example, a C1-10 aliphatic substituted with C1-6 alkyl includes n-butylene substituted with cyclohexyl.

The term "alkyl" as used herein means a saturated straight, branched or cyclic hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Unless otherwise specified, alkyl, alkenyl and alkynyl groups contain 1-20 carbon atoms. In some embodiments, alkyl, alkenyl and alkynyl groups contain 1-10 carbon atoms. In other embodiments, alkyl, alkenyl and alkynyl groups contain 1-8 carbon atoms. In still other embodiments, alkyl, alkenyl and alkynyl groups contain 1-6 carbon atoms, and in yet other embodiments alkyl, alkenyl and alkynyl groups contain 1-4 carbon atoms.

The term "cycloaliphatic" (or "carbocycle" or "carbocyclyl" or "carbocyclic") refers to a non-aromatic monocyclic or polycyclic carbon containing ring which can be saturated or contain one or more units of unsaturation, having three to fourteen ring carbon atoms. The term includes polycyclic fused, spiro or bridged carbocyclic ring systems wherein the radical or point of attachment is on the carbocyclic ring. The term also includes polycyclic ring systems in which the carbocyclic ring can be attached to one or more non-aromatic carbocyclic or heterocyclic rings or one or more aromatic rings or combination thereof, wherein the radical or point of attachment is on the carbocyclic ring. Fused bicyclic ring systems comprise two rings which share two adjoining ring atoms, bridged bicyclic group comprise two rings which share three or four adjacent ring atoms, spiro bicyclic ring systems share one ring atom. Examples of cycloaliphatic groups include, but are not limited to, cycloalkyl and cycloalkenyl groups. Specific examples include, but are not limited to, cyclohexyl, cyclopropentyl, and cyclobutyl.

The term "heterocycle" (or "heterocyclyl", or "heterocyclic") as used herein means refers to a non-aromatic monocyclic or polycyclic ring which can be saturated or contain one or more units of unsaturation, having three to fourteen ring atoms in which one or more ring carbons is replaced by a heteroatom such as, N, S, or O. The term includes polycyclic fused, spiro or bridged heterocyclic ring systems wherein the radical or point of attachment is on the heterocyclic ring. The term also includes polycyclic ring systems in which the heterocyclic ring can be attached to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azetidinylazocanyl, diazocanyl, triazocanyl, oxazolidinyl, oxetenyl, isoxazolidinyl, thiazolidinyl, imidazolinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydropyranyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as defined herein, attached to the molecule through an oxygen ("alkoxy" e.g., —O-alkyl) or sulfur ("thioalkyl" e.g., —S-alkyl) atom.

The terms "haloalkyl", "haloalkenyl", "haloaliphatic", and "haloalkoxy" (or "aminoalkyl", "hydroxyalkyl" etc.,) mean alkyl, alkenyl, aliphatic, or alkoxy, as the case may be, substituted with one or more halogen atoms (or amino or hydroxy). The terms haloalkyl etc., include, mono-di- and tri-halo substituted groups. In particular, these terms include perfluorinated alkyl groups, such as —CF$_3$ and —CF$_2$CF$_3$.

The terms "halogen", "halo", and "hal" mean F, Cl, Br, or I.

The term "acyl group" means —C(O)R wherein R is an aliphatic groups as defined herein, or an aryl group as defined herein.

The term "aryl" used alone or as part of a larger moiety as in "heteroaryl", "aralkyl", "aralkoxy", or "aryloxyalkyl" refers to both carbocyclic and or heterocyclic aromatic ring systems. The term "aryl" may be used interchangeably with the term "aryl ring".

Carbocyclic aromatic ring groups have only carbon ring atoms (typically six to fourteen) and include monocyclic aromatic rings such as phenyl and fused polycyclic aromatic ring systems in which one carbocyclic aromatic rings is fused to one or more aromatic rings in which the radical or point of attachment is on the carbocyclic aromatic ring. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the carbocyclic aromatic ring.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic heteroaryl ring is fused to one or more other aromatic ring in which the radical or point of attachment is on the heteroaryl ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the heteroaryl ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The terms "aralkyl", "heteroaralkyl", "cycloaliphaticalkyl", and "heterocyclylakyl", refer to alkyl groups as defined herein substituted with aryl, heteroaryl, cycloaliphatic, or heterocyclic groups respectively.

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, where indicated a methylene unit of an aliphatic group or alkyl group is optionally replaced with another atom or group. Examples of such atoms or groups include, but are not limited to, —N(R')—, —O—, —C(O)—, —C(=N—CN)—, —C(=NR')—, —C(=NO R')—, —S—, —S(O)—, and —S(O)$_2$—. These atoms or groups can be combined to form larger groups. Examples of such larger groups include, but are not limited to, —OC(O)—, —C(O)CO—, —CO$_2$—, —C(O)NR'—, —C(=N—CN), —N(R')C(O)—, —N(R')C(O)O—, —S(O)$_2$N(R')—, —N(R')SO$_2$—, —N(R')C(O)N(R')—, —OC(O)N(R')—, and —N(R')SO$_2$N (R')—, wherein R' is defined herein.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a $C_3$ aliphatic can be optionally replaced by —N(R')—, —C(O)—, and —N(R')— to form —N(R')C(O) N(R')—(a urea).

Unless otherwise indicated, if the replacement occurs at the terminal end, the replacement atom is bound to an H on the terminal end. For example, if a methylene unit in —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

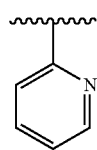

also represents

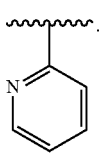

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As described herein, where indicated compounds and groups of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Therefore, where it is not indicated that a compound or group is substituted, it is understood that the group is not substituted. That is, if the terms "optionally substituted" or "substituted" is not present in an instance of the definition of a compound or group it is understood that the compound or group is not substituted in that instance. For example, Ri is alkyl, Rii is optionally substituted alkyl, and Riii is alkyl optionally substituted with halo, means that Rii, and Riii are optionally substituted and Ri is not substituted in this instance.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen, or when the structure depicts they are already bound by a hydrogen.

An optionally substituted aryl group as defined herein contains one or more substitutable ring atoms, which may be optionally bonded to one or more suitable substituent. Examples of suitable substituents on a substitutable ring carbon atom of an aryl group includes Rk. Rk is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRcCORa, —NRcNRcCO$_2$Ra, —CHO, —CON(RaRb), —OC(O)N(RaRb), —CSN(RaRb), —NRc-CORa, —NRcCOORa, —NRcCSRa, —NRcCON(RaRb), —NRcNRcC(O)N(RaRb), —NRcCSN(RaRb), —C(=NRc)—N(RaRb), —C(=S)N(RaRb), —NRd-C(=NRc)—N(RaRb), —NRcNRaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by R1. Preferably Ra-Rd are unsubstituted.

R1 is halogen, R$^m$, —OR$^m$, —SR$^m$, —NO$_2$, —CN, —N(R$^m$)$_2$, —COR$^m$, —COOR$^m$, —NHCO$_2$R$^m$, —NHC(O)R$^m$, —NHNHC(O)R$^m$, —NHC(O)N(R$^m$)$_2$, —NHNHC(O)N(R$^m$)$_2$, —NHNHCO$_2$R$^m$, —C(O)N(R$^m$)$_2$, —OC(O)R$^m$, —OC(O)N(R$^m$)$_2$, —S(O)$_2$R$^m$, —SO$_2$N(R$^m$)$_2$, —S(O)R$^m$, —NHSO$_2$N(R$^m$)$_2$, —NHSO$_2$R$^m$, —C(=S)N(R$^{m+}$)$_2$, or —C(=NH)—N(R$^m$)$_2$.

R$^m$ is —H, a C1-C4 alkyl group, a monocyclic aryl group, a non-aromatic carbocyclic or heterocyclic group each optionally substituted with unsubstituted alkyl, haloalkyl, alkoxy, haloalkoxy, halogen, —CN, —NO$_2$, amine, alkylamine or dialkylamine. Preferably R$^m$ is unsubstituted.

An optionally substituted aliphatic or a non-aromatic heterocyclic or carbocyclic group as defined herein contains one or more substitutable atoms which may optionally be bonded to one or more suitable substituents. Examples of suitable substituents for an aliphatic group or a ring carbon of a non-aromatic heterocyclic group is Rn. Rn include those substituents listed above for Rk and =O, =S, =NNHRo, =NN(Ro)2, =NNHC(O)Ro, =NNHCO2 (alkyl), =NNHSO2 (alkyl), =NRo, Spiro cycloalkyl group or fused cycloalkyl group. Each Ro is independently selected from hydrogen, an unsubstituted alkyl group or a substituted alkyl group. Examples of substituents on the alkyl group represented by Ro include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Preferably Ro is unsubstituted.

When a heterocyclyl, heteroaryl, or heteroaralkyl group contains a nitrogen atom, it may be substituted or unsubstituted as indicated herein. When a nitrogen atom in the aromatic ring of a heteroaryl group has a substituent the nitrogen may be a quaternary nitrogen.

In certain embodiments non-aromatic nitrogen-containing heterocyclic group or heteroaryl groups are optionally substituted at the nitrogen ring atom. Suitable substituents on the nitrogen of a non-aromatic heterocyclic group or heteroaryl group include —Rq, —N(Rq)$_2$, —C(O)Rq, CO$_2$Rq, —C(O)C(O)Rq, —SO$_2$Rq, SO$_2$N(Rq)$_2$, —C(=S)N(Rq)$_2$, —C(=NH)—N(Rq)$_2$, and —NRqSO$_2$Rq; wherein Rq is hydrogen, an aliphatic group, a substituted aliphatic group, aryl, substituted aryl, heterocyclic or carbocyclic ring or a substituted heterocyclic or carbocyclic ring. Examples of substituents on the group represented by R^ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R^ is not substituted.

Non-aromatic nitrogen containing heterocyclic rings and heteroaryl that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as piperazinyl that are substituted on a ring nitrogen and attached to the remainder of the molecule at a second ring nitrogen atom are said to be N' substituted-N-heterocycles. For example, an N' acyl N-piperazinyl group is attached to the remainder of the molecule at one ring nitrogen atom and substituted at the second ring nitrogen atom with an acyl group.

As used herein an optionally substituted aralkyl can be substituted on both the alkyl and the aryl portion. In certain embodiments, optionally substituted aralkyl is optionally substituted on the aryl portion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable solvates (e.g., hydrates) and clathrates of the compounds of this invention may also be employed in compositions to treat or prevent the herein identified disorders.

As used herein, the term "pharmaceutically acceptable solvate," is a solvate formed from the association of one or more pharmaceutically acceptable solvent molecules to one of the compounds the invention. The term solvate includes hydrates (e.g., hemihydrate, monohydrate, dihydrate, trihydrate, tetrahydrate, and the like).

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

In addition to the compounds of this invention, pharmaceutically acceptable derivatives or prodrugs of the compounds of this invention may also be employed in compositions to treat or prevent the herein identified disorders.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO2, —ONO, or —ONO2 moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to a subject as defined herein. These pharmaceutical compositions, which comprise an amount of the protein inhibitor effective to treat or prevent a protein kinase-mediated condition and a pharmaceutically acceptable carrier, are another embodiment of the present invention.

In one embodiment the present invention is a method of treating or preventing a protein kinase-mediated disorder in a subject in need thereof, comprising administering to the subject an effective amount of a compound composition or a pharmaceutically acceptable salt of the present invention as described herein. In another embodiment, the present invention is the use of an effective amount of a compound, composition or a pharmaceutically acceptable salt described herein for treating or preventing a disease or disorder, described herein, in a subject in need thereof. In another embodiment, the present invention is the use of an effective amount of a compound, composition or a pharmaceutically acceptable salt described herein for treating a disease or disorder, described herein, in a subject in need thereof. In yet another embodiment, the present invention is the use of an effective amount of a compound, composition or a pharmaceutically acceptable salt described herein for the manufacture of a medicament method for the treatment or prevention of a disease or disorder, described herein, in a subject in need thereof. In yet another embodiment, the present invention is the use of an effective amount of a compound, composition or a pharmaceutically acceptable salt described herein for the manufacture of a medicament method for the treatment of a disease or disorder, described herein, in a subject in need thereof. In one embodiment the protein kinase mediated disease is a protein kinase C(PKC) mediated disease. In another embodiment the protein kinase mediated disease is a protein kinase C theta (PKCtheta)-mediated disease.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a protein kinase-mediated condition, prevent the advancement of a protein kinase-mediated condition, cause the regression of a protein kinase-mediated condition, prevent the recurrence, development, onset or progression of a symptom associated with a protein kinase-mediated condition, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of protein kinase-mediated condition, and the mode of administration. The skilled artisan will be able to determine appropriate dosages depending on these and other factors. When co-administered with other agents, e.g., when co-administered with an protein kinase-mediated condition agent, an "effective amount" of the second agent, will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a protein kinase-mediated condition, or the amelioration of one or more symptoms (preferably, one or more discernible symptoms) of a protein kinase-mediated condition resulting from the administration of one or more therapies (e.g., one or more therapeutic agents such as a compound of the invention). In specific embodiments, the terms "treat", "treatment" and "treating" refer to the amelioration of at least one measurable physical parameter of a protein kinase-mediated condition. In other embodiments the terms "treat", "treatment" and "treating" refer to the inhibition of the progression of a protein kinase-mediated condition, either physically by, e.g., stabilization of a discernible symptom, physiologically by, e.g., stabilization of a physical parameter, or both. In other embodiments the terms "treat", "treatment" and "treating" refer to the reduction or stabilization of a protein kinase-mediated condition.

As used herein, the terms "prevent", "prevention" and "preventing" refer to the reduction in the risk of acquiring or developing a given protein kinase-mediated condition, or the reduction or inhibition of the recurrence or a protein kinase-mediated condition. In one embodiment, a compound of the invention is administered as a preventative measure to a patient, preferably a human, having a genetic predisposition to any of the conditions, diseases or disorders described herein.

As used herein, the terms, "disease", "disorder" and "condition" may be used interchangeably here to refer to a protein kinase-mediated condition.

In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor. In some embodiments, said protein kinase inhibitor is a PKCtheta inhibitor.

The term "protein kinase-mediated condition", as used herein means any disease or other deleterious condition in which a protein kinase plays a role. Such conditions include, without limitation, autoimmune diseases, inflammatory diseases, proliferative and hyperproliferative diseases, immunologically-mediated diseases, immuno-deficiency disorders, immunomodulatory or immunosuppressive disorder, bone diseases, metabolic diseases, neurological and neurodegenerative diseases, cardiovascular diseases, hormone related diseases, diabetes, allergies, asthma, and Alzheimer's disease. In one embodiment, the protein-kinase mediated condition is a PKC-mediated condition.

The term "PKC-mediated condition", as used herein means any disease or other deleterious condition in which PKC plays a role. Such conditions include, without limitation, those listed above, and in particular, T-cell mediated diseases, including without limitation autoimmune diseases, chronic or acute inflammatory diseases, and proliferative and hyperproliferative diseases. In one embodiment, the PKC-mediated condition is a PKCtheta-mediated condition The term "PKCtheta-mediated condition", as used herein means any disease or other deleterious condition in which PKCtheta plays a role. Such conditions include, without limitation, those listed above, and in particular, autoimmune diseases, chronic or acute inflammatory diseases, and proliferative and hyperproliferative diseases.

As used herein, the term "inflammatory disease" or "inflammatory disorder" refers to pathological states resulting in inflammation, typically caused by leukocyte infiltration. Examples of such disorders include inflammatory skin diseases, including, without limitation, psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicemia or trauma; alcoholic hepatitis; bacterial pneumonia; antigen-antibody complex mediated diseases including glomerulonephritis; sepsis; sarcoidosis; immunopathologic responses to tissue or organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc.

Proliferative or hyperproliferative diseases are characterized by excessive or abnormal cell proliferation. Such diseases include, without limitation, cancer and myeloproliferative disorders.

The term "cancers" includes, but is not limited to, the following cancers: epidermoid Oral: Cardiac: Lung: Gastrointestinal: Genitourinary tract: Liver: Bone: Nervous system: Gynecological: Hematologic: Thyroid gland: and Adrenal glands. Hematologic cancers include: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, and psoriasis. Thus, the term "cancerous cell" as provided herein, includes a cell afflicted by any one of the above-identified conditions.

The term "myeloproliferative disorders", includes disorders such as polycythemia vera, thrombocythemia, myeloid metaplasia with myelofibrosis, hypereosinophilic syndrome, juvenile myelomonocytic leukaemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Examples of neurodegenerative diseases include, without limitation, Alzheimer's disease Huntington's disease, Parkinson's disease, AIDS-associated dementia, and bipolar disorder.

In one embodiment the PKCtheta mediated disease includes, without limitation, chronic inflammation, autoimmune diabetes, rheumatoid arthritis (RA), rheumatoid spondylitis, gouty arthritis and other arthritic conditions, multiple sclerosis (MS), asthma, systemic lupus erythematosis, adult respiratory distress syndrome, Behcet's disease, psoriasis, chronic pulmonary inflammatory disease, graft versus host reaction, Crohn's Disease, ulcerative colitis, inflammatory bowel disease (IBD), which includes celiac disease and irritable bowel syndrome; Alzheimer's disease, T-cell leukaemia, lymphoma, transplant rejection, cancer and pyresis, along with any disease or disorder that relates to inflammation and related disorders.

In one embodiment the PKCtheta mediated disease includes, diseases such as, but not limited to, arthritis, rheumatoid arthritis, osteoarthritis, joint inflammation, lupus, multiple sclerosis, asthma, psoriasis, cancer, T-cell lymphomas, leukaemia, diabetes type I or II, and inflammatory bowel diseases, transplant rejection, Crohn's disease and colitis.

Examples of autoimmune diseases include, without limitation, multiple sclerosis, rheumatoid arthritis and irritable bowel disease.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The dosage regimen utilizing the compounds of Structural Formula I, IA, IB or IC can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of Structural Formula I, IA, IB or IC required to treat, for example, to prevent, inhibit (fully or partially) or arrest the progress of the disease.

Dosages of the compounds of Structural Formula I, IA, IB or IC can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of Structural Formula I, IA, IB or IC or a pharmaceutically acceptable salt or solvate (e.g., hydrate) thereof alone or in combination with an additional suitable therapeutic agent, for example, a cancer-therapeutic agent. When combination therapy is employed, an effective amount can be achieved using a first amount of a compound of Structural Formula I, IA, IB or IC or a pharmaceutically acceptable salt or solvate (e.g., hydrate) thereof and a second amount of an additional suitable therapeutic agent.

In one embodiment, the compound of Structural Formula I, IA, IB or IC and the additional therapeutic agent, are each administered in an effective amount (i.e., each in an amount which would be therapeutically effective if administered alone). In another embodiment, the compound of Structural Formula I, IA, IB or IC and the additional therapeutic agent, are each administered in an amount which alone does not provide a therapeutic effect (a sub-therapeutic dose). In yet another embodiment, the compound of Structural Formula I, IA, IB or IC can be administered in an effective amount, while the additional therapeutic agent is administered in a sub-therapeutic dose. In still another embodiment, the compound of Structural Formula I, IA, IB or IC can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapies (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of Structural Formula I, IA, IB or IC and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Structural Formula I, IA, IB or IC and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of Structural Formula I, IA, IB or IC and a second amount of an additional therapeutic agent can result in an enhanced or synergistic therapeutic effect, wherein the combined effect is greater than the additive effect that would result from separate administration of the first amount of the compound of Structural Formula I, IA, IB or IC and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

In some embodiments, said additional therapeutic agent is selected from a cancer-therapeutic agent, such as, an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In yet other embodiments, said additional therapeutic agent is selected from camptothecin, doxorubicin, idarubicin, Cisplatin, taxol, taxotere, vincristine; tarceva, the MEK inhibitor, U0126, a KSP inhibitor, vorinostat, Gleevec, dasatinib, and nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxane®).

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dekrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepeside); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the compounds of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

As inhibitors of protein kinases, the compounds and compositions of this invention are also useful in biological samples. One aspect of the invention relates to inhibiting protein kinase activity in a biological sample, which method comprises contacting said biological sample with a compound of Formula I, IA, IB or IC or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention is set forth in the Examples below.

Another aspect of the invention provides a method for modulating enzyme activity by contacting a compound of Formula I, IA, IB or IC with a protein kinase.

Abbreviations

The following abbreviations are used:
DMSO dimethyl sulfoxide
TCA trichloroacetic acid
ATP adenosine triphosphate
BSA bovine serum albumin
DTT dithiothreitol
MOPS 4-morpholinepropanesulfonic acid
NMR nuclear magnetic resonance HPLC high performance liquid chromatography
LCMS liquid chromatography-mass spectrometry
TLC thin layer chromatography
Rt retention time
In some embodiments, the compounds of this invention are represented in Table 1.
TABLE 1
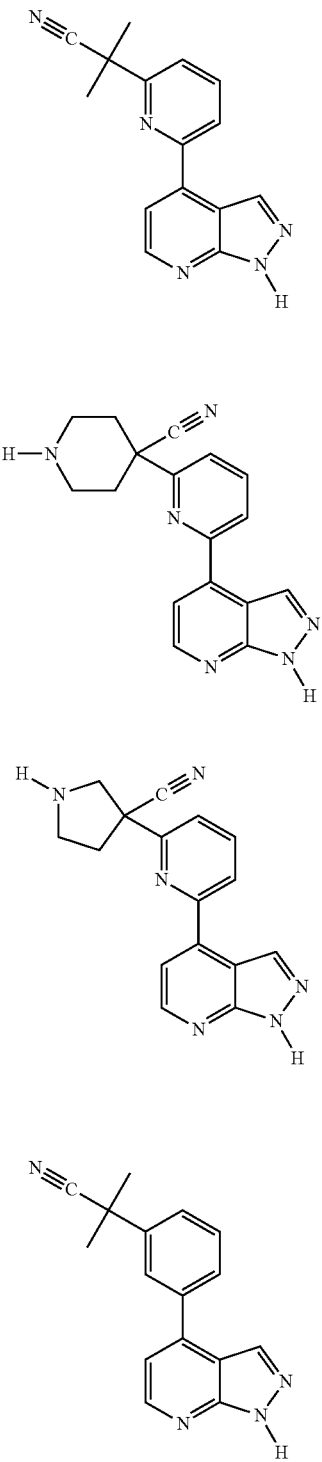
TABLE 1-continued
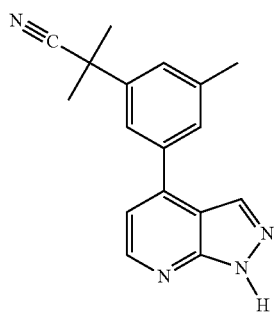 [SMILES: Cc1cc(-c2ccnc3[nH]ncc23)cc(C(C)(C)C#N)c1]
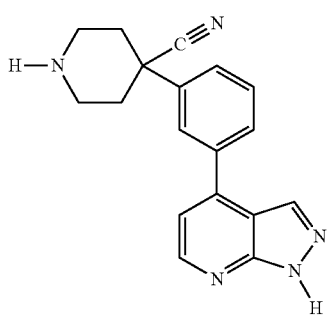 [SMILES: N#CC1(c2cccc(-c3ccnc4[nH]ncc34)c2)CCNCC1]
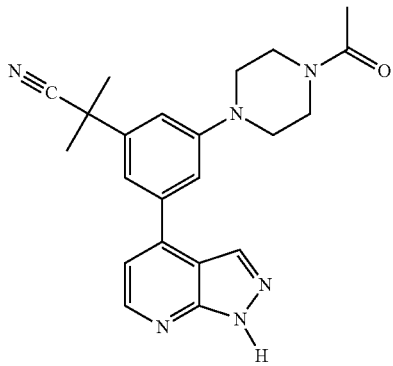 [SMILES: CC(=O)N1CCN(c2cc(-c3ccnc4[nH]ncc34)cc(C(C)(C)C#N)c2)CC1]
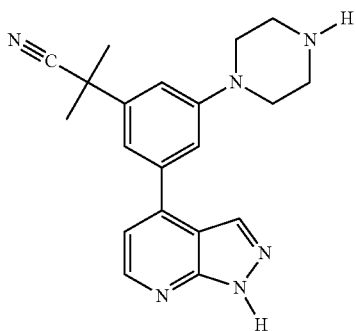 [SMILES: CC(C)(C#N)c1cc(-c2ccnc3[nH]ncc23)cc(N2CCNCC2)c1]

TABLE 1-continued
9
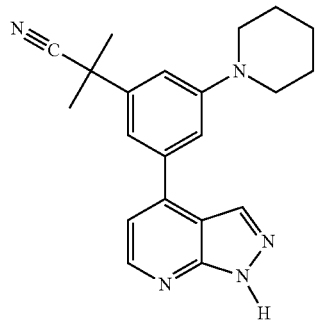 [SMILES: CC(C)(C#N)c1cc(-c2ccnc3[nH]ncc23)cc(N2CCCCC2)c1]
10
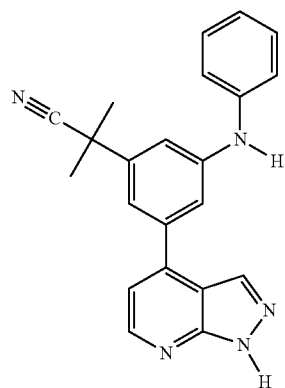 [SMILES: CC(C)(C#N)c1cc(Nc2ccccc2)cc(-c2ccnc3[nH]ncc23)c1]
11
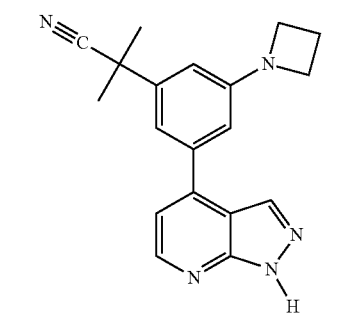 [SMILES: CC(C)(C#N)c1cc(-c2ccnc3[nH]ncc23)cc(N2CCC2)c1]
12
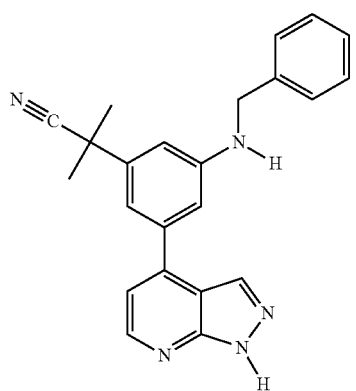 [SMILES: CC(C)(C#N)c1cc(NCc2ccccc2)cc(-c2ccnc3[nH]ncc23)c1]
TABLE 1-continued
13
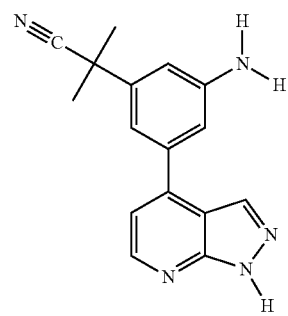 [SMILES: CC(C)(C#N)c1cc(N)cc(-c2ccnc3[nH]ncc23)c1]
14
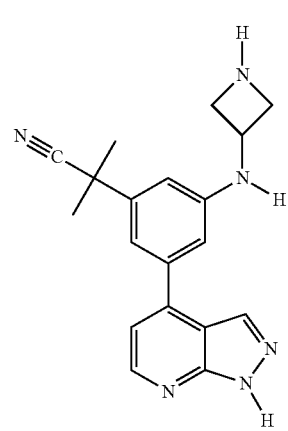 [SMILES: CC(C)(C#N)c1cc(NC2CNC2)cc(-c2ccnc3[nH]ncc23)c1]
15
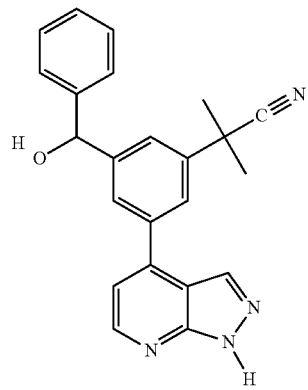
16
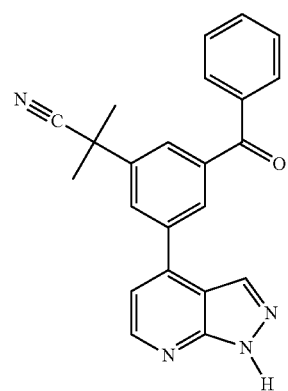

TABLE 1-continued
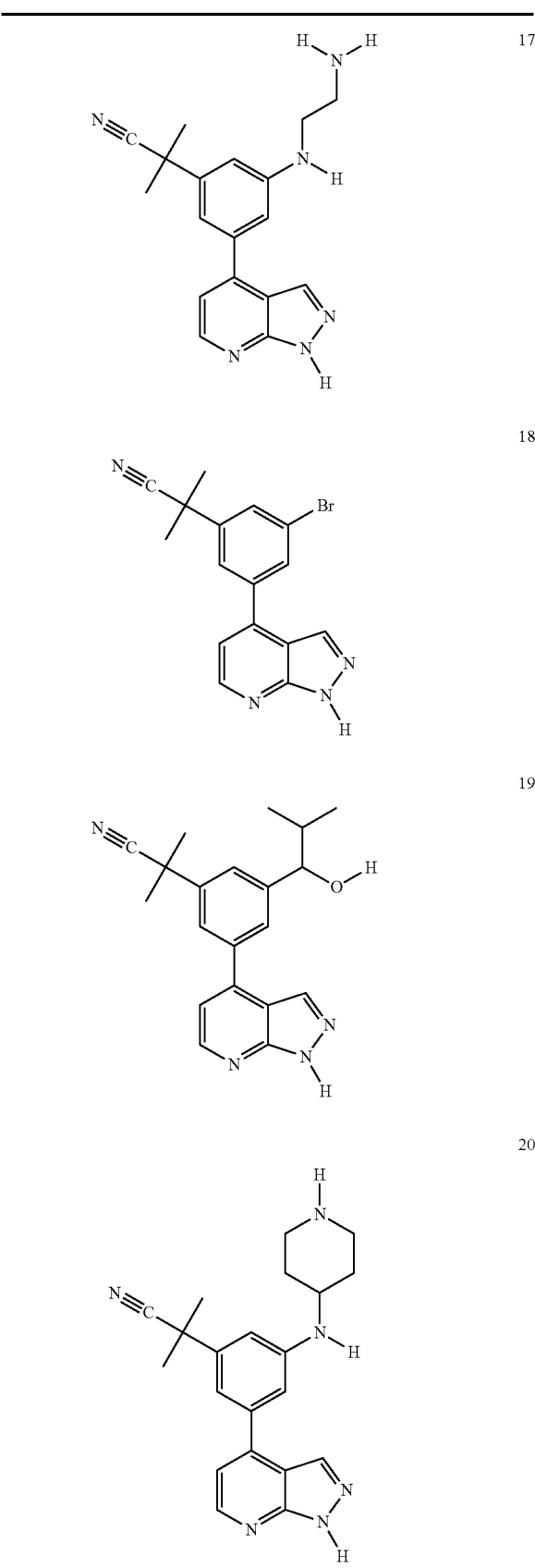
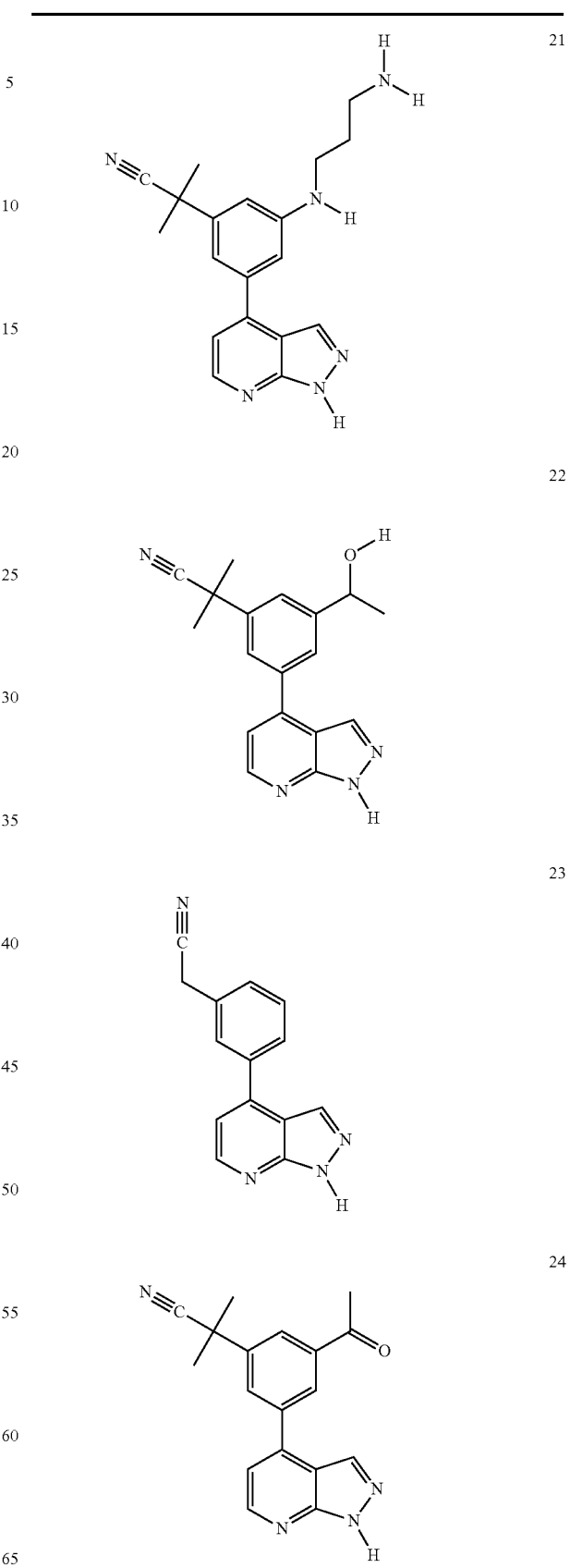

TABLE 1-continued
| | |
|---|---|
| 25 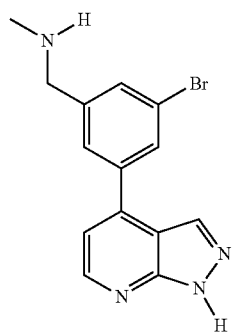 [SMILES: CNCc1cc(Br)cc(-c2ccnc3[nH]ncc23)c1] | 30 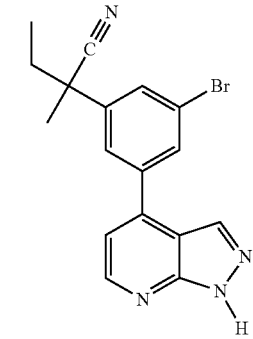 |
| 26 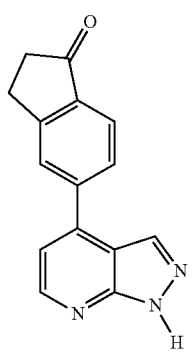 [SMILES: O=C1CCc2cc(-c3ccnc4[nH]ncc34)ccc21] | 31 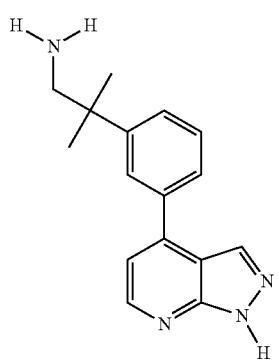 |
| 27 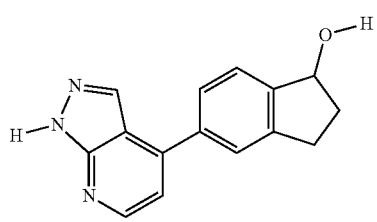 [SMILES: OC1CCc2cc(-c3ccnc4[nH]ncc34)ccc21] | 32 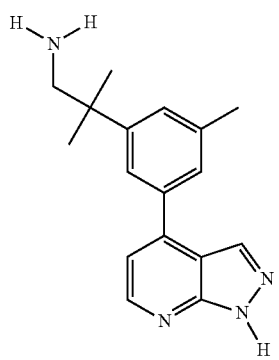 |
| 28 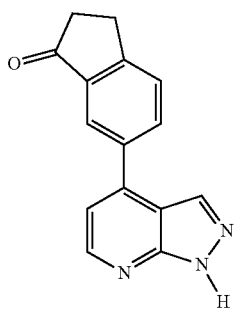 [SMILES: O=C1CCc2ccc(-c3ccnc4[nH]ncc34)cc21] | 33 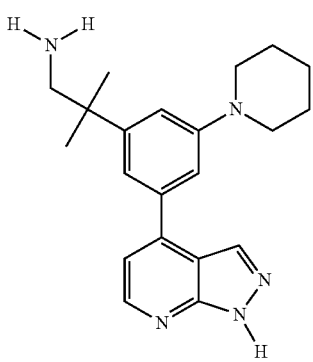 |
| 29 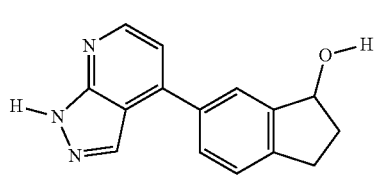 [SMILES: OC1CCc2ccc(-c3ccnc4[nH]ncc34)cc21] | |

TABLE 1-continued
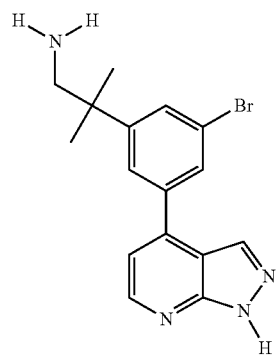 [SMILES: CC(C)(CN)c1cc(Br)cc(-c2ccnc3[nH]ncc23)c1]
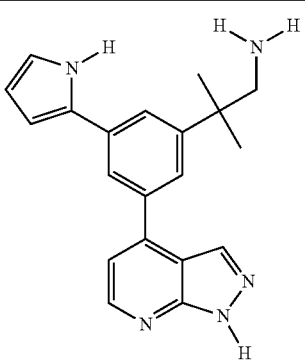

TABLE 1-continued
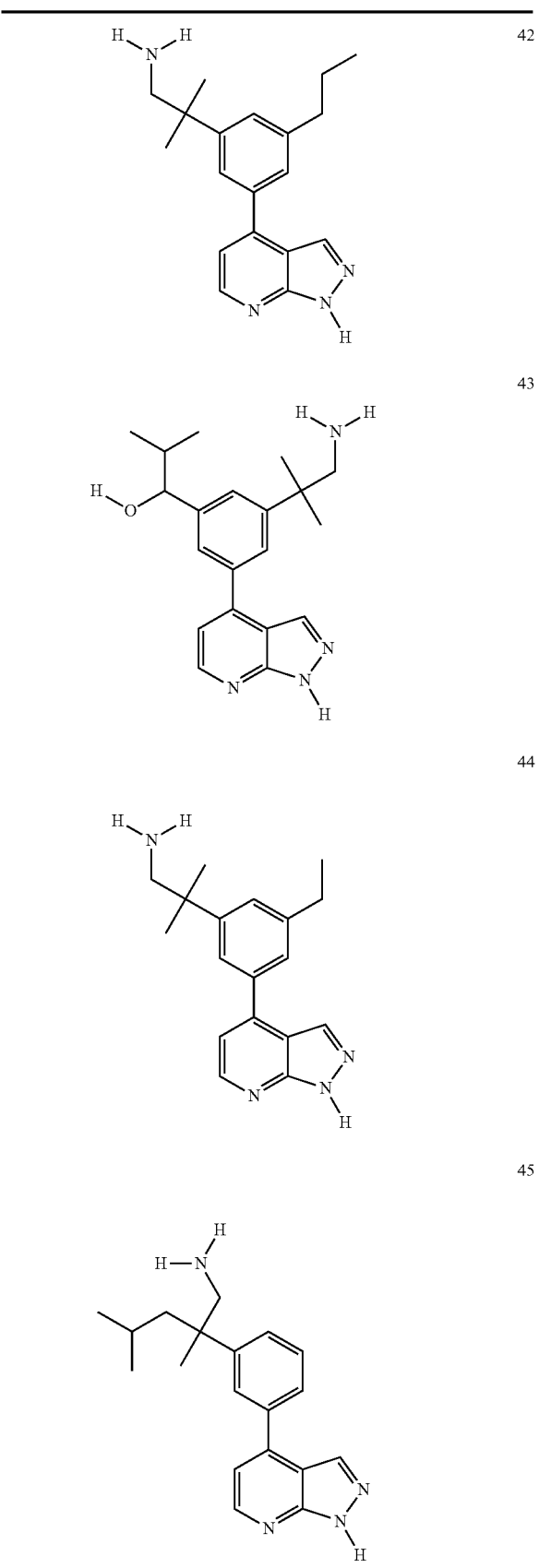
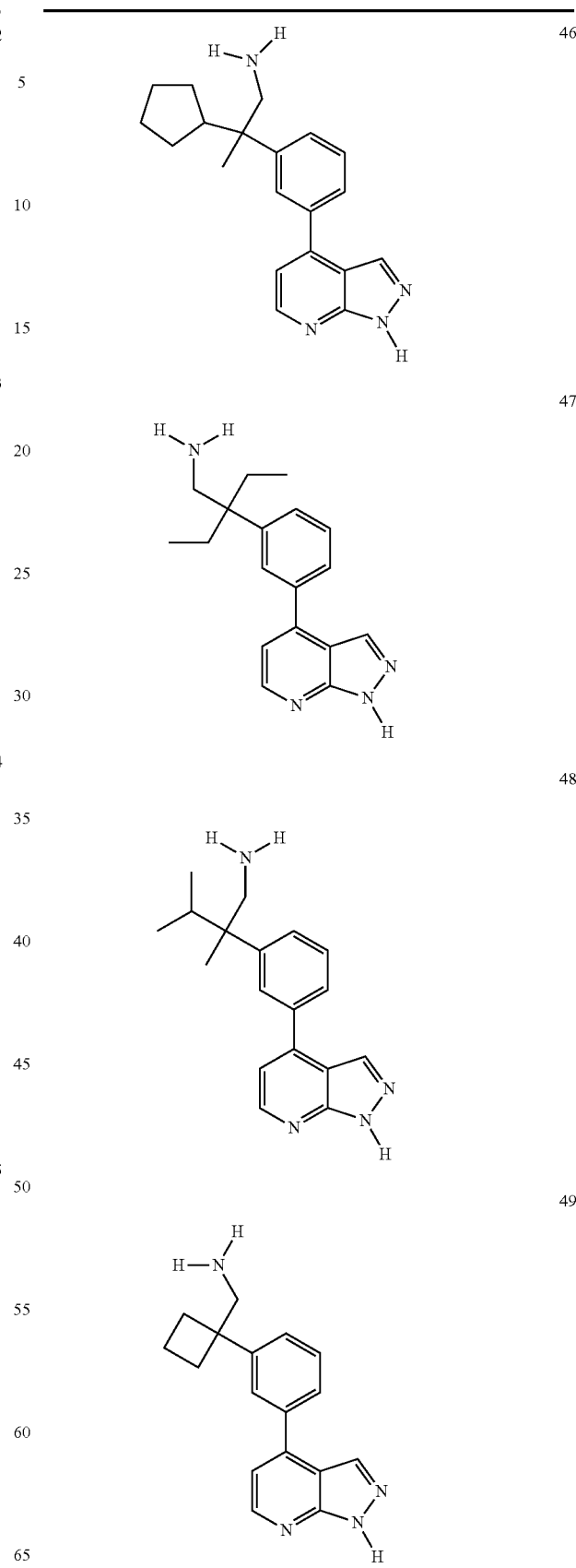

TABLE 1-continued
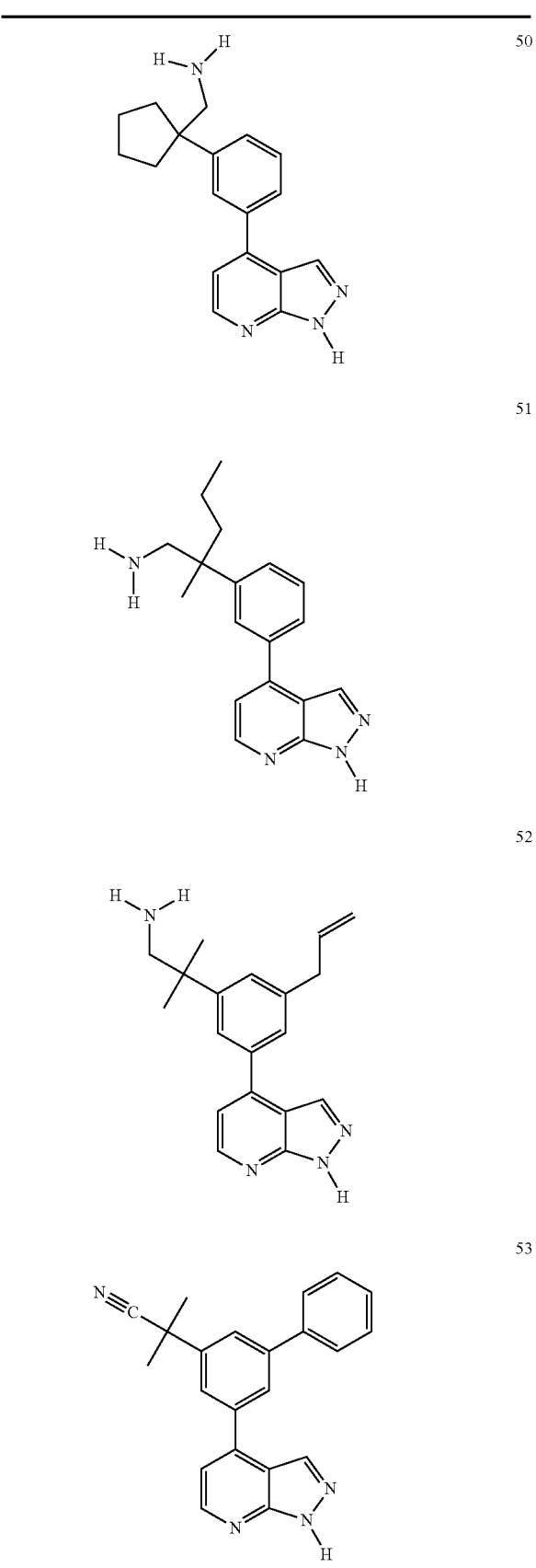

TABLE 1-continued
| | |
|---|---|
| 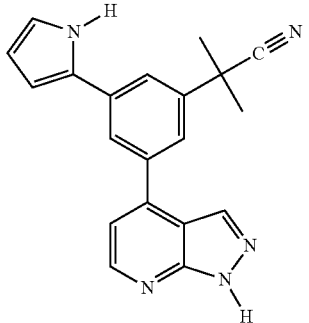 [SMILES: CC(C)(C#N)c1cc(-c2ccc[nH]2)cc(-c2ccnc3[nH]ncc23)c1] | 59 |
| 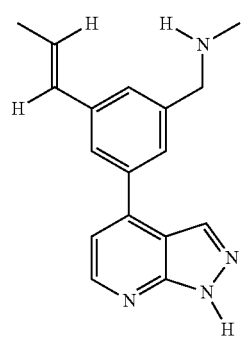 [SMILES: C/C=C/c1cc(CNC)cc(-c2ccnc3[nH]ncc23)c1] | 60 |
| 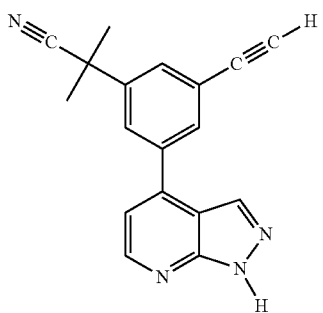 [SMILES: C#Cc1cc(-c2ccnc3[nH]ncc23)cc(C(C)(C)C#N)c1] | 61 |
| 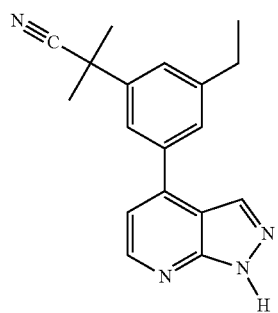 [SMILES: CCc1cc(-c2ccnc3[nH]ncc23)cc(C(C)(C)C#N)c1] | 62 |
| 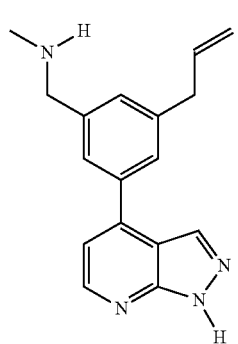 [SMILES: C=CCc1cc(CNC)cc(-c2ccnc3[nH]ncc23)c1] | 63 |
TABLE 1-continued
| | |
|---|---|
| 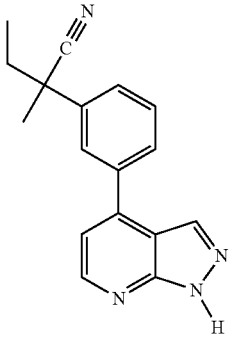 [SMILES: CCC(C)(C#N)c1cccc(-c2ccnc3[nH]ncc23)c1] | 64 |
| 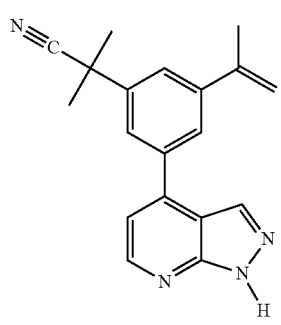 [SMILES: C=C(C)c1cc(-c2ccnc3[nH]ncc23)cc(C(C)(C)C#N)c1] | 65 |
| 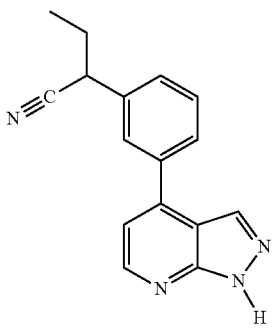 [SMILES: CCC(C#N)c1cccc(-c2ccnc3[nH]ncc23)c1] | 66 |
| 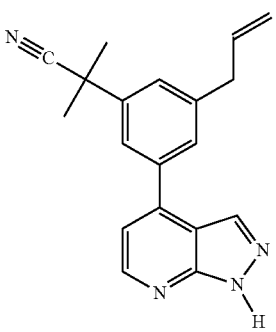 [SMILES: C=CCc1cc(-c2ccnc3[nH]ncc23)cc(C(C)(C)C#N)c1] | 67 |
| 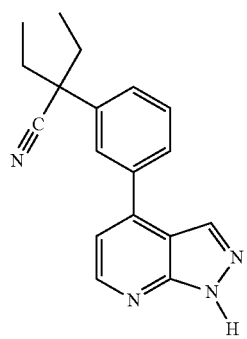 [SMILES: CCC(C#N)(CC)c1cccc(-c2ccnc3[nH]ncc23)c1] | 68 |

TABLE 1-continued
69 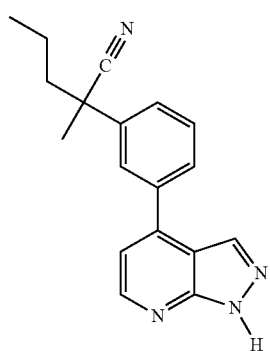 [SMILES: CCCC(C)(C#N)c1cccc(-c2ccnc3[nH]ncc23)c1]
70 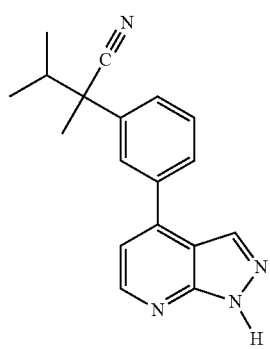 [SMILES: CC(C)C(C)(C#N)c1cccc(-c2ccnc3[nH]ncc23)c1]
71 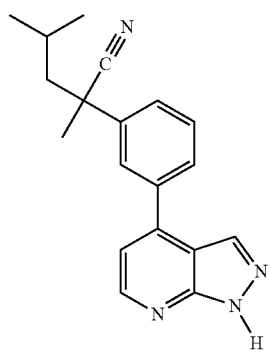 [SMILES: CC(C)CC(C)(C#N)c1cccc(-c2ccnc3[nH]ncc23)c1]
72 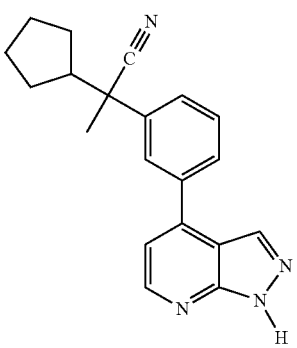 [SMILES: CC(C#N)(c1cccc(-c2ccnc3[nH]ncc23)c1)C1CCCC1]
TABLE 1-continued
73 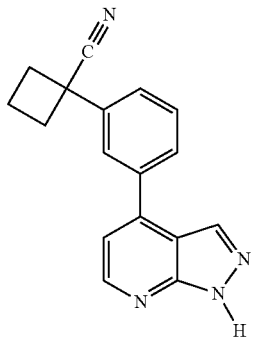 [SMILES: N#CC1(c2cccc(-c3ccnc4[nH]ncc34)c2)CCC1]
74 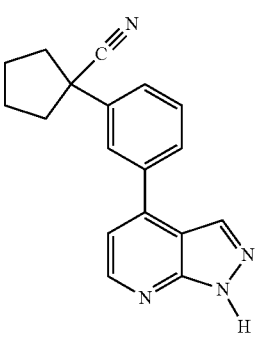 [SMILES: N#CC1(c2cccc(-c3ccnc4[nH]ncc34)c2)CCCC1]
75 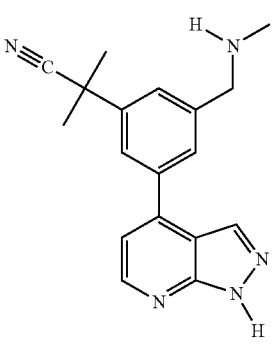 [SMILES: CNCc1cc(-c2ccnc3[nH]ncc23)cc(C(C)(C)C#N)c1]
76 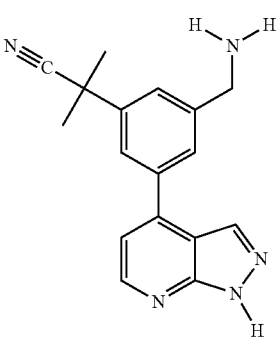 [SMILES: CC(C)(C#N)c1cc(CN)cc(-c2ccnc3[nH]ncc23)c1]

TABLE 1-continued
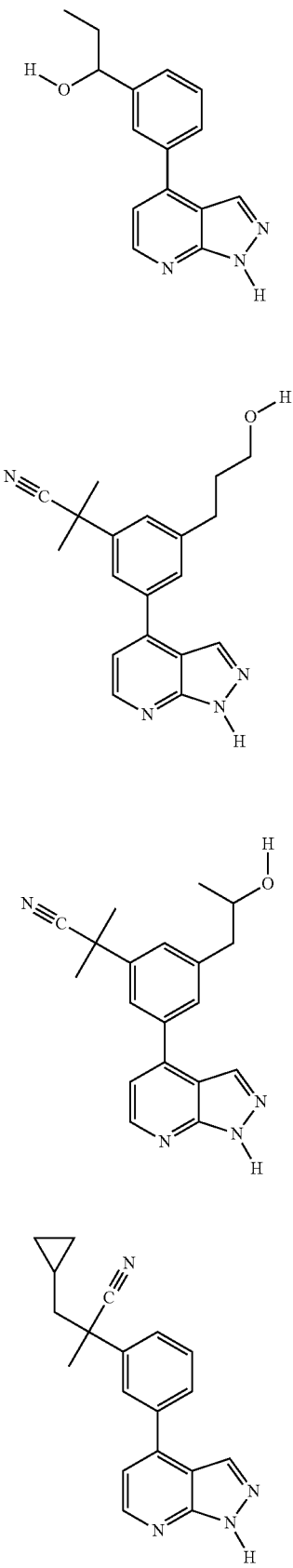
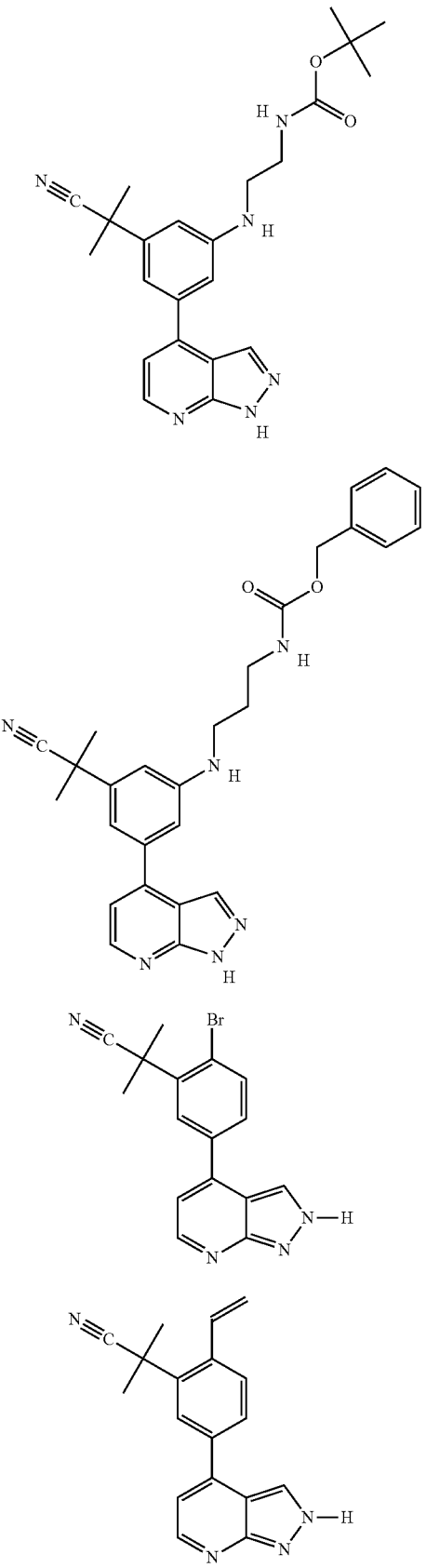

TABLE 1-continued
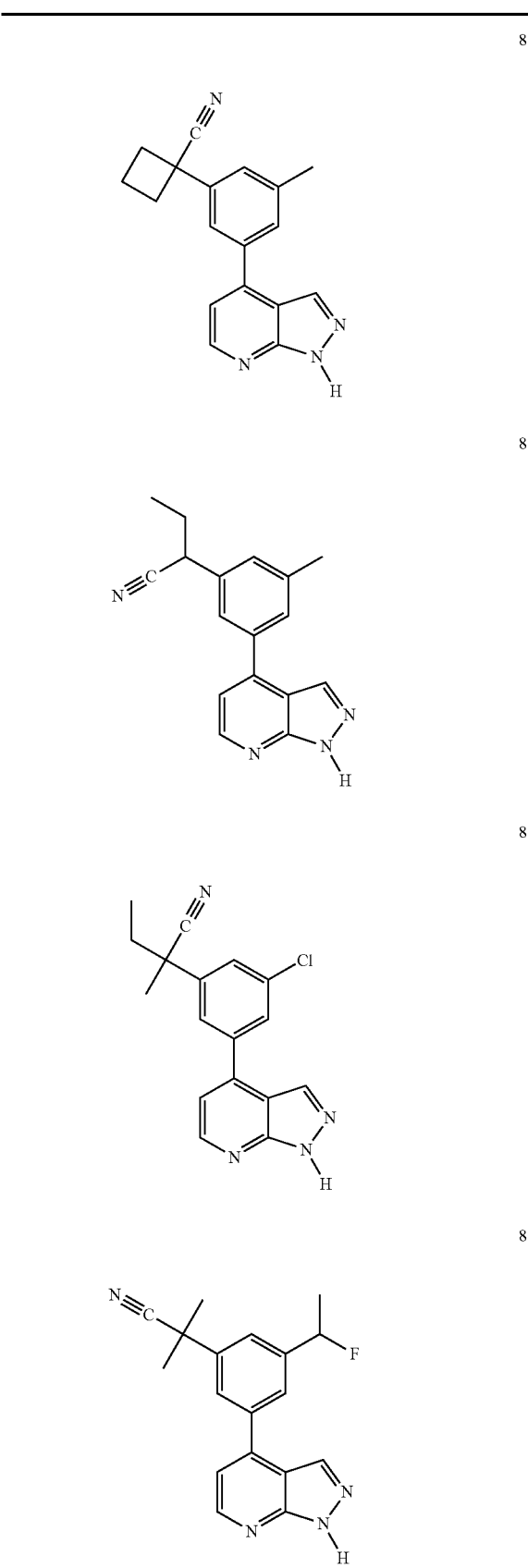
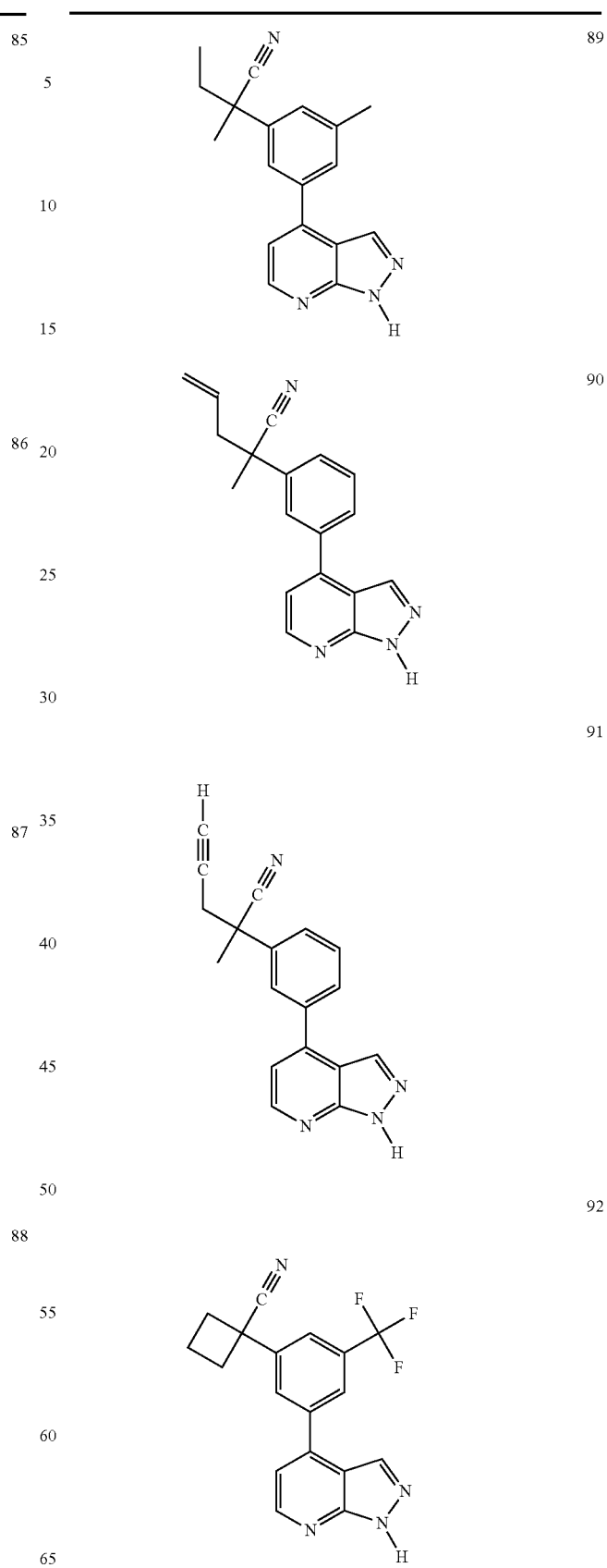

TABLE 1-continued
93 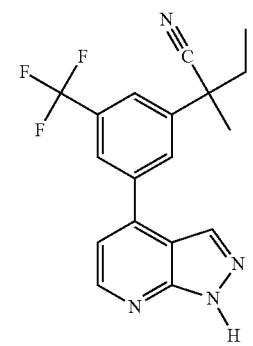 [SMILES: CCC(C)(C#N)c1cc(-c2ccnc3[nH]ncc23)cc(C(F)(F)F)c1]
94 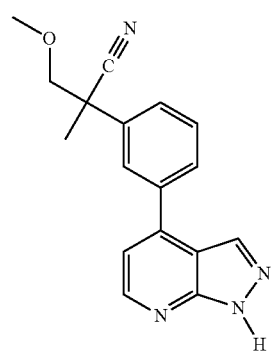 [SMILES: COCC(C)(C#N)c1cccc(-c2ccnc3[nH]ncc23)c1]
95 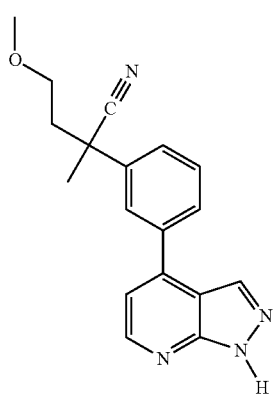 [SMILES: COCCC(C)(C#N)c1cccc(-c2ccnc3[nH]ncc23)c1]
TABLE 1-continued
97 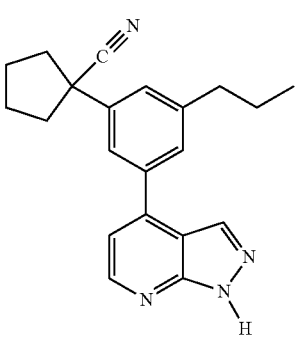 [SMILES: CCCc1cc(-c2ccnc3[nH]ncc23)cc(C2(C#N)CCCC2)c1]
98 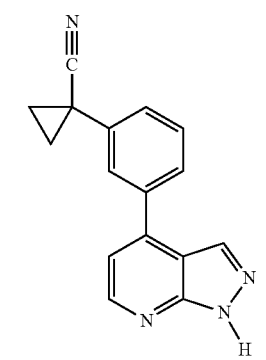 [SMILES: N#CC1(c2cccc(-c3ccnc4[nH]ncc34)c2)CC1]
99 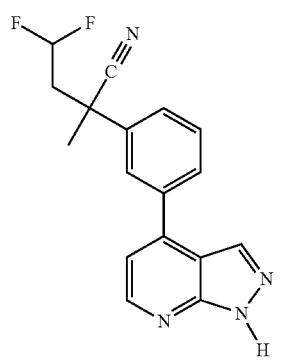 [SMILES: CC(C#N)(CC(F)F)c1cccc(-c2ccnc3[nH]ncc23)c1]
100 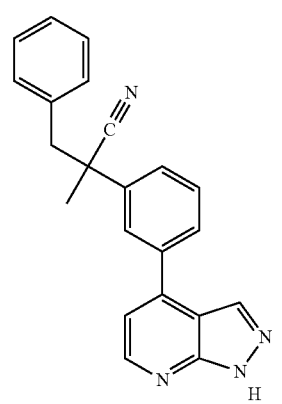

TABLE 1-continued
| | |
|---|---|
| 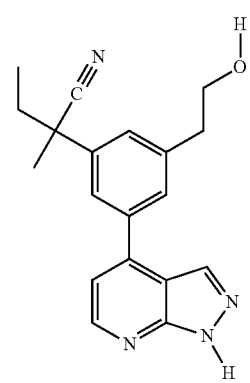 [SMILES: CCC(C)(C#N)c1cc(CCO)cc(-c2ccnc3[nH]ncc23)c1] | 101 |
| 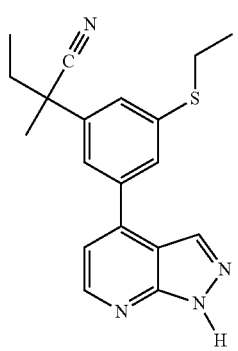 [SMILES: CCSc1cc(-c2ccnc3[nH]ncc23)cc(C(C)(C#N)CC)c1] | 102 |
| 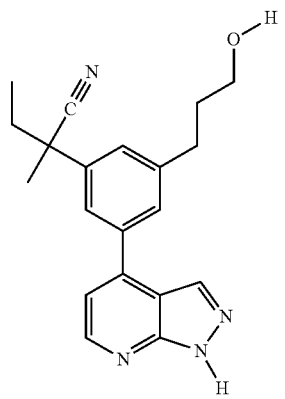 [SMILES: CCC(C)(C#N)c1cc(CCCO)cc(-c2ccnc3[nH]ncc23)c1] | 103 |
| 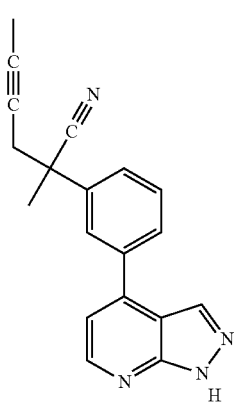 | 104 |
| 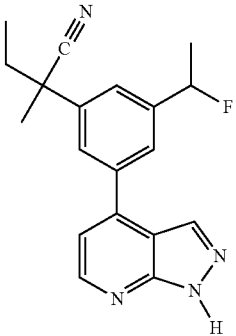 [SMILES: CCC(C)(C#N)c1cc(-c2ccnc3[nH]ncc23)cc(C(C)F)c1] | 105 |
| 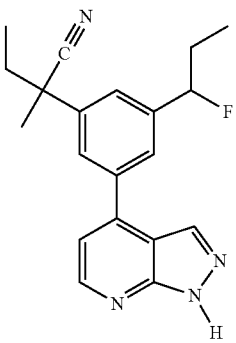 [SMILES: CCC(F)c1cc(-c2ccnc3[nH]ncc23)cc(C(C)(C#N)CC)c1] | 106 |
| 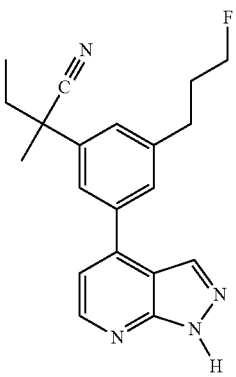 [SMILES: CCC(C)(C#N)c1cc(CCCF)cc(-c2ccnc3[nH]ncc23)c1] | 107 |
| 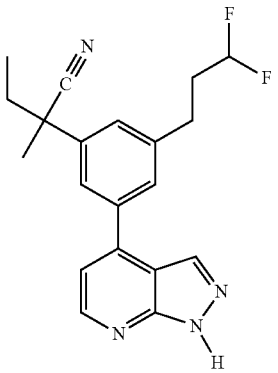 [SMILES: CCC(C)(C#N)c1cc(CCC(F)F)cc(-c2ccnc3[nH]ncc23)c1] | 108 |

TABLE 1-continued
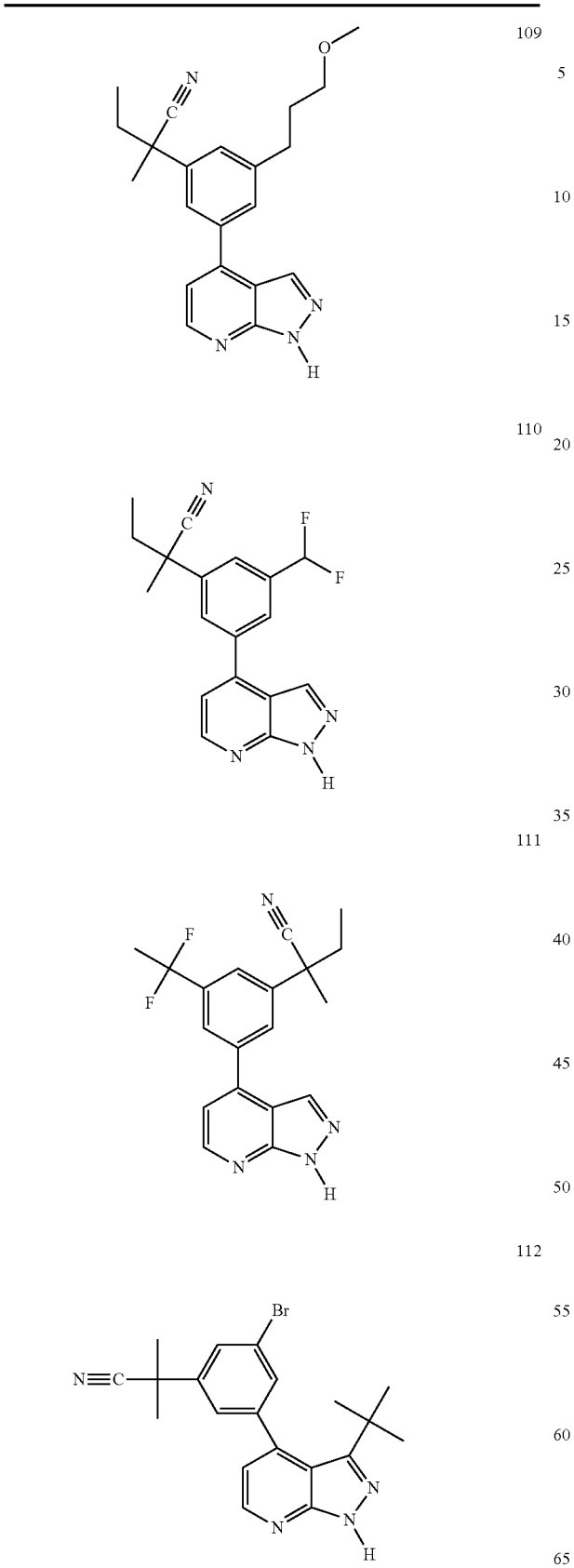
TABLE 1-continued
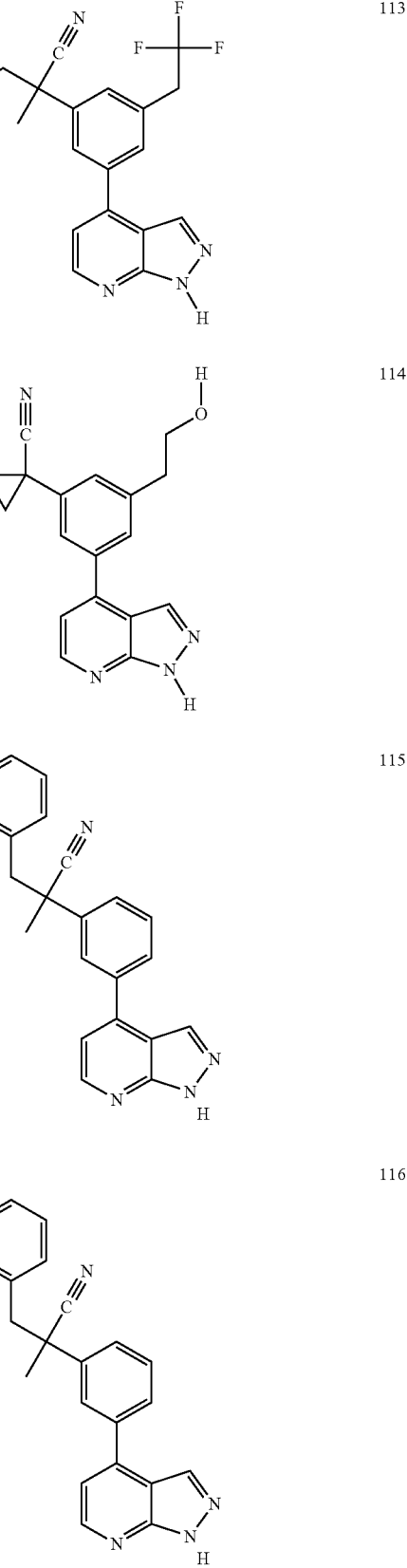

TABLE 1-continued
| | |
|---|---|
| 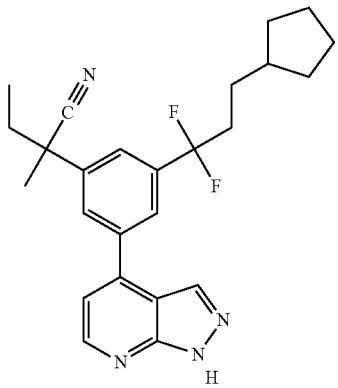 | 117 |
| 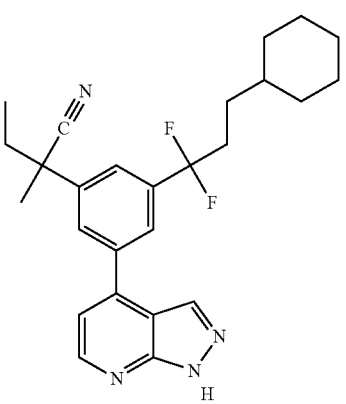 | 118 |
| 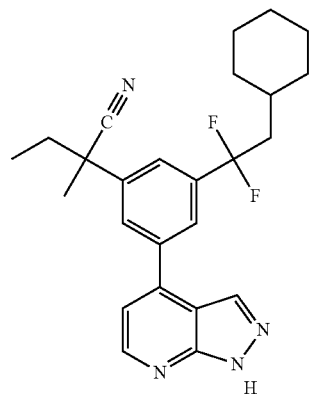 | 119 |
| 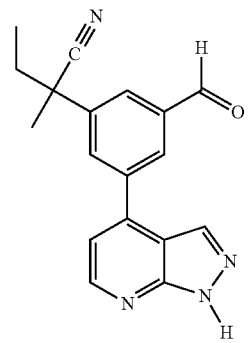 [SMILES: CCC(C)(C#N)c1cc(C=O)cc(-c2ccnc3[nH]ncc23)c1] | 120 |
TABLE 1-continued
| | |
|---|---|
| 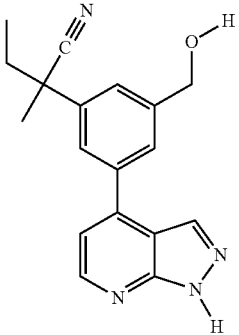 [SMILES: CCC(C)(C#N)c1cc(CO)cc(-c2ccnc3[nH]ncc23)c1] | 121 |
| 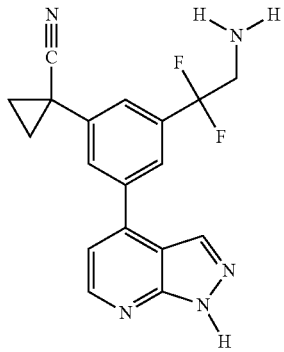 [SMILES: N#CC1(c2cc(-c3ccnc4[nH]ncc34)cc(C(F)(F)CN)c2)CC1] | 122 |
| 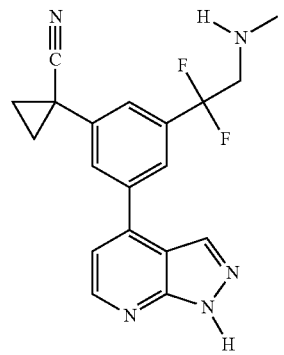 [SMILES: CNCC(F)(F)c1cc(-c2ccnc3[nH]ncc23)cc(C2(C#N)CC2)c1] | 123 |
| 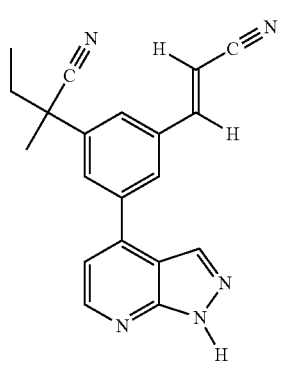 [SMILES: CCC(C)(C#N)c1cc(/C=C/C#N)cc(-c2ccnc3[nH]ncc23)c1] | 124 |

TABLE 1-continued
125
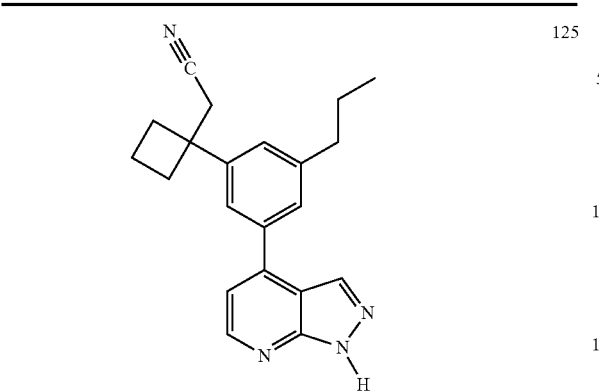
126
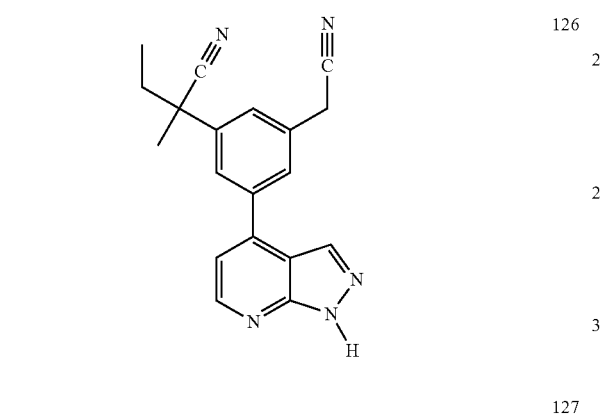
127
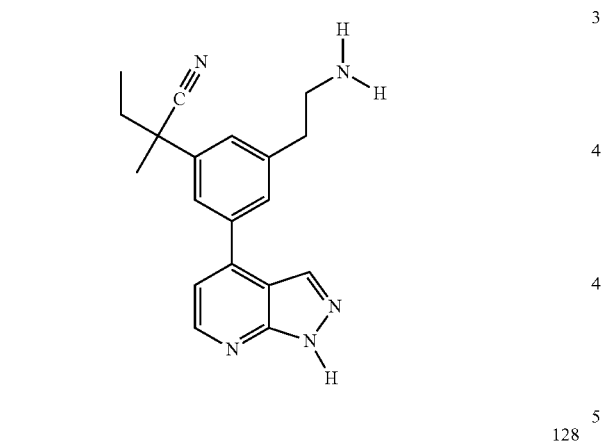
128
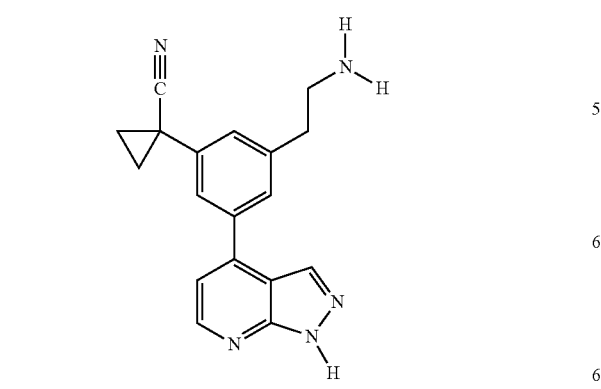
TABLE 1-continued
129
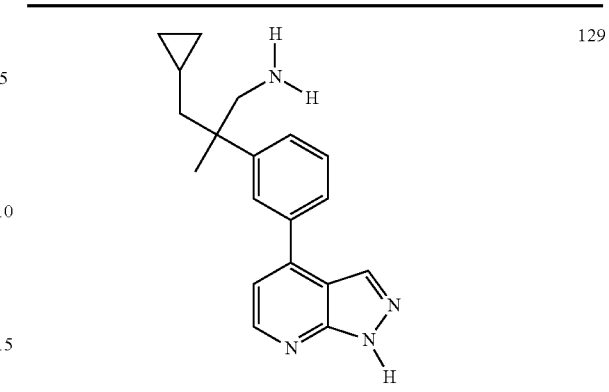
130
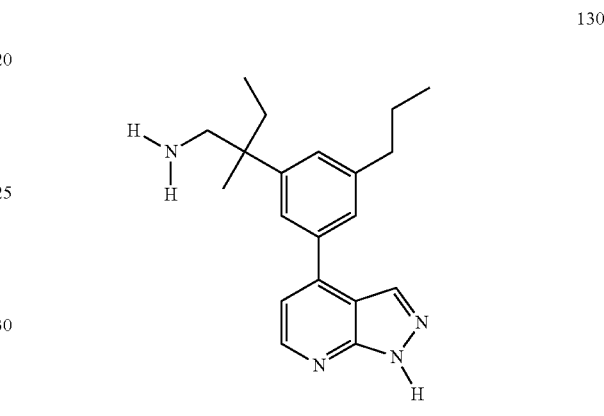
131
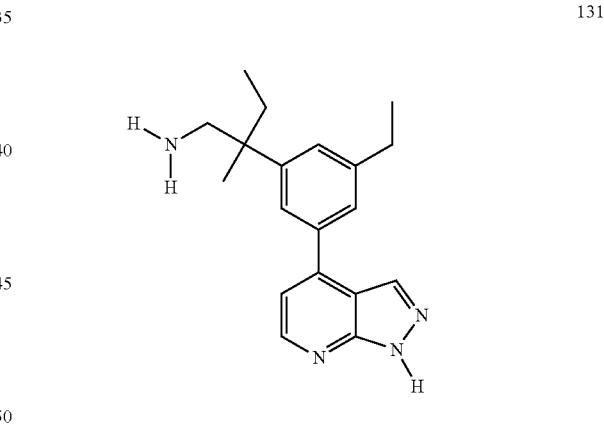
132
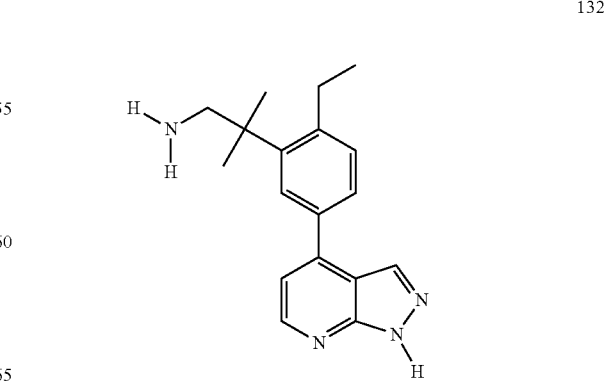

TABLE 1-continued
133 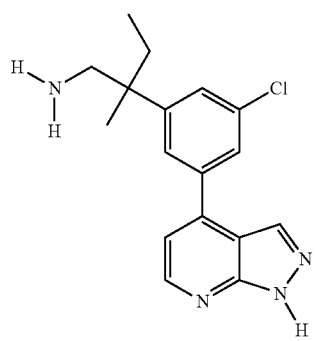
134 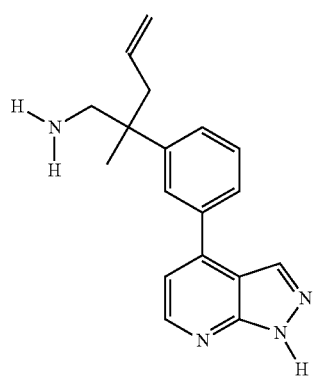 [SMILES: C=CCC(C)(CN)c1cccc(-c2ccnc3[nH]ncc23)c1]
135 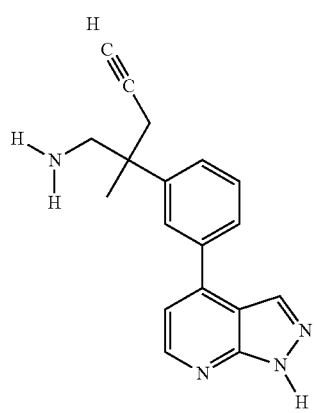
136 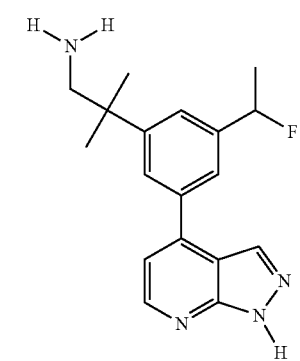 [SMILES: CC(F)c1cc(-c2ccnc3[nH]ncc23)cc(C(C)(C)CN)c1]
TABLE 1-continued
137 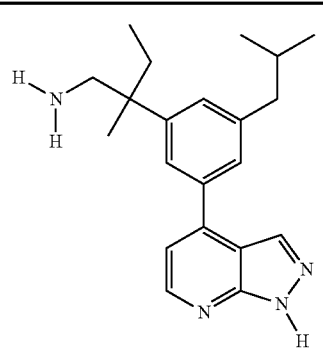
138 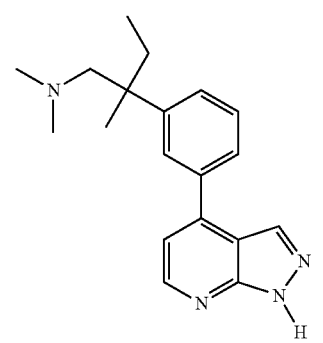 [SMILES: CCC(C)(CN(C)C)c1cccc(-c2ccnc3[nH]ncc23)c1]
139 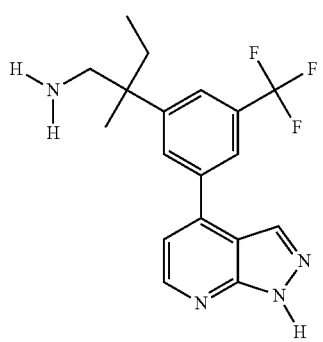 [SMILES: CCC(C)(CN)c1cc(-c2ccnc3[nH]ncc23)cc(C(F)(F)F)c1]
140 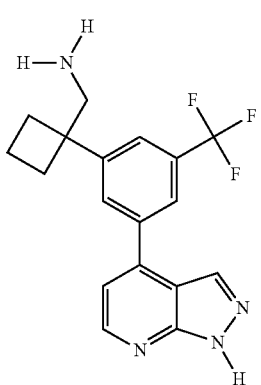 [SMILES: NCC1(c2cc(-c3ccnc4[nH]ncc34)cc(C(F)(F)F)c2)CCC1]

TABLE 1-continued
141
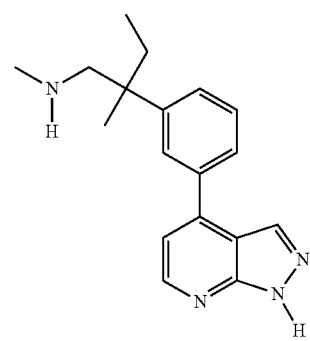 [SMILES: CCC(C)(CNC)c1cccc(-c2ccnc3[nH]ncc23)c1]
142
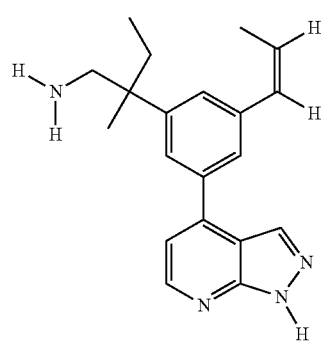 [SMILES: C/C=C\c1cc(-c2ccnc3[nH]ncc23)cc(C(C)(CC)CN)c1]
143
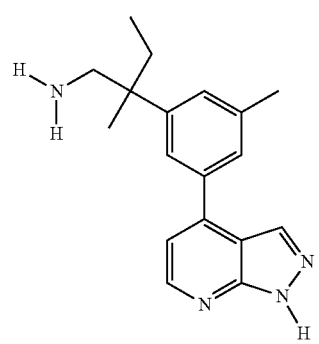 [SMILES: CCC(C)(CN)c1cc(C)cc(-c2ccnc3[nH]ncc23)c1]
144
145
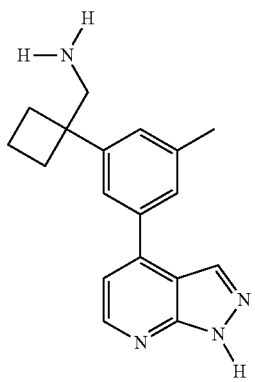 [SMILES: Cc1cc(-c2ccnc3[nH]ncc23)cc(C2(CN)CCC2)c1]
146
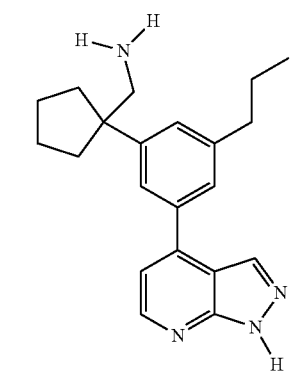 [SMILES: CCCc1cc(-c2ccnc3[nH]ncc23)cc(C2(CN)CCCC2)c1]
147
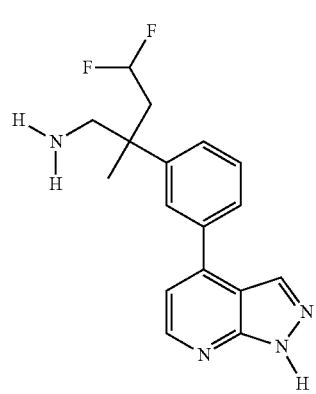 [SMILES: CC(CN)(CC(F)F)c1cccc(-c2ccnc3[nH]ncc23)c1]
148

TABLE 1-continued
| | |
|---|---|
| 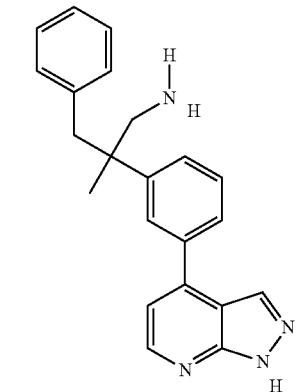 149 | 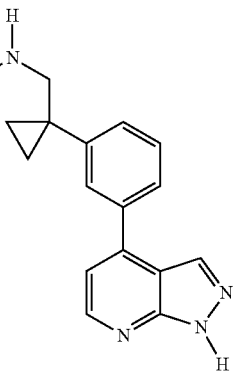 153 |
| 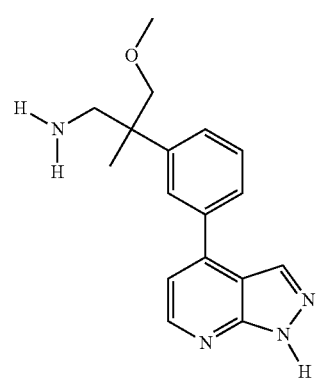 [SMILES: COCC(C)(CN)c1cccc(-c2ccnc3[nH]ncc23)c1] 150 | 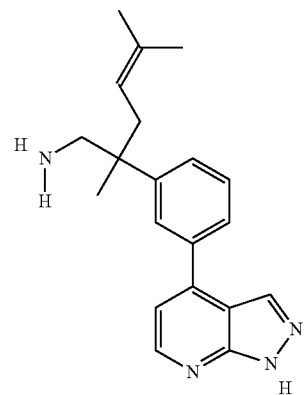 154 |
| 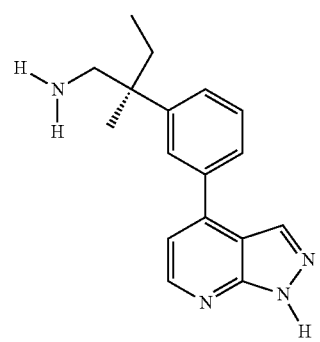 [SMILES: CC[C@](C)(CN)c1cccc(-c2ccnc3[nH]ncc23)c1] 151 | 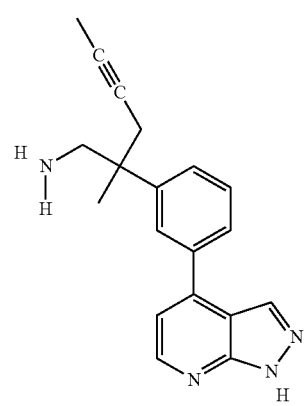 155 |
| 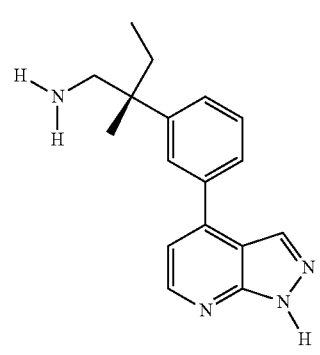 [SMILES: CC[C@@](C)(CN)c1cccc(-c2ccnc3[nH]ncc23)c1] 152 | 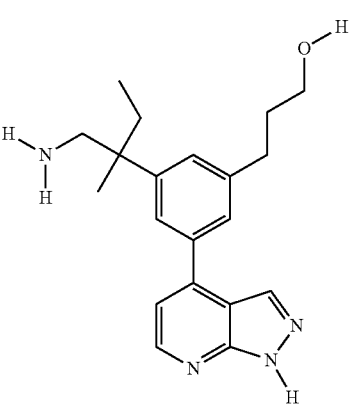 [SMILES: CCC(C)(CN)c1cc(CCCO)cc(-c2ccnc3[nH]ncc23)c1] 156 |

TABLE 1-continued
| 157 | 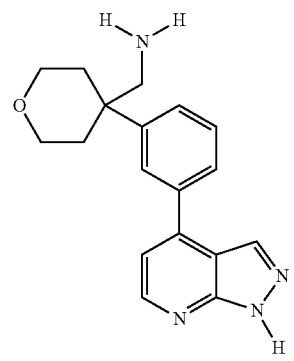 [SMILES: NCC1(c2cccc(-c3ccnc4[nH]ncc34)c2)CCOCC1] |
| 158 | 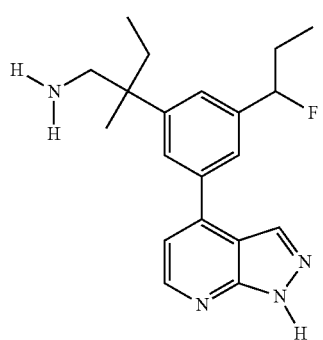 [SMILES: CCC(F)c1cc(-c2ccnc3[nH]ncc23)cc(C(C)(CC)CN)c1] |
| 159 | 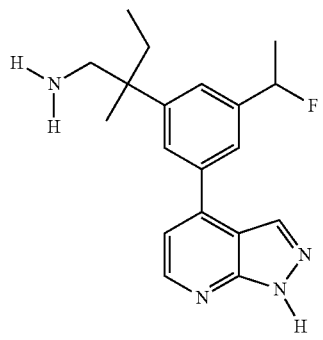 [SMILES: CCC(C)(CN)c1cc(-c2ccnc3[nH]ncc23)cc(C(C)F)c1] |
| 160 | 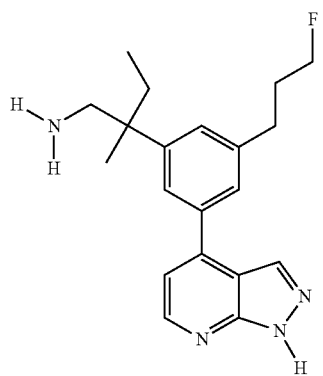 [SMILES: CCC(C)(CN)c1cc(CCCF)cc(-c2ccnc3[nH]ncc23)c1] |
TABLE 1-continued
| 161 | 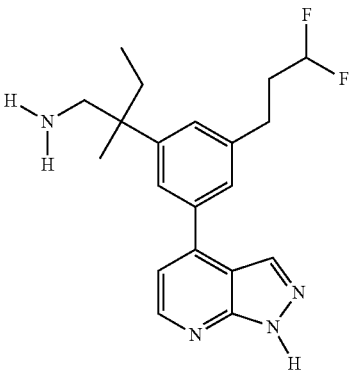 [SMILES: CCC(C)(CN)c1cc(CCC(F)F)cc(-c2ccnc3[nH]ncc23)c1] |
| 162 | 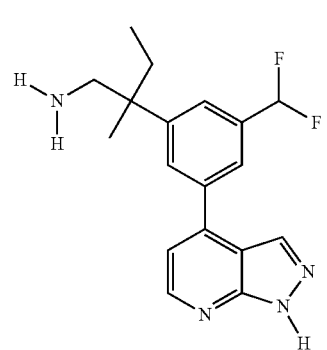 [SMILES: CCC(C)(CN)c1cc(-c2ccnc3[nH]ncc23)cc(C(F)F)c1] |
| 163 | 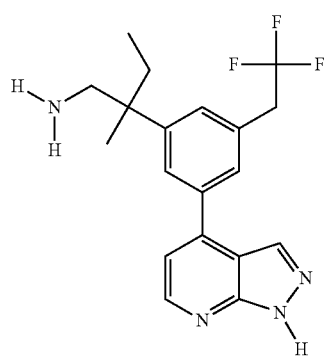 [SMILES: CCC(C)(CN)c1cc(CC(F)(F)F)cc(-c2ccnc3[nH]ncc23)c1] |
| 164 | 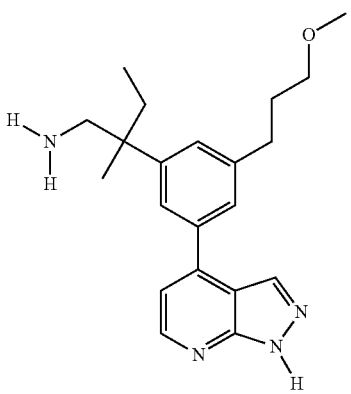 [SMILES: CCC(C)(CN)c1cc(CCCOC)cc(-c2ccnc3[nH]ncc23)c1] |

TABLE 1-continued
| | |
|---|---|
| 165 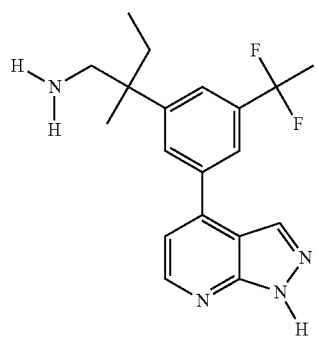 [SMILES: CCC(C)(CN)c1cc(-c2ccnc3[nH]ncc23)cc(C(C)(F)F)c1] | 169 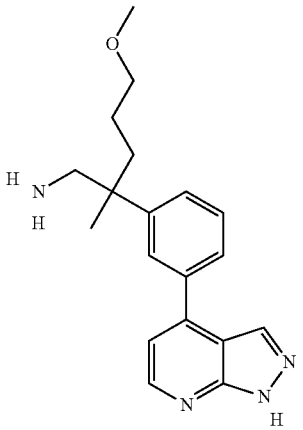 |
| 166 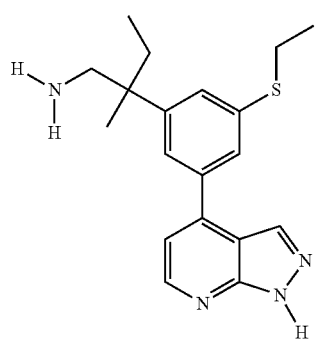 [SMILES: CCSc1cc(-c2ccnc3[nH]ncc23)cc(C(C)(CC)CN)c1] | 170 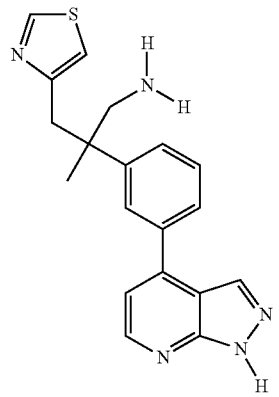 |
| 167 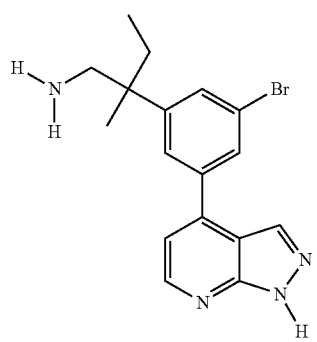 [SMILES: CCC(C)(CN)c1cc(Br)cc(-c2ccnc3[nH]ncc23)c1] | 171 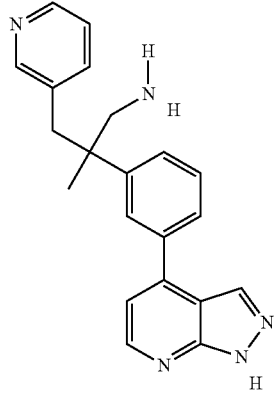 |
| 168 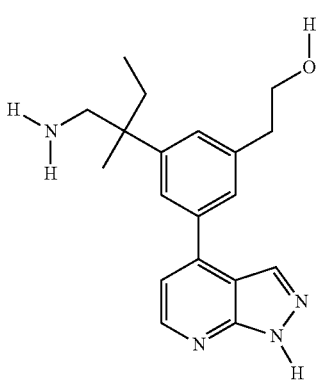 [SMILES: CCC(C)(CN)c1cc(CCO)cc(-c2ccnc3[nH]ncc23)c1] | 172 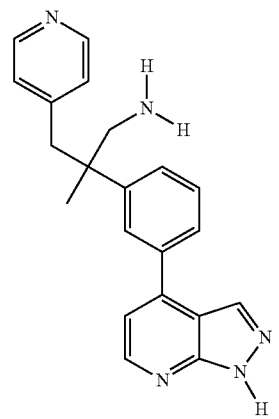 [SMILES: CC(CN)(Cc1ccncc1)c1cccc(-c2ccnc3[nH]ncc23)c1] |

TABLE 1-continued
173 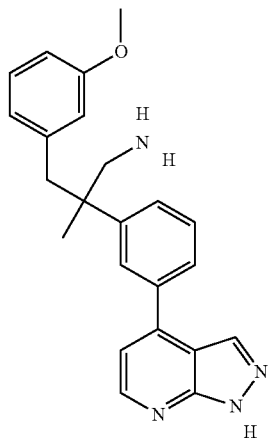
174 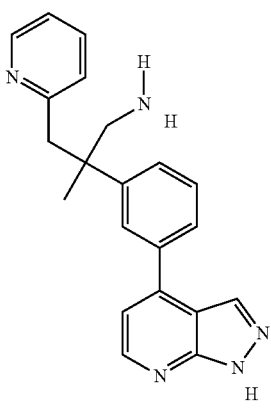
175 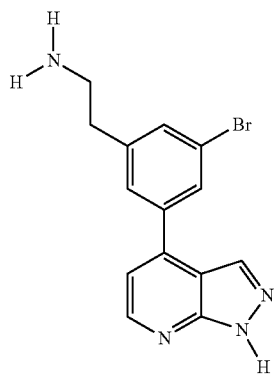 [SMILES: NCCc1cc(Br)cc(-c2ccnc3[nH]ncc23)c1]
TABLE 1-continued
176 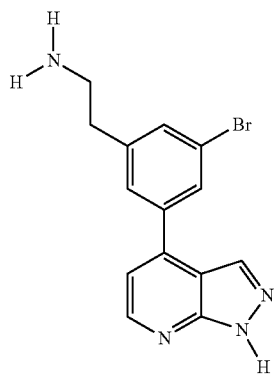 [SMILES: NCCc1cc(Br)cc(-c2ccnc3[nH]ncc23)c1]
177 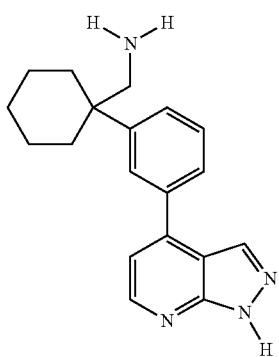 [SMILES: NCC1(c2cccc(-c3ccnc4[nH]ncc34)c2)CCCCC1]
178 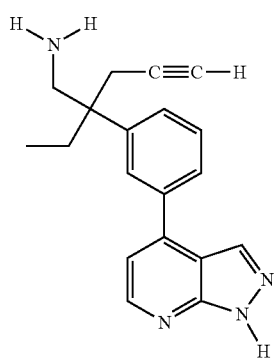 [SMILES: C#CCC(CC)(CN)c1cccc(-c2ccnc3[nH]ncc23)c1]
179 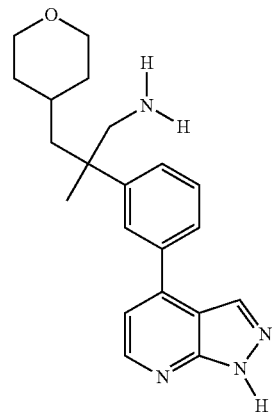 [SMILES: CC(CN)(CC1CCOCC1)c1cccc(-c2ccnc3[nH]ncc23)c1]

81
TABLE 1-continued
180
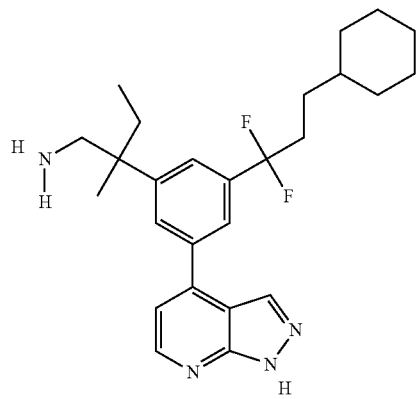
181
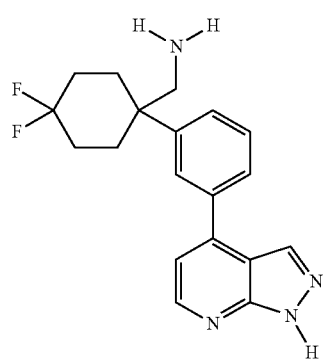 [SMILES: NCC1(c2cccc(-c3ccnc4[nH]ncc34)c2)CCC(F)(F)CC1]
182
183
82
TABLE 1-continued
184
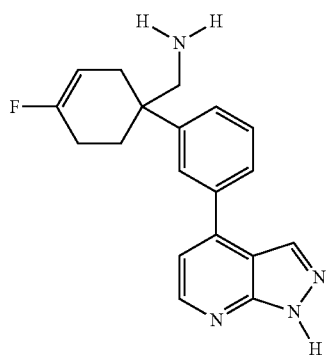 [SMILES: NCC1(c2cccc(-c3ccnc4[nH]ncc34)c2)CC=C(F)CC1]
185
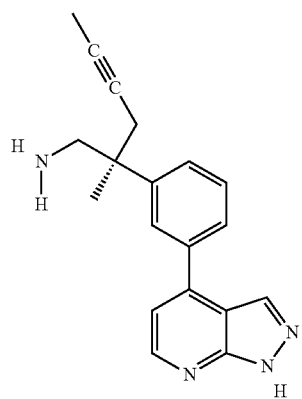
186
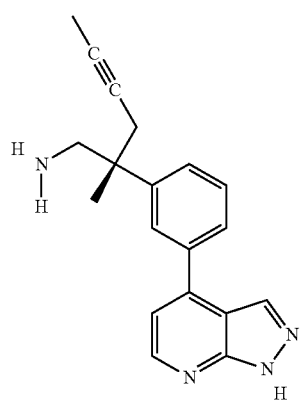
187
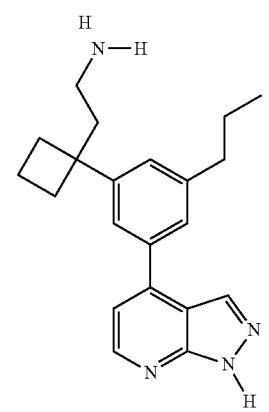

TABLE 1-continued
| | |
|---|---|
| 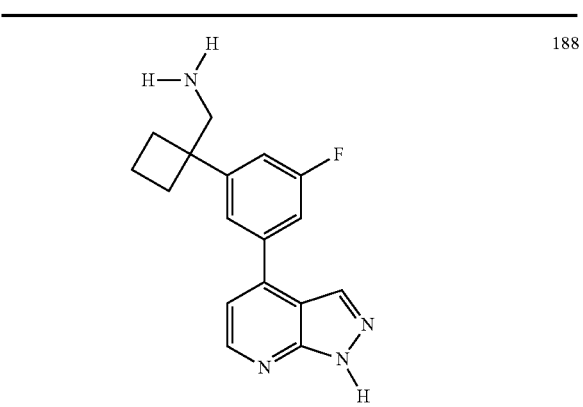 | 188 |
| 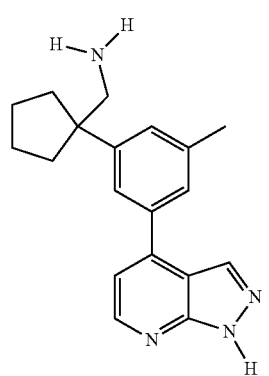 [SMILES: Cc1cc(-c2ccnc3[nH]ncc23)cc(C2(CN)CCCC2)c1] | 189 |
| 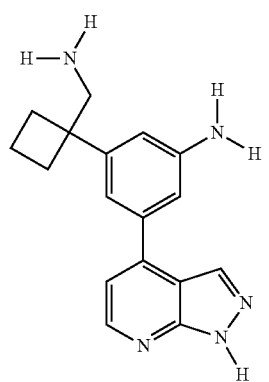 [SMILES: NCC1(c2cc(N)cc(-c3ccnc4[nH]ncc34)c2)CCC1] | 190 |
| 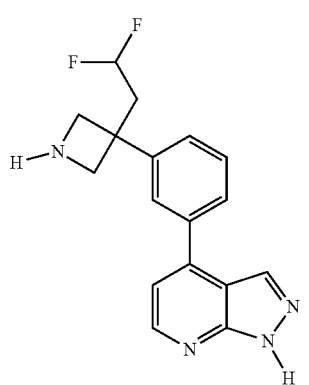 [SMILES: FC(F)CC1(c2cccc(-c3ccnc4[nH]ncc34)c2)CNC1] | 191 |
| 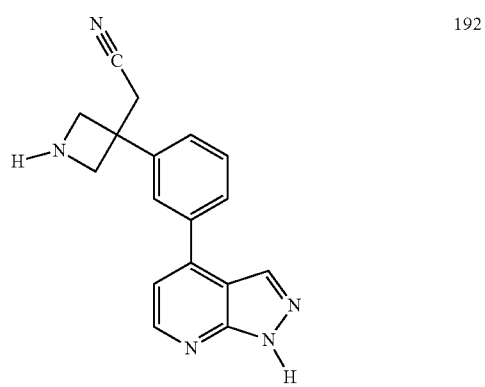 | 192 |
| 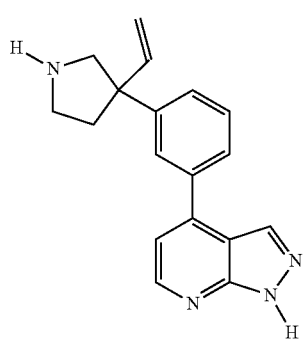 [SMILES: C=CC1(c2cccc(-c3ccnc4[nH]ncc34)c2)CCNC1] | 193 |
| 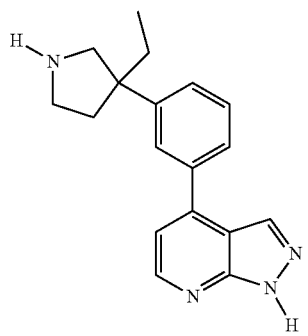 [SMILES: CCC1(c2cccc(-c3ccnc4[nH]ncc34)c2)CCNC1] | 194 |
| 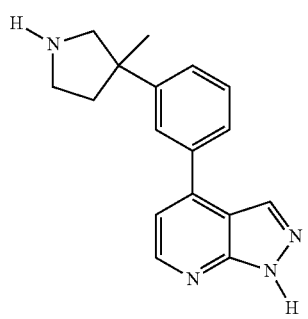 [SMILES: CC1(c2cccc(-c3ccnc4[nH]ncc34)c2)CCNC1] | 195 |

TABLE 1-continued
196 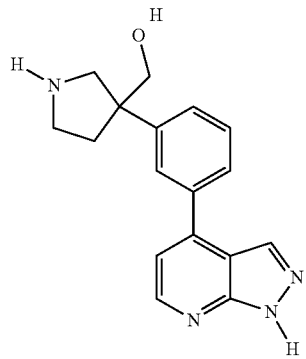
197 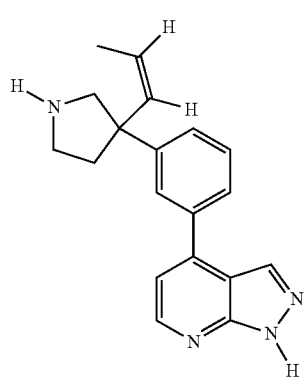 [SMILES: C/C=C\C1(c2cccc(-c3ccnc4[nH]ncc34)c2)CCNC1]
198 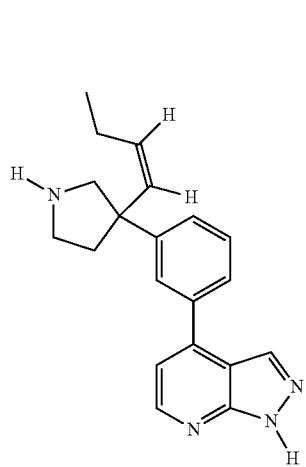 [SMILES: CC/C=C\C1(c2cccc(-c3ccnc4[nH]ncc34)c2)CCNC1]
199 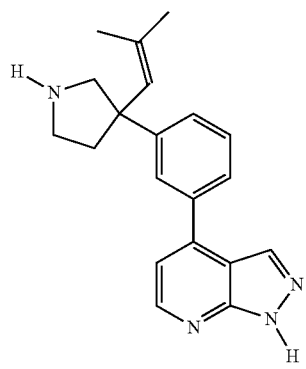 [SMILES: CC(C)=CC1(c2cccc(-c3ccnc4[nH]ncc34)c2)CCNC1]
TABLE 1-continued
200 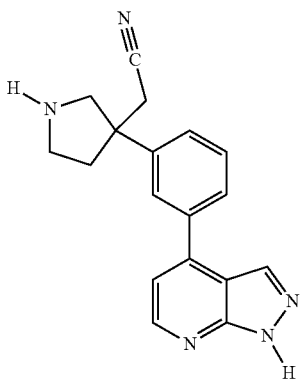 [SMILES: N#CCC1(c2cccc(-c3ccnc4[nH]ncc34)c2)CCNC1]
201 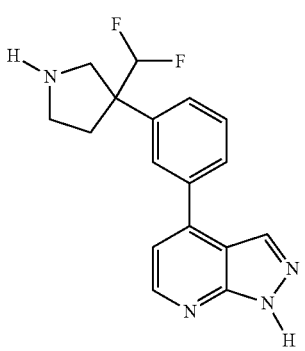 [SMILES: FC(F)C1(c2cccc(-c3ccnc4[nH]ncc34)c2)CCNC1]
202 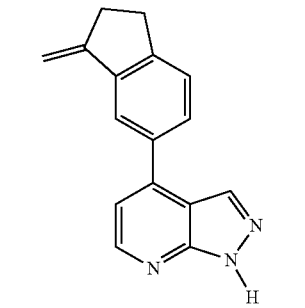 [SMILES: C=C1CCc2ccc(-c3ccnc4[nH]ncc34)cc21]
203 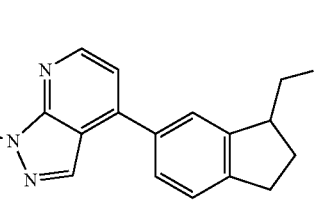
204 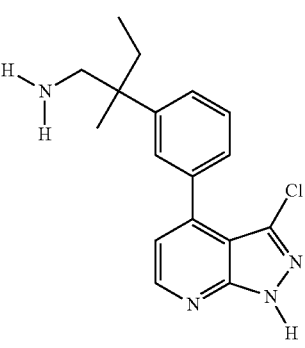 [SMILES: CCC(C)(CN)c1cccc(-c2ccnc3[nH]nc(Cl)c23)c1]

TABLE 1-continued
| 205 | 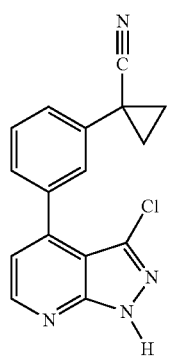 [SMILES: N#CC1(c2cccc(-c3ccnc4[nH]nc(Cl)c34)c2)CC1] |
| 206 | 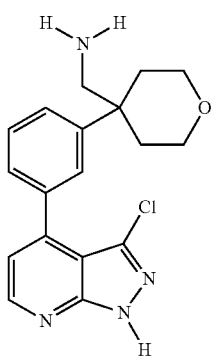 [SMILES: NCC1(c2cccc(-c3ccnc4[nH]nc(Cl)c34)c2)CCOCC1] |
| 207 | 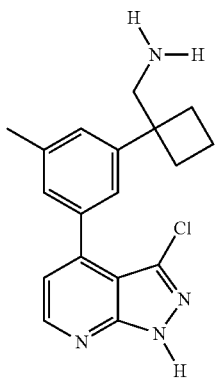 [SMILES: Cc1cc(-c2ccnc3[nH]nc(Cl)c23)cc(C2(CN)CCC2)c1] |
| 208 | 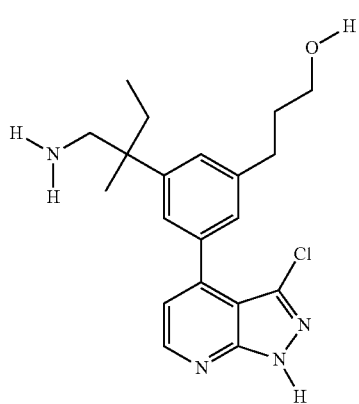 [SMILES: CCC(C)(CN)c1cc(CCCO)cc(-c2ccnc3[nH]nc(Cl)c23)c1] |
TABLE 1-continued
| 209 | 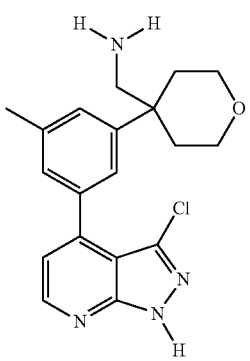 [SMILES: Cc1cc(-c2ccnc3[nH]nc(Cl)c23)cc(C2(CN)CCOCC2)c1] |
| 210 | 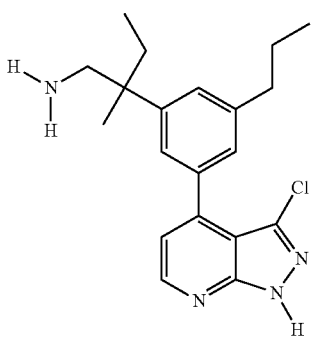 [SMILES: CCCc1cc(-c2ccnc3[nH]nc(Cl)c23)cc(C(C)(CC)CN)c1] |
| 211 | 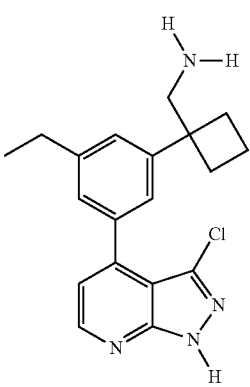 [SMILES: CCc1cc(-c2ccnc3[nH]nc(Cl)c23)cc(C2(CN)CCC2)c1] |
| 212 | 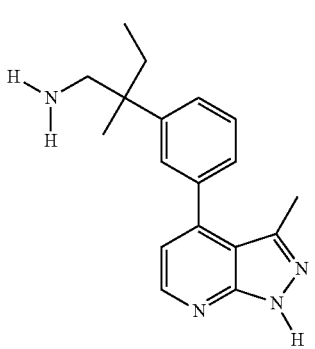 [SMILES: CCC(C)(CN)c1cccc(-c2ccnc3[nH]nc(C)c23)c1] |

TABLE 1-continued
213 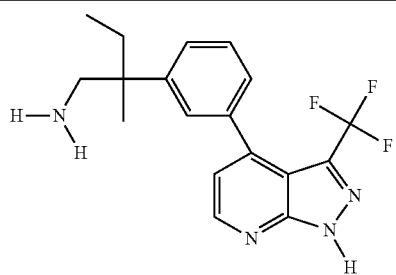
214 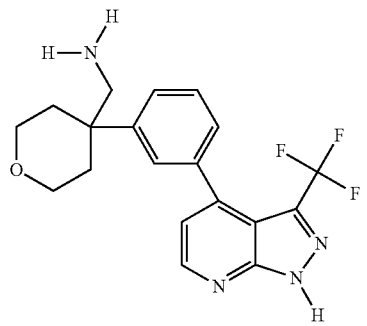 [SMILES: NCC1(c2cccc(-c3ccnc4[nH]nc(C(F)(F)F)c34)c2)CCOCC1]
215 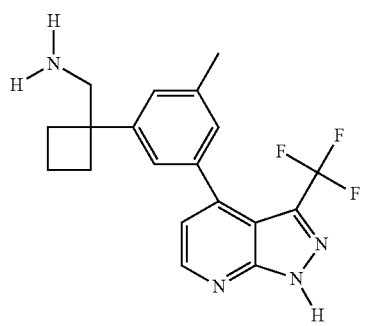 [SMILES: Cc1cc(-c2ccnc3[nH]nc(C(F)(F)F)c23)cc(C2(CN)CCC2)c1]
216 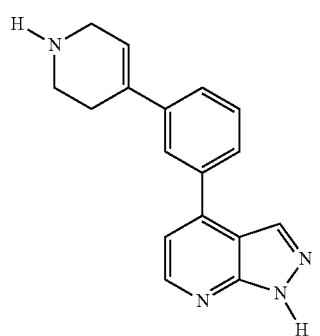 [SMILES: C1=C(c2cccc(-c3ccnc4[nH]ncc34)c2)CCNC1]
217 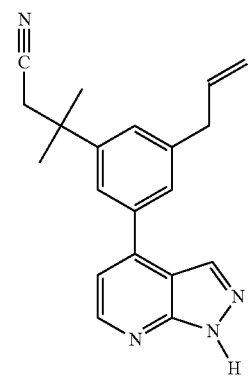 [SMILES: C=CCc1cc(-c2ccnc3[nH]ncc23)cc(C(C)(C)CC#N)c1]
TABLE 1-continued
218 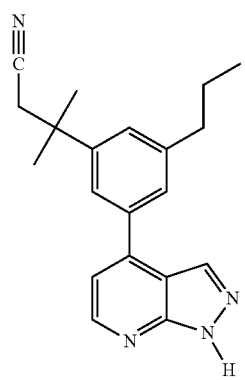 [SMILES: CCCc1cc(-c2ccnc3[nH]ncc23)cc(C(C)(C)CC#N)c1]
219 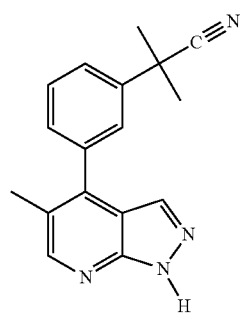 [SMILES: Cc1cnc2[nH]ncc2c1-c1cccc(C(C)(C)C#N)c1]
220 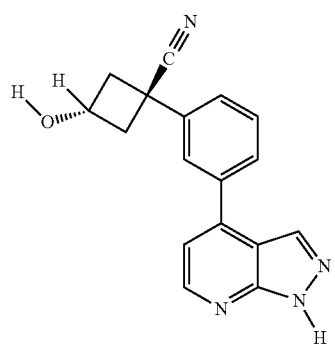 [SMILES: N#C[C@]1(c2cccc(-c3ccnc4[nH]ncc34)c2)C[C@@H](O)C1]
221 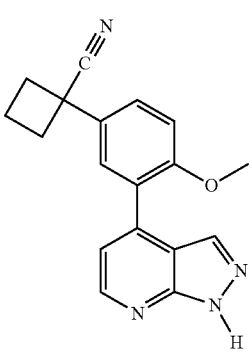 [SMILES: COc1ccc(C2(C#N)CCC2)cc1-c1ccnc2[nH]ncc12]

TABLE 1-continued
| | |
|---|---|
| 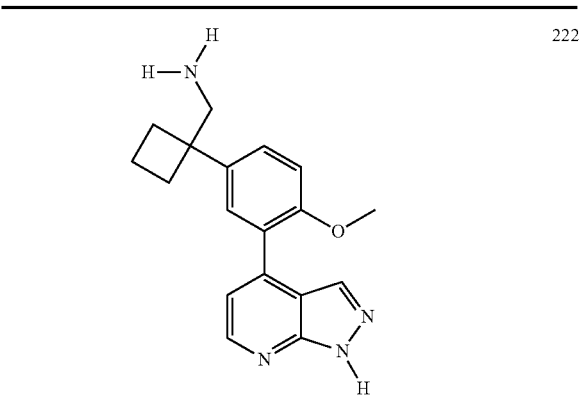 222 | 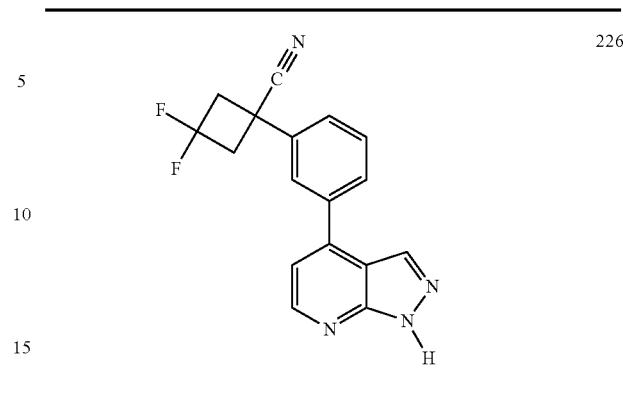 226 |
| 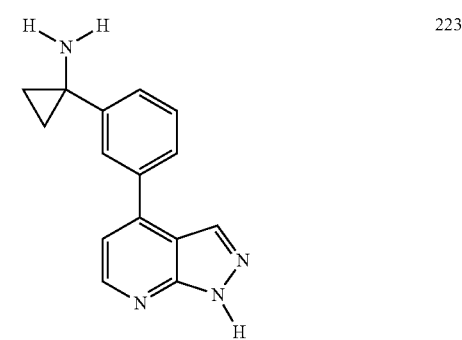 223 | 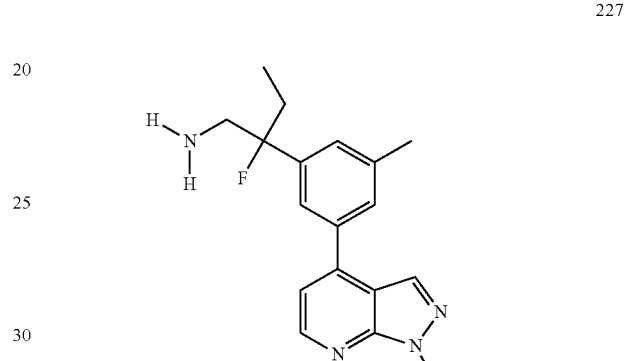 227 |
| 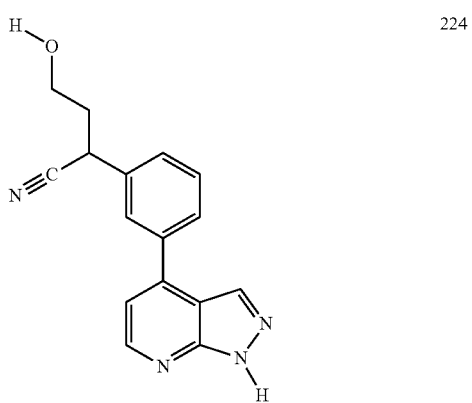 224 | 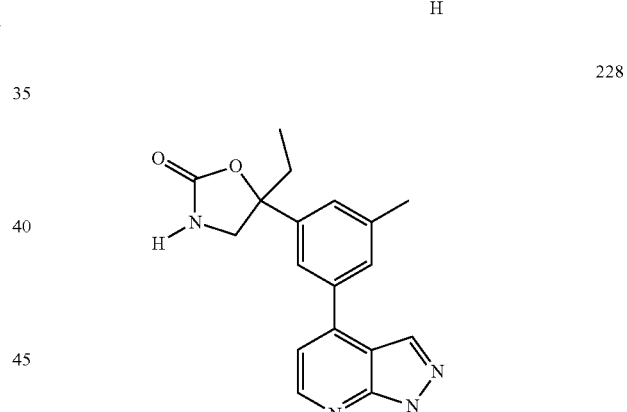 228 |
| 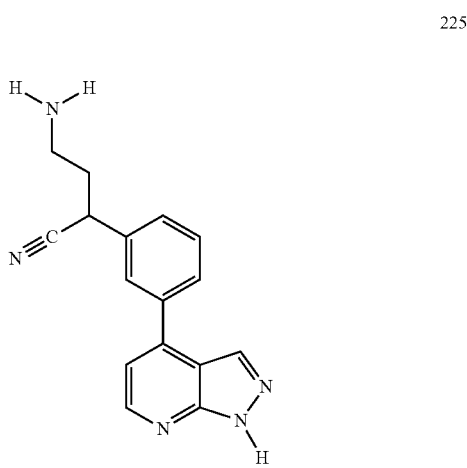 225 | 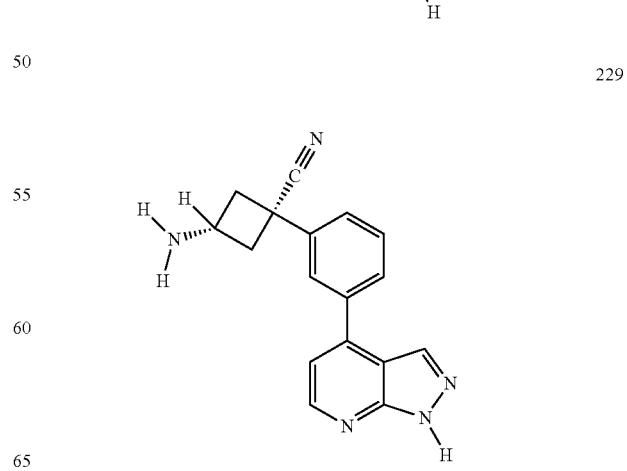 229 |

TABLE 1-continued
230 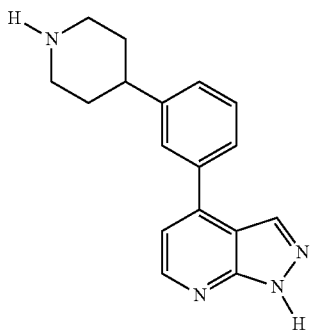 [SMILES: c1cc(-c2ccnc3[nH]ncc23)cc(C2CCNCC2)c1]
231 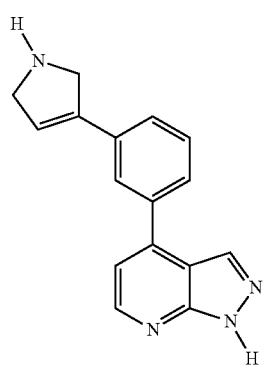 [SMILES: C1=C(c2cccc(-c3ccnc4[nH]ncc34)c2)CNC1]
232 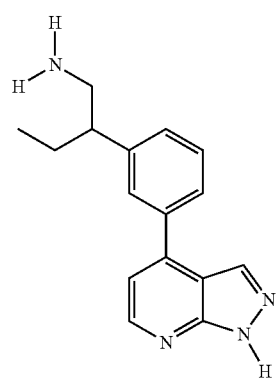 [SMILES: CCC(CN)c1cccc(-c2ccnc3[nH]ncc23)c1]
233 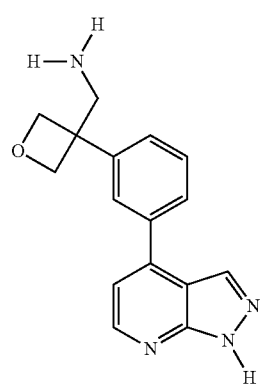 [SMILES: NCC1(c2cccc(-c3ccnc4[nH]ncc34)c2)COC1]
TABLE 1-continued
234 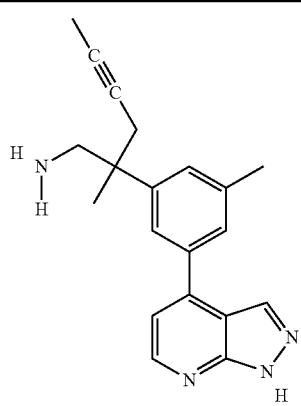
235 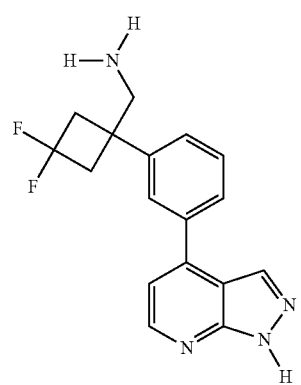 [SMILES: NCC1(c2cccc(-c3ccnc4[nH]ncc34)c2)CC(F)(F)C1]
236 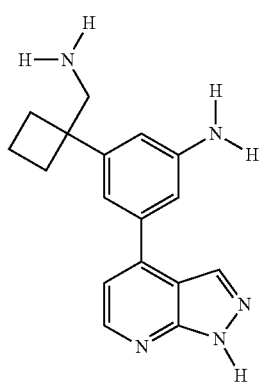 [SMILES: NCC1(c2cc(N)cc(-c3ccnc4[nH]ncc34)c2)CCC1]
237 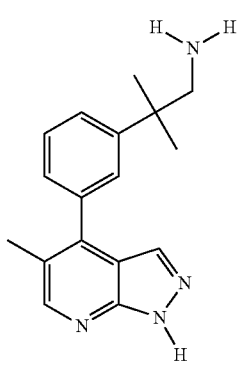 [SMILES: Cc1cnc2[nH]ncc2c1-c1cccc(C(C)(C)CN)c1]

TABLE 1-continued
| | |
|---|---|
| 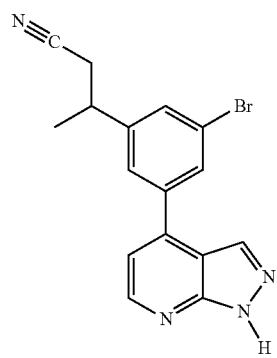 [SMILES: CC(CC#N)c1cc(Br)cc(-c2ccnc3[nH]ncc23)c1] | 238 |
| 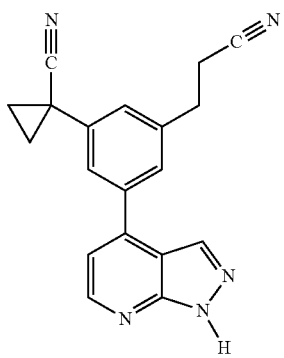 [SMILES: N#CCCc1cc(-c2ccnc3[nH]ncc23)cc(C2(C#N)CC2)c1] | 239 |
| 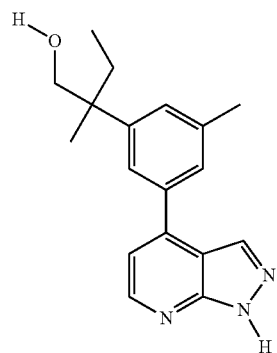 [SMILES: CCC(C)(CO)c1cc(C)cc(-c2ccnc3[nH]ncc23)c1] | 240 |
| | 241 |
TABLE 1-continued
| | |
|---|---|
| 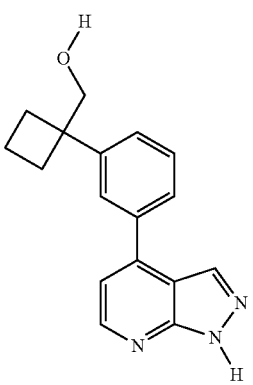 [SMILES: OCC1(c2cccc(-c3ccnc4[nH]ncc34)c2)CCC1] | 242 |
| 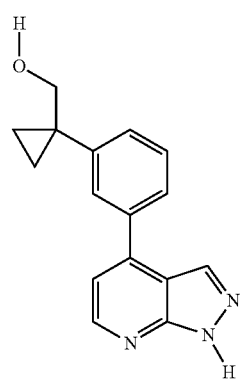 [SMILES: OCC1(c2cccc(-c3ccnc4[nH]ncc34)c2)CC1] | 243 |
| 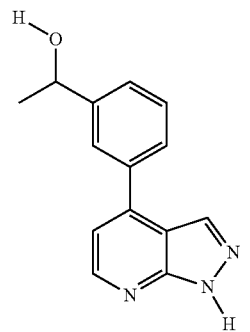 [SMILES: CC(O)c1cccc(-c2ccnc3[nH]ncc23)c1] | 244 |
| 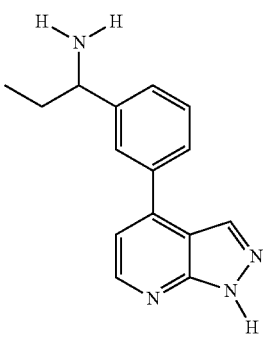 [SMILES: CCC(N)c1cccc(-c2ccnc3[nH]ncc23)c1] | 245 |

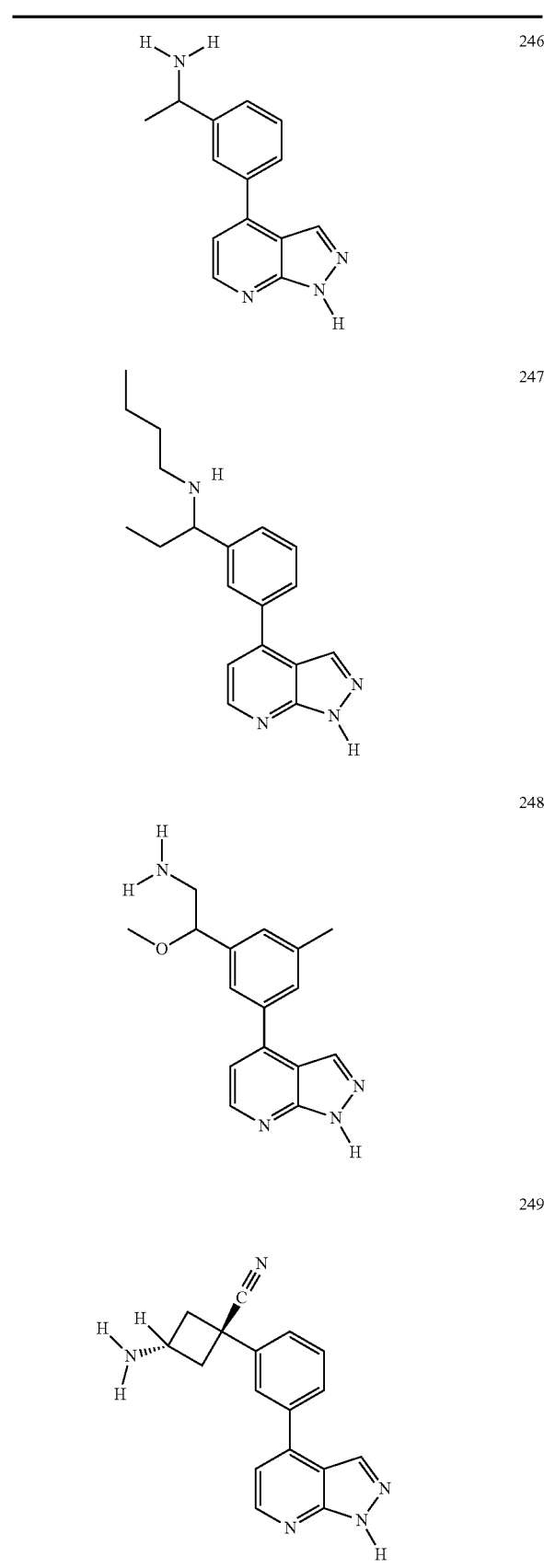
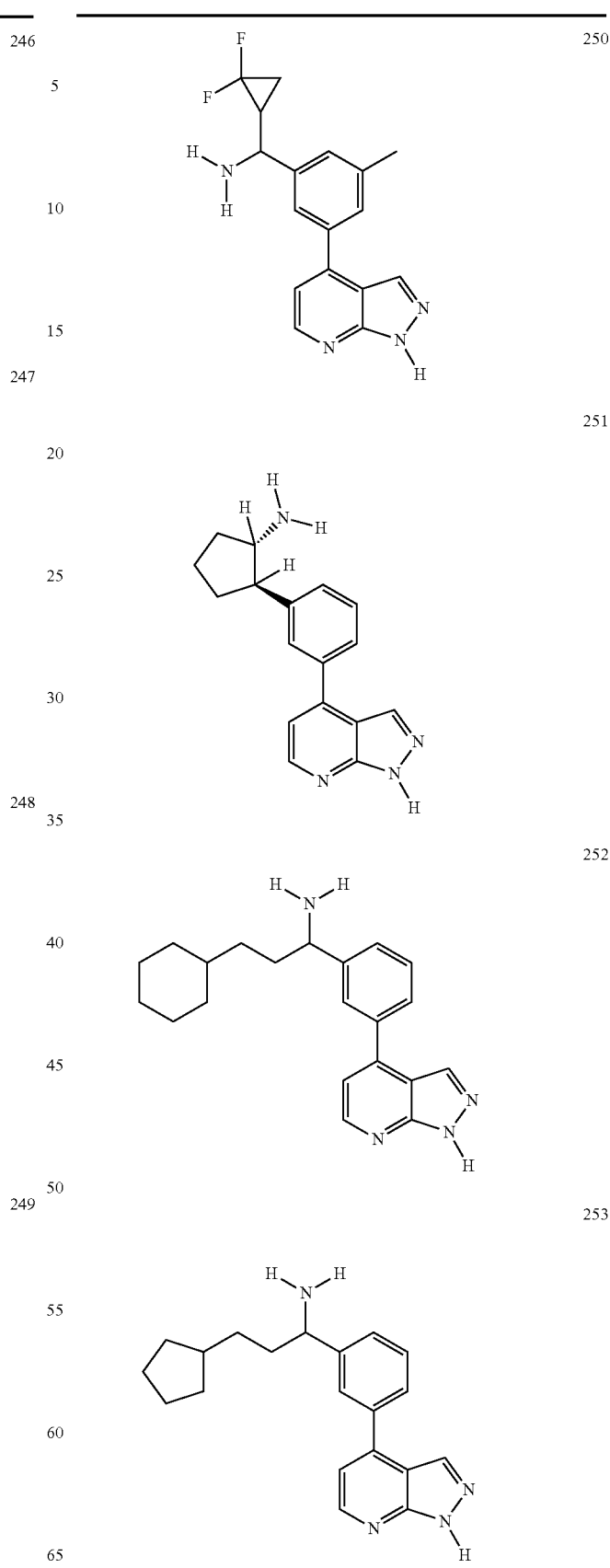

TABLE 1-continued
| | |
|---|---|
| 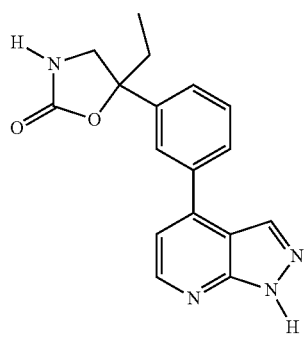 [SMILES: CCC1(c2cccc(-c3ccnc4[nH]ncc34)c2)CNC(=O)O1] | 254 |
| 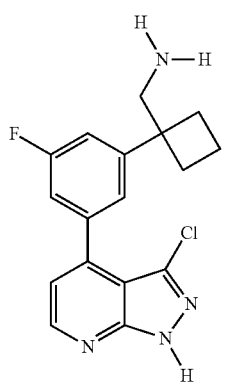 [SMILES: NCC1(c2cc(F)cc(-c3ccnc4[nH]nc(Cl)c34)c2)CCC1] | 255 |
| 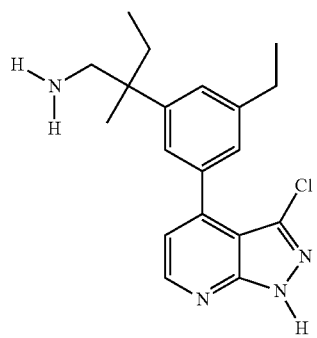 [SMILES: CCc1cc(-c2ccnc3[nH]nc(Cl)c23)cc(C(C)(CC)CN)c1] | 256 |
| 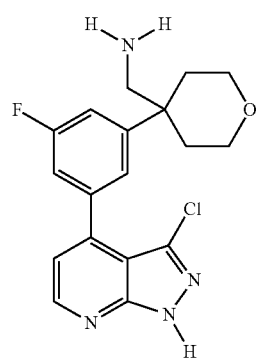 [SMILES: NCC1(c2cc(F)cc(-c3ccnc4[nH]nc(Cl)c34)c2)CCOCC1] | 257 |
TABLE 1-continued
| | |
|---|---|
| 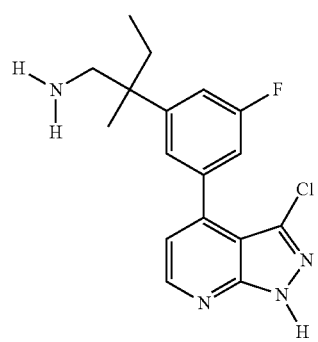 [SMILES: CCC(C)(CN)c1cc(F)cc(-c2ccnc3[nH]nc(Cl)c23)c1] | 258 |
| 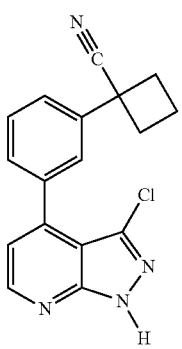 [SMILES: N#CC1(c2cccc(-c3ccnc4[nH]nc(Cl)c34)c2)CCC1] | 259 |
| 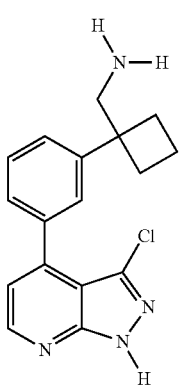 [SMILES: NCC1(c2cccc(-c3ccnc4[nH]nc(Cl)c34)c2)CCC1] | 260 |

TABLE 1-continued
262 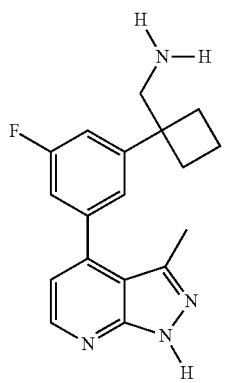 [SMILES: Cc1n[nH]c2nccc(-c3cc(F)cc(C4(CN)CCC4)c3)c12]
263 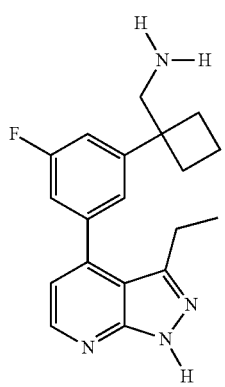 [SMILES: CCc1n[nH]c2nccc(-c3cc(F)cc(C4(CN)CCC4)c3)c12]
264 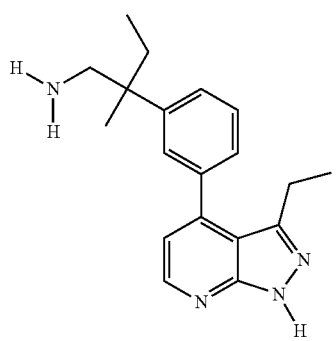 [SMILES: CCc1n[nH]c2nccc(-c3cccc(C(C)(CC)CN)c3)c12]
265 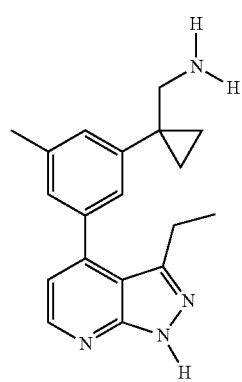 [SMILES: CCc1n[nH]c2nccc(-c3cc(C)cc(C4(CN)CC4)c3)c12]
TABLE 1-continued
266 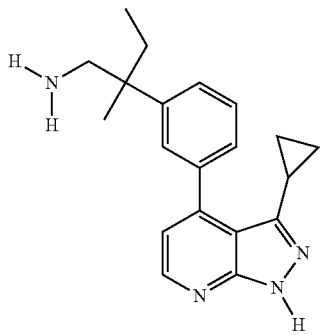 [SMILES: CCC(C)(CN)c1cccc(-c2ccnc3[nH]nc(C4CC4)c23)c1]
267 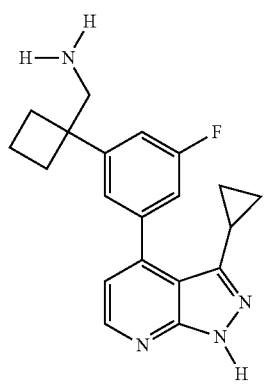 [SMILES: NCC1(c2cc(F)cc(-c3ccnc4[nH]nc(C5CC5)c34)c2)CCC1]
268 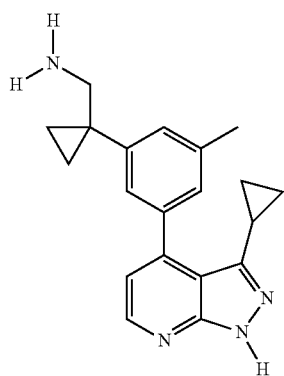 [SMILES: Cc1cc(-c2ccnc3[nH]nc(C4CC4)c23)cc(C2(CN)CC2)c1]
269 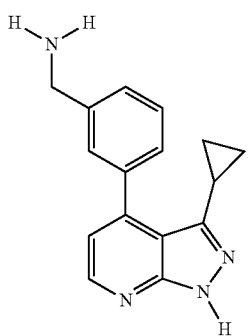 [SMILES: NCc1cccc(-c2ccnc3[nH]nc(C4CC4)c23)c1]

TABLE 1-continued
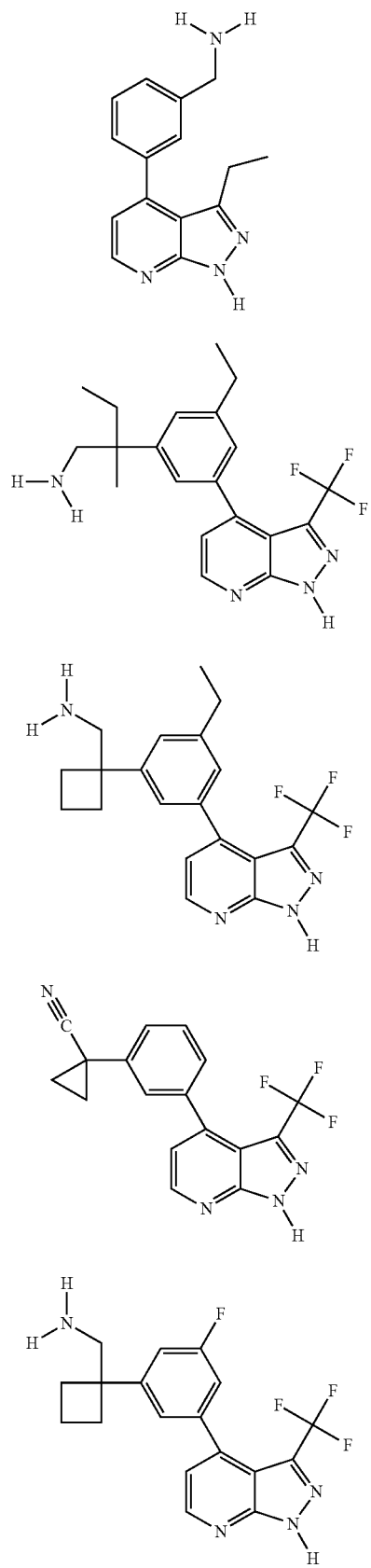
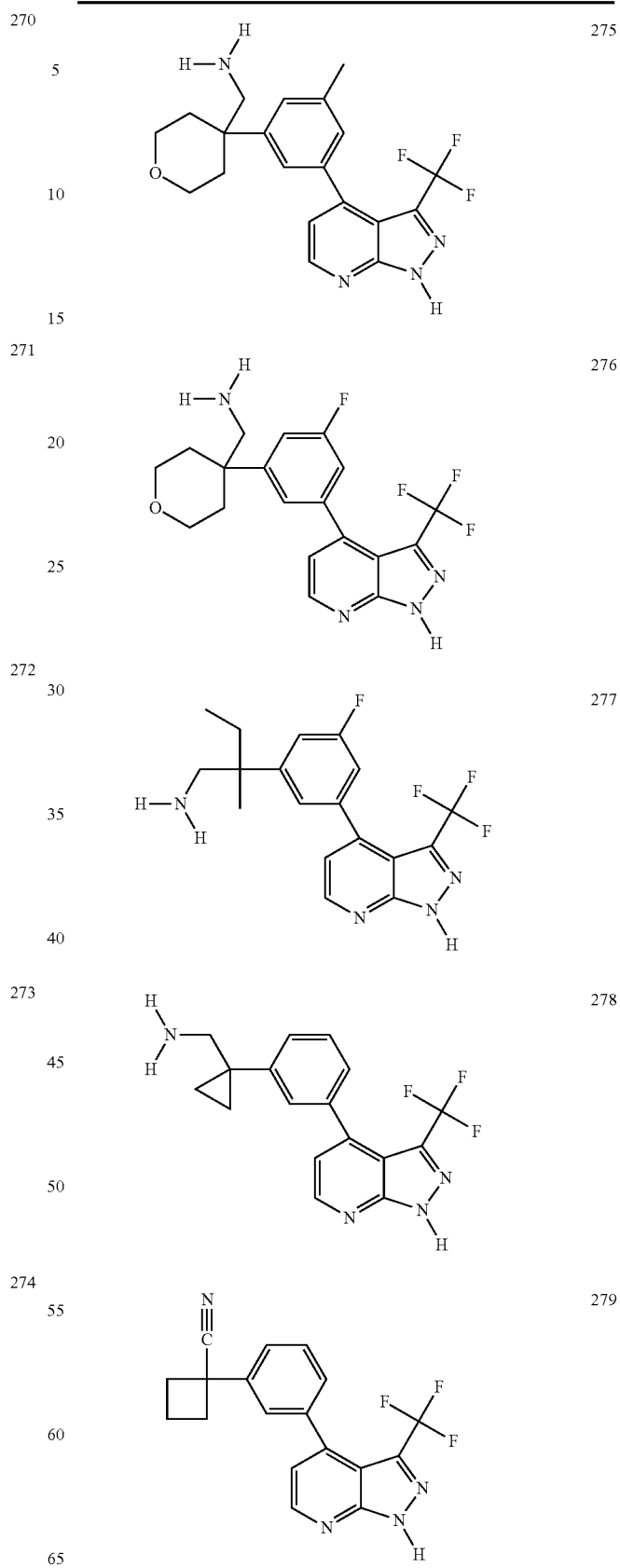

TABLE 1-continued
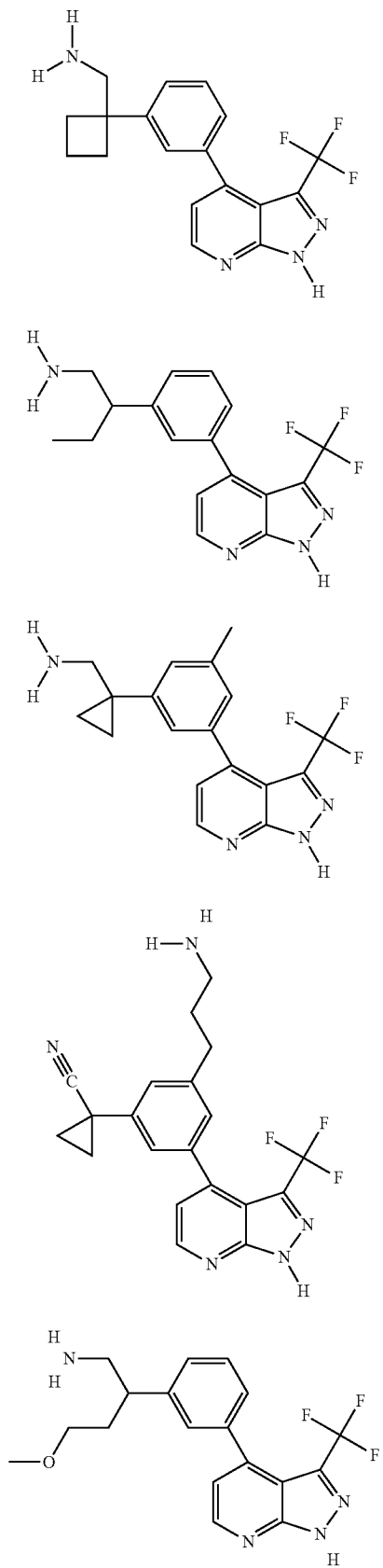
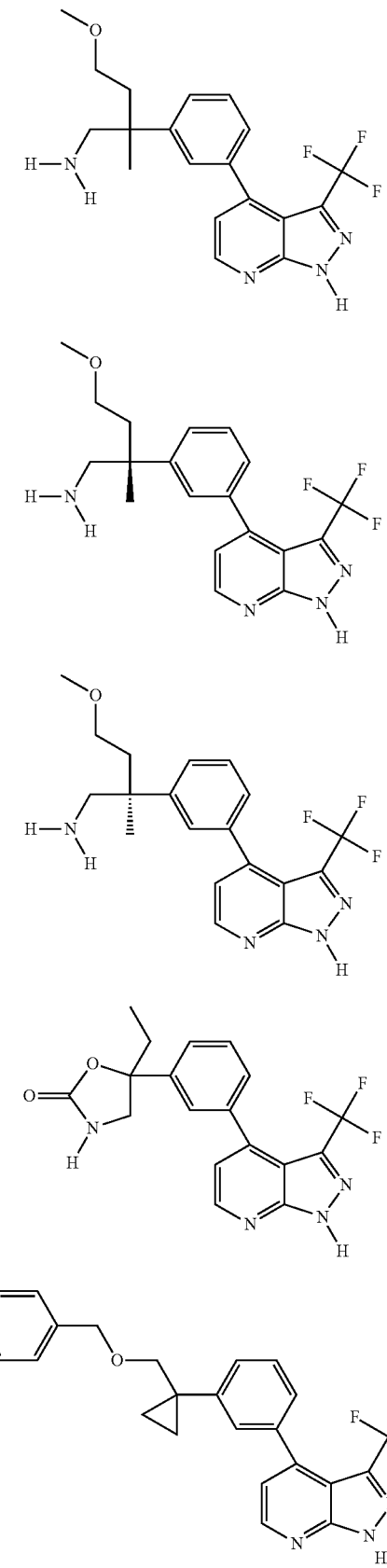

TABLE 1-continued
290 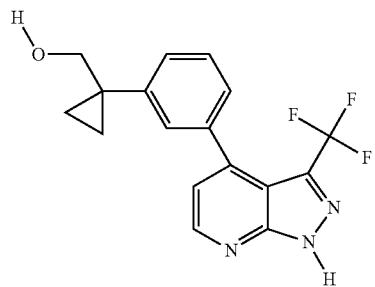 [SMILES: OCC1(c2cccc(-c3ccnc4[nH]nc(C(F)(F)F)c34)c2)CC1]
291 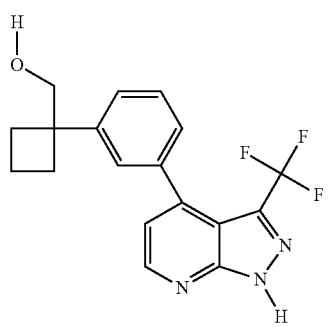 [SMILES: OCC1(c2cccc(-c3ccnc4[nH]nc(C(F)(F)F)c34)c2)CCC1]
292 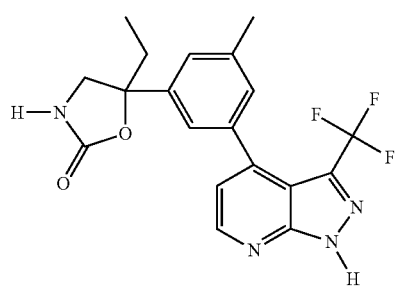 [SMILES: CCC1(c2cc(C)cc(-c3ccnc4[nH]nc(C(F)(F)F)c34)c2)CNC(=O)O1]
293 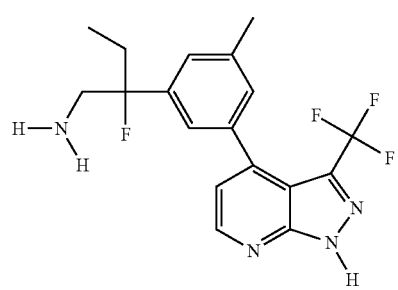 [SMILES: CCC(F)(CN)c1cc(C)cc(-c2ccnc3[nH]nc(C(F)(F)F)c23)c1]
294 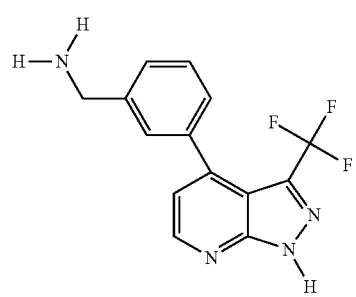 [SMILES: NCc1cccc(-c2ccnc3[nH]nc(C(F)(F)F)c23)c1]
TABLE 1-continued
295 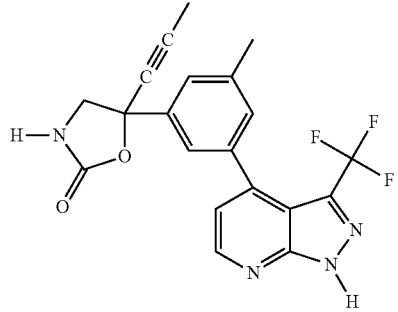 [SMILES: CC#CC1(c2cc(C)cc(-c3ccnc4[nH]nc(C(F)(F)F)c34)c2)CNC(=O)O1]
296 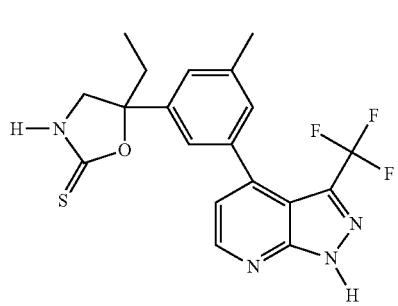 [SMILES: CCC1(c2cc(C)cc(-c3ccnc4[nH]nc(C(F)(F)F)c34)c2)CNC(=S)O1]
297 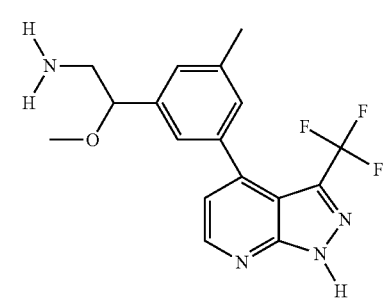 [SMILES: COC(CN)c1cc(C)cc(-c2ccnc3[nH]nc(C(F)(F)F)c23)c1]
298 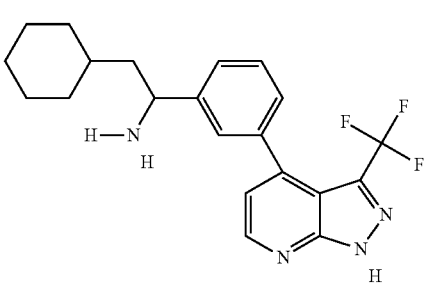
299 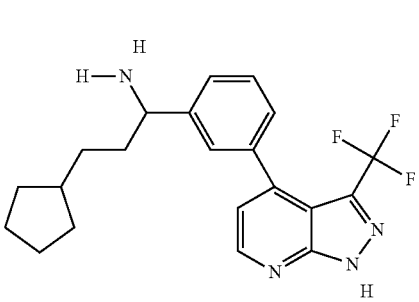

TABLE 1-continued
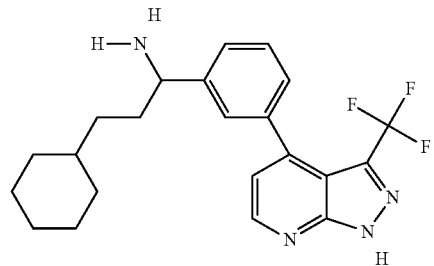 300
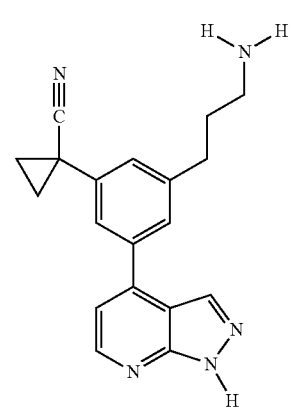 [SMILES: N#CC1(c2cc(CCCN)cc(-c3ccnc4[nH]ncc34)c2)CC1] 301
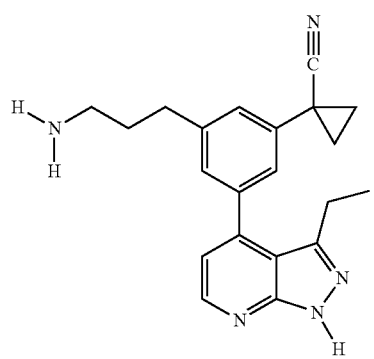 [SMILES: CCc1n[nH]c2nccc(-c3cc(CCCN)cc(C4(C#N)CC4)c3)c12] 302
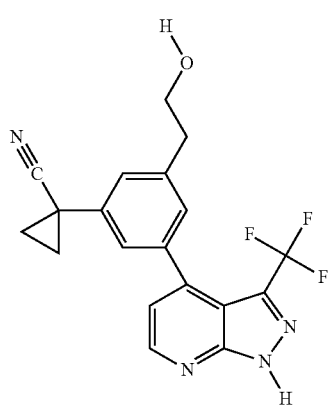 [SMILES: N#CC1(c2cc(CCO)cc(-c3ccnc4[nH]nc(C(F)(F)F)c34)c2)CC1] 303
TABLE 1-continued
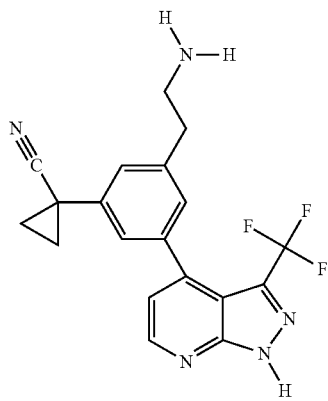 [SMILES: N#CC1(c2cc(CCN)cc(-c3ccnc4[nH]nc(C(F)(F)F)c34)c2)CC1] 304
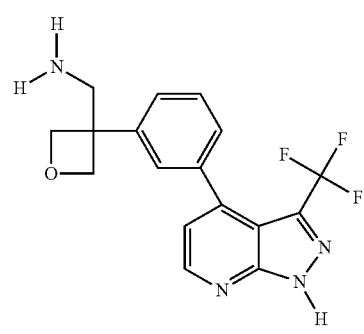 [SMILES: NCC1(c2cccc(-c3ccnc4[nH]nc(C(F)(F)F)c34)c2)COC1] 305
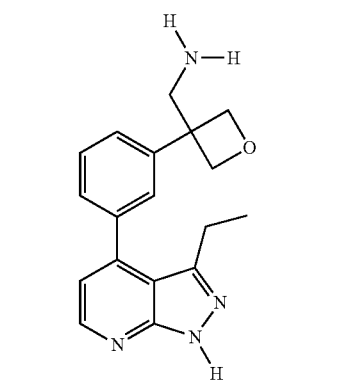 [SMILES: CCc1n[nH]c2nccc(-c3cccc(C4(CN)COC4)c3)c12] 306
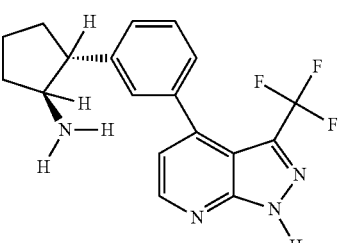 307
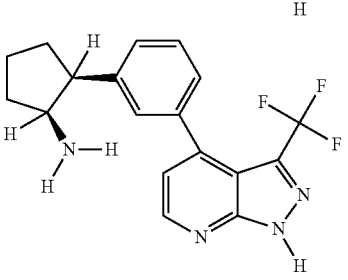

TABLE 1-continued
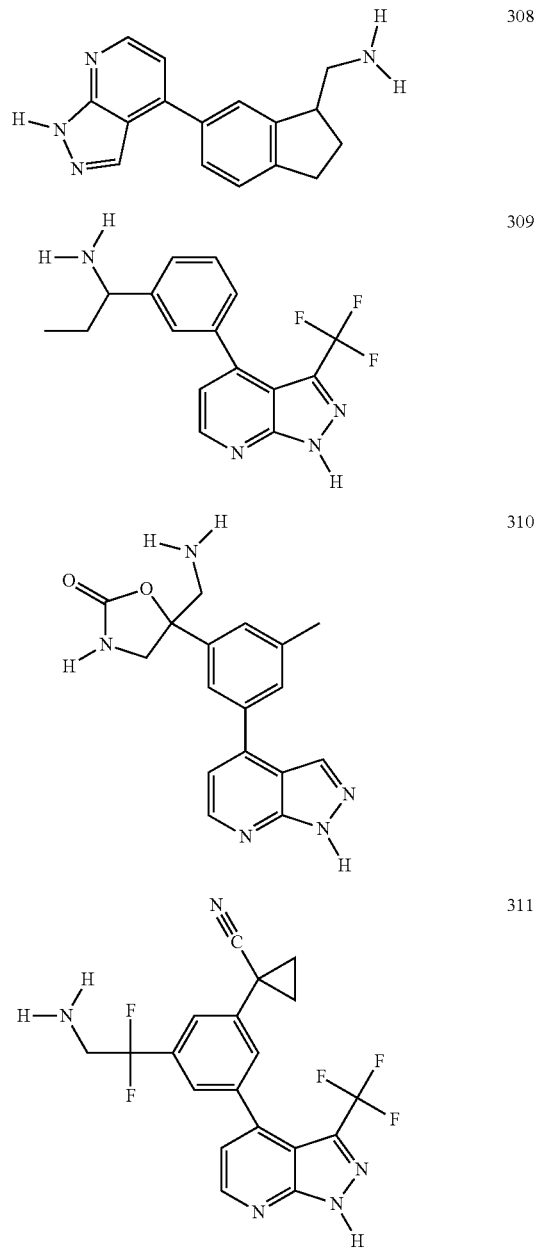
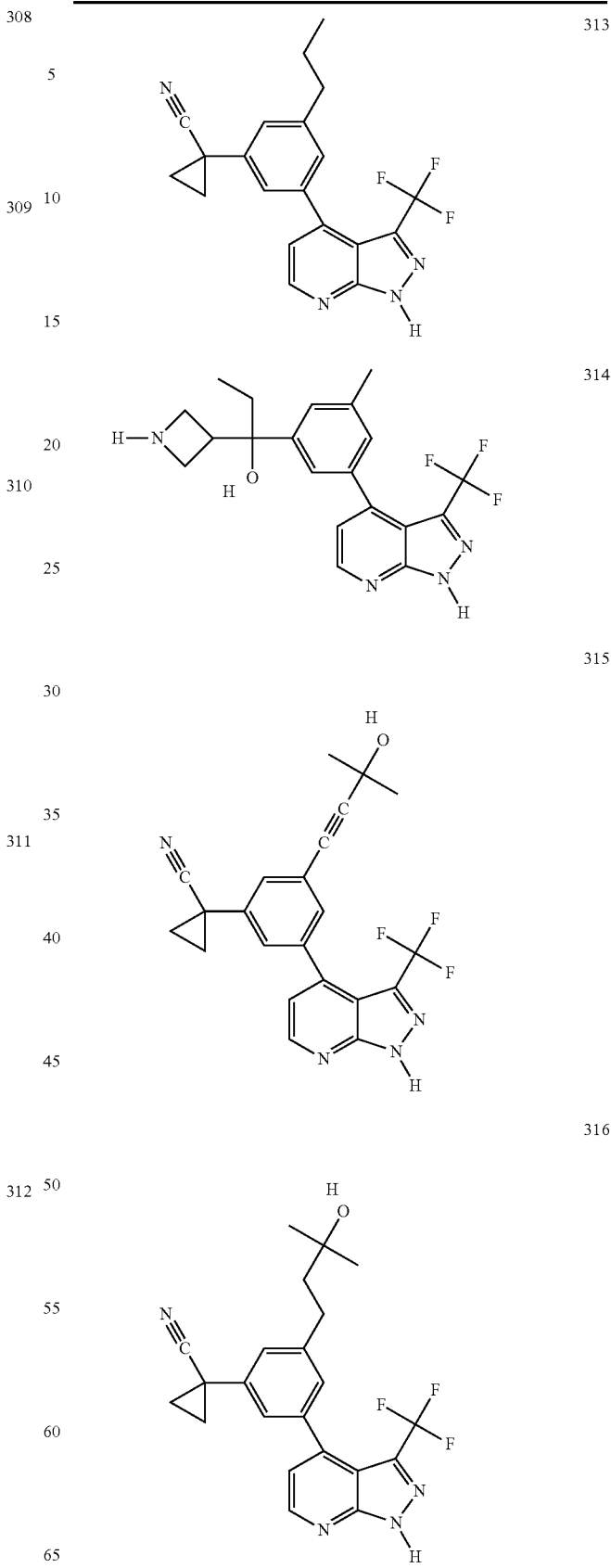

TABLE 1-continued
| | |
|---|---|
| 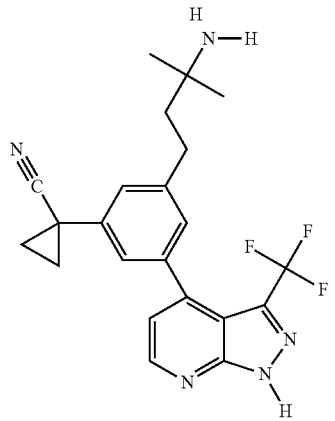 | 317 |
| 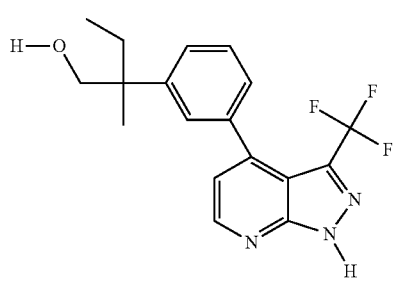 [SMILES: CCC(C)(CO)c1cccc(-c2ccnc3[nH]nc(C(F)(F)F)c23)c1] | 318 |
| 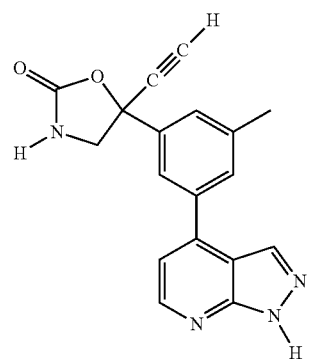 [SMILES: C#CC1(c2cc(C)cc(-c3ccnc4[nH]ncc34)c2)CNC(=O)O1] | 319 |
| 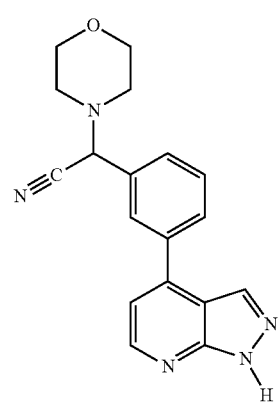 [SMILES: N#CC(c1cccc(-c2ccnc3[nH]ncc23)c1)N1CCOCC1] | 320 |
| 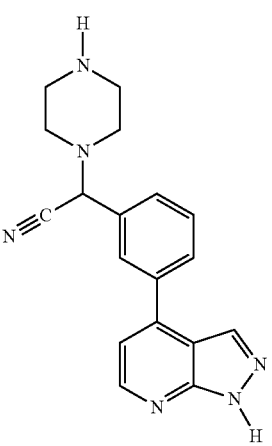 [SMILES: N#CC(c1cccc(-c2ccnc3[nH]ncc23)c1)N1CCNCC1] | 321 |
| 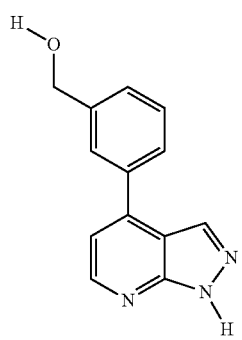 [SMILES: OCc1cccc(-c2ccnc3[nH]ncc23)c1] | 322 |
| 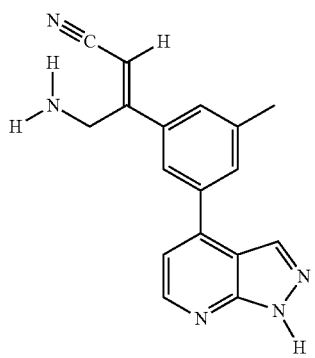 [SMILES: Cc1cc(/C(=C/C#N)CN)cc(-c2ccnc3[nH]ncc23)c1] | 323 |
| 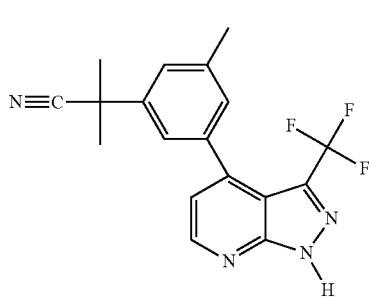 [SMILES: Cc1cc(-c2ccnc3[nH]nc(C(F)(F)F)c23)cc(C(C)(C)C#N)c1] | 324 |

TABLE 1-continued

325 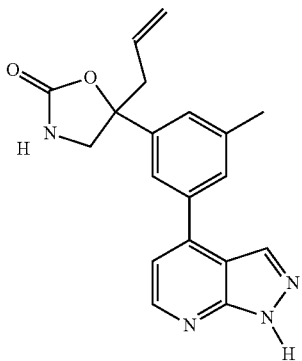

326 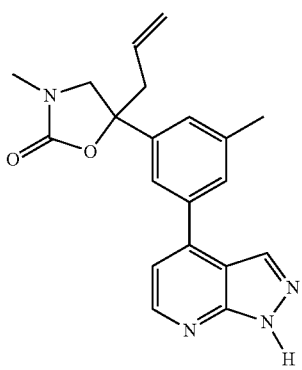 [SMILES: C=CCC1(c2cc(C)cc(-c3ccnc4[nH]ncc34)c2)CN(C)C(=O)O1]

327 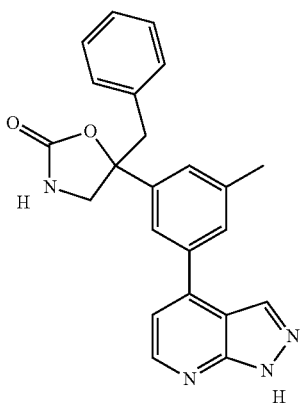

328 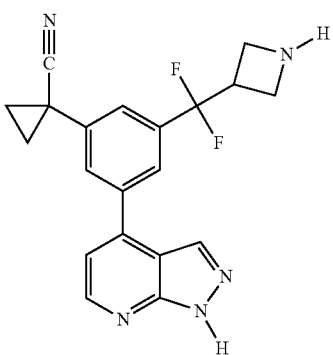 [SMILES: N#CC1(c2cc(-c3ccnc4[nH]ncc34)cc(C(F)(F)C3CNC3)c2)CC1]

TABLE 1-continued

329 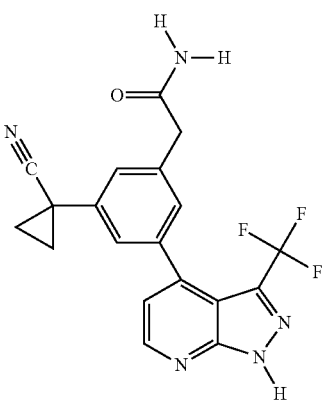 [SMILES: N#CC1(c2cc(CC(N)=O)cc(-c3ccnc4[nH]nc(C(F)(F)F)c34)c2)CC1]

330 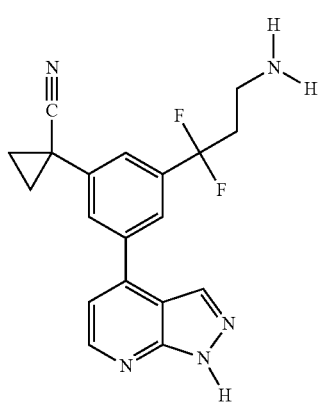 [SMILES: N#CC1(c2cc(-c3ccnc4[nH]ncc34)cc(C(F)(F)CCN)c2)CC1]

In some embodiments the variables used herein, such as, A, A', B, $R_1$, T1, Q1, $R_2$, $R_3$, $R_4$, $R_5$, $R_6$, $R_7$, $J_{T1}$, $J_{Q1}$, $R^+$, $R^{++}$, R', $R^\wedge$, R", R and R* are as defined in Table 1.

General Synthetic Methodology

The compounds of this invention may be prepared in light of the specification using steps generally known to those of ordinary skill in the art. Those compounds may be analyzed by known methods, including but not limited to LCMS (liquid chromatography mass spectrometry) HPLC and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

General Schemes:

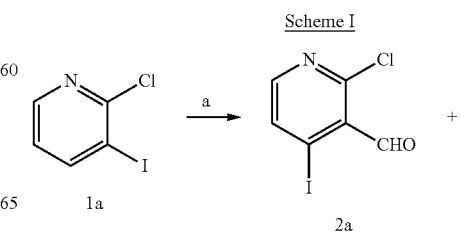

Scheme I

117

-continued

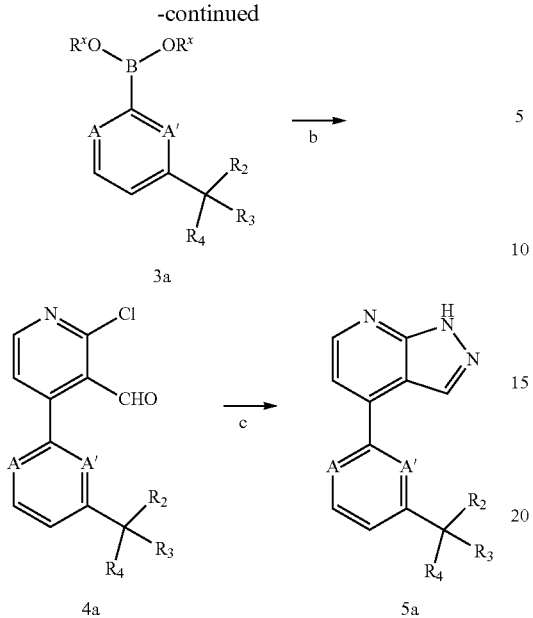

R$^x$ is -H or two R$^x$ together form:

Reagents and conditions: a) i) LDA, THF; ii) Ethyl formate; b) Pd(OAc)$_2$, CuI, Pd(o-tol)$_3$, K$_2$CO$_3$, THF, reflux; c) N$_2$H$_4$, 160° C., microwave.

Scheme 1 above shows a general synthetic route for preparing compounds of Formula I, IA, IB or IC of this invention where A, A', R$_2$, R$_3$ and R$_4$ are as described herein (it is understood that R$_1$, R$_5$ and R$_6$ can also be present and that ring B substituted with (R$_7$)$_y$ can replace the —CR$_2$R$_3$R$_4$ group). Intermediate 2a, prepared by directed ortho-lithiation of 1a followed by reaction with ethyl formate, is engaged in a Suzuki-Miyaura cross-coupling reaction to give derivative 4a. Cyclisation in presence of hydrazine yields compounds of formula 5a.

Scheme 2:

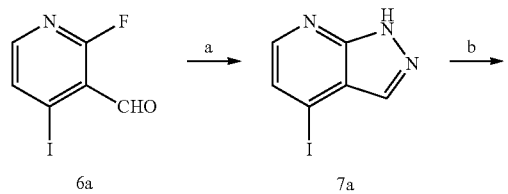

118

-continued

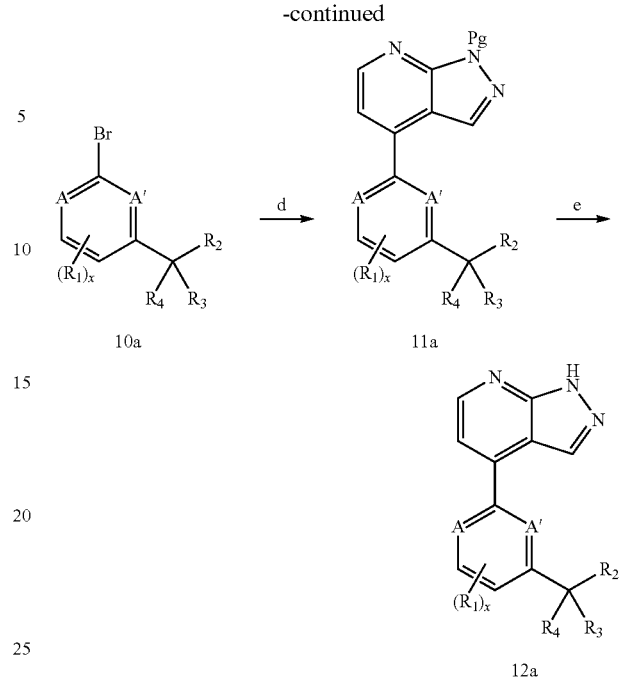

R$^x$ is -H or two R$^x$ together form:

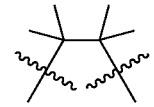

Reagents and conditions:
a) N$_2$H$_4$, THF, 90° C.; b) NaH, PgCl, DMF;
c) K$_2$CO$_3$, [B(OR$^7$)$_2$]$_2$, Pd(dppf)$_2$Cl$_2$•DCM, dioxane, 120° C.;
d) Na$_2$CO$_3$, Pd[P($^t$Bu$_3$)]$_2$ dioxane; e) deprotection conditions Scheme 2 above describes a general synthetic route for preparing compounds of Formula I, IA, IB or IC of this invention where x, A, A', R$_1$, R$_2$, R$_3$ and R$_4$ are as described herein (it is understood that R$_5$ and R$_6$ can also be present and that ring B substituted with (R$_7$)$_y$ can replace the —CR$_2$R$_3$R$_4$ group). Cyclisation of 6a in presence of hydrazine furnishes intermediate 7a. Introduction of a suitable protecting group (e.g. tosyl, trityl, Sem) followed by boronation of iodo derivative 8a gives 9a. Suzuki coupling of intermediate 9a with bromo derivative 10a [starting material for 10a are generally commercially available or be prepared by reactions well known in the art (e.g. Knochel, Buchwald)] leads to 11a, which yield compounds 12a of this invention after deprotection using conditions well know in the art.

Scheme 3:

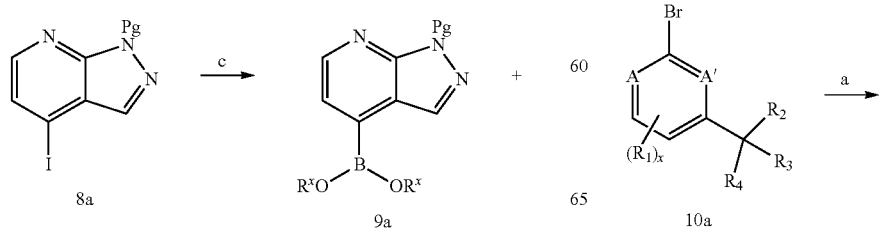

-continued

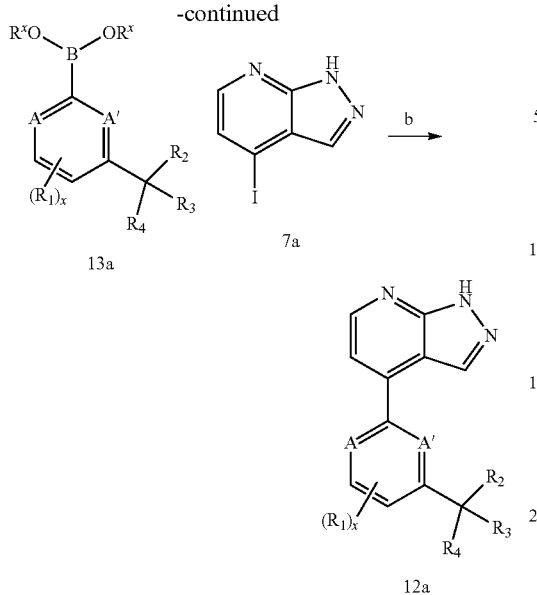

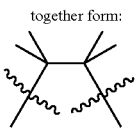

Reagents and conditions: a) K₂CO₃, [B(OR⁷)₂]₂, Pd(dppf)₂Cl₂•DCM, DME, 100° C.; b) Na₂CO₃, Pd(PPh₃)₄, DME, mwave irradiations, 150° C.

Scheme 3 above describes another general synthetic route for preparing compounds of Formula I, IA, IB or IC of this invention where x, A, A', $R_1$, $R_2$, $R_3$ and $R_4$ are as described herein (it is understood that $R_5$ and $R_6$ can also be present and that ring B substituted with $(R_7)_y$ can replace the $CR_2R_3R_4$ group). Starting materials for 10a are either commercially available or can be prepared by reactions well known in the art (e.g. Knochel, Buchwald). Boronation of derivative 10a, followed by Suzuki-Miyaura cross-coupling reaction with intermediate 7a leads to compounds 12a of this invention.

Scheme 4:

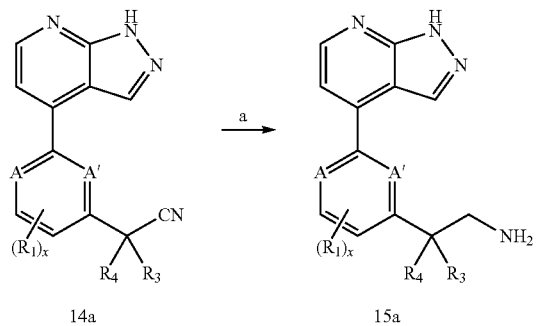

Reagents and conditions: a) LiAlH₄, THF.

Scheme 4 above shows a general synthetic route for preparing compounds of Formula I, IB or IC of this invention where x, A, A', $R_1$, $R_3$ and $R_4$ are as described herein and $R_2$ is CH₂NH₂ (it is understood that $R_5$ and $R_6$ can also be present and that ring B substituted with $(R_7)_y$ can replace the $CR_2R_3R_4$ group). Compounds 15a of this invention can be prepared by reduction of the cyano functionality using conditions well known in the art.

Scheme 5:

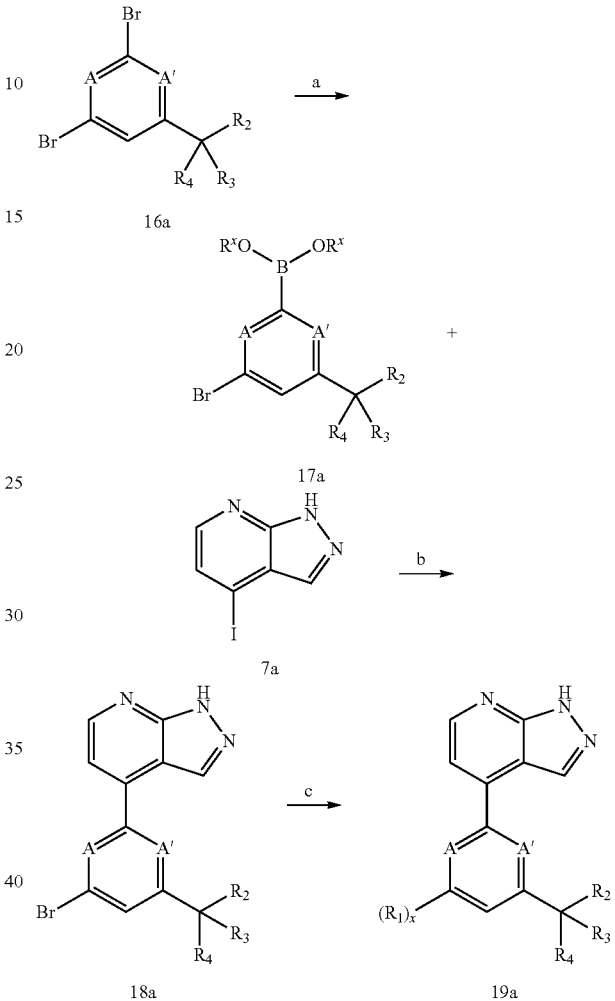

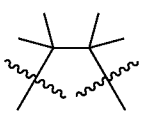

Reagents and conditions: 1) B(OR⁷)₂(OMe), ⁱPrMgCl•LiCl, THF, -20° C.; b) Na₂CO₃, Pd(PPh₃)₄, DME, mwave irradiations, 150° C.; c) R¹B(OH)₂, Na₂CO₃, Pd(PPh₃)₄, DME, mwave irradiations, 150° C.

Reagents and conditions: 1) B(OR⁷)₂(OMe), ⁱPrMgCl•LiCl, THF, -20° C.; b) Na₂CO₃, Pd(PPh₃)₄, DME, mwave irradiations, 150° C.; c) R¹B(OH)₂, Na₂CO₃, Pd(PPh₃)₄, DME, mwave irradiations, 150° C.

Scheme 5 above shows a general synthetic route for preparing compounds of Formula I, IA, IB or IC of this invention where x, A, A', $R_1$, $R_2$, $R_3$ and $R_4$ are as described herein (it is understood that $R_5$ and $R_6$ can also be present and that ring B substituted with $(R_7)_y$ can replace the $CR_2R_3R_4$ group). Derivatives 17a, obtained by boronation of 16a, undergo Suzuki-Miyaura cross-coupling reactions to form compounds of formula 18a. After introducing R' substituent by reactions well known in the art (e.g. Knochel or Suzuki-Miyaura), compounds 19a of this invention were obtained.

Scheme 6:

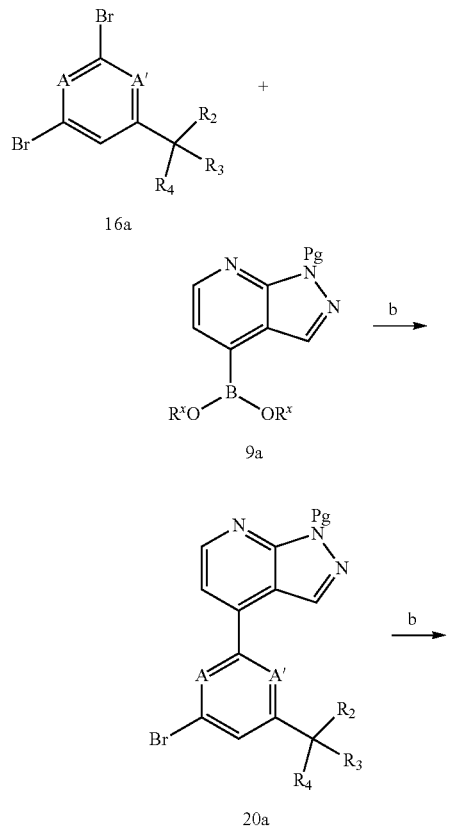

$R^x$ is -H or two $R^x$ together form:

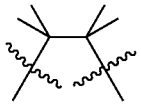

Reagents and conditions: a) Pd(AcO)$_2$, CuI, Pd(o-tol)$_3$, K$_2$CO$_3$, THF, reflux; b) R$^1$B(OH)$_2$, Na$_2$CO$_3$, Pd(PPh$_3$)$_4$, DME mwave irradiations, 150° C.; c) deprotection conditions.

Scheme 6 above shows another general synthetic route for preparing compounds of Formula I, IA, IB or IC of this invention where x, A, A', R$^1$, R$^2$, R$^3$ and R$^4$ are as described herein (it is understood that R$_5$ and R$_6$ can also be present and that ring B substituted with (R$_7$)$_y$ can replace the CR$_2$R$_3$R$_4$ group). Suzuki coupling of intermediate 9a with dibromo derivatives 16a lead to compounds 20a. R$^1$ substituents could be introduced by cross-coupling reactions well known in the art (e.g. Suzuki-Miyaura or Sonogashira). Compounds 19a of this invention were finally obtained after deprotection of intermediates 21a.

Scheme 7:

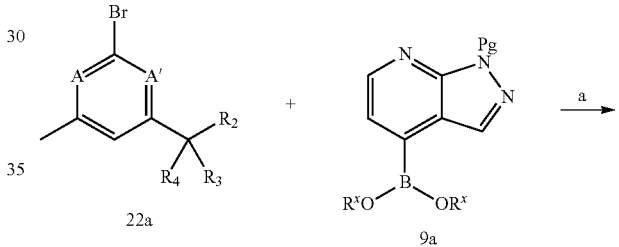

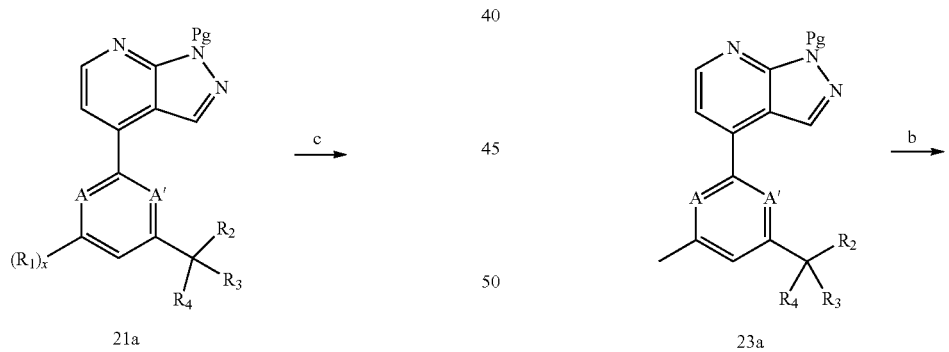

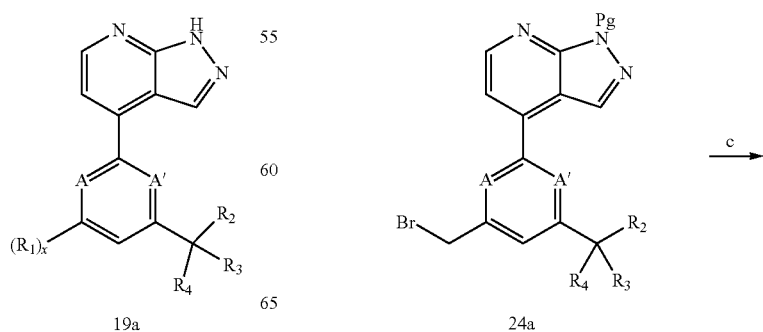

123

-continued

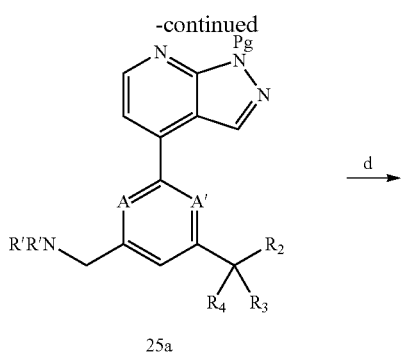

25a

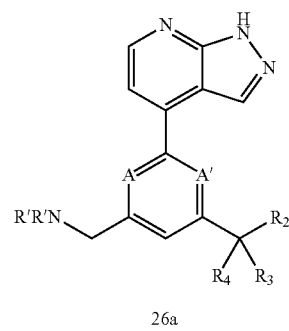

26a

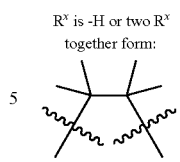

Reagents and conditions: a) Pd(AcO)$_2$, CuI, Pd(o-tol)$_3$, K$_2$CO$_3$, THF, reflux; b) bromination under radical conditions; c) R$^8$R$^9$NH, THF; d) deprotection conditions.

Scheme 7 above shows a general synthetic route for preparing compounds of Formula I, IA, IB or IC of this invention where A, A', R$_2$, R$_3$, R', and R$_4$ are as described herein and R$^1$ is represented as CH$_2$NR'R' (it is understood that R$_1$, R$_5$ and R$_6$ can also be present and that ring B substituted with (R$_7$)$_y$ can replace the CR$_2$R$_3$R$_4$ group). Suzuki-Miyaura cross-coupling of intermediates 9a with derivatives 22a lead to compounds 23a. Bromination of the methyl substituent of 23a followed by displacement with amines HNR'R' furnish compounds 25a. After deprotection under suitable conditions well known in the art, compounds 26a of this invention are prepared.

Scheme 8:

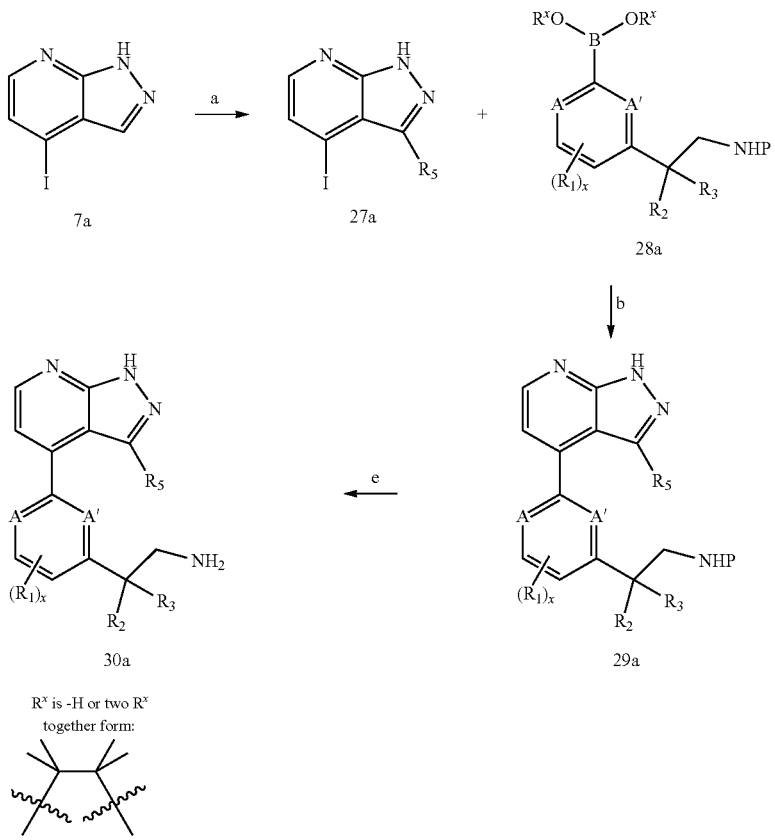

Reagents and conditions: a) NCS, MeCN, reflux; b) Na$_2$CO$_3$, Pd(PPh$_3$)$_4$, dioxane, mwave irradiations, 150° C.; c) deprotection conditions.

Scheme 8 above shows a general synthetic route for preparing compounds of formula I or IA of this invention where x, A, A', $R_1$, $R_2$, $R_3$, $R_5$ and R' are as described herein (it is understood that $R_6$ can also be present and that ring B substituted with $(R_7)_y$ can replace the $CR_2R_3R_4$ group). Chlorination of intermediates 7a led to intermediates 27a. Suzuki-Miyaura cross-coupling reaction of intermediate 27a with derivatives 28a to yield compounds of type 29a. After deprotection under suitable conditions compounds 30a of this invention were prepared.

Scheme 9:

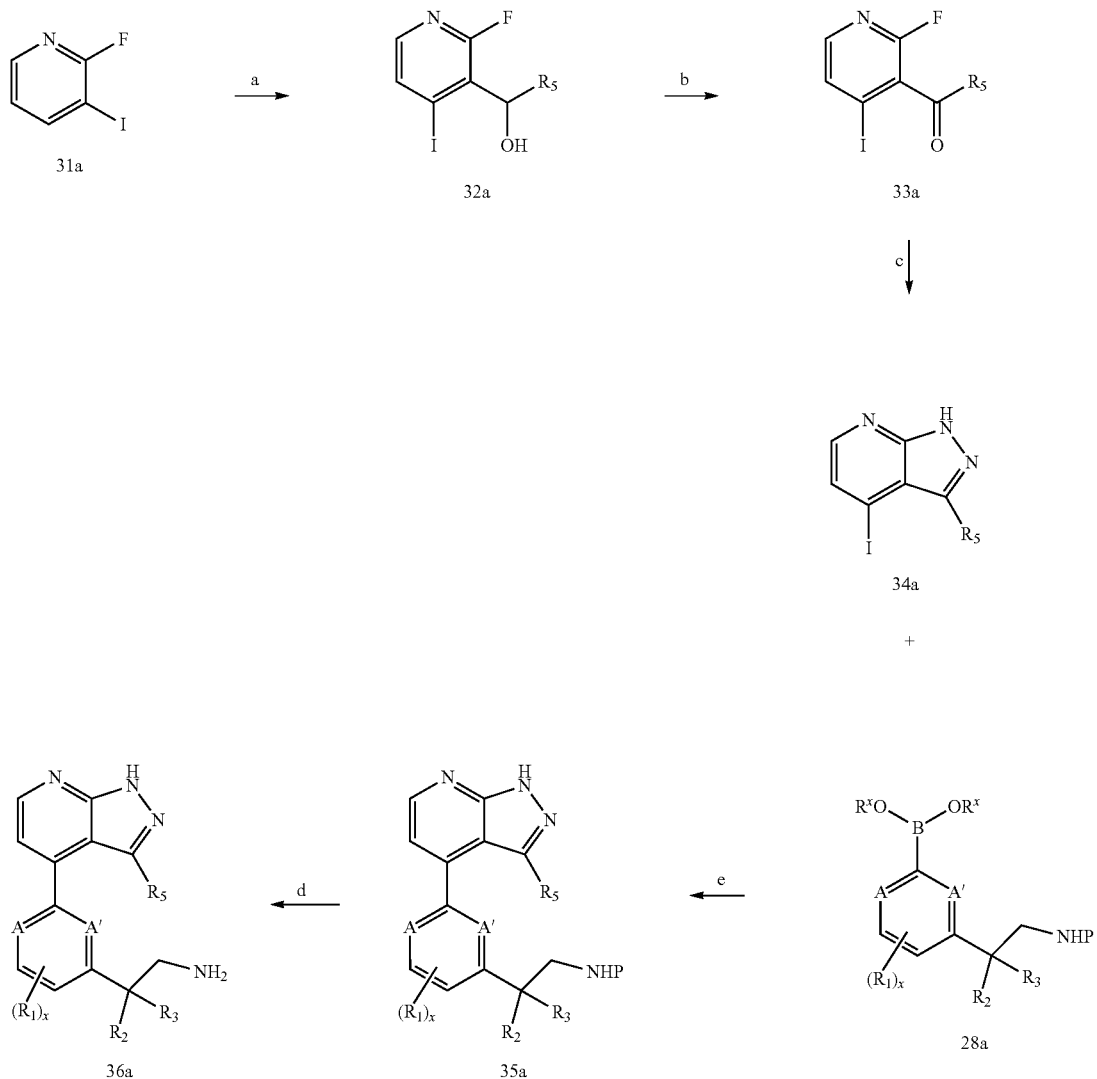

$R^x$ is -H or two $R^x$ together form:

Reagents and conditions: a) LDA, THF, acetaldehyde, −78° C.; b) MnO2, toluene, reflux; c) NH2NH2, THF, pressure tube, 90° C.; d) Na2CO3, Pd(PPh3)4, dioxane, mwave irradiation, 150° C.; e) deprotection conditions.

Scheme 9 above shows another general synthetic route for preparing compounds of formula I or IA of this invention where x, A, A', $R_1$, $R_2$, $R_3$, and $R_5$ are as described herein (it is understood that $R_6$ can also be present). Intermediate 31a was transformed to the alcohol 32a and then oxidized to ketone 33a. This was cyclised using hydrazine to give 34a which was coupled with intermediate 28a using Suzuki-Miyaura cross-coupling reactions to yield compounds 35a. Compounds 36a of this invention were finally obtained after deprotection.

Scheme 10:

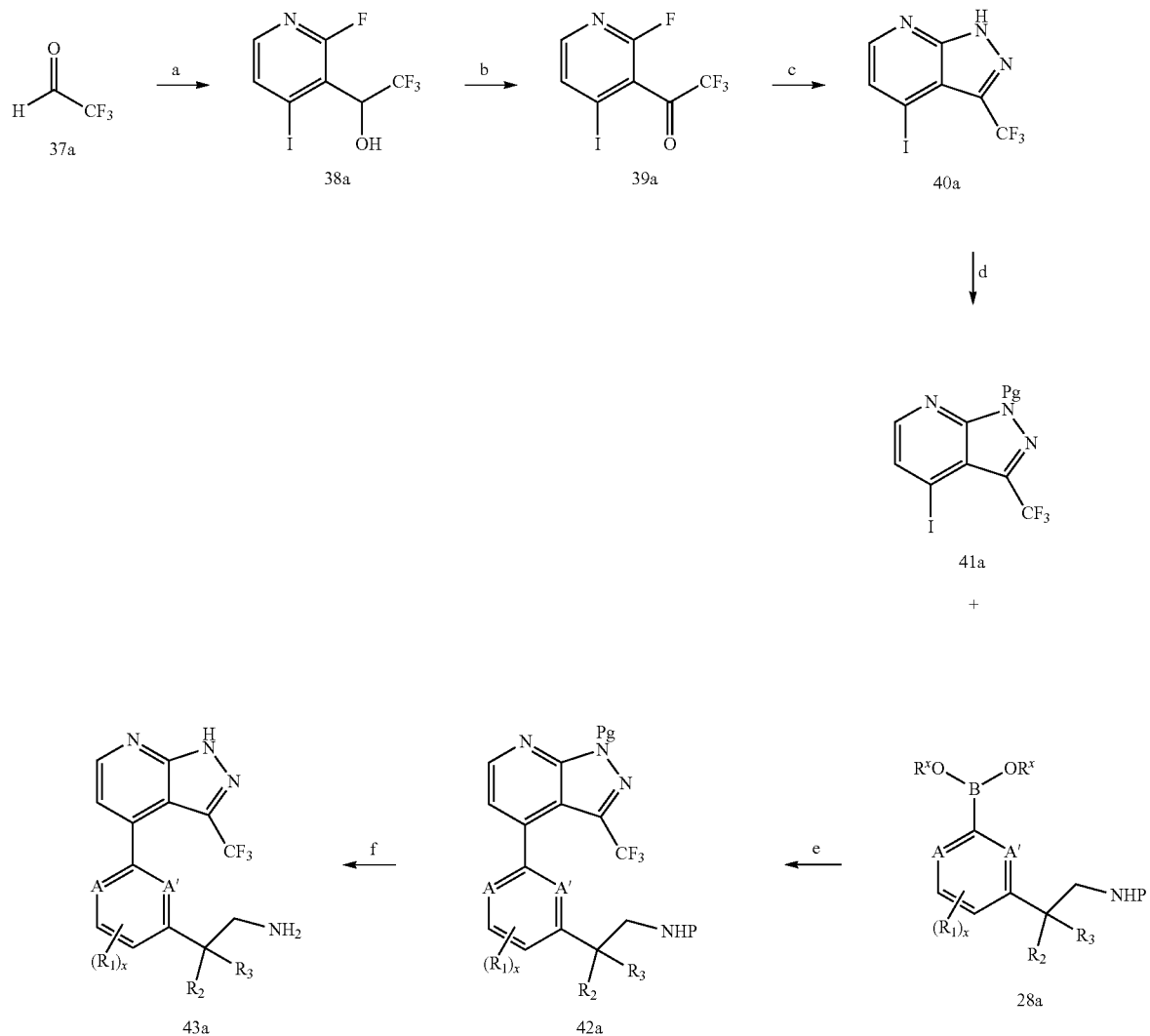

$R^x$ is -H or two $R^x$ together form:

Reagents and conditions: a) LDA, THF, 2-Fluro-3-iodo-pyridine, -78° C.; b) MnO2, toluene, reflux; c) NH2NH2, dioxane, pressure tube, reflux; d) NaH, DMF, PgCl, RT; e) Na2CO3, [P(tBu3)3]2, dioxane, 60° C.; f) deprotection conditions.

Scheme 10 above shows another general synthetic route for preparing compounds of formula I or IA of this invention where x, A, A', $R_1$, $R_2$ and $R_3$ are as described herein (it is understood that $R_6$ can also be present). Intermediate 37a was reacted with the pyridyl lithium species to yield the alcohol 38a. The compounds were then oxidized to ketone 39a, that subsequently was cyclised using hydrazine to give derivatives 40a. Compounds of formula 40a were protected and then underwent a Suzuki-Miyaura cross-coupling reaction with intermediate 28a to lead to compounds 42a. Compounds 43a of this invention were finally obtained after deprotection.

Scheme 11:

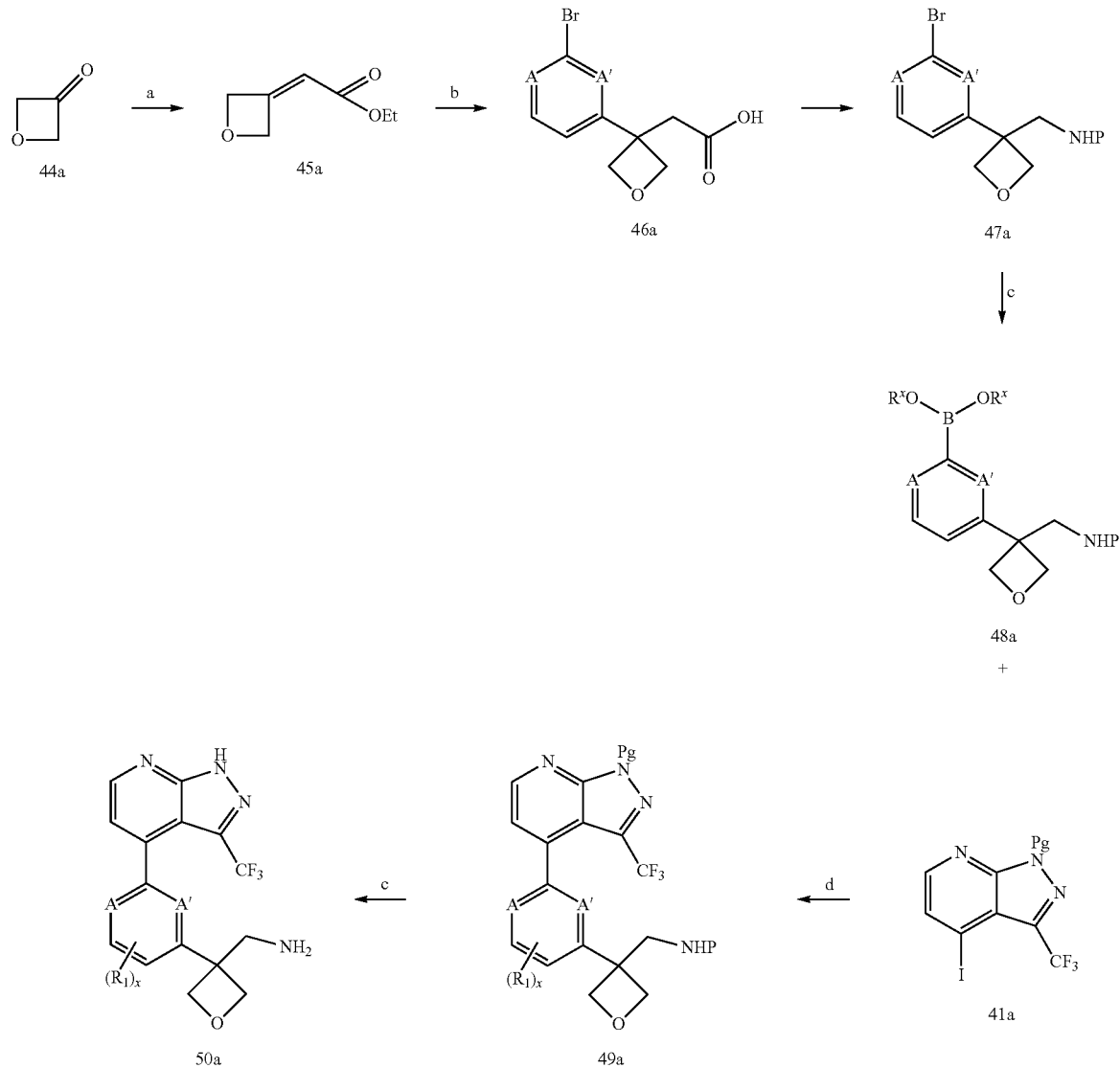

$R^X$ is -H or two $R^X$ together form:

Reagents and conditions: a) 2-triphenylphosphoranylideneacetate, DCM, 0° C.-RT; b) i) 3-bromo-phenyl boronic acid, [Rh(cod)Cl]$_2$, dioxane, KOH, ethyl 2-(oxetan-3-ylidene) acetate, ii) NaOH, MeOH, 0° C.; c) DPPA, triethylamine, tBuOH, 80° C.; d) B(OR$^7$)$_2$(OMe), Pd[dppf]Cl$_2$. DCM, dioxane, KOAc, 90° C,; e) Na$_2$CO$_3$, [P(tBu$_3$)$_3$]$_2$, dioxane, 60° C.; f) deprotection conditions.

Scheme 11 above shows another general synthetic route for preparing compounds of formula I or IA of this invention where x, A, A', and $R^1$ are as described herein it is understood that $R_6$ can also be present). Intermediate 44a was converted to 45a under Wittig reaction conditions and then coupled to form 46a, using Rh as catalyst. A Curtius reaction gave 47a, which was converted to the boronate 48b and then underwent a Suzuki-Miyaura cross-coupling reaction with intermediate 41a to lead to compounds 49a. Final compounds 50a were obtained after deprotection.

Accordingly, this invention also provides a process for preparing a compound of this invention.

In one embodiment the present invention is a method of preparing the compounds described herein.

In one embodiment the present invention is a process for preparing a compound of the present invention, comprising:

a) ortholithiation of compound represented by the following structural formula:

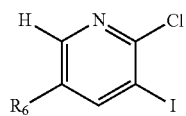

1a to give a compound represented by the following structural formula:

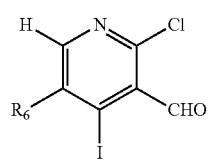

2a b) Suzuki-miyaura coupling of the compound represented by formula 2a with a compound represented by a structural formula selected from the group consisting of:

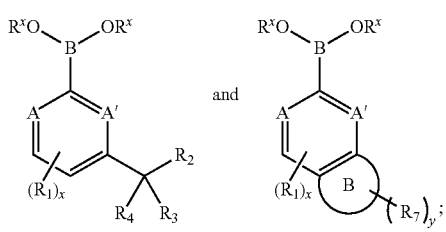

3a wherein:
each $R^x$ is —H or two $R^x$s together form

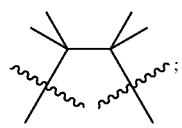 [SMILES: *C(C)(C)C(*)(C)C]

to give a compound represented a structural formula selected from the group consisting of:

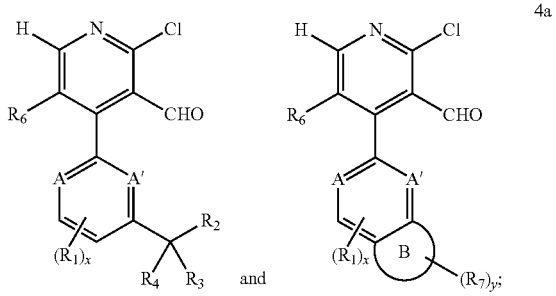

4a and c) cyclization of the compound represented by 4a in the presence of hydrazine to yield a compound of the present invention, wherein the variables are as defined herein.

In certain embodiments the above process is carried out with the following reagents and conditions: a) i) LDA (lithium diisopropyamide), THF (tetrahydrofuran); ii) Ethyl formate; b) Pd(OAc)$_2$, CuI, Pd(o-tol)$_3$, K$_2$CO$_3$, THF, reflux; c) N$_2$H$_4$ (hydrazine), 160° C., microwave.

In another embodiment the present invention is a process for preparing a compound of the present invention, comprising:

a) cyclization of compound represented by represented by the following

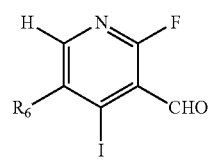

6a in the presence of hydrazine to give a compound represented by the following structural formula:

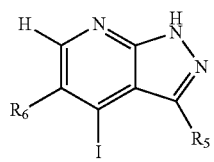

7a b) protection of a compound represented by 7a to give a compound represented by the following structural formula:

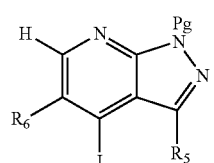

8a c) boronation of a compound represented by 8a to give a compound represented by represented by the following structural formula:

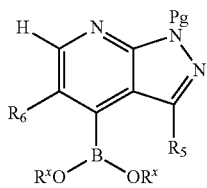

9a wherein:
each $R^X$ is —H or two $R^X$s together form

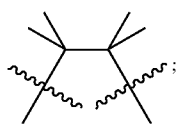 [SMILES: *C(C)(C)C(*)(C)C]

;

d) suzuki coupling of the compound represented by formula 9a with a compound represented a structural formula selected from the groups consisting of:

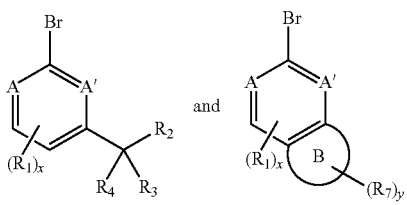

10a to give a compound represented by a structural formula selected from the group consisting of:

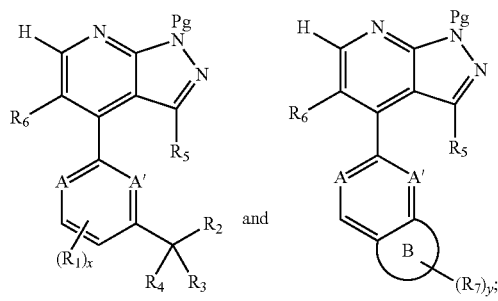

11a and e) deprotection of the compound represented by 11a in the presence of hydrazine to yield compound of the present invention, wherein the variables are as defined herein.

In certain embodiments the above process is carried out with the following reagents and conditions: a) N$_2$H$_4$, THF, 90° C.; b) NaH, PgCl, DMF; c) K$_2$CO$_3$, [B(OR$^7$)$_2$]$_2$, Pd(dppf)$_2$Cl$_2$.DCM(palladium 1,1'bis(diphenylphosphino)ferrocene dichloromethane), dioxane, 120° C.; d) Na$_2$CO$_3$, Pd[P($^t$(Bu$_3$)]$_2$ dioxane; e) deprotection conditions.

In another embodiment, the present invention is a process for preparing a compound of the present invention, comprising:

a) boronation of a compound represented by a structural formula selected from the group consisting of:

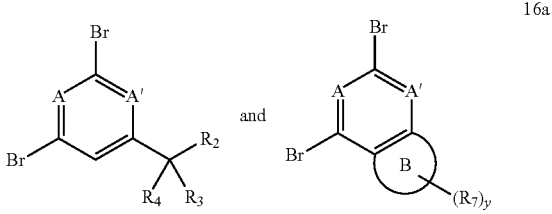

16a to give a compound represented by a structural formula selected from the group consisting of:

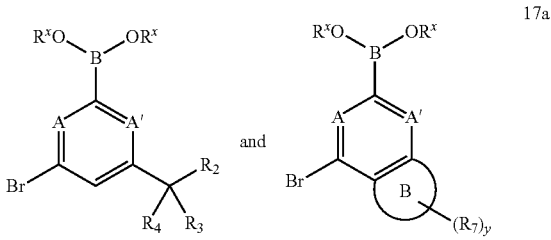

17a wherein:
each $R^X$ is —H or two $R^X$s together form

;

b) suzuki coupling of the compound represented by formula 17a with a compound represented by the following structural formula:

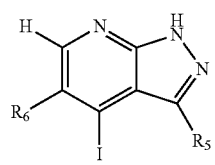

7a to give a represented by a structural formula selected from the group consisting of:

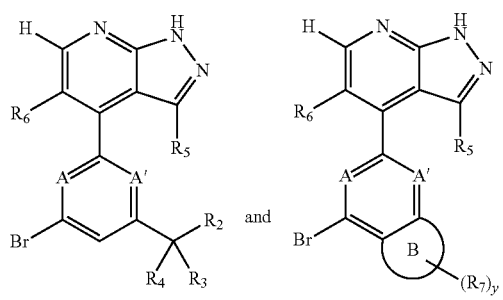

18a c) Introduction of $R_1$ by reactions well known in the art (e.g., Knochel or Suzuki coupling) to yield a compound of the present invention, wherein the variables are as defined herein.

In certain embodiments the above process is carried out with the following reagents and conditions: a) $B(OR^7)_2$ (OMe), $^iPrMgCl.LiCl$, THF, $-20°$ C.; b) $Na_2CO_3$, $Pd(PPh_3)_4$, DME, mwave irradiations, $150°$ C.; c) $R'B(OH)_2$, $Na_2CO_3$, $Pd(PPh_3)_4$, DME, mwave irradiations, $150°$ C.

In another embodiment the present invention is a process for preparing a compound of the present invention, comprising:

a) suzuki coupling of a compound represented by a structural formula selected from the group consisting of:

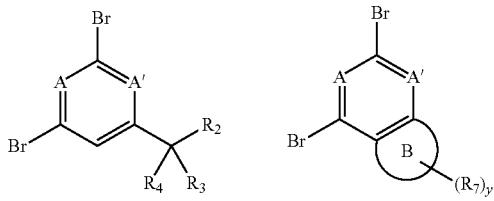

16a with a compound represented by the following structural formula:

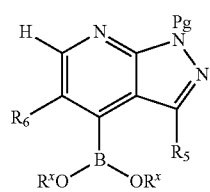

9a wherein:
each $R^x$ is —H or two $R^x$s together form

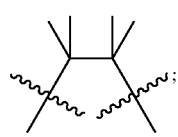

to give a compound represented by a structural formula selected from the groups consisting of:

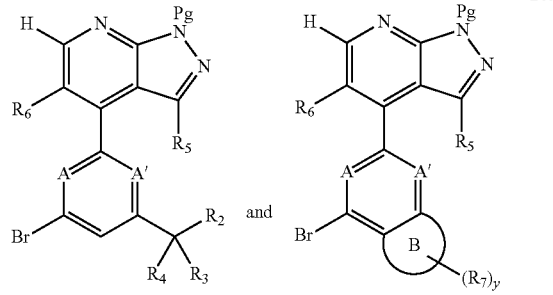

20a c) introduction of $R_1$ substituent by cross-coupling reactions well known in the art (e.g., Suzuki or Sonogashira) to give a compound of represented by formula 21a:

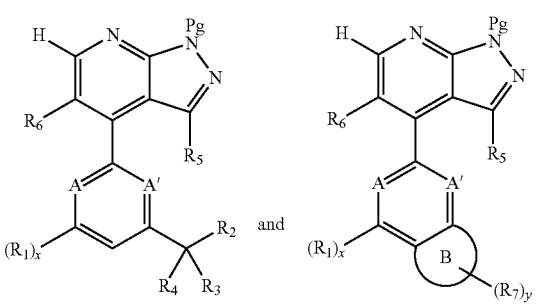

21a d) deprotection of the compound represented by formula 21a to yield a compound of the present invention, wherein the variables are as defined herein.

In certain embodiments the above process is carried out with the following reagents and conditions: a) $Pd(AcO)_2$, CuI, $Pd(o-tol)_3$, $K_2CO_3$, THF, reflux; b) $R^1B(OH)_2$, $Na_2CO_3$, $Pd(PPh_3)_4$, DME, mwave irradiations, $150°$ C.; c) deprotection conditions.

In another embodiment, the present invention is a process for preparing a compound of the present invention, comprising:

a) suzuki coupling of a compound represented by a structural formula selected from the group consisting of:

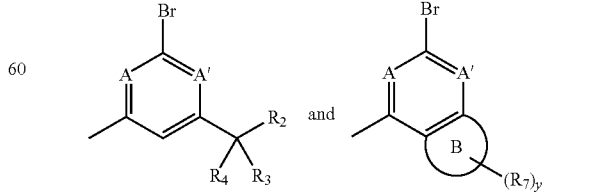

22a with a compound represented by the following structural formula:

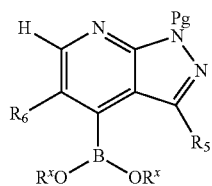

9a wherein:
each $R^x$ is —H or two $R^x$s together form

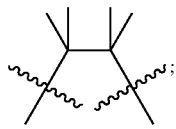 [SMILES: *C(C)(C)C(*)(C)C]

to give a compound represented by a structural formula selected from the group consisting of:

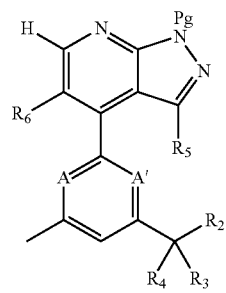 and 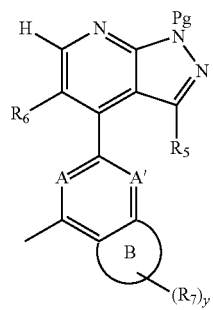

23a c) bromination of the compound represented by 23a to give a compound represented by a structural formula selected from the group consisting of:

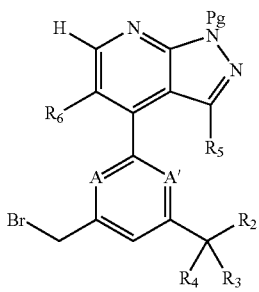 and 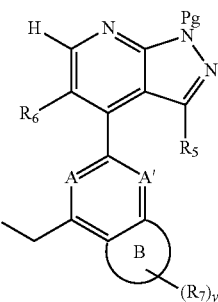

24a d) amine displacement with HNR'R' to give a compound represented by the following structural formula:

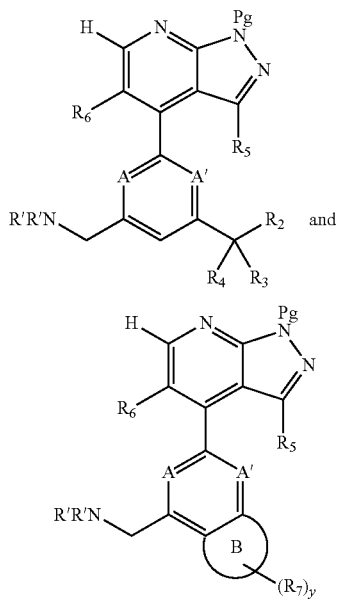

25a e) deprotection of the compound represented by formula 25a to yield a compound of the present invention, wherein the variables are as defined herein.

In certain embodiments the above process is carried out with the following reagents and conditions: a) Pd(AcO)$_2$, CuI, Pd(o-tol)$_3$, K$_2$CO$_3$, THF, reflux; b) bromination under radical conditions; c) R$^8$R$^9$NH, d) deprotection conditions.

In another embodiment, the present invention is a process for preparing a compound of the present invention, comprising:

a) boronation of a compound represented by a structural formula selected from the group consisting of:

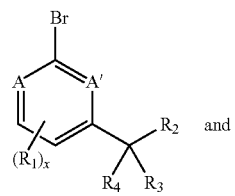 and i

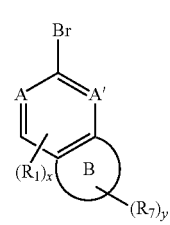

ia in the presence of a boronation agent and a solvent, to give a compound represented by a structural formula selected from the group consisting of:

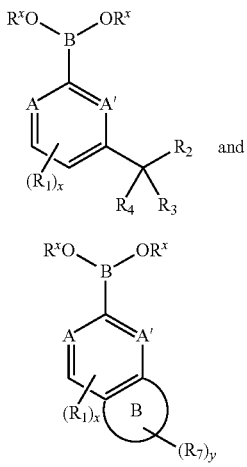

wherein:

each R$^X$ is —H or two R$^X$s together form

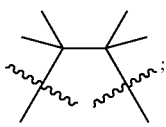

b) cyclization of a compound represented by the following structural formula:

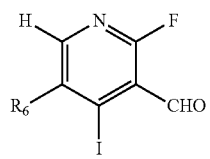

in the presence of hydrazine and a solvent to give a compound represented by the following structural formula:

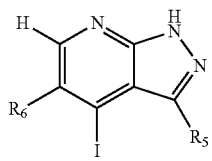

c) suzuki coupling of the compound represented by formula ii or iia with a compound represented by formula iv in the presence of a solvent, a catalyst complex and a base to give a compound of Claim 1 or 2.

In one embodiment, the boronation agent in step a) is bis(pinacolato)diboron, pinacol, or 2-methoxy-4,4,5,5-tetramethyl-1,3,2-dioxaborolane.

In another embodiments, the solvent is used in step a) is selected from the group consisting of tetrahydrofuran, dimethyl ether, dioxane, dimethyl sulfoxide and combinations thereof.

In another embodiment, a catalyst complex is used in step a).

In one embodiment, the catalyst complex comprises at least one metal and one or more ligands.

In another embodiment, the catalyst complex is Pd(dppf)Cl$_2$.DCM, Pd(PPh$_3$)$_4$ or isopropylmagnessium chloride lithium chloride complex.

In yet another embodiment, the solvent in step b) is selected from the group consisting of tetrahydrofuran, dioxane, dichloromethane, toluene, ethanol, methanol, ethylene glycol, butanol and combinations thereof.

In another embodiment, the solvent in step c) is selected from the group consisting of dioxane, dimethyl ether, toluene, ethanol, dimethylformamide, tetrahydrofuran, benzene, water and combinations thereof.

In another embodiment, the catalyst complex used in step c) comprises at least one metal and one or more ligands. In one embodiment, the metal is Pd.

In one embodiment, each ligand is independently selected from the group consisting of P(tBu)$_3$ ((tri-tet-butyl phosphone), P(Cyc)$_3$ (tricyclohexane phosphine), PPh$_3$, PPh$_2$$^t$Bu, BINAP (2,2'bis(diphenylphosphino)-1,1'binaphthyl), dppf, dba (dibenzylidenacetone), and combinations thereof.

In one embodiment, the catalyst complex is selected from the group consisting of Pd(PPh$_3$)$_4$, PdCl$_2$(PPh$_3$)$_2$, Pd(dppf)$_2$Cl$_2$, Pd$_2$(dba)$_3$, and Pd(P$^t$Bu$_3$)$_2$.

In another embodiment, the base in step c) is selected from the group consisting of Na$_2$CO$_3$, NaHCO$_3$, Cs$_2$CO$_3$, CsF, KF, K$_2$CO$_3$, KOAc, K$_3$PO$_4$, NaOEt, KOH and CsOH.

In another embodiment, the present invention is a process for preparing a compound of the present invention, comprising:

a) cyclization of compound represented by represented by the following structural formula:

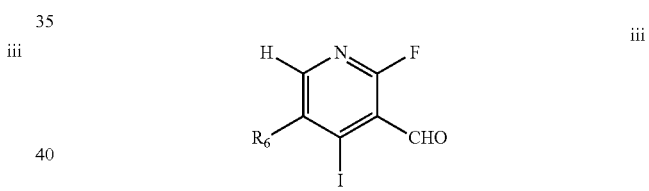

in the presence of hydrazine and a solvent to give a compound represented by the following structural formula:

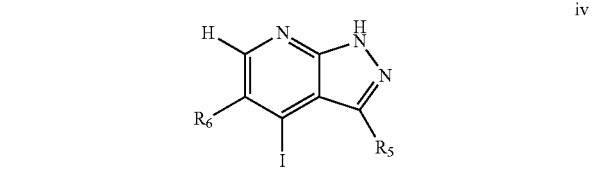

b) protection of a compound represented by iv to give a compound represented by the following structural formula:

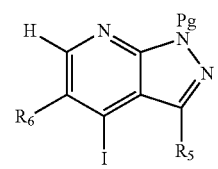

c) boronation of a compound represented by v in the presence of a boronation agent and a solvent to give a compound represented by represented by the following structural formula:

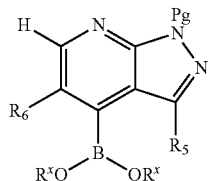

vi wherein:
each $R^x$ is —H or two $R^x$s together form

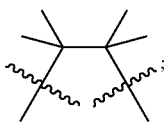

d) suzuki coupling of the compound represented by formula vi with a compound represented a structural formula selected from the groups consisting of:

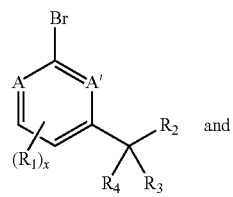

i and

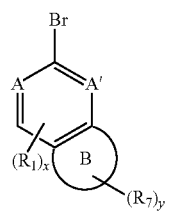

ia in the presence of solvent, a catalyst complex and a base to give a compound represented by a structural formula selected from the group consisting of:

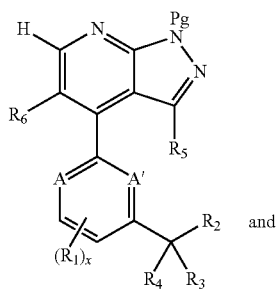

vii

-continued

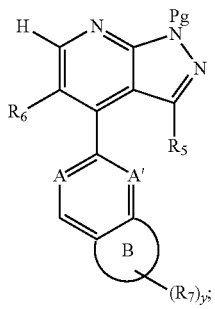

viia and e) deprotection of the compound represented by vii or viia in the presence of hydrazine to yield a compound of Claim 1 or 2.

In one embodiment, the solvent in step a) is selected from the group consisting of tetrahydrofuran, dioxane, dichloromethane, toluene, ethanol, methanol, ethylene glycol, butanol and combinations thereof.

In another embodiment, the boronation agent in step c) is bis(pinacolato)diboron, pinacol, or 2-methoxy-4,4,5,5-tetramethyl-1,3,2-dioxaborolane.

In another embodiment, the solvent used in step c) is selected from the group consisting of tetrahydrofuran, dimethyl ether, dioxane, dimethyl sulfoxide and combinations thereof.

In yet another embodiment, a catalyst complex in also used in step a). In yet another embodiment, the catalyst complex comprises at least one metal and one or more ligands. In another embodiment, the catalyst complex is Pd(dppf)Cl$_2$.DCM, Pd(PPh$_3$)$_4$ or isopropylmagnessium chloride lithium chloride complex.

In another embodiment, the solvent in step d) is selected from the group consisting of dioxane, dimethyl ether, toluene, ethanol, dimethylformamide, tetrahydrofuran, benzene, water and combinations thereof.

In another embodiment, the catalyst complex used in step d) comprises at least one metal and one or more ligands. In one embodiment, the metal is Pd. In another embodiment, each ligand is independently selected from the group consisting of P(tBu)$_3$, P(Cyc)$_3$, PPh$_3$, PPh$_2$$^t$Bu, BINAP, dppf, dba, and combinations thereof. In yet another embodiment, the catalyst complex is selected from the group consisting of Pd(PPh$_3$)$_4$, PdCl$_2$(PPh$_3$)$_2$, Pd(dppf)$_2$Cl$_2$, Pd$_2$(dba)$_3$, and Pd(P$^t$Bu$_3$)$_2$.

In one embodiment, the base in step d) is selected from the group consisting of Na$_2$CO$_3$, NaHCO$_3$, Cs$_2$CO$_3$, CsF, KF, K$_2$CO$_3$, KOAc, K$_3$PO$_4$, NaOEt, KOH and CsOH.

EXAMPLES

HPLC Methods

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture. Column gradient conditions were 5%-100% acetonitrile-methanol over 3.5 mins gradient time and 4.8 mins run time on an ACE5C8 3.0×75 mm column. Flow rate was 1.2 ml/min.

As used herein, the term "Rt(min)" refers to the LCMS retention time, in minutes, associated with the compound. Unless otherwise indicated, the LCMS method utilized to obtain the reported retention time is as detailed above.

1H-NMR spectra were recorded at 400 MHz using a Bruker DPX 400 instrument.

The following compounds of Formula I, IA, IB or IC were prepared and analyzed as follows.

Example 1

2-(6-(1H-pyrazolo[3,4-b]pyridin-4-yl)pyridin-2-yl)-2-methylpropanenitrile (Compound 1)

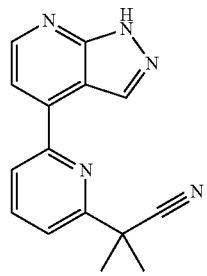 [SMILES: CC(C)(C#N)c1cccc(-c2ccnc3[nH]ncc23)n1]

Step 1:
2-(6-bromopyridin-2-yl)-2-methylpropanenitrile

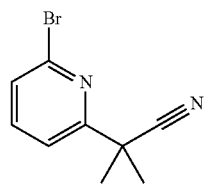

Potassium bis(trimethylsilyl)amide (0.5 M in toluene, 200 ml, 100 mmol) was added slowly to a solution of isobutyronitrile (8.55 ml, 95.26 mmol) in toluene (200 ml) cooled down to 0° C. After complete addition, the reaction mixture was allowed to warm up to room temperature over 1 hour. The resulting mixture was added to a solution of 2,6-dibromopyridine (56.42 g, 238.15 mmol) in toluene (100 ml). The reaction mixture was stirred at room temperature for 18 hours. The crude mixture was diluted with ether, washed with a saturated aqueous solution of ammonium chloride and brine. The organic phase was dried over magnesium sulfate, filtered and concentrated in vacuo. The residue was purified on silica gel by flash column chromatography to afford the title compound as an oil (14.04 g, 65% yield).

$^1$H NMR (DMSO-$d_6$, 400 MHz) δ 1.69 (6H, s), 7.66 (2H, dd), 7.85 (1H, t).

Step 2: 2-methyl-2-(6-(6-phenyl-1,3,6,2-dioxazaborocan-2-yl)pyridin-2-yl)propanenitrile

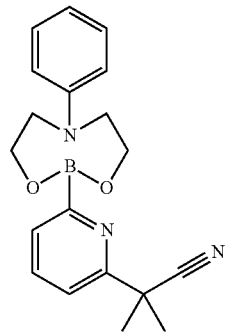 [SMILES: CC(C)(C#N)c1cccc(B2OCCN(c3ccccc3)CCO2)n1]

A stirred solution of 2-(6-bromopyridin-2-yl)-2-methylpropanenitrile (1 g, 4.44 mmol) and triisopropylborate (1.23 ml, 5.33 mmol) in tetrahydrofuran (10 ml) was cooled down to −75° C. A 2.5 M solution of n-BuLi in hexanes (2.31 ml, 5.77 mmol) was added at such a rate that the temperature did not exceed −67° C. After complete addition, the reaction was allowed to warm to room temperature and was stirred at this temperature for 16 hours. After this time, a solution of N-phenyldiethanolamine (805 mg, 4.44 mmol) in THF (8 ml) was added and the resulting mixture was heated at reflux for 4 hours. The mixture was concentrated in vacuo, diluted with isopropanol (18 ml) and refluxed for 1 hour. The reaction mixture was cooled down to room temperature and stirred for 18 hours. The newly formed solid was filtered off and dried under vacuo at 40° C. to afford the title compound as a white solid (880 mg, 59% yield).

$^1$H NMR (CD$_3$OD, 400 MHz) δ 1.79 (6H, s), 3.54 (4H, t), 3.73 (4H, t), 6.63 (1H, t), 6.75 (2H, d), 7.17 (2H, t), 7.32 (1H, d), 7.50 (1H, d), 7.60 (1H, t).

Step 3: 2-(2'-chloro-3'-formyl-2,4'-bipyridin-6-yl)-2-methylpropanenitrile

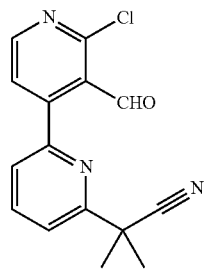 [SMILES: CC(C)(C#N)c1cccc(-c2ccnc(Cl)c2C=O)n1]

A suspension of 2-chloro-4-iodonicotinaldehyde (90.3 mg, 0.338 mmol)(prepared via *J. Org. Chem.*, 1993, 58, 7832), 2-methyl-2-(6-(6-phenyl-1,3,6,2-dioxazaborocan-2-yl)pyridin-2-yl)propanenitrile (226 mg, 0.675 mmol), tri-o-tolylphosphine (21 mg, 0.068 mmol), palladium acetate (5 mol %, 3.8 mg, 0.017 mmol), potassium carbonate (93 mg, 0.675 mmol) and copper(I) iodide (26 mg, 0.135 mmol) in tetrahydrofuran (5 ml) was heated at reflux under nitrogen for 75 minutes. The mixture was cooled down to room temperature, filtered through a path of celite and evaporated to dryness. The residue was purified on silica gel by flash column chromatography to afford the title compound as an off-white solid (71 mg, 74% yield).

¹H NMR (CDCl₃, 400 MHz) δ 1.76 (6H, s), 7.58 (1H, d), 7.70 (1H, d), 7.72 (1H, d), 7.95 (1H, t), 8.60 (1H, d), 10.39 (1H, s).

Step 4: 2-(6-(1H-pyrazolo[3,4-b]pyridin-4-yl)pyridin-2-yl)-2-methylpropanenitrile

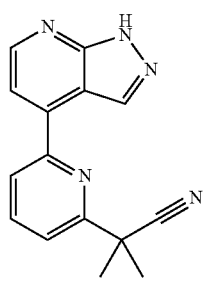 [SMILES: CC(C)(C#N)c1cccc(-c2ccnc3[nH]ncc23)n1]

A mixture of 2-(2'-chloro-3'-formyl-2,4'-bipyridin-6-yl)-2-methylpropanenitrile (71 mg, 0.25 mmol) and 1M solution of hydrazine in tetrahydrofuran (3 ml) was heated under microwave irradiation at 140° C. for 20 minutes. The mixture was cooled down to room temperature, diluted with ethanol (1 ml) and hydrazine hydrate (1 ml) was added. The reaction mixture was heated under microwave irradiation at 160° C. for 30 minutes. The mixture was cooled down to room temperature, partitioned between ethyl acetate and water. The organic phase was dried over magnesium sulfate, filtered and evaporated to dryness. The residue was purified on silica gel by flash column chromatography to afford the title compound as a white solid (14.6 mg, 22% yield).

¹H NMR (CDCl₃, 400 MHz) δ 1.83 (6H, s), 7.73 (1H, d), 7.84 (1H, d), 8.12 (1H, t), 8.27 (1H, d), 8.67 (1H, d), 8.89 (1H, s), 13.80 (1H, s); MS (ES⁺) 264.

Table 2 below depicts data for certain exemplary compounds made in general by a similar route to that outlined in Example 1.

TABLE 2

| # | M + 1 (obs) | RT (min) | 1H-NMR |
|---|---|---|---|
| 1 | 264.09 | 2.73 | (DMSO) 1.83 (6H, s), 7.73 (1H, d), 7.84 (1H, d), 8.12 (1H, t), 8.27 (1H, d), 8.67 (1H, d), 8.89 (1H, s), 13.80 (1H, s). |
| 2 | 305.15 | 2.67 | (DMSO) 2.55-2.46 (4 H, masked signal), 3.21 (2 H, m), 3.62-3.59 (2 H, m), 7.78 (1 H, d), 7.84 (1 H, d), 8.19 (1 H, t), 8.32 (1 H, d), 8.68 (1 H, d), 8.79 (1 H, s), 8.90-8.84 (1 H, br m), 13.85 (1 H, s). |
| 3 | 291.14 | 2.77 | (DMSO) 2.84-2.76 (1 H, m), 2.99-2.93 (1 H, m), 3.59-3.52 (1 H, m), 3.69-3.63 (1 H, m), 4.03 (1 H, d), 4.23 (1 H, d), 7.84 (1 H, d), 7.89 (1 H, d), 8.20 (1 H, t), 8.33 (1 H, d), 8.68 (1 H, d), 8.73 (1 H, s), 9.87 (1 H, br s), 13.87 (1 H, br s). |

Example 2

2-(3-(1H-pyrazolo[3,4-b]pyridin-4-yl)phenyl)-2-methylpropanenitrile (Compound 4)

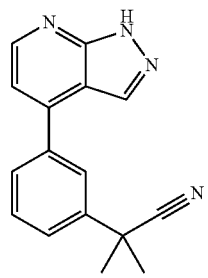 [SMILES: CC(C)(C#N)c1cccc(-c2ccnc3[nH]ncc23)c1]

Step 1: 2-(3-bromophenyl)-2-methylpropanenitrile

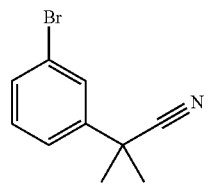

Lithium bis(trimethylsilyl)amide (1 M in tetrahydrofuran, 58.7 ml, 58.7 mmol) was added slowly to a solution of 2-(3-bromophenyl)acetonitrile (5.75 g, 29.33 mmol) in tetrahydrofuran (60 ml) cooled down to 0° C. After complete addition, the reaction mixture was stirred at 0° C. for a further 20 minutes. Methyl iodide (9.14 ml, 146.82 mmol) was then added to the reaction mixture and the reaction was stirred at room temperature for 1 hour. The crude mixture was quenched with water and extracted with ethyl acetate. The organic phase was washed with brine, dried over magnesium sulfate, filtered and concentrated in vacuo. The residue was purified on silica gel by flash column chromatography to afford the title compound as a colourless oil (6.629 g, quantitative yield).

¹H NMR (MeOH-d₄, 400 MHz) δ 1.57 (6H, s), 7.19 (1H, t), 7.33-7.38 (2H, m), 7.53 (1H, t); MS (ES⁺) 225.

Step 2: 2-methyl-2-(3-(4,4,5,5-tetramethyl-1,3,2-dioxaborolan-2-yl)phenyl)propanenitrile

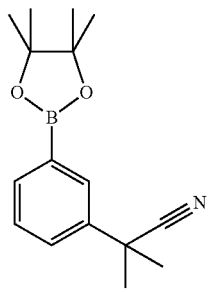

A suspension of 2-(3-bromophenyl)-2-methylpropanenitrile (6.33 g, 28.25 mmol), bis(pinacolato)diboron (8.61 g, 33.90 mmol), potassium acetate (8.32 g, 84.80 mmol), 1,1'-bis(diphenylphosphino)ferrocene-palladium(II)dichloride dichloromethane complex (692 mg, 0.85 mmol), in ethylene glycol dimethyl ether (120 ml) was heated at 100° C. under nitrogen for 30 minutes. The mixture was cooled down to room temperature, filtered through a path of celite and evaporated to dryness. The residue was purified on silica gel by flash column chromatography to afford the title compound as a white solid (6.39 g, 83% yield).

$^1$H NMR (CD$_3$OD, 400 MHz) δ 1.37 (12H, s), 1.77 (6H, s), 7.42 (1H, t), 7.61 (1H, d), 7.79 (1H, d), 7.89 (1H, s); MS (ES$^+$) 272.

Step 3: 4-iodo-1H-pyrazolo[3,4-b]pyridine

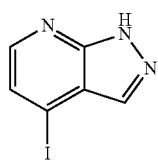

To a cooled solution of 2-fluoro-4-iodonicotinaldehyde (19.75 g, 78.7 mmol) in anhydrous tetrahydrofuran (100 ml) at 10° C. was carefully added 1M hydrazine in tetrahydrofuran (100 ml, 100 mmol) at such a rate that the temperature of the reaction mixture remained below 30° C. After complete addition a precipitate started to form and this was allowed to stir for a few minutes and then the vessel was sealed and heated to 90° C. for 2 hours behind a blast shield. After this time, the reaction mixture was allowed to cool down to room temperature and concentrated to dryness. The resulting yellow solid was triturated with a small amount of ethyl acetate to give the product as a pale yellow powder (17.68 g, 92% yield).

$^1$H NMR (DMSO-d$_6$, 400 MHz) δ 7.7 (1H, d), 8.0 (1H, s), 8.2 (1H, d) and 12.0 (1H, br s); MS (ES$^+$) 246, (ES$^-$) 244.

Step 4: 2-(3-(1H-pyrazolo[3,4-b]pyridin-4-yl)phenyl)-2-methylpropanenitrile

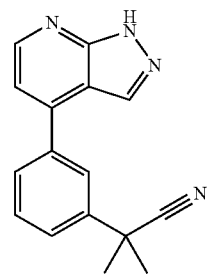 [SMILES: CC(C)(C#N)c1cccc(-c2ccnc3[nH]ncc23)c1]

A suspension of 4-iodo-1H-pyrazolo[3,4-b]pyridine (50 mg, 0.204 mmol), 2-methyl-2-(3-(4,4,5,5-tetramethyl-1,3,2-dioxaborolan-2-yl)phenyl)propanenitrile (66 mg, 0.245 mmol), 2 M aqueous solution of sodium carbonate (0.31 ml, 0.612 mmol), tetrakis(triphenylphosphine)palladium(0) (5 mol %, 12 mg, 0.01 mmol), in ethylene glycol dimethyl ether (2.5 ml) was heated under microwave irradiation at 150° C. for 30 minutes. The mixture was cooled down to room temperature, filtered through a path of celite and evaporated to dryness. The residue was partitioned between ethyl acetate and water. The organic phase was dried over magnesium sulfate, filtered and concentrated in vacuo. The residue was purified on silica gel by flash column chromatography to afford the title compound as a white solid (28.4 mg, 53% yield).

$^1$H NMR (CDCl$_3$, 400 MHz) δ 1.79 (6H, s), 7.42 (1H, d), 7.67-7.72 (2H, m), 7.86 (1H, d), 7.95 (1H, s), 8.31 (1H, s), 8.61 (1H, d), 13.85 (1H, br s); MS (ES$^+$) 263.

Table 3 below depicts data for certain exemplary compounds made in general by a similar route to that outlined in Example 2.

TABLE 3

| # | M + 1 (obs) | RT (min) | 1H-NMR |
|---|---|---|---|
| 4 | 263.08 | 2.89 | (DMSO) 1.79 (6H, s), 7.42 (1H, d), 7.67-7.72 (2H, m), 7.86 (1H, d), 7.95 (1H, s), 8.31 (1H, s), 8.61 (1H, d), 13.85 (1H, br s). |
| 5 | 277.1 | 3.06 | (DMSO, 400 MHz) 1.77 (6H, s), 2.48 (3H, s), 7.40 (1H, d), 7.52 (1H, s), 7.66 (1H, d), 7.74 (1H, s), 8.31 (1H, s), 8.60 (1H, d), 13.83 (1H, br s) |
| 6 | | | (DMSO, 400 MHz) 2.05-2.10 (2H, m), 2.18-2.22 (2H, m), 2.90 (2H, t), 3.15-3.18 (2H, m), 7.43 (1H, d), 7.67-7.70 (2H, m), 7.88-7.89 (1H, m), 7.95 (1H, s), 8.31 (1H, s), 8.62 (1H, d), 13.86 (1H, br s). |
| 7 | | | (DMSO, 400 MHz) 1.78 (6H, s), 2.06 (3H, s), 3.27-3.35 (4H, m), 3.62-3.64 (4H, m), 7.23 (1H, s), 7.30 (1H, s), 7.36 (1H, s), 7.41 (1H, d), 8.29 (1H, s), 8.59 (1H, d), 13.82 (1H, br s). |
| 8 | 347.18 | 2.97 | (DMSO, 400 MHz) 1.76 (6H, s), 2.88 (4H, app s), 3.32-3.39 (4H, m), 7.18 (1H, s), 7.24 (1H, s), 7.32 (1H, s), 7.40 (1H, d), 8.26 (1H, s), 8.58 (1H, d), 13.81 (1H, br s). |
| 9 | | | (DMSO, 400 MHz) 1.54-1.59 (2H, m), 1.63-1.68 (4H, m), 1.76 (6H, s), 3.29 (2H, t), 7.18 (1H, s), 7.25 (1H, s), 7.29 (1H, s), 7.39 (1H, d), 8.25 (1H, s), 8.57 (1H, d), 13.80 (1H, br s). |
| 10 | 354.23 | 3.75 | (DMSO, 400 MHz) 1.77 (6H, s), 6.92 (1H, t), 7.20 (1H, d), 7.29-7.38 (5H, m), 7.45 (1H, s), 8.28 (1H, s), 8.59 (1H, t), 13.84 (1H, br s). |
| 11 | 318.21 | 3.05 | (DMSO, 400 MHz) 1.75 (6H, s), 2.35 (2H, t), 3.94 (4H, t), 6.63 (1H, s), 6.74 (1H, s), 7.20 (1H, s), 7.36 (1H, d), 8.26 (1H, s), 8.58 (1H, d), 13.81 (1H, s). |

TABLE 3-continued

| # | M + 1 (obs) | RT (min) | 1H-NMR |
|---|---|---|---|
| 12 | | | (DMSO, 400 MHz) 1.70 (6H, s), 4.39 (2H, d), 6.80 (1H, t), 6.92 (2H, d), 7.05 (1H, s), 7.27 (2H, d), 7.34-7.43 (4H, m), 7.95 (1H, s), 8.53 (1H, d), 13.73 (1H, br s). |
| 13 | 278.1 | 2.31 | (DMSO, 400 MHz) 1.71 (6H, s), 5.56 (2H, br s), 6.88 (1H, s), 7.03 (2H, d), 7.30 (1H, s), 8.26 (1H, s), 8.56 (1H, s), 13.77 (1H, br s). |
| 14 | | | (DMSO, 400 MHz) 1.74 (6H, s), 3.74 (2H, t), 4.13 (2H, t), 4.45-4.51 (1H, m), 6.83-6.87 (2H, m), 7.15 (1H, s), 7.35 (1H, d), 8.26 (1H, s), 8.58 (1H, d), 13.82 (1H, br s). |
| 15 | 369.23 | 3.01 | (DMSO, 400 MHz) 1.77 (6H, s), 5.91 (1H, d), 6.16 (1H, d), 7.23 (1H, t), 7.32-7.38 (3H, m), 7.48 (2H, d), 7.78 (3H, s), 8.16 (1H, s), 8.60 (1H, d), 13.85 (1H, br s). |
| 16 | 367.23 | 3.31 | (DMSO, 400 MHz) 1.85 (6H, s), 7.49 (1H, d), 7.61 (2H, t), 7.73 (1H, t), 7.88 (2H, d), 8.05 (2H, d), 8.25 (1H, s), 8.31 (1H, s), 8.64 (1H, s), 13.98 (1H, br s). |
| 17 | | | (DMSO, 400 MHz) 1.73 (6H, s), 2.78 (2H, t), 3.14 (2H, t), 6.16 (1H, t), 6.86 (1H, s), 6.97 (1H, s), 7.06 (1H, s), 7.34 (1H, d), 8.27 (1H, s), 8.57 (1H, d). |
| 18 | 343 | 3.67 | 1H (DMSO) 1.80 (6H, s), 7.46 (1H, d), 7.89 (1H, s), 7.96 (1H, s), 8.01 (1H, s), 8.30 (1H, s), 8.62 (1H, d), 14.05 (1H, bs). |
| 19 | 335.2 | 2.97 | (DMSO, 400 MHz) 0.85 (3H, d), 0.89 (3H, d), 1.79 (6H, s), 1.89-1.93 (1H, m), 4.48 (1H, d), 5.35 (1H, d), 7.41 (1H, d), 7.62 (1H, s), 7.75 (1H, s), 7.80 (1H, s), 8.27 (1H, s), 8.61 (1H, s), 13.86 (1H, br s). |
| 20 | 361.24 | 2.13 | (DMSO, 400 MHz) 1.28-1.33 (2H, m), 1.72 (6H, s), 1.91 (2H, d), 2.63 (2H, t), 3.00 (2H, d), 3.40-3.44 (1H, m), 6.05 (1H, d), 6.87 (1H, s), 6.96 (1H, s), 7.02 (1H, s), 7.33 (1H, d), 8.24 (1H, s), 8.57 (1H, d), 13.81 (1H, br s) |
| 21 | 335.22 | 2.1 | (DMSO, 400 MHz) 1.65-1.70 (2H, m), 1.73 (6H, s), 2.67 (2H, t), 3.14-3.18 (2H, m), 6.12 (1H, t), 6.85 (1H, s), 6.95 (1H, s), 7.05 (1H, s), 7.34 (1H, d), 8.27 (1H, s), 8.57 (1H, d). |
| 22 | 307.16 | 2.6 | (DMSO, 400 MHz) 1.42 (3H, d), 1.79 (6H, s), 4.91 (1H, d), 5.41 (1H, br s), 7.40 (1H, d), 7.68 (1H, s), 7.79 (2H, s), 8.30 (1H, s), 8.61 (1H, d), 13.85 (1H, br s). |
| 23 | 235.07 | 3.04 | (DMSO) 4.20 (2H, m), 7.39 (1H, m), 7.54 (1H, m), 7.67 (1H, m), 7.87 (2H, m), 8.36 (1H, m), 8.61 (1H, m) |
| 24 | 305.14 | 2.86 | (DMSO, 400 MHz) 1.83 (6H, s), 2.74 (3H, s), 7.46 (1H, d), 8.17 (1H, s), 8.21 (1H, s), 8.34 (1H, s), 8.36 (1H, s), 8.61 (1H, d). |
| 25 | 317 | 2.84 | (400 MHz, DMSO) 2.29 (3H, s), 3.76 (2H, s), 7.36-7.43 (1H, m), 7.66-7.72 (1H, m), 7.79-7.88 (2H, m), 8.32-8.35 (1H, m), 8.57-8.64 (1H, m), 13.86 (1H, brs). |
| 26 | 250.09 | 2.51 | (DMSO, 400 MHz) 2.73 (2H, t), 3.24 (2H, t), 7.45 (1H, d), 7.82 (1H, d), 7.90 (1H, d), 8.07 (1H, d), 8.38 (1H, s), 8.63 (1H, d), 13.89 (1H, s). |
| 27 | 252.05 | 2.26 | (DMSO, 400 MHz) 1.84-1.90 (1H, m), 2.37-2.43 (1H, m), 2.79-2.87 (1H, m), 3.01-3.06 (1H, m), 5.13 (1H, app s), 5.37 (1H, app br s), 7.34 (1H, d), 7.53 (1H, d), 7.69-7.71 (2H, m), 8.31 (1H, s), 8.56 (1H, d), 13.77 (1H, br s). |
| 28 | 250.06 | 2.49 | (DMSO, 400 MHz) 2.72-2.76 (2H, m), 3.19-3.23 (2H, m), 7.43 (1H, d), 7.81 (1H, d), 8.01 (1H, d), 8.18 (1H, d), 8.29 (1H, s), 8.60 (1H, d), 13.87 (1H, br s). |
| 29 | 252.17 | 2.28 | (DMSO, 400 MHz) 1.85-1.88 (1H, m), 2.41-2.44 (1H, m), 2.79-2.85 (1H, m), 2.97-3.00 (1H, m), 5.10-5.13 (1H, m), 5.38-5.40 (1H, m), 7.34 (1H, d), 7.44 (1H, d), 7.72 (1H, d), 7.82 (1H, s), 8.32 (1H, s), 8.57 (1H, d), 13.78 (1H, br s). |
| 30 | 357.1 | 3.79 | 1H (DMSO) 0.92 (3H, t), 1.78 (3H, s), 2.09 (2H, dq), 7.43 (1H, d), 7.83 (1H, s), 7.92 (1H, s), 8.01 (1H, s), 8.25 (1H, s), 8.62 (1H, d), 13.70 (1H, bs). |
| 81 | 421.39 | 3.11 | (DMSO) 1.37 (9H, s), 1.73 (6H, s), 3.13-3.19 (4H, m), 6.87 (1H, s), 6.98 (1H, s), 7.07 (1H, s), 7.36 (1H, d), 8.26 (1H, s), 8.57 (1H, d), 13.79 (1H, s). |
| 82 | 469.39 | 3.18 | (DMSO, 400 MHz) 1.70-1.80 (8H, m), 3.12-3.19 (4H, m), 5.01 (2H, s), 6.11 (1H, t), 6.85 (1H, s), 6.94 (1H, s), 7.06 (1H, s), 7.26-7.39 (7H, m), 8.26 (1H, s), 8.56 (1H, d), 13.79 (1H, br s). |
| 88 | 309 | 3.38 | (d6-DMSO, 400 MHz) 1.66 (1.5H, d), 1.72 (1.5H, d), 1.75 (6H, s), 5.86 (0.5H, q), 5.98 (0.5H, q), 7.45 (1H, d), 7.72 (1H, s), 7.83 (1H, s), 7.93 (1H, s), 8.31 (1H, s), 8.63 (1H, d), 13.88 (1H, brs) |
| 91 | 287.12 | 3.2 | 1H NMR (400.0 MHz, DMSO) d 13.86 (br s, 1H), 8.62 (d, 1H), 8.33 (s, 1H), 7.99 (s, 1H), 7.88 (d, 1H), 7.74-7.66 (m, 2H), 7.42 (d, 1H), 3.11 (s, 3H) and 1.84 (s, 3H) ppm |
| 94 | 317.2 | 3.79 | 1H NMR (400.0 MHz, DMSO) d 0.93 (t, J = 7.2 Hz, 3H), 1.78 (s, 3H), 1.93 (dd, 3H), 2.03-2.12 (m, 2H), 5.95 (dd, J = 7.3, 11.6 Hz, 1H), 6.62 (d, J = 11.7 Hz, 1H), 7.41 (d, J = 4.8 Hz, 1H), 7.57 (s, 1H), 7.72 (s, 1H), 7.78 (s, 1H), 8.26 (s, 1H), 8.61 (d, J = 4.7 Hz, 1H) and 13.86 (bs, 1H) ppm |

TABLE 3-continued

| # | M + 1 (obs) | RT (min) | 1H-NMR |
|---|---|---|---|
| 97 | 331.3 | 3.92 | 1H NMR (400.0 MHz, DMSO) d 0.95 (t, J = 7.3 Hz, 3H), 1.68 (dt, J = 22.4, 7.4 Hz, 2H), 1.91-1.95 (m, 4H), 2.18-2.21 (m, 2H), 2.47-2.51 (m, 2H), 2.73 (t, 2H), 7.39 (d, J = 4.7 Hz, 1H), 7.50 (s, 1H), 7.66 (s, 1H), 7.74 (s, 1H), 8.28 (s, 1H), 8.59 (d, J = 4.9 Hz, 1H) and 13.71 (bs, 1H) ppm. |
| 101 | 321.2 | 3.1 | 1H (DMSO) 0.93 (3H, t), 1.76 (3H, s), 2.06 (2H, dt), 2.90 (2H, t), 3.72 (2H, t), 4.73 (1H, bs, OH), 7.39 (1H, d), 7.49 (1H, s), 7.71 (1H, s), 7.73 (1H, s), 8.28 (1H, s), 8.59 (1H, d). |
| 102 | 337.2 | 3.79 | 1H NMR (400.0 MHz, DMSO) d 0.92 (t, J = 7.3 Hz, 3H), 1.31 (t, J = 7.3 Hz, 3H), 1.77 (s, 3H), 2.03-2.07 (m, 2H), 3.15 (q, J = 7.3 Hz, 2H), 7.40 (d, J = 4.7 Hz, 1H), 7.50 (s, 1H), 7.68 (d, J = 8.4 Hz, 2H), 8.23 (s, 1H), 8.59 (d, J = 4.8 Hz, 1H) and. 13.80 (bs, 1H) ppm. |
| 103 | | | 1H NMR (400.0 MHz, DMSO) d 0.92 (t, J = 7.3 Hz, 3H), 1.76 (s, 3H), 1.77-1.85 (m, 2H), 2.00-2.10 (m, 2H), 2.79 (t, J = 7.6 Hz, 2H), 3.47 (t, J = 6.3 Hz, 2H), 4.21 (bs, 1H, OH), 7.39 (d, J = 4.8 Hz, 1H), 7.47 (s, 1H), 7.67 (s, 1H), 7.72 (s, 1H), 8.27 (s, 1H), 8.59 (d, J = 4.8 Hz, 1H) and 13.75 (bs, 1H, NH) ppm. |
| 112 | 397.2 | 3.84 | 1H NMR (400.0 MHz, DMSO) d 1.71 (s, 9H), 1.79 (s, 6H), 7.33 (d, J = 4.4 Hz, 1H), 7.86 (t, J = 1.7 Hz, 1H), 7.94 (d, J = 1.5 Hz, 1H), 8.00 (d, J = 1.6 Hz, 1H), 8.56 (s, 1H) and 8.69 (d, J = 4.5 Hz, 1H) ppm |
| 216 | 277.21 | 2.86 | (DMSO, 400 MHz) 2.42-2.45 (2H, app s), 2.94 (2H, app s), 3.40 (2H, app s), 6.37 (1H, app s), 7.40 (1H, d), 7.54-7.59 (2H, m), 7.74 (1H, d), 7.81 (1H, s), 8.29 (1H, s), 8.58 (1H, d), 13.83 (1H, br s). |

Example 3

2-(3-(1H-pyrazolo[3,4-b]pyridin-4-yl)phenyl)-2-methylpropan-1-amine (Compound 31)

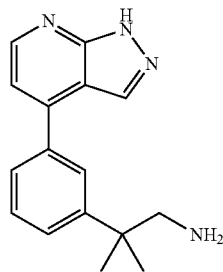 [SMILES: CC(C)(CN)c1cccc(-c2ccnc3[nH]ncc23)c1]

To 2-(3-(1H-pyrazolo[3,4-b]pyridin-4-yl)phenyl)-2-methylpropanenitrile (22 mg, 0.084 mmol) was added slowly a 2 M solution of lithium aluminium hydride (167.70 ml, 0.336 mmol) in tetrahydrofuran (3 ml). The reaction mixture was stirred at room temperature for 18 hours. The reaction mixture was allowed to cool down to room temperature and was partitioned between water and ethyl acetate. The organic phase was dried over magnesium sulfate, filtered and concentrated in vacuo. The residue was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were freeze-dried to give the title compound as a white solid (12 mg, 54% yield).

$^1$H NMR (DMSO-$d_6$, 400 MHz) δ 1.44 (6H, s), 3.19 (2H, d), 7.41 (1H, d), 7.59-7.62 (2H, m), 7.70 (3H, br s), 7.78 (1H, s), 7.85 (1H, s), 8.33 (1H, s), 8.60 (1H, d), 13.81 (1H, br s); MS (ES$^+$) 267, (ES$^-$) 265.

Table 4 below depicts data for certain exemplary compounds made in general by a similar route to that outlined in Example 3.

TABLE 4

| # | M + 1 (obs) | RT (min) | 1H-NMR |
|---|---|---|---|
| 31 | 267 | 2.9 | (d6-DMSO, 400 MHz) 1.44 (6H, s), 3.19 (2H, d), 7.41 (1H, d), 7.59-7.62 (2H, m), 7.70 (3H, brs), 7.78 (1H, s), 7.85 (1H, s), 8.33 (1H, s), 8.60 (1H, d), 13.81 (1H, brs) |
| 32 | 281 | 3.42 | (d6-DMSO, 400 MHz) 1.40 (6H, s), 2.46 (3H, s), 3.17 (2H, d), 7.39 (1H, d), 7.43 (1H, s), 7.58 (1H, s), 7.63-7.67 (4H, m), 8.34 (1H, s), 8.59 (1H, d), 13.80 (1H, brs) |
| 33 | 350 | 3.42 | (d6-DMSO, 400 MHz) 1.42 (6H, s), 1.61 (2H, brs), 1.73 (4H, brs), 3.18 (2H, d), 3.36 (4H, brs), 7.12-7.47 (4H, m), 7.66 (3H, brs), 8.32 (1H, s), 8.59 (1H, d), 13.82 (1H, brs) |
| 34 | 345.1 | 3.23 | 1H (DMSO) 1.28 (6H, d), 3.22 (2H, d), 7.34-7.40 (1H, m), 7.64 (1H, d), 7.79 (1H, s), 7.80 (1H, d), 8.26 (1H, d), 8.53-8.57 (1H, m). |
| 35 | 343.2 | 3.54 | 1H (DMSO) 1.37 (6H, s), 3.30 (2H, d), 7.41 (1H, t), 7.46-7.55 (3H, m), 7.72-7.88 (5H, m), 8.35 (1H, d), 8.57-8.62 (1H, m). |

TABLE 4-continued

| # | M + 1 (obs) | RT (min) | 1H-NMR |
|---|---|---|---|
| 36 | 293.2 | 3.02 | 1H (DMSO) 1.31 (6H, d), 3.26 (2H, d), 5.34 (1H, dd), 5.98 (1H, dd), 6.89 (1H, ddd), 7.41 (1H, d), 7.60 (1H, s), 7.68-7.76 (2H, m), 8.29 (1H, d), 8.55-8.59 (1H, m). |
| 37 | 347.3 | 3.6 | 1H (DMSO) 1.30 (6H, d), 1.59-1.66 (2H, m), 1.73-1.78 (2H, m), 2.18-2.26 (2H, m), 2.44-2.51 (2H, m), 3.23 (2H, d), 6.28 (1H, s), 7.39 (1H, d), 7.51 (1H, s), 7.60 (1H, s), 7.65 (1H, s), 8.26 (1H, d), 8.54-8.58 (1H, m). |
| 38 | 332.2 | 3.09 | 1H (DMSO) 1.33 (6H, d), 3.32-3.36 (2H, m), 6.15 (1H, s), 6.65 (1H, s), 6.91 (1H, s), 7.43 (1H, d), 7.56 (1H, s), 7.73-7.88 (2H, m), 8.32 (1H, d), 8.59 (1H, t), 11.46 (1H, d), 13.78 (1H, bs). |
| 39 | 311.15 | 1.97 | (DMSO, 400 MHz) 1.30 (6H, s), 1.37-1.41 (3H, m), 2.72 (2H, s), 4.82-4.86 (1H, m), 5.28 (1H, s), 7.34-7.38 (1H, s), 7.49 (1H, s), 7.60-7.66 (2H, m), 8.27 (1H, s), 8.54-8.58 (1H, m). |
| 40 | 291.2 | 2.95 | 1H (DMSO) 1.29 (6H, d), 3.24 (2H, d), 4.28 (1H, d), 7.40 (1H, d), 7.58 (1H, d), 7.70 (1H, d), 7.82 (1H, s), 8.28 (1H, d), 8.55-8.59 (1H, m). |
| 41 | 281 | 2.9 | (d6-DMSO, 400 MHz) 0.66 (3H, t), 1.44 (3H, s), 1.64-1.71 (1H, m), 1.83-1.90 (1H, m), 3.07-3.11 (1H, m), 3.29-3.33 (1H, m), 7.42 (1H, d), 7.56-7.65 (5H, m), 7.79 (2H, s), 8.32 (1H, s), 8.61 (1H, d), 13.84 (1H, brs) |
| 42 | 309.2 | 3.38 | 1H (DMSO) 0.95 (3H, t), 1.30 (6H, s), 1.67 (2H, dt), 2.68 (2H, t), 3.24 (2H, d), 7.33 (1H, s), 7.36 (1H, d), 7.48 (1H, s), 7.59 (1H, s), 8.26 (1H, s), 8.56 (1H, d). |
| 43 | 339.22 | 2.2 | (DMSO, 400 MHz) 0.82 (3H, d), 0.89 (3H, d), 1.31 (6H, s), 1.32-1.41 (1H, m), 1.89 (2H, s), 4.38-4.42 (1H, m), 5.21-5.23 (1H, m), 7.34-7.69 (4H, m), 8.25 (1H, s), 8.58 (1H, d), 13.82 (1H, br s). |
| 44 | 295.2 | 3.2 | 1H (DMSO) 1.26 (3H, t), 1.29 (6H, d), 2.72 (2H, q), 3.30 (2H, d), 7.34-7.39 (2H, m), 7.50 (1H, s), 7.59 (1H, s), 8.28 (1H, d), 8.56 (1H, t). |
| 45 | 309.23 | 3.32 | 1H NMR (400.0 MHz, DMSO) d 13.84 (br s, 1H), 8.61 (d, 1H), 8.31 (s, 1H), 7.83 (s, 1H), 7.78 (d, 1H), 7.64-7.60 (m, 4H), 7.41 (d, 1H), 3.32-3.27 (m, 1H), 3.06-3.02 (m, 1H), 1.81 (dd, 1H), 1.59-1.45 (m, 5H), 0.82 (d, 3H) and 0.51 (d, 3H) ppm |
| 46 | 321.23 | 3.35 | 1H NMR (400.0 MHz, DMSO) d 13.84 (br s, 1H), 8.61 (d, 1H), 8.31 (s, 1H), 7.81-7.78 (m, 2H), 7.64-7.57 (m, 4H), 7.42 (d, 1H), 3.09-3.04 (m, 1H), 2.50 (masked signal, 1H), 2.33-2.23 (m, 1H), 1.68-1.65 (m, 1H), 1.52-1.43 (m, 7H) and 1.39-1.14 (m, 3H) ppm |
| 47 | 295.17 | 3.1 | 1H NMR (400.0 MHz, DMSO) d 13.84 (br s, 1H), 8.60 (d, 1H), 8.30 (s, 1H), 7.78 (s, 2H), 7.65-7.56 (m, 4H), 7.42 (d, 1H), 3.25 (partially masked signal, 2H), 1.85-1.81 (m, 4H) and 0.70 (t, 6H) ppm |
| 48 | 295.21 | 3.09 | 1H NMR (400.0 MHz, DMSO) d 13.84 (br s, 1H), 8.61 (d, 1H), 8.31 (s, 1H), 7.79 (d, 1H), 7.65-7.52 (m, 5H), 7.42 (s, 1H), 3.21-3.09 (m, 2H), 2.10-2.07 (m, 1H), 1.38 (s, 3H), 0.90 (d, 3H) and 0.60 (d, 3H) ppm |
| 49 | 279.21 | 2.9 | 1H NMR (400.0 MHz, DMSO) d 13.82 (s, 1H), 8.61-8.58 (d, 1H), 8.35 (s, 1H), 7.78 (d, 1 H), 7.69-7.60 (m, 5H), 7.42-7.38 (m, 2H), 3.32 (d, 2H), 2.45-2.34 (m, 4H), 2.19-2.08 (m, 1H) and 1.88-1.80 (m, 1H) ppm |
| 50 | 293.2 | 3.09 | 1H NMR (400.0 MHz, DMSO) d 13.83 (s, 1H), 8.61 (d, 1H), 8.34 (s, 1H), 7.79 (d, 2H), 7.63-7.55 (m, 4H), 7.42 (d, 1H), 3.15-3.13 (m, 2H), 2.09-1.98 (m, 4H) and 1.77-1.66 (m, 4H) ppm |
| 51 | 295.22 | 3.17 | 1H NMR (400.0 MHz, DMSO) d 13.84 (br s, 1H), 8.61 (d, 1H), 8.31 (s, 1H), 7.79-7.77 (m, 2H), 7.65-7.56 (m, 4H), 7.41 (d, 1H), 3.33-3.28 (m, 1H), 3.11-3.08 (m, 1H), 1.80 (td, 1H), 1.61 (td, 1H), 1.45 (s, 3H), 1.22-1.14 (m, 1H), 0.93-0.88 (m, 1H) and 0.83-0.80 (m, 3H) ppm |
| 52 | 307.2 | 3.23 | 1H (DMSO) 1.29 (6H, d), 3.23 (2H, d), 3.51 (2H, d), 5.09 (1H, d), 5.17 (1H, d), 6.00-6.09 (1H, m), 7.32-7.37 (2H, m), 7.48 (1H, d), 7.62 (1H, s), 8.26 (1H, d), 8.53-8.58 (1H, m), 13.80 (1H, bs). |
| 129 | 307.16 | 3.72 | 1H NMR (400.0 MHz, DMSO) d 13.83 (br s, 1H), 8.60 (d, 1H), 8.31 (s, 1H), 7.83 (s, 1H), 7.78 (t, 1H), 7.66-7.61 (m, 4H), 7.41 (d, 1H), 3.43-3.39 (m, 1H), 3.16-3.10 (m, 1H), 1.86 (dd, 1H), 1.55 (s, 3H), 1.47 (dd, 1H), 0.42-0.34 (m, 2H), 0.30-0.23 (m, 1H), 0.06-0.02 (m, 1H) and −0.13 (m, 1H) ppm |
| 130 | 323 | 3.27 | (d6-DMSO, 400 MHz) 0.57 (3H, t), 0.88 (3H, t), 1.34 (3H, s), 1.52-1.66 (3H, m), 1.73-1.80 (1H, m), 2.63 (2H, t), 2.97-3.01 (1H, m), 3.19-3.24 (1H, m), 7.29 (1H, s), 7.32 (1H, d), 7.51-7.55 (5H, m), 8.22 (1H, s), 8.51 (1H, d), 13.74 (1H, brs) |
| 131 | 309 | 3.07 | (d6-DMSO, 400 MHz) 0.66 (3H, t), 1.29 (3H, t), 1.42 (3H, s), 1.63-1.69 (1H, m), 1.84-1.91 (1H, m), 2.76 (2H, q), 3.05-3.10 (1H, m), 3.28-3.37 (1H, m), 7.39-7.41 (1H, m), 7.60 (5H, brm), 8.31 (1H, s), 8.59 (1H, d), 13.82 (1H, brs) |

TABLE 4-continued

| # | M + 1 (obs) | RT (min) | 1H-NMR |
|---|---|---|---|
| 132 | 295.22 | 2.17 | (DMSO, 400 MHz) 0.57 (3H, t), 0.83 (6H, s), 2.19 (2H, q), 2.60 (2H, s), 6.58 (1H, d), 6.76 (1H, d), 6.96-7.00 (2H, m), 7.50 (1H, s), 7.77 (1H, s). |
| 133 | 315.1 | 3.05 | 1H NMR (400.0 MHz, DMSO) d 0.68 (t, J = 7.2 Hz, 3H), 1.30 (s, 3H), 1.57 (dt, J = 21.1, 7.0 Hz, 1H), 1.83 (dd, J = 7.2, 13.9 Hz, 1H), 2.68 (d, J = 12.9 Hz, 1H), 2.87 (d, J = 12.9 Hz, 1H), 3.34 (s, 2H), 7.42 (d, J = 4.6 Hz, 1H), 7.49 (s, 1H), 7.70 (s, 2H), 8.25 (s, 1H) and 8.60 (d, J = 4.6 Hz, 1H) ppm |
| 134 | 293.15 | 2.84 | 1H NMR (400.0 MHz, DMSO) d 8.58-8.55 (m, 1H), 8.31-8.27 (m, 1H), 7.77 (s, 1H), 7.68 (d, 1H), 7.56-7.50 (m, 2H), 7.37 (d, 1H), 5.62-5.55 (m, 1H), 5.05-4.92 (m, 2H), 2.85 (d, 1H), 2.71 (d, 1H), 2.59 (m, 1H), 2.36 (m, 1H) and 1.31 (s, 3H) ppm |
| 135 | 291.15 | 2.63 | 1H NMR (400.0 MHz, DMSO) d 8.58 (m, 1H), 8.33 (s, 1H), 7.83 (s, 1H), 7.70-7.69 (m, 1H), 7.55-7.52 (m, 2H), 7.38 (d, 1H), 2.88-2.84 (m, 1H), 2.79-2.73 (m, 3H), 2.58 (dd, 1H) and 1.42 (s, 3H) ppm |
| 136 | 313.1 | 2.79 | 1H (DMSO) 1.32 (6H, s), 1.62-1.66 (1.5H, m), 1.68-1.72 (1.5H, m), 3.26 (2H, d), 5.77-5.82 (0.5H, m), 5.89-5.94 (0.5H, m), 7.40 (1H, d), 7.53 (1H, s), 7.66 (1H, s), 7.77 (1H, s), 8.29 (1H, d), 8.57-8.61 (1H, m). |
| 137 | 337.2 | 3.5 | 1H (DMSO) 0.63-0.70 (3H, m), 0.92 (6H, d), 1.29 (3H, s), 1.52-1.58 (1H, m), 1.78-1.94 (2H, m), 2.59 (2H, d), 3.33 (2H, d, hidden under water peak), 7.24 (1H, s), 7.36 (1H, d), 7.45 (1H, s), 7.56 (1H, s), 8.25 (1H, d), 8.55-5.58 (1H, m). |
| 139 | 349 | 3.38 | (400 MHz, DMSO) 0.69 (3h, t), 1.34 (3H, s), 1.54-1.67 (1H, m), 1.82-1.95 (1H, m), 2.67-2.74 (1H, m), 2.85-2.93 (1H, m), 7.44-7.53 (1H, m), 7.72-7.77 (1H, m), 7.90-7.98 (1H, m), 8.03-8.09 (1H, m), 8.25 (1H, s), 8.59-8.70 (1H, m). |
| 140 | 347 | 3.2 | (400 MHz, DMSO) 1.76-1.89 (1H, m), 1.99-2.13 (1H, m), 2.21-2.35 (4H, m), 2.90 (2H, s), 7.44-7.49 (1H, m), 7.51-7.55 (1H, m), 7.78-7.82 (1H, m), 7.90-7.94 (1H, m), 8.27 (1H, s), 8.60-8.64 (1H, m). |
| 142 | 297 | 2.63 | (400 MHz, DMSO) 1.29 (6H, s), 2.72 (2H, s), 3.87 (3H, s), 7.00-7.06 (1H, m), 7.15-7.20 (1H, m), 7.33-7.41 (2H, m), 8.26-8.30 (1H, m), 8.55-8.60 (1H, m). |
| 143 | 321.2 | 3.22 | 1H NMR (400.0 MHz, DMSO) d 0.68 (t, 3H), 1.31 (s, 3H), 1.55-1.61 (m, 1H), 1.78-1.86 (m, 1H), 1.94 (dd, J = 1.5, 7.1 Hz, 3H), 2.68 (d, J = 12.8 Hz, 1H), 2.85 (d, J = 12.8 Hz, 1H), 5.83-5.90 (m, 1H), 6.56-6.61 (m, 1H), 7.37-7.39 (m, 2H), 7.56 (s, 1H), 7.62 (s, 1H), 8.26 (d, 1H) and 8.57 (dd, J = 4.8, 8.7 Hz, 1H) ppm |
| 144 | 295 | 2.92 | (400 MHz, DMSO) 0.68 (3H, t), 1.29 (3H, s), 1.49-1.63 (1H, m), 1.74-1.87 (1H, m), 2.44 (3H, s), 2.63-2.69 (1H, m), 2.80-2.88 (1H, m), 7.25-7.38 (2H, m), 7.44-7.55 (2H, m), 8.26 (1H, s), 8.53-8.60 (1H, m), 13.70 (1H, vbrs). |
| 145 | 293 | 2.87 | (400 MHz, DMSO) 1.74-1.86 (1H, m), 1.95-2.10 (1H, m), 2.17-2.32 (4H, m), 2.43 (3H, s), 2.83 (2H, s), 7.02-7.10 (1H, m), 7.28-7.37 (2H, m), 7.43-7.49 (1H, m), 8.28 (1H, s), 8.53-8.60 (1H, m), 13.80 (1H, vbrs). |
| 146 | 311.17 | 2.52 | 1H NMR (400.0 MHz, DMSO) d 13.80 (br s, 1H), 8.59-8.57 (m, 1H), 8.29 (d, 1H), 7.77 (s, 1H), 7.69 (d, 1H), 7.57-7.49 (m, 2H), 7.40-7.38 (m, 1H), 3.35-3.20 (masked signal, 2H), 3.13-3.07 (m, 5H), 2.82 (d, 1H), 2.69 (d, 1H), 2.10-2.03 (m, 1H), 1.89-1.82 (m, 1H) and 1.34 (s, 3H) ppm |
| 147 | 335.2 | 3.43 | 1H (DMSO) 0.95 (3H, t), 1.59-1.72 (6H, m), 1.73-1.85 (2H, m), 2.01-2.09 (2H, m), 2.64-2.71 (2H, m), 3.28-3.39 (2H, m, hidden by water peak), 7.24 (1H, s), 7.36 (1H, d), 7.48 (1H, s), 7.51 (1H, s), 8.27 (1H, d), 8.53-8.57 (1H, m) and 13.75 (1H, bs). |
| 148 | 317.08 | 2.8 | (DMSO) 1.44 (s, 3H), 2.33-2.19 (m, 1H), 2.54-2.41 (masked signal, 1H), 2.80 (d, 1H), 2.88 (d, 1H), 3.32 (masked signal, 2H), 6.07-5.77 (m, 1H), 7.39 (d, 1H), 7.57 (d, 2H), 7.73-7.72 (m, 1H), 7.81 (s, 1H), 8.31-8.28 (m, 1H), 8.59 (d, 1H), 13.79 (brs, 1H). |
| 149 | 343.17 | 3.2 | (DMSO) 1.28 (s, 3H), 2.08 (s, 2H), 2.79 (d, 1H), 2.93 (d, 1H), 3.06-3.00 (m, 2H), 3.17 (d, 1H), 6.87-6.81 (m, 2H), 7.14-7.12 (m, 3H), 7.32 (d, 1H), 7.57-7.50 (m, 2H), 7.70-7.64 (m, 2H), 8.03 (s, 1H), 8.57 (d, 1H), 13.77 (br s, 1H). |
| 150 | 297.17 | 2.65 | (DMSO) 1.32 (s, 3H), 2.85 (q, 2H), 3.27 (s, 3H), 3.32 (masked signal, 2H), 3.53 (d, 1H), 3.63 (d, 1H), 7.37 (d, 1H), 7.53 (d, 2H), 7.69-7.68 (m, 1H), 7.82 (s, 1H), 8.28 (s, 1H), 8.58 (d, 1H), 13.81 (br s, 1H). |
| 153 | 265.2 | 2.54 | 1H NMR (400.0 MHz, DMSO) d 0.80-0.92 (m, 4H), 3.29 (d, J = 6.0 Hz, 2H), 7.37 (t, J = 4.5 Hz, 1H), 7.44-7.53 (m, 2H), |

TABLE 4-continued

| # | M + 1 (obs) | RT (min) | 1H-NMR |
|---|---|---|---|
| | | | 7.68 (d, J = 7.5 Hz, 1H), 7.78 (d, J = 6.3 Hz, 1H), 8.32 (d, J = 4.2 Hz, 1H), 8.57 (dd, J = 2.2, 4.7 Hz, 1H) and 13.75 (bs, 1H) ppm |
| 154 | 321.24 | 3.34 | 1H NMR (400.0 MHz, DMSO) d 1.29 (d, 3H), 1.52 (d, 3H), 1.59 (d, 3H), 2.28-2.33 (m, 1H), 2.48-2.51 (masked signal, 1H), 2.70 (d, 1H), 2.85 (d, 1H), 3.35 (masked signal, 2H), 4.93-4.95 (m, 1H), 7.36-7.38 (m, 1H), 7.49-7.55 (m, 2H), 7.67 (d, 1H), 7.75 (s, 1H), 8.26 (d, 1H), 8.56-8.58 (m, 1H) and 13.80 (br s, 1H) ppm |
| 155 | 305.18 | 2.92 | 1H NMR (400.0 MHz, DMSO) d 1.39 (s, 3H), 1.70 (s, 3H), 2.50-2.55 (masked signal, 1H), 2.64-2.68 (m, 1H), 2.76 (d, 1H), 2.85 (d, 1H), 7.38 (d, 1H), 7.54 (d, 2H), 7.68-7.70 (m, 1H), 7.83 (s, 1H), 8.32 (s, 1H), 8.59 (d, 1H) and 13.77 (br s, 1H) ppm |
| 156 | 339.3 | 2.08 | 1H NMR (400.0 MHz, DMSO) d 0.68 (t, 3H), 1.29 (s, 3H), 1.77-1.81 (m, 4H), 2.66 (d, 1H), 2.74 (t, 2H), 2.83 (d, 1H), 3.46 (t, 2H), 4.52 (bs, 1H, OH), 7.29 (s, 1H), 7.37 (d, 1H), 7.49 (s, 1H), 7.55 (s, 1H), 8.25 (d, 1H), 8.57 (d, 1H) and 13.80 (bs, 1H, NH) ppm. |
| 157 | 309.13 | 1.92 | 1H NMR (400.0 MHz, DMSO) d 1.85-1.91 (m, 2H), 2.09-2.15 (t, 2H), 2.74 (s, 2H), 3.25-3.48 (masked signal, 4H), 3.69-3.74 (m, 2H), 7.40 (d, 1H), 7.50-7.52 (m, 1H), 7.56-7.60 (m, 1H), 7.69-7.76 (m, 2H), 8.27 (s, 1H), 8.58 (d, 1H) and 13.79 (br s, 1H) ppm |
| 158 | 341 | 2.35 | 400 MHz, DMSO, 0.58-0.73 (3H, m), 0.92-1.02 (3H, m), 1.20-1.37 (3H, m), 1.52-2.08 (4H, m), 2.81-3.17 (2H, m), 5.52-5.73 (1H, m), 7.23-7.49 (3H, m), 7.60-7.77 (2H, m), 7.84-7.91 (1H, m), 8.21-8.27 (1H, m), 8.53-8.61 (1H, m). |
| 159 | 327 | 2.24 | 400 MHz, DMSO, 0.61-0.72 (3H, m), 1.26-1.36 (3H, m), 1.53-1.88 5H, m), 2.90-3.30 (2H, m), 5.73-5.97 (1H, m), 7.22-7.52 (3H, m), 7.62-7.77 (2H, m), 7.84-7.90 (1H, m), 8.24-8.28 (1H, m), 8.53-8.61 (1H, m). |
| 160 | 341.2 | 2.34 | 1H NMR (400.0 MHz, DMSO) d 0.69 (t, 3H), 1.29 (s, 3H), 1.57 (dd, J = 7.3, 13.8 Hz, 1H), 1.82 (dd, J = 7.4, 13.8 Hz, 1H), 1.99-2.09 (m, 2H), 2.66 (d, J = 12.8 Hz, 1H), 2.77-2.85 (m, 3H), 4.44 (t, J = 5.9 Hz, 1H), 4.56 (t, J = 5.9 Hz, 1H), 7.32 (s, 1H), 7.38 (d, J = 4.7 Hz, 1H), 7.52 (d, J = 6.7 Hz, 1H), 7.57 (s, 1H), 8.28 (d, J = 11.0 Hz, 1H), 8.52-8.58 (m, 1H) and 13.80 (bs, 1H) ppm |
| 161 | 359.2 | 2.4 | 1H (DMSO) 0.63-0.71 (3H, m), 1.28 (3H, d), 1.53-1.60 (1H, m), 1.77-1.86 (1H, m), 2.19-2.28 (2H, m), 2.82-2.87 (2H, m), 3.30-3.40 (2H, m, hidden under water peak), 5.98-6.30 (1H, m), 7.35 (1H, s), 7.36-7.40 (1H, m), 7.55 (1H, d), 7.58 (1H, s), 8.29 (1H, d), 8.54-8.58 (1H, m). |
| 162 | 331 | 2.23 | (400 MHz, DMSO) 0.64-0.73 (3H, m), 1.33 (3H, s), 1.54-1.67 (1H, m), 1.79-1.93 (1H, m), 2.66-2.91 (2H, m), 6.99-7.33 (1H, t), 7.41-7.46 (1H, m), 7.63-7.69 (1H, m), 7.82-7.94 (2H, m), 8.28 (1H, s), 8.60-8.63 (1H, m). |
| 163 | 363.3 | 3.09 | 1H NMR (400.0 MHz, DMSO) d 0.68 (t, J = 7.4 Hz, 3H), 1.30 (d, J = 4.5 Hz, 3H), 1.57-1.61 (m, 1H), 1.79 (s, 1H), 2.67 (d, J = 12.9 Hz, 1H), 2.84 (d, J = 12.8 Hz, 1H), 3.82 (d, J = 11.6 Hz, 2H), 7.38-7.40 (m, 1H), 7.47 (s, 1H), 7.70-7.73 (m, 2H), 8.29 (d, J = 10.4 Hz, 1H), 8.59 (dd, J = 4.8, 7.9 Hz, 1H) and 13.80 (bs, 1H) ppm |
| 164 | 353.3 | 2.97 | 1H NMR (400.0 MHz, DMSO) d 0.68 (t, 3H), 1.29 (s, 3H), 1.55-1.59 (m, 1H), 1.81-1.89 (m, 3H), 2.65 (d, 1H), 2.72-2.76 (m, 2H), 2.83 (d, 1H), 3.25 (s, 3H), 3.31-3.37 (m, 2H), 7.29 (s, 1H), 7.37 (d, 1H), 7.49 (d, 1H), 7.56 (s, 1H), 8.27 (d, 1H) and 8.56 (dd, 1H) ppm |
| 165 | 345 | 2.36 | (400 MHz, DMSO) 0.64-0.73 (3H, m), 1.33 (3H, s), 1.54-1.66 (1H, m), 1.80-1.93 (1H, m), 1.93-2.15 (3H, m), 2.65-2.74 (1H, m), 2.84-2.91 (1H, m), 7.43-7.47 (1H, m), 7.59-7.62 (1H, m), 7.77-7.80 (1H, m), 7.86-7.89 (1H, m), 8.26 (1H, s), 8.59-8.63 (1H, m). |
| 166 | 341.3 | 3.23 | 1H (DMSO) 0.69 (3H, t), 1.23-1.31 (6H, m), 1.56 (1H, dt), 1.81 (1H, dt), 2.66 (1H, d), 2.83 (1H, d), 3.08 (2H, dq), 7.34 (1H, t), 7.39 (1H, d), 7.51-7.54 (2H, m), 8.24 (1H, d), 8.56-8.59 (1H, m). |
| 167 | 359.2 | 3.1 | 1H (DMSO) 0.68 (3H, t), 1.29 (3H, s), 1.57 (1H, dt), 1.81 (1H, dt), 2.66 (1H, d), 2.84 (1H, d), 7.41 (1H, d), 7.62 (1H, t), 7.74 (1H, t), 7.81 (1H, t), 8.27 (1H, d), 8.60 (1H, d). |
| 168 | 325.1 | 2.55 | 1H (DMSO) 0.69 (3H, t), 1.29 (3H, s), 1.56 (1H, dq), 1.81 (1H, dq), 2.65 (1H, d), 2.82 (1H, d), 2.81-2.87 (2H, m), 3.69 (2H, t), 4.70 (1H, bs, OH), 7.32 (1H, s), 7.36 (1H, d), 7.54 (1H, s), 7.56 (1H, s), 8.27 (1H, d), 8.57 (1H, d), 13.80 (1H, bs, NH). |
| 169 | 325.26 | 2.63 | 1H NMR (400.0 MHz, DMSO) d 8.59-8.57 (m, 1H), 8.29 (s, 1H), 7.76 (s, 1H), 7.68 (d, 1H), 7.59-7.52 (m, 1H), 7.47 (d, |

TABLE 4-continued

| # | M + 1 (obs) | RT (min) | 1H-NMR |
|---|---|---|---|
| | | | 1H), 7.39-7.37 (m, 1H), 3.25-3.21 (m, 3H), 3.16-3.14 (m, 4H), 2.84 (d, 1H), 2.68 (d, 1H), 1.88-1.81 (m, 1H), 1.59-1.52 (m, 1H), 1.42-1.32 (m, 4H) and 1.22-1.11 (m, 1H) ppm |
| 170 | 350.22 | 2.57 | 1H NMR (400.0 MHz, DMSO) d 13.84 (br s, 1H), 8.94 (m, 1H), 8.58-8.55 (m, 1H), 8.24 (s, 1H), 7.79-7.78 (m, 1H), 7.68-7.64 (m, 1H), 7.55-7.47 (m, 2H), 7.35 (d, 1H), 7.06-7.05 (m, 1H), 3.43-3.15 (masked signals, 4H), 2.88 (d, 1H), 2.78 (d, 1H) and 1.34 (s, 3H) ppm |
| 171 | 344.06 | 2.42 | 1H NMR (400.0 MHz, DMSO) d 1.27 (s, 3H), 2.78 (d, 1H), 2.89-3.07 (m, 3H), 3.35 (masked signal, 2H), 7.12-7.25 (m, 2H), 7.34 (d, 1H), 7.45-7.57 (m, 2H), 7.66-7.71 (m, 2H), 8.00-8.12 (m, 2H), 8.29-8.32 (m, 1H), 8.55-8.58 (m, 1H) and 13.82 (br s, 1H) ppm |
| 172 | 344.12 | 2.48 | 1H NMR (400.0 MHz, DMSO) d 13.74 (br s, 1H), 8.57 (d, 1H), 8.31-8.28 (m, 2H), 8.10 (s, 1H), 7.71-7.69 (m, 2H), 7.57-7.47 (m, 2H), 7.35-7.34 (m, 1H), 6.87-6.85 (m, 2H), 3.07 (d, 1H), 2.97 (t, 2H), 2.78 (d, 1H) and 1.28 (s, 3H) ppm |
| 173 | 373.19 | 2.33 | 1H NMR (400.0 MHz, DMSO) d 13.75 (br s, 1H), 8.57-8.55 (m, 1H), 8.03 (s, 1H), 7.70-7.64 (m, 2H), 7.58-7.50 (m, 2H), 7.33-7.32 (m, 1H), 7.06 (t, 1H), 6.67 (dd, 1H), 6.49 (d, 1H), 6.28 (s, 1H), 3.50 (s, 3H), 3.05-2.97 (m, 2H), 2.89-2.76 (m, 2H) and 1.28 (s, 3H) ppm |
| 174 | 373.19 | 2.34 | 1H NMR (400.0 MHz, DMSO) d 1.26 (s, 3H), 2.73-3.02 (m, 4H), 3.65 (s, 3H), 6.68-6.72 (m, 2H), 6.74-6.78 (m, 2H), 7.32-7.34 (m, 1H), 7.49-7.57 (m, 2H), 7.63-7.69 (m, 2H), 8.04 (s, 1H), 8.55-8.57 (m, 1H) and 13.83 (br s, 1H) ppm |
| 175 | 344.06 | 2.62 | 1H NMR (400.0 MHz, DMSO) d 1.32 (s, 3H), 2.81 (d, 1H), 2.89 (d, 1H), 3.16-3.17 (m, 2H), 3.35 (masked signal, 2H), 6.88 (d, 1H), 7.11-7.16 (m, 1H), 7.34 (d, 1H), 7.47-7.56 (m, 3H), 7.64-7.68 (m, 1H), 7.77 (s, 1H), 8.20 (s, 1H), 8.41-8.45 (m, 1H) and 8.57 (d, 1H) ppm |
| 176 | 317 | 2.14 | (400 MHz, DMSO) 2.75-2.89 (2H, m), 3.17-3.25 (2H, m), 7.23-7.39 (1H, m), 7.54-7.61 (1H, m), 7.66-7.74 (1H, m), 7.78-7.89 (1H, m), 8.31 (1H, s), 8.52-8.59 (1H, m). |
| 177 | 307.04 | 3.04 | (DMSO) 1.36-1.27 (m, 3H), 1.61-1.47 (m, 5H), 2.18-2.15 (m, 2H), 2.61 (s, 2H), 3.10 (d, 2H), 7.38-7.36 (m, 1H), 7.58-7.50 (m, 2H), 7.69-7.65 (m, 1H), 7.77 (s, 1H), 8.29-8.26 (m, 1H), 8.59-8.56 (m, 1H). |
| 178 | 305.02 | 2.87 | 1H NMR (400.0 MHz, DMSO) d 0.69 (t, 3H), 1.79-1.85 (m, 2H), 2.68-2.83 (m, 3H), 2.93 (s, 2H), 7.39 (d, 1H), 7.50-7.58 (m, 2H), 7.70-7.72 (m, 1H), 7.78 (s, 1H), 8.30 (s, 1H), 8.59 (d, 1H) and 13.81 (br s, 1H) ppm |
| 179 | 351.1 | 2.59 | 1H NMR (400.0 MHz, DMSO) d 0.90-1.07 (m, 2H), 1.13-1.21 (m, 1H), 1.38-1.54 (m, 6H), 1.74-1.82 (m, 1H), 2.63 (d, 1H), 2.82 (d, 1H), 3.01-3.08 (m, 1H), 3.11-3.21 (m, 2H), 3.31-3.36 (masked signal, 2H), 3.56-3.59 (m, 1H), 3.68-3.71 (m, 1H), 7.38 (d, 1H), 7.51-7.55 (m, 2H), 7.68 (d, 1H), 7.77 (s, 1H), 8.27 (s, 1H) and 8.58 (d, 1 H) ppm |
| 180 | 441 | 3 | 1H NMR (400.0 MHz, DMSO) d 13.80 (s, 1H), 8.61 (d, J = 4.7 Hz, 1H), 8.22 (s, 1H), 7.86 (s, 1H), 7.74 (s, 1H), 7.54 (s, 1H), 7.44 (d, J = 4.7 Hz, 1H), 2.85 (d, 1H), 2.71 (d, 1H), 2.40-2.23 (m, 2H), 1.93-1.78 (m, 1H), 1.73-1.52 (m, 6H), 1.39-1.03 (m, 9H), 0.95-0.76 (m, 2H) and 0.68 (t, J = 7.3 Hz, 3H) ppm |
| 181 | 343.08 | 2.92 | 1H NMR (400.0 MHz, DMSO) d 1.64-1.72 (m, 2H), 1.84 (t, 2H), 2.00-2.08 (m, 2H), 2.30-2.34 (m, 2H), 2.66 (s, 2H), 7.38-7.41 (m, 1H), 7.57-7.62 (m, 2H), 7.74 (d, 1H), 7.82 (s, 1H), 8.27 (s, 1H), 8.57-8.59 (m, 1H) and 13.78 (br s, 1H) ppm |
| 182 | 323.05 | 2.05 | 1H NMR (400.0 MHz, DMSO) d 1.10-1.18 (m, 2H), 1.43-1.55 (m, 2H), 1.71 (br s, 2H), 2.33 (t, 2H), 2.54 (s, 2H), 3.05 (d, 1H), 3.47 (s, 1H), 4.36 (s, 1H), 7.37 (t, 1H), 7.52-7.60 (m, 2H), 7.69 (t, 1H), 7.78 (s, 1H), 8.27 (d, 1H), 8.58-8.60 (m, 1H) and 13.79 (br s, 1H) ppm |
| 183 | 323.05 | 2.34 | 1H NMR (400.0 MHz, DMSO) d 8.58-8.56 (m, 1H), 8.27 (d, 1H), 7.78 (s, 1H), 7.69-7.67 (m, 1H), 7.57-7.52 (m, 2H), 7.37-7.35 (m, 1H), 4.43 (s, 1H), 3.57 (s, 1H), 3.32-3.20 (masked signal, 2H), 2.71 (s, 2H), 2.07-2.01 (m, 2H), 1.82-1.80 (m, 2H) and 1.51 (m, 4H) ppm |
| 184 | 323.05 | 2.8 | 1H NMR (400.0 MHz, DMSO) d 13.82 (br s, 1H), 8.58 (d, 1H), 8.25 (s, 1H), 7.79 (s, 1H), 7.70 (m, 1H), 7.56-7.52 (m, 2H), 7.38 (d, 1H), 5.33 (d, 1H), 2.83 (d, 1H), 2.71 (d, 1H), 2.69-2.67 (d, 1H), 2.36-2.33 (m, 1H), 2.20-2.09 (m, 2H), 2.05-1.98 (m, 1H) and 1.87-1.76 (m, 1H) ppm |
| 185 | 305.1 | 2.8 | 1H (DMSO) 1.38 (3H, s), 1.71 (3H, s), 2.55-2.68 (2H, m), 2.77 (1H, d), 2.84 (1H, d), 7.37 (1H, s), 7.53 (2H, bs), 7.68 (1H, s), 7.83 (1H, s), 8.32 (1H, d), 8.57 (1H, s). |

TABLE 4-continued

| # | M + 1 (obs) | RT (min) | 1H-NMR |
|---|---|---|---|
| 186 | 305 | 2.8 | 1H (DMSO) 1.38 (3H, s), 1.71 (3H, s), 2.53-2.68 (2H, m), 2.77 (1H, d), 2.85 (1H, d), 7.38 (1H, t), 7.53-7.56 (2H, m), 7.68 (1H, d), 7.83 (1H, s), 8.33 (1H, d), 8.58 (1H, d), 13.82 (1H, bs, NH). |
| 187 | 335 | 2.54 | 1H NMR (400.0 MHz, DMSO) d 8.56 (m, 1H), 8.23 (d, J = 8.2 Hz, 1H), 7.45 (s, 1H), 7.39-7.30 (m, 2H), 7.13-7.04 (m, 1H), 3.14-2.80 (m, 2H), 2.69-2.65 (m, 2H), 2.41-1.56 (m, 10H) and 0.94 (t, J = 7.2 Hz, 3H) ppm |
| 188 | 297.05 | 2.87 | 1H NMR (400.0 MHz, DMSO) d 1.49 (br s, 2H), 1.82 (m, 1H), 1.99-2.06 (m, 1H), 2.20-2.31 (m, 4H), 2.87 (s, 2H), 7.07 (d, 1H), 7.37 (s, 1H), 7.40 (d, 1H), 7.48 (d, 1H), 8.30 (s, 1H) and 8.59 (d, 1H) ppm |
| 189 | 307.1 | 3.04 | 1H (DMSO) 1.55-1.85 (6H, m), 1.97-2.06 (2H, m), 2.42 (3H, s), 3.16 (2H, d), 7.24 (1H, s), 7.35 (1H, d), 7.48 (1H, s), 7.49 (1H, s), 8.29 (1H, d), 8.55 (1H, d), 13.75 (1H, bs, NH). |
| 190 | 294.07 | 2.35 | 1H NMR (400.0 MHz, DMSO) d 1.79-1.86 (m, 1H), 2.04-2.15 (m, 1H), 2.28-2.40 (m, 4H), 3.24 (d, 2H), 6.71 (s, 1H), 6.98 (s, 1H), 7.15 (s, 1H), 7.33 (d, 1H), 7.69 (br s, 3H), 8.33 (s, 1H), 8.57 (d, 1H) and 13.84 (br s, 1H) ppm |
| 232 | 267.06 | 2.59 | 1H NMR (400.0 MHz, DMSO) d 0.79 (t, 3H), 1.52-1.63 (m, 1H), 1.76-1.86 (m, 1H), 2.51-2.62 (m, 1H), 2.76-2.85 (m, 2H), 7.35-7.38 (m, 2H), 7.53 (t, 1H), 7.66 (s, 1H), 7.69-7.71 (m, 1H), 8.29 (s, 1H) and 8.58 (d, 1H) ppm |
| 234 | 319.09 | 2.26 | (DMSO, 400 MHz) 1.30 (3H, s), 1.72 (3H, s), 2.40-2.70 (2H, m), 2.44 (3H, s), 2.75 (1H, d), 2.85 (1H, d), 7.35-7.36 (2H, m), 7.49 (1H, s), 7.62 (1H, s), 8.32 (1H, s), 8.57 (1H, d), 13.80 (1H, br s). |
| 235 | 315.1 | 2.82 | 1H NMR (400.0 MHz, DMSO) d 2.82-2.84 (m, 2H), 2.87-3.06 (m, 4H), 7.37-7.41 (m, 2H), 7.55-7.60 (m, 1H), 7.65 (d, J = 1.5 Hz, 1H), 7.71-7.76 (m, 1H), 8.31-8.34 (m, 1H), 8.57-8.60 (m, 1H) and 13.81 (bs, 1H, NH) ppm |
| 236 | 294.07 | 2.35 | 1H NMR (400.0 MHz, DMSO) d 1.79-1.86 (m, 1H), 2.04-2.15 (m, 1H), 2.28-2.40 (m, 4H), 3.24 (d, 2H), 6.71 (s, 1H), 6.98 (s, 1H), 7.15 (s, 1H), 7.33 (d, 1H), 7.69 (br s, 3H), 8.33 (s, 1H), 8.57 (d, 1H) and 13.84 (br s, 1H) ppm |

Example 4

2-(5-(1H-pyrazolo[3,4-b]pyridin-4-yl)biphenyl-3-yl)-2-methylpropanenitrile (Compound 53)

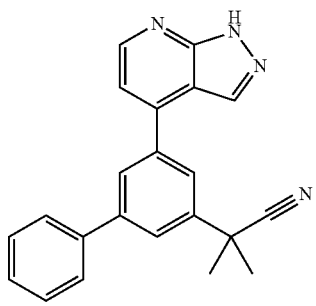 [SMILES: CC(C)(C#N)c1cc(-c2ccccc2)cc(-c2ccnc3[nH]ncc23)c1]

Step 1: 2-(3-bromo-5-(4,4,5,5-tetramethyl-1,3,2-dioxaborolan-2-yl)phenyl)-2-methylpropanenitrile

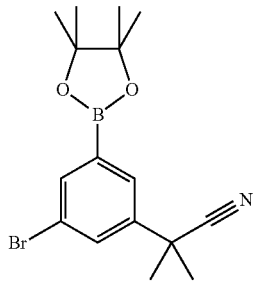 [SMILES: CC(C)(C#N)c1cc(Br)cc(B2OC(C)(C)C(C)(C)O2)c1]

A solution of isopropylmagnesium chloride lithium chloride complex (1.71 ml, 1.65 mmol) in tetrahydrofuran (10 ml) was cooled down to −20° C. 2-(3,5-dibromophenyl)-2-methylpropanenitrile (500 mg, 1.65 mmol, preparation as described in Example 2 step 1) was added in one portion and the reaction stirred for 1.5 hours at −15 to −5° C. 2-Methoxy-4,4,5,5-tetramethyl-1,3,2-dioxaborolane (260.7 mg, 269.9 µL, 1.65 mmol) was added and the reaction was allowed to warm up to room temperature. The reaction mixture was stirred at room temperature for 18 hours. The mixture was partitioned between a diluted solution of ammonium chloride and ethyl acetate. The organic phase was dried over magnesium sulfate and the solvent removed under reduced pressure to afford the title compound as a light yellow solid (551 mg, 95% yield).

$^1$H NMR (CDCl$_3$, 400 MHz) δ 1.36 (12H, s), 1.77 (6H, s), 7.72 (1H, s), 7.80 (1H, s), 7.90 (1H, s); MS (ES$^+$) 351.

Step 2: 2-(3-bromo-5-(1H-pyrazolo[3,4-b]pyridin-4-yl)phenyl)-2-methylpropanenitrile

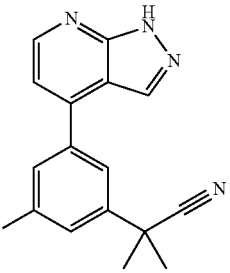

A suspension of 4-iodo-1H-pyrazolo[3,4-b]pyridine (116 mg, 0.47 mmol), 2-(3-bromo-5-(4,4,5,5-tetramethyl-1,3,2-dioxaborolan-2-yl)phenyl)-2-methylpropanenitrile (137 mg, 0.39 mmol), 2 M aqueous solution of sodium carbonate (0.79 ml, 1.58 mmol), tetrakis(triphenylphosphine)palladium(0) (5 mol %, 23 mg, 0.02 mmol), in ethylene glycol dimethyl ether (4 ml) was heated under microwave irradiation at 150° C. for 30 minutes. The mixture was cooled down to room temperature, filtered through a path of celite and evaporated to dryness. The residue was partitioned between ethyl acetate and water. The organic phase was dried over magnesium sulfate, filtered and concentrated in vacuo. The residue was purified on silica gel by flash column chromatography to afford the title compound as a white solid (102.5 mg, 77% yield).

$^1$H NMR (CDCl$_3$, 400 MHz) δ 1.84 (6H, s), 7.35 (1H, d), 7.79 (1H, s), 7.85 (1H, s), 7.90 (1H, s), 8.29 (1H, s), 8.72 (1H, d); MS (ES$^+$) 341.

Step 3: 2-(5-(1H-pyrazolo[3,4-b]pyridin-4-yl)biphenyl-3-yl)-2-methylpropanenitrile

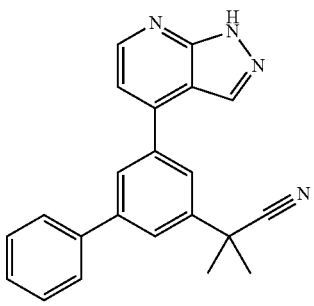 [SMILES: CC(C)(C#N)c1cc(-c2ccccc2)cc(-c2ccnc3[nH]ncc23)c1]

A mixture of 2-(3-bromo-5-(1H-pyrazolo[3,4-b]pyridin-4-yl)phenyl)-2-methylpropanenitrile (50 mg, 0.147 mmol) and phenyl boronic acid (26.76 mg, 0.220 mmol) were placed in a microwave vial. Ethylene glycol dimethyl ether (1.5 ml) was then added followed by sodium carbonate (269.0 mg, 243.9 µL of 2 M, 0.488 mmol) and tetrakis(triphenylphosphine)palladium(0) (14.2 mg, 0.012 mmol). The reaction mixture was heated under microwave irradiation at 150° C. for 60 minutes. The reaction mixture was allowed to cool down to room temperature and was diluted with ethyl acetate and water. The organic phase was dried over magnesium sulfate, filtered and concentrated in vacuo. The residue was purified by reverse phase preparative HPLC [Waters Sunfire C18, 10 µM, 100 Å column, gradient 10%-95% B (solvent A: 0.05% TFA in water; solvent B: CH3CN) over 16 minutes at 25 mL/min]. The fractions were collected, passed through a sodium bicarbonate cartridge and freeze-dried to give the title compound as a white solid (17 mg, 34% yield).

$^1$H NMR (CDCl$_3$, 400 MHz) δ 1.81 (6H, s), 7.30 (1H, d), 7.37 (1H, t), 7.45 (2H, t), 7.59 (2H, d), 7.74-7.79 (2H, m), 7.86 (1H, s), 8.24 (1H, s), 8.63 (1H, d); MS (ES$^+$) 339, (ES$^-$) 337.

Table 5 below depicts data for certain exemplary compounds made in general by a similar route to that outlined in Example 4.

TABLE 5

| # | M + 1 (obs) | RT (min) | 1H-NMR |
|---|---|---|---|
| 53 | 339.2 | 3.8 | 1H (CDCl3) 1.81 (6H, s), 7.30 (1H, d), 7.37 (1H, t), 7.45 (2H, t), 7.59 (2H, d), 7.74-7.79 (2H, m), 7.86 (1H, s), 8.24 (1H, s), 8.63 (1H, d). |
| 54 | 303.1 | 3.73 | 1H (CDCl3) 1.84 (6H, s), 1.97 (3H, d), 6.37-6.49 (1H, m), 6.51-6.58 (1H, m), 7.32 (1H, d), 7.59 (1H, s), 7.68 (2H, d), 8.27 (1H, s), 8.68 (1H, d), 11.69 (1H, bs). |
| 55 | 289.1 | 3.63 | 1H (CDCl3) 1.86 (6H, s), 5.46 (1H, d), 5.93 (1H, d), 6.86 (1H, dd), 7.34 (1H, d), 7.67 (1H, s), 7.77 (2H, d), 8.28 (1H, s), 8.71 (1H, d). |
| 56 | 343.2 | 3.98 | 1H (CDCl3) 1.65-1.76 (4H, m), 1.85 (6H, s), 2.25-2.33 (2H, m), 2.47-2.55 (2H, m), 6.28 (1H, s), 7.33 (1H, d), 7.65 (1H, s), 7.72 (2H, d), 8.28 (1H, s), 8.70 (1H, d), 12.15 (1H, bs). |
| 57 | 305.2 | 3.79 | 1H (DMSO) 0.96 (3H, t), 1.68 (2H, q), 1.78 (6H, s), 2.73 (2H, t), 7.38 (1H, d), 7.51 (1H, s), 7.66 (1H, s), 7.76 (1H, s), 8.28 (1H, s), 8.58 (1H, d). |
| 58 | 345.2 | 4.03 | 1H (DMSO) 1.24-1.60 (5H, m), 1.68-1.93 (5H, m), 1.78 (6H, s), 2.64-2.73 (1H, m), 7.39 (1H, d), 7.53 (1H, s), 7.66 (1H, s), 7.76 (1H, s), 8.27 (1H, s), 8.58 (1H, d). |
| 59 | 328.1 | 3.54 | 1H (DMSO) 1.83 (6H, s), 6.18 (1H, d), 6.74 (1H, s), 6.96 (1H, s), 7.47 (1H, d), 7.71 (1H, s), 7.89 (1H, s), 8.03 (1H, s), 8.34 (1H, s), 8.63 (1H, d), 11.56 (1H, s), 13.70 (1H, bs). |
| 60 | 279 | 2.9 | (400 MHz, DMSO) 1.85-1.91 (3H, m), 2.36 (3H, s), 3.82 (2H, s), 6.36-6.62 (2H, m), 7.29-7.43 (1H, m), 7.49-7.56 (1H, m), 7.65-7.74 (2H, m), 8.35 (1H, s), 8.53-8.62 (1H, m), 13.85 (1H, brs). |
| 61 | 287.1 | 3.5 | 1H (DMSO) 1.80 (6H, s), 4.44 (1H, s), 7.45 (1H, d), 7.78 (1H, s), 7.89 (1H, s), 7.99 (1H, s), 8.29 (1H, s), 8.62 (1H, d), 13.90 (1H, s). |
| 62 | 291.2 | 3.68 | 1H (DMSO) 1.28 (3H, t), 1.78 (6H, s), 2.78 (2H, t), 7.40 (1H, d), 7.54 (1H, s), 7.67 (1H, s), 7.76 (1H, s), 8.30 (1H, s), 8.60 (1H, d). |

TABLE 5-continued

| # | M + 1 (obs) | RT (min) | 1H-NMR |
|---|---|---|---|
| 63 | 279 | 2.87 | (400 MHz, DMSO) 2.37 (3H, s), 3.51-3.60 (2H, m), 3.80 (2H, s), 5.09-5.29 (2H, m), 6.03-6.18 (1H, m), 7.22-7.45 (2H, m), 7.54-7.77 (2H, m), 8.33-8.40 (1H, m), 8.60-8.68 (1H, m), 13.88 (1H, brs). |
| 238 | 342 | 3.13 | (400 MHz, DMSO) 13.89 (1H, brs), 8.67-8.56 (1H, m), 8.35 (1H, s), 7.95-7.72 (3H, m), 7.45-7.38 (1H, m), 3.42-3.27 (1H, m), 3.00-2.94 (2H, m), 1.42-1.35 (3H, m). |
| 239 | 437 | 4.12 | 1H NMR (400.0 MHz, DMSO) d 13.72 (s, 1H), 8.60 (d, J = 4.6 Hz, 1H), 8.24 (s, 1H), 7.94 (s, 1H), 7.81 (s, 1H), 7.65 (s, 1H), 7.42 (d, J = 4.5 Hz, 1H), 7.23 (d, J = 2.1 Hz, 1H), 3.32 (s, 1H), 3.22 (s, 1H), 2.40-2.20 (m, 2H), 2.00-1.61 (m, 5H), 1.58-1.31 (m, 8H), 1.10-0.95 (m, 2H) and 0.70 (t, J = 7.3 Hz, 3H) ppm |

Example 5

2-(3-(1H-pyrazolo[3,4-b]pyridin-4-yl)phenyl)-2-methylbutanenitrile (Compound 64)

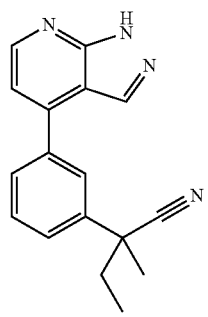

Step 1: 4-iodo-1-trityl-1H-pyrazolo[3,4-b]pyridine

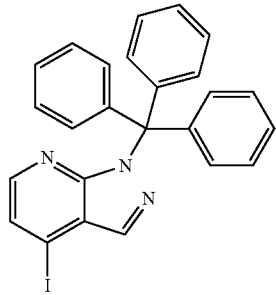 [SMILES: N=Cc1c(I)ccnc1NC(c1ccccc1)(c1ccccc1)c1ccccc1]

4-iodo-1H-pyrazolo[3,4-b]pyridine (15 g, 61.22 mmol) was dissolved in dimethylformamide (300 mL) and the solution was cooled down in an ice bath to 5° C. Sodium hydride (60%, 2.938 g, 73.46 mmol) was added portionwise and left to stir at this temperature for 2 hours. After this time a solution of trityl chloride (18.77 g, 67.34 mmol) in dimethylformamide (150 mL) was added dropwise over 30 minutes. After an additional 2 hours of stirring, the solvent was removed by evaporation, and the residue was partitioned between ethyl acetate and saturated bicarbonate (2×100 ml). The organic layer was further washed with brine (100 ml), dried over magnesium sulfate and concentrated in vacuo to give a brown oil. This residue was purified on silica gel by flash column chromatography to afford the title compound as a white solid (less polar fraction: 2-regioisomer, 13.71 g, 46% yield; more polar fraction: 3-regioisomer, pale yellow solid, 8.06 g, 27% yield).

$^1$H NMR (DMSO-$d_6$, 400 MHz) δ 7.16-7.31 (15H, m), 7.59 (1H, d), 7.89 (1H, d), 8.10 (1H, s); MS (ES$^+$) 488.

Step 2: 4-(4,4,5,5-tetramethyl-1,3,2-dioxaborolan-2-yl)-1-trityl-1H-pyrazolo[3,4-b]pyridine

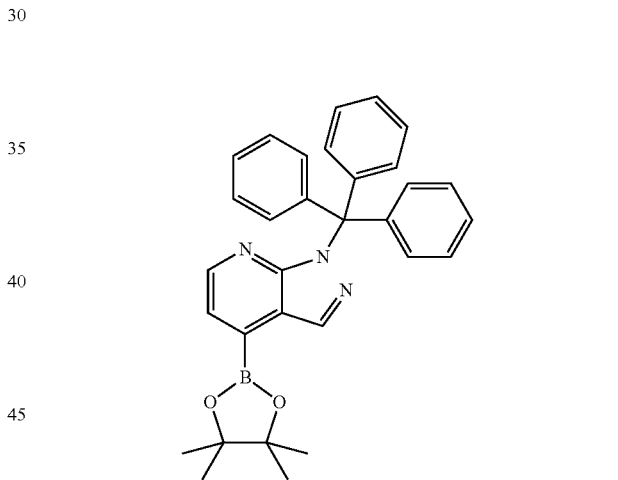

A mixture of 4-iodo-1-trityl-1H-pyrazolo[3,4-b]pyridine (9.61 g, 19.72 mmol), potassium acetate (5.806 g, 59.16 mmol) and bis(pinacol)diboron (6.008 g, 23.66 mmol) was dissolved in dioxane (100 mL). Nitrogen was bubbled through the reaction mixture for 20 minutes then 1,1'-bis (diphenylphosphino)ferrocene-palladium(II)dichloride dichloromethane complex (805.2 mg, 0.99 mmol) was added in one portion and the reaction mixture was sealed and heated to 120° C. behind a blast shield for 24 hours. The reaction mixture was cooled down to room temperature, filtered through a path of celite and washed with ethyl acetate. The filtrate was concentrated in vacuo and the residue was purified on silica gel by flash column chromatography to afford the title compound as a beige solid (7.08 g, 74% yield).

$^1$H NMR (DMSO-$d_6$, 400 MHz) δ 1.35 (12H, s), 7.19-7.32 (16H, m), 8.25-8.29 (2H, m);

MS (ES$^+$) 488.

Step 3: 2-(3-bromophenyl)propanenitrile

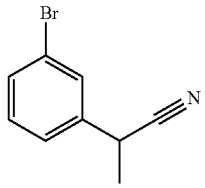

To a solution of 3-bromophenylacetonitrile (12 g, 61.2 mmol) in tetrahydrofuran (150 ml) cooled down to 0° C., was added 60% sodium hydride in mineral oil (2.25 g, 56.3 mmol) portionwise over 10 minutes. The reaction mixture was stirred at 0° C. for 40 minutes. Methyl iodide (5.71 ml, 91.8 mmol) was added dropwise at 0° C. and the reaction mixture was stirred at 0° C. for a further 1 hour. The reaction mixture was diluted with ethyl acetate (250 ml), washed with water and brine. The organic phase was dried over magnesium sulfate, filtered and concentrated in vacuo. The residue was purified on silica gel by flash column chromatography (ISCO Companion, 330 g column, 0-20% EtOAc/Petrol) to afford the title compound as a colourless oil (7.06 g, 55% yield).

$^1$H NMR (DMSO-$d_6$, 400 MHz) δ 1.55 (3H, d), 4.35 (1H, q), 7.37-7.46 (2H, m), 7.56 (1H, d), 7.63 (1H, t).

Step 4: 2-(3-bromophenyl)-2-methylbutanenitrile

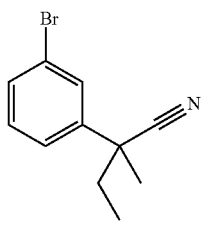

To a solution of 2-(3-bromophenyl)propanenitrile (600 mg, 3.06 mmol) in tetrahydrofuran (15 ml) cooled down to 0° C., was added 60% sodium hydride in mineral oil (184 mg, 4.59 mmol) in one portion. The reaction mixture was stirred at 0° C. for 40 minutes. Ethyl iodide (0.49 ml, 6.12 mmol) was added dropwise at 0° C. and the reaction mixture was stirred at 0° C. for a further 2 hours. The reaction mixture was diluted with ethyl acetate (250 ml), washed with water and brine. The organic phase was dried over magnesium sulfate, filtered and concentrated in vacuo. The residue was purified on silica gel by flash column chromatography (ISCO Companion, 40 g column, 0-10% EtOAc/Petrol) to afford the title compound as a colourless sticky oil (0.526 g, 72% yield).

$^1$H NMR (DMSO-$d_6$, 400 MHz) δ 0.84 (3H, t), 1.67 (3H, s), 1.98 (2H, q), 7.41 (1H, t), 7.51 (1H, m), 7.57 (1H, m), 7.65 (1H, t).

Step 5: 2-methyl-2-(3-(1-trityl-1H-pyrazolo[3,4-b]pyridin-4-yl)phenyl)butanenitrile

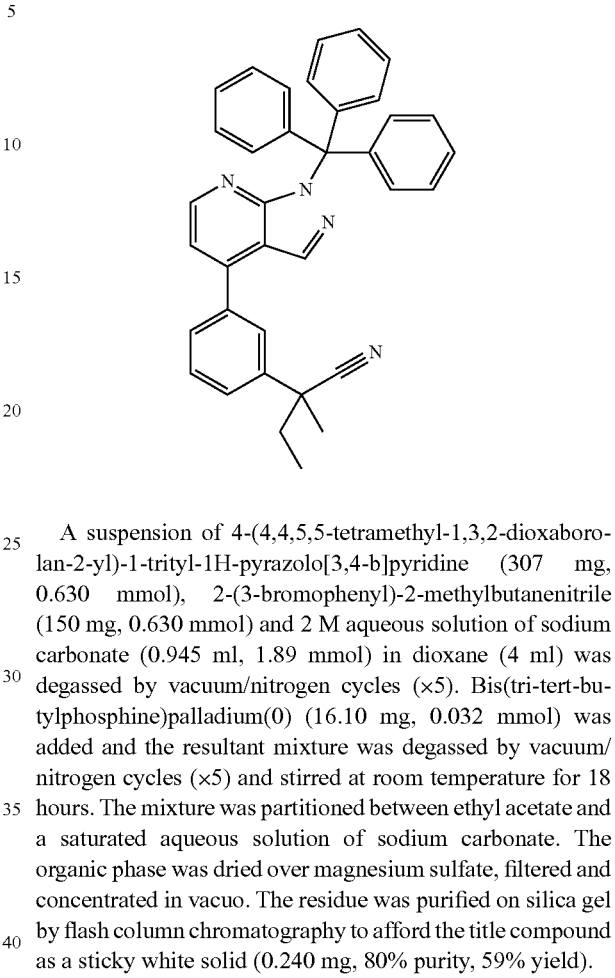

A suspension of 4-(4,4,5,5-tetramethyl-1,3,2-dioxaborolan-2-yl)-1-trityl-1H-pyrazolo[3,4-b]pyridine (307 mg, 0.630 mmol), 2-(3-bromophenyl)-2-methylbutanenitrile (150 mg, 0.630 mmol) and 2 M aqueous solution of sodium carbonate (0.945 ml, 1.89 mmol) in dioxane (4 ml) was degassed by vacuum/nitrogen cycles (×5). Bis(tri-tert-butylphosphine)palladium(0) (16.10 mg, 0.032 mmol) was added and the resultant mixture was degassed by vacuum/nitrogen cycles (×5) and stirred at room temperature for 18 hours. The mixture was partitioned between ethyl acetate and a saturated aqueous solution of sodium carbonate. The organic phase was dried over magnesium sulfate, filtered and concentrated in vacuo. The residue was purified on silica gel by flash column chromatography to afford the title compound as a sticky white solid (0.240 mg, 80% purity, 59% yield).

MS (ES$^+$) 519.

Step 6: 2-(3-(1H-pyrazolo[3,4-b]pyridin-4-yl)phenyl)-2-methylbutanenitrile

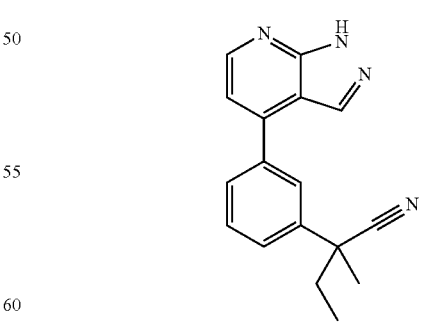

2-Methyl-2-(3-(1-trityl-1H-pyrazolo[3,4-b]pyridin-4-yl)phenyl)butanenitrile (240 mg, 0.46 mmol) was dissolved in dichloromethane (10 ml) and cooled down in an ice-bath. Triethylsilane (2.5 ml) was added followed by trifluoroacetic acid (2.5 ml). The resulting mixture was stirred at 0° C. for 2 hours and then concentrated under reduced pressure. The residue was partitioned between ethyl acetate and a saturated aqueous solution of sodium carbonate. The organic phase was dried over sodium sulfate, filtered and concentrated in vacuo. The residue was purified on silica gel by flash column chromatography to afford the title compound as a white solid (92 mg, 70% yield).

$^1$H NMR (DMSO-$d_6$, 400 MHz) δ 0.92 (3H, t), 1.77 (3H, s), 2.02-2.13 (2H, m), 7.42 (1H, d), 7.66-7.68 (2H, m), 7.85-7.88 (1H, m), 7.92 (1H, s), 8.28 (1H, s), 8.61 (1H, d), 13.87 (1H, s); MS (ES$^+$) 277, (ES$^-$) 275.

Table 6 below depicts data for certain exemplary compounds made in general by a similar route to that outlined in Example 5.

TABLE 6

| # | M + 1 (obs) | RT (min) | 1H-NMR |
|---|---|---|---|
| 64 | 277 | 3.52 | (d6-DMSO, 400 MHz) 0.92 (3H, t), 1.77 (3H, s), 2.02-2.13 (2H, m), 7.42 (1H, d), 7.66-7.68 (2H, m), 7.85-7.88 (1H, m), 7.92 (1H, s), 8.28 (1H, s), 8.61 (1H, d). 13.87 (1H, s) |
| 65 | 303.2 | 3.77 | 1H (DMSO) 1.81 (6H, s), 2.23 (3H, s), 5.26 (1H, s), 5.62 (1H, s), 7.42 (1H, d), 7.76 (1H, s), 7.84-7.89 (2H, m), 8.27 (1H, s), 8.59 (1H, d). |
| 66 | 263.23 | 3.43 | 1H NMR (400.0 MHz, DMSO) d 13.85 (s, 1H), 8.61 (d, 1H), 8.34 (d, 1H), 7.87-7.86 (m, 2H), 7.65 (t, 1H), 7.57 (d, 1H), 7.41 (d, 1H), 4.38 (t, 1H), 2.01-1.94 (m, 2H) and 1.03 (t, 3H) ppm |
| 67 | 303.3 | 3.73 | 1H (DMSO) 1.78 (6H, s), 3.56 (2H, d), 5.13 (1H, dd), 5.18 (1H, dd), 6.01-6.10 (1H, m), 7.41 (1H, d), 7.53 (1H, s), 7.66 (1H, s), 7.79 (1H, s), 8.29 (1H, s), 8.61 (1H, d), 13.85 (1H, s). |
| 68 | 291.2 | 3.68 | 1H NMR (400.0 MHz, DMSO) d 13.73 (br s, 1H), 8.60 (d, J = 4.8 Hz, 1H), 8.24 (s, 1H), 7.87 (m, 2H), 7.67 (t, 1H), 7.61 (d, 1H), 7.39 (d, 1H), 2.11 (m, 4H) and 0.86 (t, 6H) ppm |
| 69 | 291.2 | 3.73 | 1H NMR (400.0 MHz, DMSO) d 13.86 (br s, 1H), 8.61 (d, 1H), 8.28 (s, 1H), 7.92 (s, 1H), 7.87-7.85 (m, 1H), 7.67 (d, 2H), 7.41 (d, 1H), 2.08-1.94 (m, 2H), 1.78 (s, 3H), 1.47-1.38 (m, 1H), 1.25-1.17 (m, 1H) and 0.89 (t, 3H) ppm |
| 70 | 291.2 | 3.7 | 1H NMR (400.0 MHz, DMSO) d 13.87 (br s, 1H), 8.61 (d, 1H), 8.26 (s, 1H), 7.91 (s, 1H), 7.87-7.85 (m, 1H), 7.67-7.66 (m, 2H), 7.42 (d, 1 H), 2.33 (m, 1H), 1.77 (s, 3H), 1.10 (d, 3H) and 0.82 (d, 3H) ppm |
| 71 | 305.26 | 3.82 | 1H NMR (400.0 MHz, DMSO) d 13.78 (br s, 1H), 8.61 (d, 1H), 8.26 (s, 1H), 7.95 (s, 1H), 7.85 (d, 1H), 7.70-7.65 (m, 2H), 7.40 (d, 1H), 2.08 (dd, 1H), 1.92 (dd, 1H), 1.78 (s, 3H), 1.63-1.57 (m, 1H), 0.96 (d, 3 H) and 0.76 (d, 3H) ppm |
| 72 | 317.25 | 3.87 | 1H NMR (400.0 MHz, DMSO) d 13.85 (br s, 1H), 8.61 (d, 1H), 8.27 (s, 1H), 7.94 (s, 1H), 7.85 (d, 1H), 7.69-7.64 (m, 2H), 7.41 (d, 1H), 2.60-2.50 (m, 1H), 1.98-1.94 (m, 1H), 1.77 (s, 3H), 1.74-1.69 (m, 1H), 1.60-1.48 (m, 4H), 1.45-1.36 (m, 1H) and 1.26-1.22 (m, 1H) ppm |
| 73 | 275.17 | 3.5 | 1H NMR (400.0 MHz, DMSO) d 13.85 (br s, 1H), 8.61 (d, 1H), 8.31 (s, 1H), 7.88-7.86 (m, 2H), 7.70-7.63 (m, 2H), 7.43 (d, 1H), 2.82-2.75 (m, 4H), 2.36-2.29 (m, 1H) and 2.08-2.04 (m, 1H) ppm |
| 74 | 289.19 | 3.62 | 1H NMR (400.0 MHz, DMSO) d 13.85 (brs, 1H), 8.61 (d, 1H), 8.30 (s, 1H), 7.93 (s, 1H), 7.87-7.85 (m, 1H), 7.69-7.66 (m, 2H), 7.42 (d, 1H), 2.50 (masked signal, 2H), 2.23-2.18 (m, 2H) and 1.95-1.93 (m, 4H) ppm |
| 75 | 306 | 2.72 | (400 MHz, DMSO) 1.78 (6H, s), 2.33 (3H, s), 3.80 (2H, s), 7.38-7.45 (1H, m), 7.62-7.68 (1H, m), 7.75-7.83 (2H, m), 8.32-8.35 (1H, m), 8.58-8.64 (1H, m), 13.84 (1H, brs). |
| 76 | 290 | 2.7 | 1H NMR (400.0 MHz, DMSO) d 13.83 (s, 1H), 8.61 (d, J = 4.7 Hz, 1H), 8.34 (s, 1H), 7.82 (s, 1H), 7.77 (s, 1H), 7.65 (s, 1H), 7.41 (d, J = 4.8 Hz, 1H), 3.87 (s, 2H) and 1.77 (s, 6H) ppm |
| 77 | 254.11 | 3.18 | 1H NMR (400.0 MHz, DMSO) d 13.80 (br s, 1H), 8.59 (d, 1H), 8.31 (s, 1H), 7.81 (s, 1H), 7.73 (d, 1H), 7.54 (t, 1H), 7.48 (d, 1H), 7.37 (d, 1H), 4.60 (t, 1H), 1.73-1.66 (m, 2H) and 0.88 (t, 3H) ppm |
| 78 | 321.2 | 3.29 | 1H (DMSO) 1.78 (6H, s), 1.81 (2H, dt), 2.79 (2H, t), 3.47 (2H, t), 4.55 (1H, bs), 7.39 (1H, d), 7.52 (1H, s), 7.67 (1H, s), 7.76 (1H, s), 8.29 (1H, s), 8.59 (1H, d), 13.70 (1H, bs). |
| 79 | 321.2 | 3.32 | 1H (DMSO) 0.85 (3H, t), 1.55-1.66 (2H, m), 1.67 (6H, s), 4.58 (1H, t), 5.31 (1H, bs), 7.33 (1H, d), 7.58 (1H, s), 7.71 (1H, s), 7.74 (1H, s), 8.22 (1H, s), 8.53 (1H, s), 13.75 (1H, bs). |
| 80 | 303.2 | 3.72 | 1H NMR (400.0 MHz, DMSO) d 13.86 (s, 1H), 8.61 (d, 1H), 8.28 (s, 1H), 7.95 (s, 1H), 7.85 (d, 1H), 7.71-7.64 (m, 2H), 7.41 (d, 1H), 2.06 (dd, 1H), 1.88-1.82 (m, 4H), 0.73-0.63 (m, 1H), 0.51-0.44 (m, 1H), 0.41-0.35 (m, 1H), 0.27-0.22 (m, 1H) and 0.08-0.04 (m, 1H) ppm |
| 83 | 341.05 | 3.15 | (400 MHz, DMSO) 1.83 (6H, s), 7.46 (1H, d), 8.17 (1H, s), 8.21 (1H, s), 8.34 (1H, s), 8.36 (1H, s), 8.61 (1H, d). |
| 84 | 289.12 | 3.14 | 1H NMR (400.0 MHz, DMSO) d 13.85 (br s, 1H), 8.59 (d, 1H), 8.39 (s, 1H), 7.91-7.81 (m, 3H), 7.51 (dd, 1H), 7.43 (d, 1H), 5.91 (d, 1H), 5.57 (d, 1H) and 1.86 (s, 6H) ppm |

TABLE 6-continued

| # | M + 1 (obs) | RT (min) | 1H-NMR |
|---|---|---|---|
| 85 | 289 | 4.24 | (400 MHz, DMSO) 1.98-2.11 (1H, m), 2.25-2.38 (1H, m), 2.48 (3H, s), 2.69-2.83 (4H, m), 7.35-7.47 (2H, m), 7.62-7.69 (2H, m), 8.31 (1H, s), 8.54-8.61 (1H, m), 13.82 (1H, brs). |
| 86 | 277 | 4.2 | (400 MHz, DMSO) 1.03 (3H, t), 1.89-2.03 (2H, m), 2.47 (3H, s), 4.28-4.36 (1H, m), 7.33-7.42 (2H, m), 7.63-7.69 (2H, m), 8.34 (1H, m), 8.55-8.63 (1H, m), 13.78 (1H, brs). |
| 87 | 311.1 | 3.62 | 1H NMR (400.0 MHz, DMSO) d 0.99 (t, J = 7.3 Hz, 3H), 1.85 (s, 3H), 2.15 (m, 2H), 7.53 (d, J = 4.7 Hz, 1H), 7.79 (s, 1H), 7.96 (d, J = 6.2 Hz, 2H), 8.34 (s, 1H), 8.70 (d, J = 4.7 Hz, 1H) and 14.00 (br s, 1H) ppm |
| 89 | 291 | 3.55 | (400 MHz, DMSO) 0.88-0.95 (3H, m), 1.75 (3H, s), 1.97-2.15 (2H, m), 2.48 (3H, s), 7.35-7.49 (2H, m), 7.63-7.74 (2H, m), 8.25-8.32 (1H, m), 8.57-8.63 (1H, m), 13.85 (1H, brs). |
| 90 | 289.19 | 3.43 | 1H NMR (400.0 MHz, DMSO) d 1.78 (s, 3H), 2.76-2.89 (m, 2H), 5.17-5.23 (m, 2H), 5.68-5.75 (m, 1H), 7.41 (d, 1H), 7.67-7.68 (m, 2H), 7.85-7.87 (m, 1H), 7.94 (s, 1H), 8.29 (s, 1H), 8.61 (d, 1H) and 13.84 (br s, 1H) ppm |
| 92 | 343 | 3.63 | (400 MHz, DMSO) 1.98-2.12 (1H, m), 2.27-2.42 (1H, m), 2.77-2.90 (4H, m), 7.50-7.57 (1H, m), 7.93-8.00 (1H, m), 8.10-8.26 (2H, m), 8.34 (1H, s), 8.61-8.70 (1H, m), 13.95 (1H, brs). |
| 93 | 345 | 3.68 | (400 MHz, DMSO) 0.88-0.96 (3H, m), 1.83 (3H, s), 2.03-2.25 (2H, m), 7.49-7.56 (1H, m), 7.93-8.00 (1H, m), 8.13-8.29 (3H, m), 8.62-8.68 (1H, m), 13.96 (1H, brs). |
| 95 | 293.09 | 3.17 | 1H NMR (400.0 MHz, DMSO) d 13.80 (br s, 1H), 8.61 (d, 1H), 8.30 (s, 1H), 7.95 (s, 1H), 7.87-7.86 (m, 1H), 7.70-7.64 (m, 2H), 7.41 (d, 1H), 3.82 (d, 1H), 3.75 (d, 1H), 3.34 (masked signal, 3H) and 1.76 (s, 3H) ppm |
| 96 | 307.11 | 3.22 | 1H NMR (400.0 MHz, DMSO) d 13.78 (br s, 1H), 8.61 (d, 1H), 8.29 (s, 1H), 7.96 (s, 1H), 7.87-7.86 (m, 1H), 7.70-7.65 (m, 2H), 7.41 (d, 1H), 3.41-3.38 (masked signal, 2H), 3.18 (s, 3H), 2.32 (t, 2H) and 1.81 (s, 3H) ppm |
| 98 | 261.1 | 3.17 | 1H NMR (400.0 MHz, DMSO) d 1.67-1.71 (m, 2H), 1.81-1.84 (m, 2H), 7.40 (d, J = 4.8 Hz, 1H), 7.52-7.54 (m, 1H), 7.63 (t, J = 7.7 Hz, 1H), 7.71 (s, 1H), 7.82 (d, J = 7.7 Hz, 1H), 8.30 (s, 1H), 8.59 (d, J = 4.6 Hz, 1H) ppm and 13.70 (bs, 1H) ppm. |
| 99 | 313.06 | 3.25 | 1.87 (3 H, s), 2.92-2.67 (2 H, m), 6.08 (1 H, tt), 7.43 (1H, d), 7.69 (1H, t), 7.75 (1H, d), 7.88 (1H, d), 8.02 (1 H, s), 8.31 (1H, s), 8.62 (1 H, d), 13.85 (1H, s). |
| 100 | 339.18 | 3.6 | 1H NMR (400.0 MHz, DMSO) d 13.66 (br, 1H), 8.59 (d, 1H), 8.08 (s, 1H), 7.85-7.84 (m, 2H), 7.67-7.65 (m, 2H), 7.35 (d, 1H), 7.28-7.25 (m, 3H), 7.12-7.10 (m, 2H), 3.32 (masked signal, 2H) and 1.82 (s, 3H) ppm |
| 104 | 301.16 | 3.4 | (DMSO) 1.77 (t, 3H), 1.83 (s, 3H), 3.02-3.01 (m, 2H), 7.42 (d, 1H), 7.72-7.65 (m, 2H), 7.87 (d, 1H), 7.98 (s, 1H), 8.32 (s, 1H), 8.62 (d, 1H), 13.85 (s, 1H). |
| 105 | 323 | 3.55 | (400 MHz, DMSO) 0.87-0.97 (3H, m), 1.63-1.82 (6H, m), 2.01-2.18 (2H, m), 5.82-6.04 (1H, m), 7.42-7.48 (1H, m), 7.64-7.71 (1H, m), 7.81-7.94 (2H, m), 8.59-8.68 (1H, m), 13.89 (1H, brs). |
| 106 | 337 | 3.7 | (400 MHz, DMSO) 0.87-1.01 (6H, m), 1.74-1.81 (3H, m), 1.87-2.18 (4H, m), 5.58-5.81 (1H, m), 7.41-7.48 (1H, m), 7.60-7.68 (1H, m), 7.78-7.92 (2H, m), 8.23-8.32 (1H, m), 8.59-8.66 (1H, m), 13.89 (1H, brs). |
| 107 | 337.2 | 3.3 | 1H NMR (400.0 MHz, DMSO) d 0.92 (t, J = 7.3 Hz, 3H), 1.76 (s, 3H), 1.99-2.12 (m, 4H), 2.83-2.87 (m, 2H), 4.45 (t, J = 5.9 Hz, 1H), 4.57 (t, J = 5.9 Hz, 1H), 7.41 (d, J = 4.7 Hz, 1H), 7.50 (s, 1H), 7.71 (s, 1H), 7.75 (s, 1H), 8.29 (s, 1H), 8.60 (d, J = 4.7 Hz, 1H) and 13.80 (bs, 1H) ppm |
| 108 | 355 | 3.34 | 1H (DMSO) 0.91 (3H, t), 1.76 (3H, s), 2.00-2.12 (2H, m), 2.20-2.30 (2H, m), 2.89 (2H, dd), 6.03 (0.25H, t), 6.17 (0.5H, t), 6.31 (0.25H, t), 7.41 (1H, d), 7.53 (1H, s), 7.74-7.76 (2H, m), 8.30 (1H, s), 8.60 (1H, d), 13.80 (1H, bs, NH). |
| 109 | 349.2 | 3.22 | 1H NMR (400.0 MHz, DMSO) d 0.92 (t, J = 7.4 Hz, 3H), 1.76 (s, 3H), 1.89 (dd, J = 6.4, 9.1 Hz, 2H), 2.06 (dd, J = 7.4, 9.2 Hz, 2H), 2.77-2.81 (m, 2H), 3.26 (s, 3H), 3.37 (t, J = 6.3 Hz, 2H), 7.38 (d, J = 4.8 Hz, 1H), 7.47 (s, 1H), 7.67 (s, 1H), 7.73 (t, J = 1.5 Hz, 1H), 8.27 (s, 1H), 8.58 (d, J = 4.7 Hz, 1H) and 13.80 (bs, NH, 1H) ppm |
| 110 | 327 | 3.22 | 1H NMR (400.0 MHz, DMSO) d 13.93 (s, 1H), 8.65 (d, J = 4.8 Hz, 1H), 8.30 (s, 1H), 8.09 (s, 1H), 8.04 (s, 1H), 7.85 (s, 1H), 7.48 (d, J = 4.7 Hz, 2H), 7.30-7.06 (t, 1H), 2.15-2.05 (m, 2H), 1.81 (s, 3H) and 0.92 (t, J = 7.3 Hz, 3H) ppm |
| 111 | 341 | 3.33 | (400 MHz, DMSO) 0.90-0.97 (3H, m), 1.80 (3H, s), 2.00-2.20 (5H, m), 7.43-7.54 (1H, m), 7.76-7.82 (1H, m), 7.94-8.09 (2H, m), 8.24-8.30 (1H, m), 8.60-8.69 (1H, m), 13.93 (1H, brs). |
| 113 | 359.2 | 3.59 | 1H NMR (400.0 MHz, DMSO) d 0.78 (t, 3H), 1.64 (s, 3H), 1.93 (dd, 2H), 3.20 (d, 2H), 3.75 (dd, 2H), 7.29 (d, 1H), 7.53 (s, |

TABLE 6-continued

| # | M + 1 (obs) | RT (min) | 1H-NMR |
|---|---|---|---|
| | | | 1H), 7.75-7.76 (m, 2H), 8.16 (s, 1H), 8.49 (d, 1H) and 13.76 (bs, 1H) ppm |
| 114 | 305.2 | 2.82 | 1H (DMSO) 1.65-1.69 (2H, m), 1.78-1.82 (2H, m), 2.87 (2H, t), 3.70 (2H, t), 4.74 (1H, s, OH), 7.37-7.40 (2H, m), 7.53 (1H, s), 7.67 (1H, s), 8.30 (1H, s), 8.58 (1H, d), 13.80 (1H, bs, NH). |
| 115 | 340.1 | 3.1 | 1H NMR (400.0 MHz, DMSO) d 1.86 (s, 3H), 3.48-3.56 (m, 2H), 7.20 (d, 1H), 7.23-7.27 (m, 1H), 7.37 (d, 1H), 7.60-7.72 (m, 3H), 7.81-7.83 (m, 1H), 7.90-7.92 (m, 1H), 8.22 (s, 1H), 8.49-8.51 (m, 1H), 8.61 (d, 1H) and 13.84 (br s, 1H) ppm |
| 116 | 340.08 | 3.07 | 1H NMR (400.0 MHz, DMSO) d 1.85 (s, 3H), 3.35-3.39 (masked signal, 2H), 7.32 (dd, 1H), 7.38 (d, 1H), 7.52 (dt, 1H), 7.65-7.69 (m, 2H), 7.85-7.88 (m, 2H), 8.13 (s, 1H), 8.27 (d, 1H), 8.45 (dd, 1H), 8.61 (d, 1H) and 13.87 (br s, 1H) ppm |
| 117 | 423 | 4.19 | (400 MHz, DMSO) 0.87-0.96 (3H, m), 1.00-1.12 (2H, m), 1.37-1.60 (5H, m), 1.67-1.85 (5H, m), 2.04-2.20 (2H, m), 2.27-2.43 (2H, m), 7.46-7.51 (1H, m), 7.72-7.78 (1H, m), 7.90-7.93 (1H, m), 8.02-8.06 (1H, m), 8.20-8.26 (1H, m), 8.61-8.67 (1H, m), 13.92 (1H, brs). |
| 118 | 437 | 4.33 | 1H NMR (400.0 MHz, DMSO) d 13.77 (s, 1H), 8.61 (d, J = 4.8 Hz, 1H), 8.22 (s, 1H), 8.04 (s, 1H), 7.92 (s, 1H), 7.73 (s, 1H), 7.44 (d, J = 4.8 Hz, 1H), 2.39-2.28 (m, 2H), 2.17-2.05 (m, 2H), 1.81 (s, 3H), 1.70-1.52 (m, 5H), 1.36-1.04 (m, 6H), 0.92 (t, J = 7.3 Hz, 3H) and 0.86-0.81 (m, 2H) ppm |
| 119 | 423 | 4.15 | 1H NMR (400.0 MHz, DMSO) d 13.92 (s, 1H), 8.64 (d, 1H), 8.23 (s, 1H), 8.03 (s, 1H), 7.92 (s, 1H), 7.74 (s, 1H), 7.48 (d, 1H), 2.38-2.02 (m, 4H), 1.81 (s, 3H), 1.75-1.46 (m, 6H), 1.26-0.96 (m, 5H) and 0.91 (t, 3H) ppm |
| 120 | 305 | 2.99 | 1H NMR (400.0 MHz, DMSO) d 13.93 (s, 1H), 10.20 (s, 1H), 8.66 (d, 1H), 8.39 (d, 1H), 8.24 (s, 1H), 8.15 (s, 1H), 7.52 (d, 1H), 2.24-2.04 (m, 2H), 1.83 (s, 3H) and 0.93 (t, J = 7.3 Hz, 3H) ppm |
| 121 | 307 | 2.65 | 1H NMR (400.0 MHz, DMSO) d 13.84 (s, 1H), 8.61 (d, J = 4.7 Hz, 1H), 8.29 (s, 1H), 7.78 (s, 1H), 7.59 (s, 1H), 7.40 (d, J = 4.8 Hz, 1H), 5.42 (t, 1H), 4.67 (d, J = 5.7 Hz, 2H), 2.15-1.99 (m, 2H), 1.77 (s, 3H) and 0.93 (t, J = 7.3 Hz, 3H) ppm |
| 122 | 340 | 2.95 | 1H NMR (400.0 MHz, DMSO) d 1.76 (d, J = 8.3 Hz, 2H), 1.85 (d, J = 4.2 Hz, 2H), 3.26 (s, 2H), 7.46 (d, J = 4.7 Hz, 1H), 7.63 (s, 1H), 7.80 (s, 1H), 7.88 (s, 1H), 8.29 (s, 1H), 8.62 (d, J = 4.7 Hz, 1H) and 13.88 (bs, 1H, NH) ppm |
| 123 | 354 | 3.05 | 1H NMR (400.0 MHz, DMSO) d 1.74-1.77 (m, 2H), 1.85-1.88 (m, 2H), 2.08 (s, 1H), 2.33 (s, 3H), 3.23-3.27 (m, 2H), 7.46 (d, J = 4.7 Hz, 1H), 7.64 (s, 1H), 7.79 (s, 1H), 7.89 (s, 1H), 8.28 (s, 1H), 8.63 (d, J = 4.7 Hz, 1H) and 13.83 (bs, 1H, NH) ppm |
| 124 | 328 | 3.18 | 1H NMR (400.0 MHz, DMSO) d 13.89 (s, 1H), 8.67-8.61 (m, 1H), 8.34 (s, 1H), 8.14 (s, 1H), 8.00-7.79 (m, 3H), 7.50-7.43 (m, 1H), 6.80-6.71 (m, 1H), 2.19-2.01 (m, 2H), 1.79 (s, 3H) and 0.93 (t, 3H) ppm |
| 125 | 331 | 3.48 | 1H NMR (400.0 MHz, DMSO) d 13.78 (s, 1H), 8.58 (d, J = 4.7 Hz, 1H), 8.34 (s, 1H), 7.54 (s, 1H), 7.46 (s, 1H), 7.37 (d, J = 4.6 Hz, 1H), 7.21 (s, 1H), 3.12 (s, 2H), 2.71-2.67 (m, 2H), 2.50 (s, 2H), 2.31-2.13 (m, 3H), 1.90-1.61 (m, 3H) and 0.95 (t, J = 7.3 Hz, 3H) ppm |
| 126 | 316 | 2.96 | 1H NMR (400.0 MHz, DMSO) d 13.88 (s, 1H), 8.63 (d, J = 4.8 Hz, 1H), 8.32 (s, 1H), 7.86 (d, J = 8.6 Hz, 2H), 7.66 (s, 1H), 7.43 (d, J = 4.7 Hz, 1H), 4.25 (s, 2H), 2.15-2.00 (m, 2H), 1.78 (s, 3H) and 0.93 (t, J = 7.3 Hz, 3H) ppm |
| 127 | 320 | 2.16 | 1H NMR (400.0 MHz, DMSO) d 8.55 (d, J = 4.7 Hz, 1H), 8.27 (s, 1H), 7.73-7.71 (m, 1H), 7.64 (s, 1H), 7.34 (d, J = 4.7 Hz, 1H), 7.25-7.23 (m, 1H), 3.23-3.17 (m, 2H), 2.87-2.81 (m, 2H), 2.09-1.99 (m, 2H), 1.75 (s, 3H) and 0.92 (t, J = 7.3 Hz, 3H) ppm |
| 128 | 304.1 | 2.47 | 1H NMR (400.0 MHz, DMSO) d 1.68-1.71 (m, 2H), 1.82-1.85 (m, 2H), 2.99-3.03 (m, 2H), 3.17-3.21 (m, 2H), 7.42-7.43 (m, 2H), 7.60 (s, 1H), 7.71 (s, 1H), 7.82 (bs, 3H, NH3), 8.35 (s, 1H), 8.61 (d, J = 4.7 Hz, 1H) and 13.85 (s, 1H, NH) ppm |
| 217 | 317 | 3.32 | 1H NMR (400.0 MHz, DMSO) d 13.80 (s, 1H), 8.59 (d, J = 4.7 Hz, 1H), 8.31 (s, 1H), 7.70 (d, J = 1.6 Hz, 2H), 7.63 (s, 1H), 7.41 (d, J = 4.9 Hz, 1H), 6.56 (m, 3H), 3.04 (s, 2H), 1.90 (d, J = 5.8 Hz, 2H) and 1.49 (s, 6H) ppm |
| 218 | 319 | 3.38 | 1H NMR (400.0 MHz, DMSO) d 13.79 (s, 1H), 8.58 (d, J = 4.8 Hz, 1H), 8.31 (s, 1H), 7.69 (s, 1H), 7.55 (s, 1H), 7.46 (s, 1H), 7.38 (d, J = 4.7 Hz, 1H), 3.02 (s, 2H), 2.70 (t, 2H), 1.69 (m, 2H), 1.48 (s, 6H) and 0.96 (t, J = 7.3 Hz, 3H) ppm |
| 220 | 291 | 2.82 | 1H NMR (400.0 MHz, DMSO) d 2.53-2.57 (m, 2H), 3.13-3.18 (m, 2H), 4.46 (t, J = 7.2 Hz, 1H), 5.65 (bs, 1H, OH), |

TABLE 6-continued

| # | M + 1 (obs) | RT (min) | 1H-NMR |
|---|---|---|---|
| | | | 7.41 (d, J = 4.7 Hz, 1H), 7.61-7.70 (m, 2H), 7.86 (t, J = 1.3 Hz, 1H), 7.88 (s, 1H), 8.30 (s, 1H), 8.61 (d, J = 4.9 Hz, 1H) and 13.84 (bs, 1H, NH) ppm |
| 221 | 305 | 3.29 | 1H NMR (400.0 MHz, DMSO) d 1.97-2.08 (m, 1H), 2.22-2.27 (m, 1H), 2.66-2.76 (m, 4H), 3.82 (s, 3H), 7.25-7.31 (m, 2H), 7.52 (d, J = 2.5 Hz, 1H), 7.59 (dd, J = 2.5, 8.7 Hz, 1H), 7.95 (s, 1H), 8.56 (d, J = 4.6 Hz, 1H) and 13.64 (bs, 1H, NH) ppm |
| 222 | 309.1 | 2.7 | 1H NMR (400.0 MHz, DMSO) d 1.75-1.84 (m, 1H), 1.96-2.01 (m, 1H), 2.17-2.24 (m, 4H), 3.31 (d, J = 6.1 Hz, 2H), 3.78 (s, 3H), 7.14-7.25 (m, 4H), 7.95-8.00 (m, 1H), 8.52 (dd, J = 3.3, 4.7 Hz, 1H) and 13.59 (bs, 1H, NH) ppm |
| 223 | 251 | 1.92 | 1H NMR (400.0 MHz, DMSO) d 13.18 (s, 1H), 8.58 (d, J = 4.9 Hz, 1H), 8.37 (s, 1H), 7.88 (t, J = 1.7 Hz, 1H), 7.64-7.62 (m, 1H), 7.48 (t, J = 7.7 Hz, 1H), 7.39-7.33 (m, 2H) and 1.03 (dd, J = 2.6, 4.2 Hz, 4H) ppm |
| 224 | 279 | 2.73 | 1H NMR (400.0 MHz, DMSO) d 2.01-2.13 (m, 1H), 2.13-2.26 (m, 1H), 3.51-3.56 (m, 2H), 4.45 (dd, J = 6.6, 8.7 Hz, 1H), 4.85 (bs, 1H, OH), 7.40 (d, J = 4.8 Hz, 1H), 7.59 (d, J = 7.8 Hz, 1H), 7.66 (t, J = 7.6 Hz, 1H), 7.86-7.89 (m, 2H), 8.35 (s, 1H), 8.60 (d, J = 4.8 Hz, 1H) and 13.84 (bs, 1H, NH) ppm |
| 225 | 278.1 | 2.35 | 1H NMR (400.0 MHz, DMSO) d 1.94-2.17 (m, 2H), 2.68 (t, J = 6.7 Hz, 1H), 3.08-3.17 (m, 1H), 4.39-4.43 (m, 0.5H), 4.52 (dd, J = 6.7, 8.5 Hz, 0.5H), 6.86 (s, 0.4H), 7.38-7.42 (m, 1H), 7.58 (d, J = 7.6 Hz, 0.6H), 7.66 (t, J = 7.7 Hz, 1H), 7.86-7.90 (m, 2H), 8.35 (d, J = 5.0 Hz, 1H) and 8.60 (t, J = 4.8 Hz, 1H) ppm |
| 226 | 311.1 | 3.23 | 1H NMR (400.0 MHz, DMSO) d 3.53-3.65 (m, 4H), 7.46 (d, J = 4.9 Hz, 1H), 7.70-7.72 (m, 2H), 7.92-7.94 (m, 1H), 7.96 (s, 1H), 8.35 (s, 1H), 8.63 (d, J = 4.9 Hz, 1H) and 13.87 (bs, 1H, NH) ppm |
| 227 | 299.09 | 2.21 | 1H (DMSO, 400 MHz) 0.76 (3H, t), 1.43 (2H, br s), 1.95-2.12 (2H, m), 2.47 (3H, s), 2.98-3.08 (2H, m), 7.32 (1H, s), 7.38 (1H, d), 7.56 (1H, s), 7.61 (1H, s), 8.28 (1H, s), 8.58 (1H, d), 13.81 (1H, br s). |
| 228 | 323.06 | 2.66 | (DMSO, 400 MHz) 0.81 (3H, t), 2.06 (2H, q), 2.47 (3H, s), 3.63 (1H, d), 3.75 (1H, d), 7.36 (1H, d), 7.38 (1H, d), 7.60 (1H, s), 7.64 (1H, s), 7.68 (1H, s), 8.27 (1H, s), 8.59 (1H, d), 13.82 (1H, br s). |
| 229 | 290.1 | 2.52 | 1H NMR (400.0 MHz, DMSO) d 2.59-2.65 (m, 1.45H), 2.77-2.82 (m, 0.55H), 2.95-3.00 (m, 2H), 3.41-3.49 (m, 0.8H), 4.06-4.12 (m, 0.2H), 7.22-7.25 (m, 0.1H), 7.44-7.46 (m, 1H), 7.68-7.72 (m, 1.9H), 7.86-7.95 (m, 2H), 8.29-8.30 (m, 1H), 8.61 (d, 1H) and 13.80 (1H, bs, NH) ppm. |
| 230 | 279.28 | 2.61 | (DMSO, 400 MHz) 1.15-1.26 (2H, m), 1.37-1.43 (2H, m), 2.26-2.31 (1H, m), 2.36-2.43 (2H, m), 2.72-2.78 (2H, m), 6.59 (1H, d), 6.68 (1H, d), 6.80 (1H, t), 6.95-6.98 (2H, m), 7.49 (1H, s), 7.80 (1H, d). |
| 231 | 263.12 | 1.93 | (DMSO, 400 MHz) 3.83 (2H, app s), 4.06 (2H, app s), 6.56 (1H, app s), 7.41 (1H, d), 7.57-7.61 (2H, m), 7.75-7.82 (2H, m), 8.30 (1H, s), 8.59 (1H, d), 13.84 (1H, br s). |
| 240 | 314 | 3 | 1H NMR (400.0 MHz, DMSO) d 1.67-1.71 (m, 2H), 1.81-1.84 (m, 2H), 2.92-2.96 (m, 2H), 3.03-3.06 (m, 2H), 7.42-7.45 (m, 2H), 7.61 (d, 1H), 7.77 (s, 1H), 8.38 (s, 1H), 8.61 (d, 1H) and 13.85 (bs, 1H) ppm |
| 241 | 296 | 82.8 | 1H NMR (400.0 MHz, DMSO) d 13.77 (s, 1H), 8.56 (d, J = 4.7 Hz, 1H), 8.26 (s, 1H), 7.58 (s, 1H), 7.47 (s, 1H), 7.34 (d, J = 4.8 Hz, 1H), 7.30 (s, 1H), 4.69 (t, J = 5.2 Hz, 1H), 3.58 (dd, 1H), 3.49 (dd, 1H), 2.43 (s, 3H), 1.81 (dd, J = 7.4, 13.9 Hz, 1H), 1.60 (dd, J = 7.4, 13.9 Hz, 1H), 1.28 (s, 3H) and 0.69 (t, J = 7.4 Hz, 3H) ppm |
| 242 | 279 | 2.64 | 1H NMR (400.0 MHz, DMSO) d 13.80 (s, 1H), 8.58 (d, J = 4.8 Hz, 1H), 8.28 (s, 1H), 7.66-7.64 (m, 1H), 7.56-7.49 (m, 2H), 7.35 (d, J = 4.9 Hz, 1H), 7.29-7.27 (m, 1H), 4.88 (t, J = 5.5 Hz, 1H), 3.61 (d, J = 5.3 Hz, 2H), 2.30-2.26 (m, 4H), 2.08-2.00 (m, 1H) and 1.85-1.80 (m, 1H) ppm |
| 243 | 265 | 2.54 | 1H NMR (400.0 MHz, DMSO) d 13.81 (s, 1H), 8.58 (m, 1H), 8.31 (s, 1H), 7.83 (m, 1H), 7.68-7.44 (m, 4H), 4.81 (m, 1H), 3.60 (d, J = 5.7 Hz, 2H) and 0.88 (d, J = 7.3 Hz, 4H) ppm |
| 244 | 240 | 2.35 | 1H NMR (400.0 MHz, DMSO) d 13.83 (s, 1H), 8.59 (d, J = 4.8 Hz, 1H), 8.32 (s, 1H), 7.84 (s, 1H), 7.73 (dt, J = 7.2, 2.2 Hz, 1H), 7.56-7.51 (m, 2H), 7.37 (d, J = 4.9 Hz, 1H), 5.33 (d, J = 4.3 Hz, 1H), 4.84 (m, 1H) and 1.40 (d, J = 6.4 Hz, 3H) ppm |
| 245 | 253 | 1.99 | 1H NMR (400.0 MHz, DMSO) d 13.83 (s, 1H), 8.58 (d, J = 4.9 Hz, 1H), 8.32 (s, 1H), 7.89 (m, 1H), 7.73 (m, 1H), 7.54 (m, 2H), 7.37 (s, 1H), 3.84 (m, 1H), 1.62 (m, 2H) and 0.84 (m, 3H) ppm |

| # | M + 1 (obs) | RT (min) | 1H-NMR |
|---|---|---|---|
| 246 | 239 | 1.84 | 1H NMR (400.0 MHz, DMSO) d 13.83 (s, 1H), 8.58 (d, J = 4.9 Hz, 1H), 8.34 (s, 1H), 7.88 (s, 1H), 7.71-7.68 (m, 1H), 7.53-7.51 (m, 2H), 7.37 (d, J = 4.7 Hz, 1H), 4.12 (m, J = 6.6 Hz, 1H) and 1.32 (d, J = 6.6 Hz, 3H) ppm |
| 247 | 309 | 2.26 | 1H NMR (400.0 MHz, DMSO) d 13.82 (s, 1H), 8.58 (d, J = 4.7 Hz, 1H), 8.27 (s, 1H), 7.80 (s, 1H), 7.72 (d, J = 7.7 Hz, 1H), 7.52 (t, J = 7.6 Hz, 1H), 7.43 (m, 1H), 7.37 (d, J = 4.7 Hz, 1H), 3.58 (m, 1H), 2.38-2.30 (m, 2H), 1.72 (t, J = 7.2 Hz, 1H), 1.57 (dd, J = 7.4, 20.9 Hz, 1H), 1.36 (q, J = 7.0 Hz, 1H), 1.29-1.23 (m, 4H) and 0.80 (td, J = 7.3, 3.9 Hz, 6H) ppm |
| 248 | 283.11 | 2.09 | (DMSO, 400 MHz) 2.45 (3H, s), 2.75 (2H, ddd), 3.24 (3H, s), 4.21 (1H, dd), 7.27 (1H, s), 7.37 (1H, d), 7.55 (1H, s), 7.60 (1H, s), 8.31 (1H, s), 8.58 (1H, d), 13.85 (1H, br s). |
| 249 | 290.1 | 2.54 | 1H NMR (400.0 MHz, MeOH) d 2.52 (dd, J = 9.3, 12.1 Hz, 2H), 3.12-3.17 (m, 2H), 3.83-3.88 (m, 1H), 7.43 (d, J = 4.9 Hz, 1H), 7.66-7.69 (m, 2H), 7.85 (d, J = 7.0 Hz, 1H), 7.90 (s, 1H), 8.29 (s, 1H) and 8.62 (d, J = 4.7 Hz, 1H) ppm. |
| 250 | 315 | 2.23 | 1H NMR (400.0 MHz, DMSO) d 13.81 (s, 1H), 8.58 (d, J = 4.9 Hz, 1H), 8.32 (s, 1H), 7.70 (s, 1H), 7.59 (s, 1H), 7.36 (d, J = 4.9 Hz, 2H), 3.65 (d, 1H), 2.51 (s, 3H), 2.20 (brs, 2H), 2.02 (m, 1H) and 1.66-1.52 (m, 2H).) ppm |
| 251 | 279.1 | 2.11 | (DMSO, 400 MHz) 1.40-1.50 (1H, m), 1.71-1.82 (3H, m), 1.95-2.12 (2H, m), 2.66-2.71 (1H, m), 3.16 (1H, q), 7.38 (1H, d), 7.43 (1H, d), 7.52 (1H, t), 7.68-7.73 (2H, m), 8.31 (1H, s), 8.58 (1H, d), 13.79 (1H, br s). |
| 252 | 335 | 2.6 | 1H NMR (400.0 MHz, DMSO) d 13.70 (brs, 1H), 8.58 (d, J = 4.8 Hz, 1H), 8.31 (s, 1H), 7.88 (s, 1H), 7.69 (dd, J = 1.5, 5.8 Hz, 1H), 7.49 (s, 2H), 7.36 (d, J = 4.9 Hz, 1H), 3.85 (t, J = 6.7 Hz, 1H), 3.34 (s, 2H) and 1.76-0.69 (m, 15H) ppm |
| 253 | 321 | 2.5 | 1H NMR (400.0 MHz, DMSO) d 13.77 (brs, 1H), 8.58 (d, J = 4.8 Hz, 1H), 8.31 (s, 1H), 7.84 (s, 1H), 7.69 (d, J = 7.3 Hz, 1H), 7.50 (dd, J = 7.6, 20.1 Hz, 1H), 7.49 (s, 1H), 7.36 (d, J = 4.7 Hz, 1H), 3.88 (t, J = 6.7 Hz, 1H), 3.34 (s, 2H) and 1.80-0.77 (m, 13H) ppm |
| 254 | 309.06 | 2.5 | (DMSO, 400 MHz) 0.81 (3H, t), 2.08 (2H, q), 3.66 (1H, d), 3.77 (1H, d), 7.41 (1H, d), 7.55 (1H, d), 7.65 (1H, t), 7.70 (1H, s), 7.82-7.85 (2H, m), 8.26 (1H, s), 8.61 (1H, d), 13.85 (1H, br s). |
| 308 | 265 | 2.04 | (DMSO, 400 MHz) 1.85-1.95 (1H, m), 2.18-2.27 (1H, m), 2.72-2.77 (1H, m), 2.83-3.01 (3H, m), 3.16-3.23 (1H, m), 7.33 (1H, d), 7.42 (1H, d), 7.65 (1H, d), 7.78 (1H, s), 8.30 (1H, s), 8.55 (1H, d). |
| 320 | 319 | 2.76 | H NMR (400.0 MHz, DMSO) d 13.85 (brs, 1H), 8.61 (d, J = 4.7 Hz, 1H), 8.31 (s, 1H), 7.94-7.93 (m, 2H), 7.72-7.68 (m, 2H), 7.39 (d, J = 4.8 Hz, 1H), 5.57 (s, 1H), 3.68-3.63 (m, 4H) and 2.51-2.45 (m, 4H) ppm |
| 321 | 318 | 2.1 | H NMR (400.0 MHz, DMSO) d 13.90 (brs, 1H), 8.62 (d, J = 4.7 Hz, 1H), 8.30 (s, 1H), 7.92 (t, J = 2.3 Hz, 2H), 7.65 (m, 2H), 7.39 (d, J = 4.9 Hz, 1H), 5.50 (s, 1H), 2.78-2.71 (m, 4H) and 2.43-2.38 (m, 4H) ppm |
| 322 | 226 | 2.21 | H NMR (400.0 MHz, DMSO) d 13.82 (brs, 1H), 8.59 (d, J = 4.9 Hz, 1H), 8.34 (s, 1H), 7.84 (m, 1H), 7.76 (m, 1H), 7.62 (m, 1H), 7.56 (m, 1H), 7.36 (s, 1H), 5.36 (m, 1H) and 4.64 (d, J = 5.9 Hz, 2H) ppm |
| 328 | 366.03 | 6.55 | 1H NMR (400.0 MHz, DMSO) d 1.86 (d, 4H), 3.44 (d, 2H), 3.69 (m, 4H), 7.46 (s, 1H), 7.61 (s, 1H), 7.82 (d, 2H), 8.25 (s, 1H), 8.62 (s, 1H) and 13.91 (s, 1H) ppm |

Example 6

4-(3-(3-(2,2-Difluoroethyl)azetidin-3-yl)phenyl)-1H-pyrazolo[3,4-b]pyridine (Compound 191)

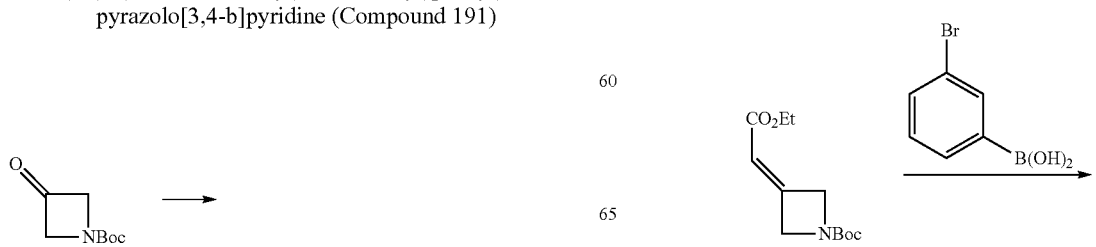

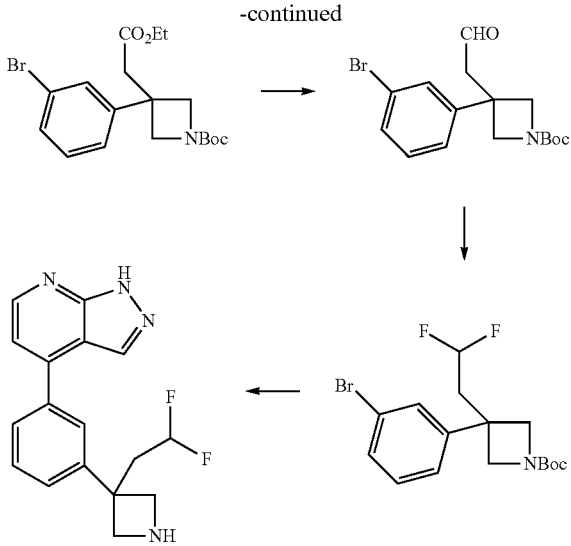

tert-Butyl 3-(2-ethoxy-2-oxoethylidene)azetidine-1-carboxylate

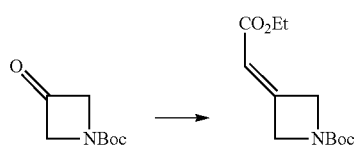 [SMILES: CC(C)(C)OC(=O)N1CC(=O)C1 ; CCOC(=O)C=C1CN(C(=O)OC(C)(C)C)C1]

To an ice-cold solution of ethyl 2-diethoxyphosphorylacetate (25.9 g, 116 mmol) in THF (200 mL) was added carefully NaH (60% dispersion in mineral oil, 4.62 g, 116 mmol) over 25 min. The cold bath was removed and after 30 min, tert-butyl 3-oxoazetidine-1-carboxylate (9.88 g, 57.7 mmol) in THF (40 mL) was added over 5 min. After 30 min, the reaction mixture was quenched with water and extracted twice with ethyl acetate. The combined organics were washed with brine, dried (MgSO4), filtered and concentrated. Purification by column chromatography (6/1 Pet ether/ethyl acetate) gave the ester (8.59 g, 62%) as a colourless oil.

1H NMR (400 MHz, CDCl3): 1.30 (3H, t), 1.46 (9H, s), 4.20 (2H, q), 4.61-4.62 (2H, m), 4.83-4.84 (2H, m).

tert-Butyl 3-(3-bromophenyl)-3-(2-ethoxy-2-oxoethyl)azetidine-1-carboxylate

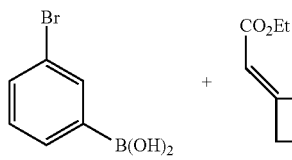

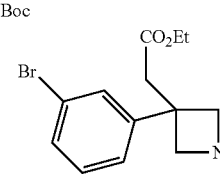

To a solution of [RhCl(COD)]2 (63 mg, 0.031 mmol) in dioxane (10 mL) was added aqueous KOH (1.5M, 8.29 mmol, 5.53 mL), followed by (3-bromophenyl)boronic acid (1.67 g, 8.29 mmol). Then a solution of the tert-butyl 3-(2-ethoxy-2-oxoethylidene)azetidine-1-carboxylate in dioxane (7.5 mL) was added. The reaction mixture was microwaved at 100° C. for 5 min at 300 W. Brine was added and the mixture was extracted twice with ethyl acetate. The combined organics were washed with brine and then dried (MgSO4), filtered and concentrated. Purification by column chromatography (4/1 Pet ether/ethyl acetate) gave the Michael adduct (1.31 g, 79%) as a light yellow oil.

1H NMR (400 MHz, CDCl3): 1.14 (3H, t), 1.44 (9H, s), 2.95 (2H, s), 4.02 (2H, q), 4.17 (2H, d), 4.23 (2H, d), 7.13 (1H, d), 7.21 (1H, t), 7.33 (1H, s), 7.38 (1H, d).

tert-Butyl 3-(3-bromophenyl)-3-(2-oxoethyl)azetidine-1-carboxylate

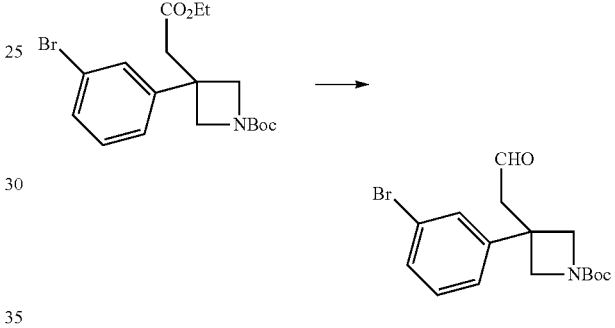

To a solution of tert-butyl 3-(3-bromophenyl)-3-(2-ethoxy-2-oxoethyl)azetidine-1-carboxylate (3.85 g, 9.68 mmol) in DCM (30 mL) was added diisobutylalumane (1M solution in DCM, 11.6 mmol, 11.6 mL) dropwise at −78° C. under nitrogen over 5 min. After 45 min at this temperature, MeOH (11.6 mmol, 0.476 mL) and water (58.1 mmol, 1.34 mL) were added and the ice-bath was removed. Sat. aq. sodium potassium tartrate (32 mL) was added and the cold bath was removed. Ether was added and the reaction mixture was stirred and left overnight. In the morning, the emulsion had vanished to give two layers which were separated. The aqueous was extracted with ether and the combined organics were dried (MgSO4), filtered and concentrated. Column chromatography (4/1 Pet ether/ethyl acetate) gave the product (2.12 g, 62%) as a colourless oil.

1H NMR (400 MHz, CDCl3): 1.45 (9H, s), 3.14 (2H, s), 4.09 (2H, d), 4.27 (2H, d), 7.15-7.40 (4H, m), 9.66 (1H, s).

tert-Butyl 3-(3-bromophenyl)-3-(2,2-difluoroethyl)azetidine-1-carboxylate

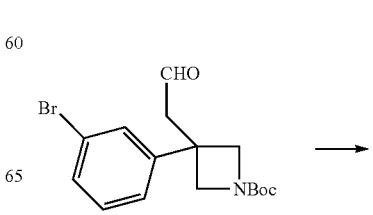

181
-continued

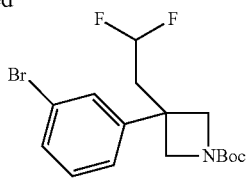

To an ice-cooled solution of tert-butyl 3-(3-bromophenyl)-3-(2-oxoethyl)azetidine-1-carboxylate (408 mg, 1.15 mmol) in DCM (8 mL) was added Deoxofluor (765 mg, 3.46 mmol) dropwise and then the ice-bath was removed. After 1 hr, the reaction mixture was poured into stirring sat. aq. sodium bicarbonate carefully to quench. After 30 min, the aqueous layer was extracted with DCM twice and the organics were dried (MgSO4), filtered and concentrated. Purification by column chromatography (3/1 Pet ether/ethyl acetate) yielded the product (172 mg, 40%) as a colourless oil.

1H NMR (400 MHz, CDCl3): 1.46 (9H, s), 2.49 (2H, td), 4.13 (2H, d), 4.25 (2H, d), 5.41 (1H, tt), 7.10 (1H, d), 7.26-7.46 (3H, m).

4-(3-(3-(2,2-Difluoroethyl)azetidin-3-yl)phenyl)-1H-pyrazolo[3,4-b]pyridine

To a mixture of tert-butyl 3-(3-bromophenyl)-3-(2,2-difluoroethyl)azetidine-1-carboxylate (172 mg, 0.457 mmol) and 4-(4,4,5,5-tetramethyl-1,3,2-dioxaborolan-2-yl)-1-trityl-1H-pyrazolo[3,4-b]pyridine (322 mg, 0.594 mmol) in DME (5 mL) was added aq. sodium carbonate (2M, 1.37 mmol, 0.686 mL) followed by tetrakistriphenylphosphine palladium (21.1 mg, 18.3 μmol). The mixture of reagents was microwaved at 150° C. for 20 min and then diluted with water and extracted twice with ethyl acetate. The organics were dried (MgSO4), filtered and concentrated to give a cream foam.

The crude Suzuki coupling adduct was dissolved in DCM (6 mL) and triethylsilane (2 mL), and TFA (2 mL) was added dropwise at rt. After 45 min, the reaction was concentrated at <40° C. and then purified by column chromatography (70/9/1, DCM/MeOH/aq. NH3) to give the azetidine (64.4 mg, 45%) as a white solid.

1H NMR (400 MHz, DMSO): 2.64 (2H, td), 3.64 (2H, d), 3.87 (2H, d), 5.87 (1H, tt), 7.34 (1H, d), 7.40 (1H, d), 7.56-7.61 (2H, m), 7.74 (1H, d), 8.27 (1H, s), 8.59 (1H, d), 13.82 (1H, br s).

182

Table 7 below depicts data for certain exemplary compounds made in general by a similar route to that outlined in Example 6.

TABLE 7

| # | M + 1 (obs) | RT (min) | 1H-NMR |
|---|---|---|---|
| 191 | 315.09 | 2.06 | (DMSO, 400 MHz) 2.64 (2H, td), 3.64 (2H, d), 3.87 (2H, d), 5.87 (1H, td), 7.34 (1H, d), 7.40 (1H, d), 7.58 (1H, t), 7.61 (1H, s), 7.74 (1H, d), 8.27 (1H, s), 8.59 (1H, d), 13.82 (1H, br s). |
| 192 | | | (400 MHz, DMSO) 3.34 (2H, s), 3.58 (2H, d), 3.91 (2H, d), 7.40 (2H, d), 7.60-7.66 (2H, m), 7.78 (1H, d), 8.36 (1H, s), 8.60 (1H, d), 13.83 (1H, br s). |

Example 7

4-(3-(3-Vinylpyrrolidin-3-yl)phenyl)-1H-pyrazolo[3,4-b]pyridine (Compound 193)

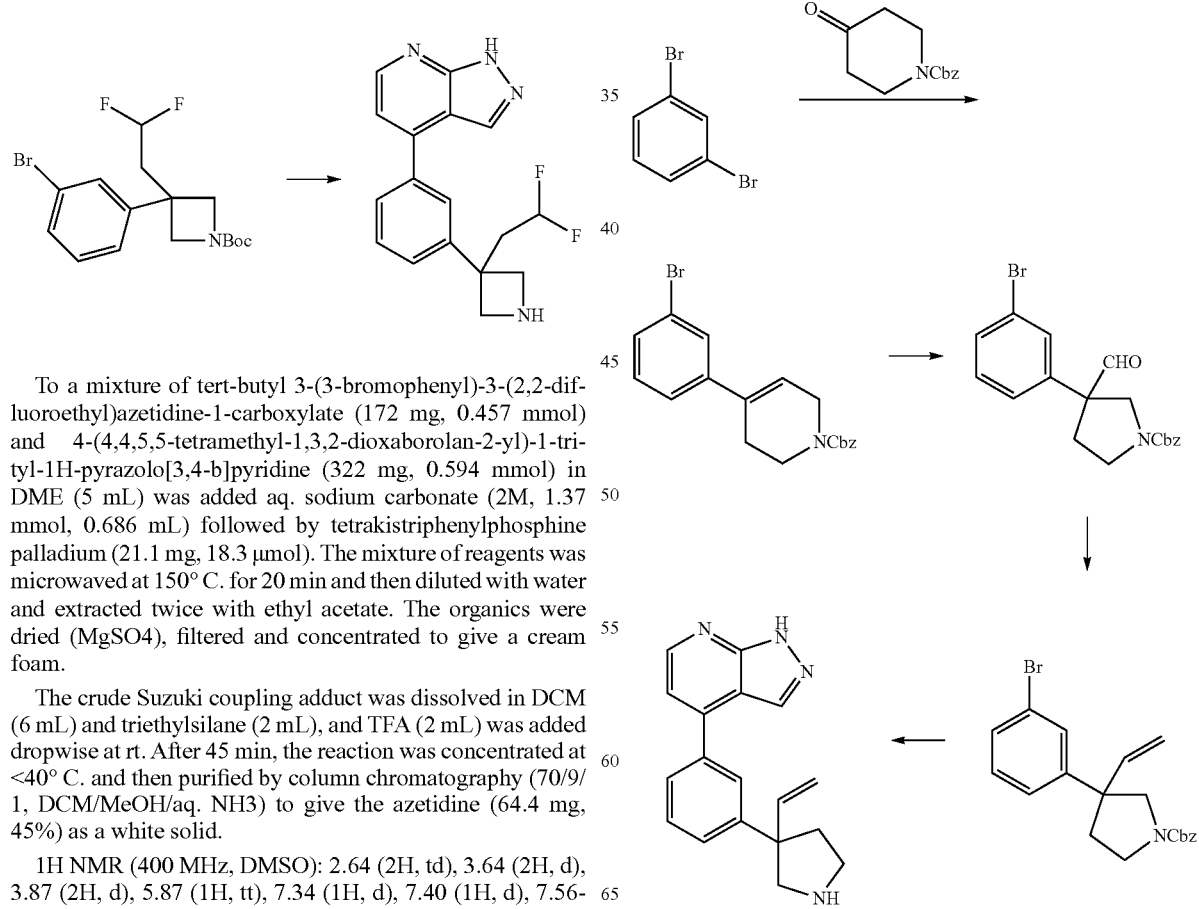

Benzyl 4-(3-bromophenyl)-5,6-dihydropyridine-1 (2H)-carboxylate

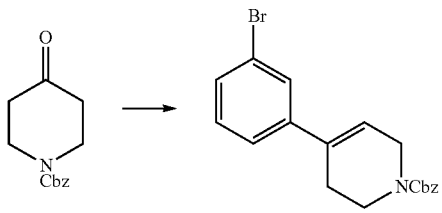 [SMILES: O=C1CCN(C(=O)OCc2ccccc2)CC1 ; O=C(OCc1ccccc1)N1CC=C(c2cccc(Br)c2)CC1]

Isopropylmagnesium chloride-lithium chloride complex (18.0 mL of 14% w/v, 17.4 mmol) was placed in a 100 mL 3-neck flask under nitrogen and cooled between −15 and −20° C. 1,3-Dibromobenzene (2 mL, 16.6 mmol) was added and the reaction mixture maintained at below −5° C. After 2 h, the reaction mixture was cooled to −25° C., THF (20 mL) was added followed by benzyl 4-oxopiperidine-1-carboxylate (3.94 g, 16.9 mmol). After 5 min, the cold bath was removed. After 1.5 h, water was added to the reaction mixture followed by sat. aq. NH4Cl. and then extraction with ethyl acetate was carried out twice. The combined organics were dried (MgSO4), filtered and concentrated.

The colourless residue was dissolved in DCM (50 mL) and BF3-OEt2 (7.57 mL, 59.7 mmol) was added under nitrogen with ice-bath cooling. After 5 min, the cold bath was removed. After 2 h, the reaction was quenched with sat. aq. sodium bicarbonate with ice-bath cooling. The mixture was extracted twice with DCM and the combined organics were dried (MgSO4), filtered and concentrated.

Purification by column chromatography (5/1 Pet ether/ethyl acetate) gave the desired alkene as a colourless oil.

1H NMR (400 MHz, CDCl3): 2.53 (2H, app br s), 3.74 (2H, t), 4.19 (2H, t), 5.20 (2H, s), 6.03-6.09 (1H, m), 7.22 (1H, t), 7.28-7.41 (7H, m), 7.52 (1H, s).

Benzyl 3-(3-bromophenyl)-3-formylpyrrolidine-1-carboxylate

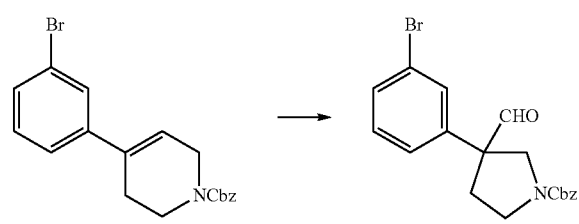 [SMILES: O=C(OCc1ccccc1)N1CC=C(c2cccc(Br)c2)CC1 ; O=CC1(c2cccc(Br)c2)CCN(C(=O)OCc2ccccc2)C1]

mCPBA (2.28 g, 13.2 mmol) was added in one portion to a solution of benzyl 4-(3-bromophenyl)-5,6-dihydropyridine-1(2H)-carboxylate (2.94 g, 7.90 mmol) in ethyl acetate (60 mL) and the mixture heated at 40° C. After 4 h, a further portion of mCPBA (1 g, 5.79 mmol) was added and the reaction continued to be stirred overnight. Sat. aq. sodium carbonate was added and the mixture was extracted twice with ethyl acetate. The combined organics were washed with a further portion of sat. aq. sodium carbonate and then dried (MgSO4), filtered and concentrated.

BF3.OEt2 (3.95 mL, 31.17 mmol) was added to a solution of the residue in DCM (100 mL) with ice-bath cooling (colourless to yellow). The ice-bath was removed and after 1 h the reaction was quenched with sat. aq. sodium bicarbonate. The layers were separated and then the aqueous layer was extracted with DCM. The combined organics were washed with sat. aq. sodium bicarbonate and then dried, filtered and concentrated. Purification by column chromatography (2/1 Pet ether/ethyl acetate) gave the product as a white solid.

1H NMR (400 MHz, CDCl3): 2.17-2.28 (1H, m), 2.77-2.87 (1H, m), 3.40 (1H, quin), 3.51-3.73 (2H, m), 4.43 (1H, dd), 5.12-5.22 (2H, m), 7.14 (1H, t), 7.27-7.51 (8H, m), 9.46 (1H, d).

Benzyl 3-(3-bromophenyl)-3-vinylpyrrolidine-1-carboxylate

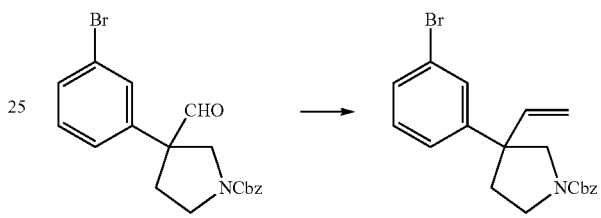

KHMDS (0.5M in toluene, 6.536 mL, 3.268 mmol) was added to a suspension of Ph3PCH3Br (1.216 g, 3.404 mmol) in THF (15 mL) at rt. After 1 h, benzyl 3-(3-bromophenyl)-3-formylpyrrolidine-1-carboxylate was added at −20 and then the cold bath was removed. After 2 h, the reaction was quenched with MeOH (2 mL) and sat. aq. sodium bicarbonate was added. The mixture was extracted twice with ethyl acetate and then dried (MgSO4), filtered and concentrated.

Purification by column chromatography (3/1 Pet ether/ethyl acetate) gave the product as a colourless oil.

1H NMR (400 MHz, CDCl3): 2.08-2.11 (2H, m), 3.32-3.48 (3H, m), 3.77 (1H, dd), 4.84 (1H, dd), 4.96-5.03 (3H, m), 5.74 (1H, dd), 6.98-7.23 (9H, m).

4-(3-(3-Vinylpyrrolidin-3-yl)phenyl)-1H-pyrazolo[3,4-b]pyridine

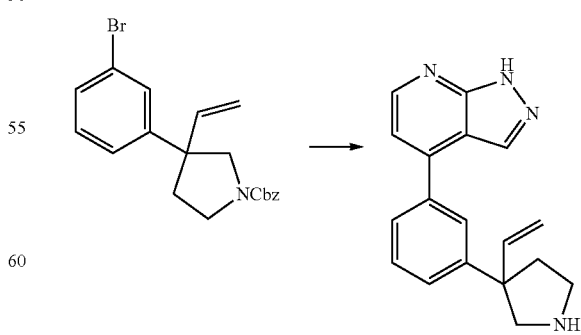

To a mixture of benzyl 3-(3-bromophenyl)-3-vinylpyrrolidine-1-carboxylate (203 mg, 0.526 mmol) and 4-(4,4,5,5-tetramethyl-1,3,2-dioxaborolan-2-yl)-1-trityl-1H-pyrazolo

[3,4-b]pyridine (307 mg, 0.631 mmol) in DME (4 mL) was added aq. sodium carbonate (2M, 1.58 mmol, 0.789 mL) followed by tetrakistriphenylphosphine palladium (60.7 mg, 52.6 µmol). The mixture of reagents was microwaved at 150° C. for 40 min and then diluted with water and extracted twice with ethyl acetate. The organics were dried (MgSO4), filtered and concentrated.

The residue from above was dissolved in DCM (6 mL) and triethylsilane (1 mL then TFA (1 mL) were added. After 5 min, the reaction mixture was concentrated in vacuo and then purified by column chromatography (1/3 Pet ether/ethyl acetate) giving the pyrazolopyridine that was taken on crude into the next step.

The carbamate product from above was dissolved in EtOH (3 mL) and conc. HCl (4 mL) and heated to 80° C. After 2 h, the reaction was concentrated at <50° C. Aqueous 2M sodium carbonate and DCM were added and the layers separated. The aqueous was extracted again with DCM and the combined organics, dried (MgSO4), filtered and concentrated.

The residue was purified by Fractionlynx prep HPLC and the resulting fractions passed through a bicarbonate SPE cartridge to give the desired amine (42 mg, 28%) as a white solid after concentration and trituration with ether.

1H NMR (400 MHz, DMSO): 2.10-2.25 (2H, m), 2.91-3.07 (3H, m), 3.27-3.35 (1H, m), 5.01 (1H, d), 5.07 (1H, d), 6.10 (1H, dd), 7.37 (1H, d), 7.45 (1H, d), 7.54 (1H, t), 7.71 (2H, s), 8.24 (1H, s), 8.58 (1H, d), 13.8 (1H, br s).

Table 8 below depicts data for certain exemplary compounds made in general by a similar route to that outlined in Example 7.

TABLE 8

| # | M + 1 (obs) | RT (min) | 1H-NMR |
|---|---|---|---|
| 193 | 291.2 | 2.06 | (DMSO, 400 MHz) 2.10-2.15 (1H, m), 2.22-2.25 (1H, m), 2.91-2.99 (2H, m), 3.05 (1H, d), 3.28 (1H, d), 5.01 (1H, d), 5.07 (1H, d), 6.10 (1H, dd), 7.37 (1H, d), 7.45 (1H, d), 7.54 (1H, t), 7.71 (2H, s), 8.24 (1H, s), 8.58 (1H, d), 13.30-14.20 (1H, br s) |
| 194 | 293.18 | 2.05 | (DMSO, 400 MHz) 0.63 (3H, t), 1.71 (2H, q), 2.02 (2H, t), 2.84-3.27 (4H, m), 7.37-7.42 (2H, m), 7.53 (1H, t), 7.66-7.67 (2H, m), 8.25 (1H, s), 8.58 (1H, s). |
| 195 | | | (DMSO, 400 MHz) 1.35 (3H), 1.94-2.08 (2H, m), 2.93-3.03 (3H, m), 3.52-3.63 (1H, m), 7.38 (1H, d), 7.50-7.55 (2H, m), 7.67-7.74 (2H, m), 8.27 (1H, s), 8.58 (1H, d), 13.55-14.10 (1H, br s). |
| 196 | | | (400 MHz, DMSO) 1.94-1.99 (1H, m), 2.07-2.11 (1H, m), 2.85-2.90 (2H, m), 2.96-2.98 (1H, m), 3.27-3.30 (1H, m), 3.49 (1H, d), 3.54 (1H, d), 7.27-7.53 (3H, m), 7.66-7.71 (2H, m), 8.29 (1H, s), 8.58 (1H, d), 13.72 (1H, br s). |
| 197 | 305.09 | 2.09 | (DMSO, 400 MHz) 1.33 (3H, d), 2.07-2.14 (1H, m), 2.27-2.34 (1H, m), 2.90-3.00 (2H, m), 3.07-3.14 (2H, m), 5.50-5.58 (1H, m), 5.92 (1H, d, J = 11.6 Hz), 7.37 (1H, d), 7.50-7.56 (2H, m), 7.68 (1H, d), 7.83 (1H, s), 8.22 (1H, s), 8.58 (1H, d). |
| 198 | 319.19 | 2.25 | (DMSO, 400 MHz) 0.66 (3H, t), 1.71 (2H, t), 2.09-2.12 (1H, m), 2.28-2.33 (1H, m), 2.97 (2H, q), 3.14 (2H, q), 5.37-5.43 (1H, m), 5.88 (1H, d, J = 11.2 Hz), 7.36 (1H, d), 7.51-7.69 (3H, m), 7.83 (1H, s), 8.23 (1H, s), 8.58 (1H, d), 13.85 (1H, br s). |
| 199 | 319.19 | 2.24 | (DMSO, 400 MHz) 1.36 (3H, s), 1.72 (3H, s), 2.05-2.12 (1H, m), 2.27-2.33 (1H, m), 2.94-2.99 (2H, m), 3.09 (1H, d), 3.16 (1H, d), 5.73 (1H, s), 7.36 (1H, d), 7.51-7.82 (4H, m), 8.20 (1H, s), 8.58 (1H, d), 13.83 (1H, br s). |
| 200 | 304.14 | 1.93 | (DMSO, 400 MHz) 2.11-2.18 (2H, m), 2.93-3.09 (5H, m), 3.25 (1H, d), 7.40 (1H, d), 7.52-7.62 (2H, m), 7.76-7.79 (2H, m), 8.36 (1H, s), 8.60 (1H, d), 13.81 (1H, br s). |
| 201 | 315.08 | 2.03 | (DMSO, 400 MHz) 2.18-2.36 (2H, m), 2.87-3.13 (3H, m), 3.50 (1H, d), 6.24 (1H, t, J = 57 Hz), 7.39 (1H, d), 7.51 (1H, d), 7.59 (1H, t), 7.75 (1H, s), 7.79 (1H, d), 8.26 (1H, s), 8.60 (1H, d), 13.83 (1H, br s). |

Example 8

4-(3-Methylene-2,3-dihydro-1H-inden-5-yl)-1H-pyrazolo[3,4-b]pyridine (Compound 202) and (6-(1H-Pyrazolo[3,4-b]pyridin-4-yl)-2,3-dihydro-1H-inden-1-yl)methanol (Compound 203)

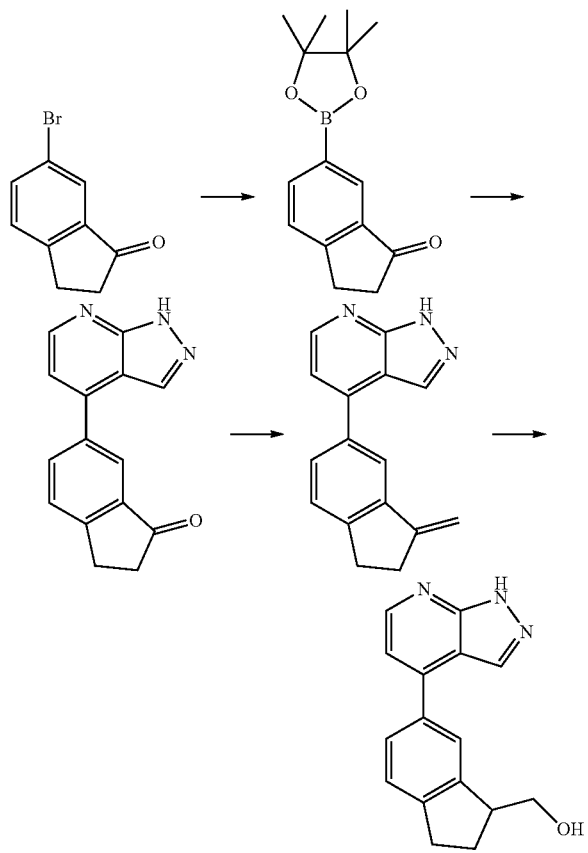

6-(4,4,5,5-Tetramethyl-1,3,2-dioxaborolan-2-yl)-2,3-dihydro-1H-inden-1-one

A mixture of 6-bromo-2,3-dihydro-1H-inden-1-one (4.60 g, 21.8 mmol), potassium acetate (6.42 g, 65.4 mmol), bis(pinacolato)diboron (6.64 g, 26.2 mmol), dichloro[1,1'-bis(diphenylphosphino)ferrocene]palladium(II) dichloromethane adduct (690 mg, 0.943 mmol) in DME (100 mL) was heated at 110° C. After 2 h, water was added and the mixture extracted with ethyl acetate twice. The combined organics were washed with brine, dried (MgSO4), filtered and concentrated. Purification by column chromatography (3/1, Pet ether/ethyl acetate) yielded the product (5.13 g, 91%) as an off-white solid.

1H NMR (400 MHz, DMSO): 1.31 (12H, s), 2.65 (2H, t), 3.14 (2H, t), 7.62 (1H, d), 7.90-7.93 (2H, m).

6-(1H-Pyrazolo[3,4-b]pyridin-4-yl)-2,3-dihydro-1H-inden-1-one

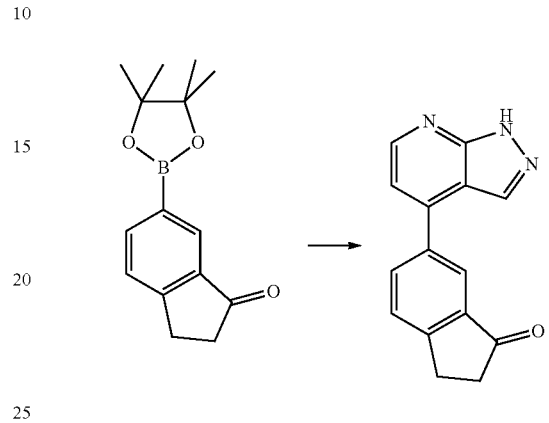

To a mixture of 6-(4,4,5,5-tetramethyl-1,3,2-dioxaborolan-2-yl)-2,3-dihydro-1H-inden-1-one (3 g, 11.6 mmol) and 4-iodo-1H-pyrazolo[3,4-b]pyridine (3.13 g, 12.8 mmol) in DME (20 mL) was added aq. sodium carbonate (2M, 11.62 mL, 23.2 mmol) followed by tetrakistriphenylphosphine palladium (978 mg, 0.846 mmol). The mixture was microwaved for 90 min at 150° C. The reaction mixture was diluted with ethyl acetate and water and the layers separated. The organic layer was filtered off since it contained a yellow precipitate (desired prod ca. 85% pure) and then it was washed with water and then dried (MgSO4), filtered and concentrated and added to the precipitate above. The solids were recrystallised from boiling MeOH-TRF to provide the pure ketone (1.62 g, 56%) as a yellow solid.

1H NMR (400 MHz, DMSO): 2.74 (2H, br s), 3.21 (2H, br s), 7.43 (1H, d), 7.82 (1H, d), 8.01 (1H, s), 8.18 (1H, d), 8.29 (1H, s), 8.60 (1H, d), 13.87 (1H, br s).

(Compound 202) 4-(3-Methylene-2,3-dihydro-1H-inden-5-yl)-1H-pyrazolo[3,4-b]pyridine

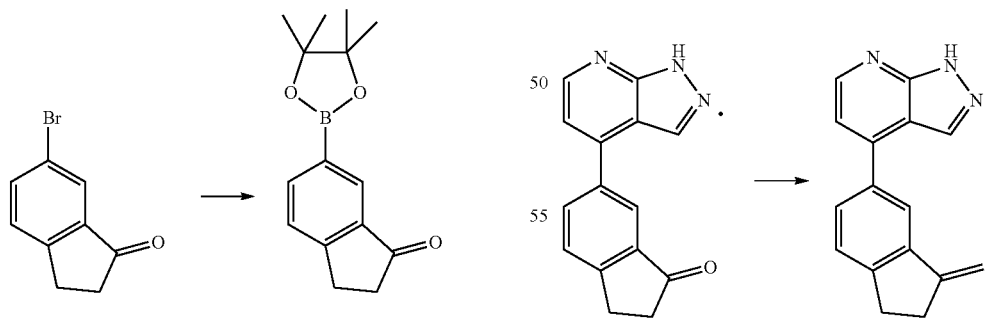

KHMDS (0.5M in toluene, 3.46 mL, 1.73 mmol) was added to a suspension of Ph3PCH3Br (644 mg, 1.80 mmol) in THF (15 mL) at rt. After 1 hr, pyrazolo[3,4-b]pyridin-4-yl)-2,3-dihydro-1H-inden-1-one (257 mg, 103 mmol) was added at rt. After 1 h, MeOH (2 mL) was added followed shortly afterwards by sat. aq. sodium bicarbonate. The mixture was extracted twice with ethyl acetate and then the combined organics were dried (MgSO4), filtered and concentrated. Column chromatography (1/2 Pet ether/ethyl acetate) gave the product (150 mg, 59%) as a white solid.

1H NMR (400 MHz, DMSO): 2.10-2.13 (2H, m), 2.27-2.30 (2H, m), 4.35 (1H, s), 4.84 (1H, t), 6.59 (1H, d), 6.70 (1H, d), 6.92 (1H, dd), 7.15 (1H, s), 7.47 (1H, s), 7.77 (1H, d).

(6-(1H-Pyrazolo[3,4-b]pyridin-4-yl)-2,3-dihydro-1H-inden-1-yl)methanol

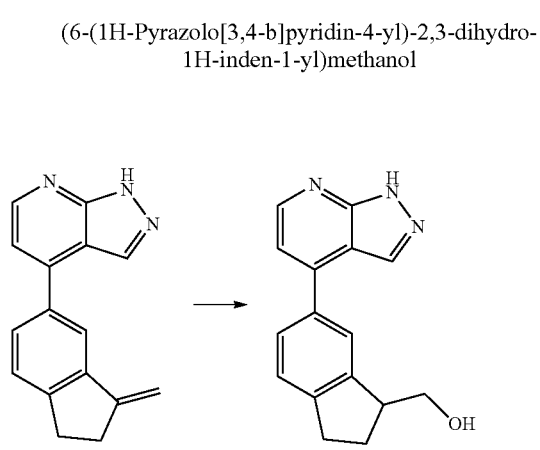

To a solution of the 4-(3-methylene-2,3-dihydro-1H-inden-5-yl)-1H-pyrazolo[3,4-b]pyridine (86 mg, 0.348 mmol) in THF (2.5 mL) with ice-bath cooling was added 9-BBN (0.5M in THF, 1.39 mL, 0.696 mmol) over 3 min giving a straw coloured solution. The cold bath was removed after 5 min.

After 3 h, 1 M NaOH (1 mL) was added followed by 30% aq. hydrogen peroxide (0.4 mL) at rt. After 15 min, sat. aq. sodium bicarbonate was added and the mixture was extracted twice with ethyl acetate. The combined organics were dried (MgSO4), filtered and concentrated. The residue was purified by Fractionlynx HPLC purification and the fractions passed through a bicarbonate SPE cartridge. Concentration gave the alcohol (36 mg, 39%) as a white solid.

1H NMR (400 MHz, DMSO): 1.82-1.84 (1H, m), 2.18-2.24 (1H, m), 2.84-3.01 (2H, m), 3.30-3.34 (1H, m), 3.57-3.69 (2H, m), 7.32 (1H, d), 7.41 (1H, d), 7.64 (1H, d), 7.80 (1H, s), 8.30 (1H, s), 8.55 (1H, d), 13.75 (1H, br s).

Table 9 below depicts data for certain exemplary compounds made in general by a similar route to that outlined in Example 8.

TABLE 9

| # | M + 1 (obs) | RT (min) | 1H-NMR |
|---|---|---|---|
| 202 | 248.13 | 3.26 | (DMSO, 400 MHz) 2.07-2.12 (2H, m), 2.25-2.30 (2H, m), 4.35 (1H, s), 4.84 (1H, s), 6.59 (1H, d), 6.70 (1H, d), 6.92 (1H, dd), 7.15 (1H, s), 7.47 (1H, s), 7.77 (1H, d). |
| 203 | 266.09 | 2.48 | (DMSO, 400 MHz) 1.88-1.94 (1H, m), 2.17-2.25 (1H, m), 2.82-3.00 (2H, m), 3.31-3.35 (1H, m), 3.57-3.69 (2H, m), 7.32 (1H, d), 7.42 (1H, d), 7.65 (1H, d), 7.80 (1H, s), 8.30 (1H, s), 8.55 (1H, d). 13.89 (1H, s). |

Example 9

Preparation of 2-(3-(3-chloro-1H-pyrazolo[3,4-b]pyridin-4-yl)phenyl)-2-methylbutan-1-amine (Compound 204)

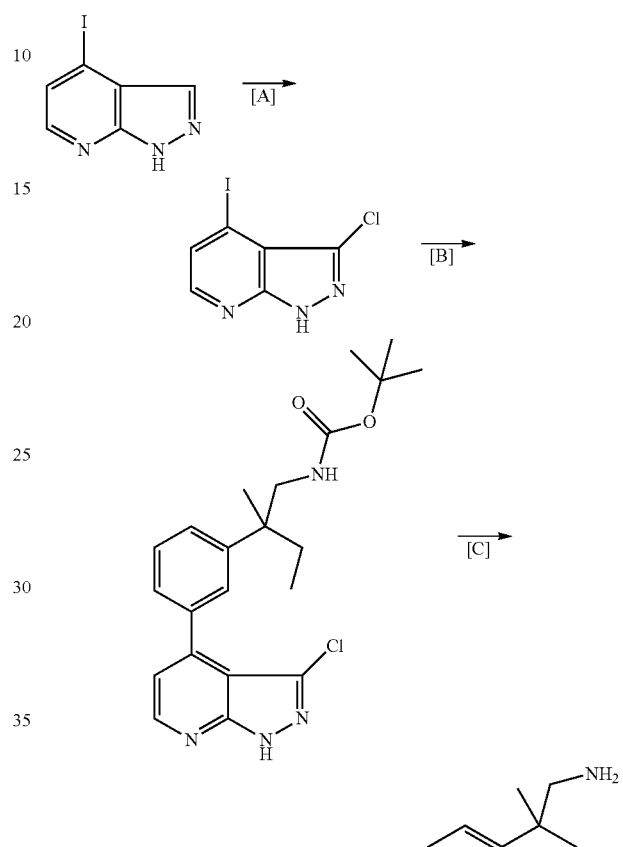

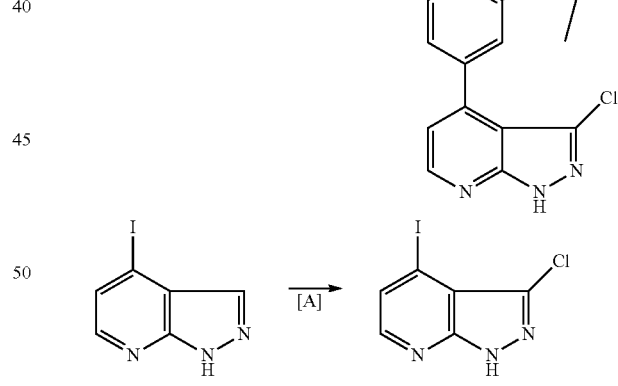

[A]—Preparation of 3-chloro-4-iodo-1H-pyrazolo[3,4-b]pyridine 4-iodo-1H-pyrazolo[3,4-b]pyridine (1 g, 4.081 mmol) and NCS (653.9 mg, 4.897 mmol) were dissolved/suspended in dry CH3CN (20 mL) and refluxed overnight (material dissolves as temperature reaches reflux point to give slightly cloudy solution). The reaction mixture was allowed to cool to RT and concentrated under reduced pressure to give a dark yellow solid. This material was partitioned between EtOAc (~300 mL) and brine. The organic layer was washed with brine (1×50 mL), saturated Na2S2O3 (1×50 mL) and brine (1×50 mL) and then dried over Na2SO4, filtered and concentrated under reduced pressure to give a yellow solid. The resulting solid was purified by column chromatography (25% EtOAc in DCM, ~100 mL silica) to give a white solid (641 mg, 56% Yield).

1H NMR (400.0 MHz, DMSO: 7.88 (1H, d), 8.23 (1H, d).

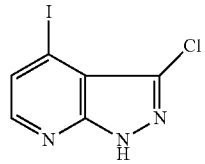

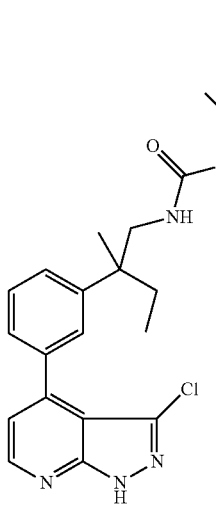

[B]—Preparation of tert-butyl 2-(3-(3-chloro-1H-pyrazolo[3,4-b]pyridin-4-yl)phenyl)-2-methylbutyl-carbamate 3-chloro-4-iodo-1H-pyrazolo[3,4-b]pyridine (100 mg, 0.3578 mmol), tert-butyl 2-methyl-2-(3-(4,4,5,5-tetramethyl-1,3,2-dioxaborolan-2-yl)phenyl)butylcarbamate (139.3 mg, 0.3578 mmol), Na2CO3 (536.5 µL of 2 M, 1.073 mmol) and Pd(PPh3)4 (41.35 mg, 0.03578 mmol) were placed in a microwave tube and Dioxane (1 mL) was added. The resulting suspension was stirred at 150° C. in the microwave (using a 10 minute ramp and nitrogen cooling) for 45 minutes. Reaction mixture partitioned between EtOAc and brine. The aqueous layer was extracted with EtOAc (3×20 mL) and the combined organics were dried over Na2SO4, filtered, and concentrated under reduced pressure to give a dark yellow gum. This material was purified by column chromatography (35% EtOAc in hexanes, loaded in DCM, ~75 mL silica) to give a slightly yellow gum (68.4 mg, 46% Yield).

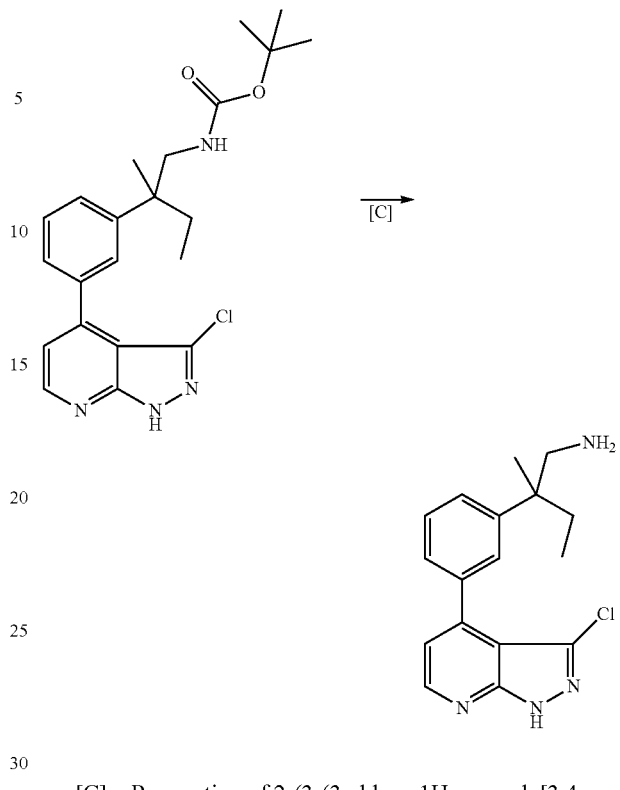

[C]—Preparation of 2-(3-(3-chloro-1H-pyrazolo[3,4-b]pyridin-4-yl)phenyl)-2-methylbutan-1-amine (compound 204)

tert-butyl 2-(3-(3-chloro-1H-pyrazolo[3,4-b]pyridin-4-yl)phenyl)-2-methylbutylcarbamate (60 mg, 0.1446 mmol) was dissolved in dry DCM (2 mL) and cooled in an ice-bath. TFA (2 mL,) was added slowly dropwise and the resultant was stirred at 0° C. for ~25 minutes and at RT for ~45 minutes. The reaction mixture was concentrated under reduced pressure and partitioned between EtOAc and saturated Na2CO3. The aqueous layer was extracted with EtOAc (3×10 mL) and the combined organics were dried over Na2SO4, filtered and concentrated under reduced pressure to give a slightly yellow gum. The resulting mixture was purified by column chromatography (9% MeOH/1% NH4OH in DCM, ~50 mL silica) to give a white solid (25.2 mg, 55% Yield).

1H NMR (400.0 MHz, DMSO): 0.64 (t, J=7.4 Hz, 3H), 1.27 (s, 3H), 1.56 (dd, J=7.4, 13.8 Hz, 1H), 1.79 (dd, J=7.3, 13.8 Hz, 1H), 2.65 (d, J=12.9 Hz, 1H), 2.82 (d, J=12.8 Hz, 1H), 7.22 (d, J=4.8 Hz, 1H), 7.40-7.51 (m, 4H) and 8.62 (d, J=4.6 Hz, 1H) ppm Table 10 below depicts data for certain exemplary compounds made in general by a similar route to that outlined in Example 9.

TABLE 10

| # | M + 1 (obs) | RT (min) | 1H-NMR |
|---|---|---|---|
| 204 | 315.1 | 2.27 | 1H NMR (400.0 MHz, DMSO) d 0.64 (t, J = 7.4 Hz, 3H), 1.27 (s, 3H), 1.56 (dd, J = 7.4, 13.8 Hz, 1H), 1.79 (dd, J = 7.3, 13.8 Hz, 1H), 2.65 (d, J = 12.9 Hz, 1H), 2.82 (d, J = 12.8 Hz, 1H), 7.22 (d, J = 4.8 Hz, 1H), 7.40-7.51 (m, 4H) and 8.62 (d, J = 4.6 Hz, 1H) ppm |
| 205 | 295 | 3.35 | 1H NMR (400.0 MHz, DMSO) d 1.62-1.65 (m, 2H), 1.79-1.82 (m, 2H), 7.24 (d, 1H), 7.50-7.60 (m, 4H), 8.63 (d, 1H) and 14.00 (bs, 1H, NH) ppm |

TABLE 10-continued

| # | M + 1 (obs) | RT (min) | 1H-NMR |
|---|---|---|---|
| 206 | 343.02 | 2.57 | 1H NMR (400.0 MHz, DMSO) d 8.62 (d, 1H), 7.55-7.44 (m, 4H), 7.23 (d, 1H), 3.73-3.66 (m, 2H), 3.46-3.19 (masked signal, 4H), 2.72 (s, 2H), 2.09-2.06 (m, 2H) and 1.88-1.81 (m, 2H) ppm |
| 207 | 327 | 3.13 | 1H NMR (400.0 MHz, DMSO) d 1.75-1.82 (m, 1H), 1.97-2.04 (m, 1H), 2.15-2.28 (m, 4H), 2.40 (s, 3H), 2.82 (s, 2H), 7.05 (s, 1H), 7.08 (s, 1H), 7.21-7.22 (m, 2H) and 8.60 (d, 1H) ppm |
| 208 | 373 | 2.77 | 1H NMR (400.0 MHz, DMSO) d 0.65 (t, 3H), 1.26 (s, 3H), 1.55 (dd, 1H), 1.76-1.82 (m, 3H), 2.64 (d, 1H), 2.69-2.73 (m, 2H), 2.81 (d, 1H), 3.44 (t, 2H), 4.51 (bs, 1H, OH), 7.19-7.31 (m, 4H) and 8.59 (d, 1H) ppm |
| 209 | 357.04 | 2.73 | 1H NMR (400.0 MHz, DMSO) d 1.81-1.85 (m, 2H), 2.05-2.08 (m, 2H), 2.42 (s, 3H), 2.71 (s, 2H), 3.44 (t, 2H), 3.67-3.70 (m, 2H), 7.22 (d, 1H), 7.26 (s, 1H), 7.30 (s, 2H) and 8.61 (d, 1H) ppm |
| 210 | 357.05 | 3.5 | 1H NMR (400.0 MHz, MeOH) d 0.77 (t, 3H), 1.02 (t, 3H), 1.51 (s, 3H), 1.70-1.80 (m, 3H), 1.93-1.98 (m, 1H), 2.77 (t, 2H), 3.14 (d, 2H), 3.33 (masked signal, 2H), 7.23 (d, 1H), 7.40 (s, 2H), 7.43 (s, 1H) and 8.60 (d, 1H) ppm |
| 211 | 341.1 | 3.32 | 1H (DMSO) 1.25 (3H, t), 1.76-1.82 (1H, m), 1.97-2.03 (1H, m), 2.16-2.35 (4H, m), 2.69 (2H, q), 2.82 (2H, s), 7.07 (1H, s), 7.10 (1H, s), 7.22 (1H, d), 7.25 (1H, s), 8.60 (1H, d). |
| 255 | 330.96 | 3.02 | 1H NMR (400.0 MHz, DMSO) d 1.75-1.84 (m, 1H), 1.94-2.08 (m, 1H), 2.16-2.34 (m, 4H), 2.83 (s, 2H), 7.03-7.07 (m, 1H), 7.12 (s, 1H), 7.25-7.28 (m, 2H) and 8.64 (d, 1H) ppm |
| 256 | 343.1 | 3.34 | 1H NMR (400.0 MHz, CDCl3) d 0.78 (t, 3H), 1.33 (t, 3H), 1.37 (s, 3H), 1.57-1.61 (m, 1H), 1.86 (dd, 1H), 2.75-2.81 (m, 3H), 3.03 (d, 1H), 7.18 (d, 1H), 7.25-7.28 (m, 2H), 7.32 (s, 1H), 8.62 (d, 1H) and 11.85 (bs, 1H, NH) ppm |
| 257 | 361 | 2.82 | 1H NMR (400.0 MHz, DMSO) d 1.81-1.87 (m, 2H), 2.05 (m, 2H), 2.73 (s, 2H), 3.42 (dd, J = 2.5, 20.2 Hz, 2H), 3.69 (dd, J = 3.6, 16.9 Hz, 2H), 7.27 (d, J = 4.7 Hz, 1H), 7.34 (dd, J = 9.5, 11.3 Hz, 3H) and 8.64 (d, J = 4.6 Hz, 1H) ppm |
| 258 | 333 | 3.27 | 1H NMR (400.0 MHz, DMSO) d 0.64 (t, 3H), 1.26 (s, 3H), 1.55 (dd, 1H), 1.78 (dd, 1H), 2.66 (d, 1H), 2.83 (d, 1H), 7.25-7.32 (m, 4H) and 8.63 (d, J = 4.6 Hz, 1H) ppm |
| 259 | 309.1 | 3.48 | 1H NMR (400.0 MHz, DMSO) d 2.01-2.09 (m, 1H), 2.27-2.36 (m, 1H), 2.69-2.82 (m, 4H), 7.27 (d, J = 4.6 Hz, 1H), 7.59-7.64 (m, 3H), 7.69 (d, J = 1.4 Hz, 1H), 8.65 (d, J = 4.6 Hz, 1H) and 14.01 (bs, 1H, NH) ppm |
| 260 | 313.1 | 2.93 | 1H NMR (400.0 MHz, DMSO) d 1.76-1.84 (m, 1H), 1.98-2.03 (m, 1H), 2.18-2.30 (m, 4H), 2.83 (s, 2H), 7.21-7.29 (m, 3H), 7.41 (dd, J = 1.3, 6.5 Hz, 1H), 7.43-7.47 (m, 1H) and 8.62 (d, J = 4.6 Hz, 1H) ppm |
| 261 | 375 | 3 | (400 MHz, DMSO) 1.76-1.83 (1H, m), 1.88-2.03 (1H, m), 2.15-2.30 (4H, m), 2.84 (2H, s), 7.03-7.08 (2H, m), 7.20-7.25 (2H, m), 8.61 (1H, d). |

Example 10

Preparation of 2-methyl-2-(3-(3-methyl-1H-pyrazolo[3,4-b]pyridin-4-yl)phenyl)butan-1-amine (Compound 212)

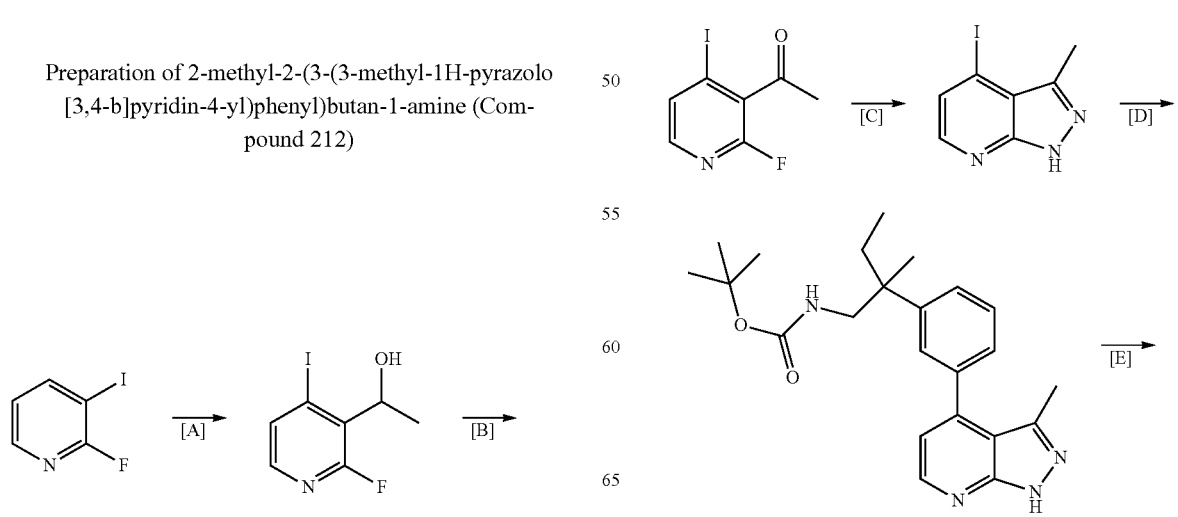

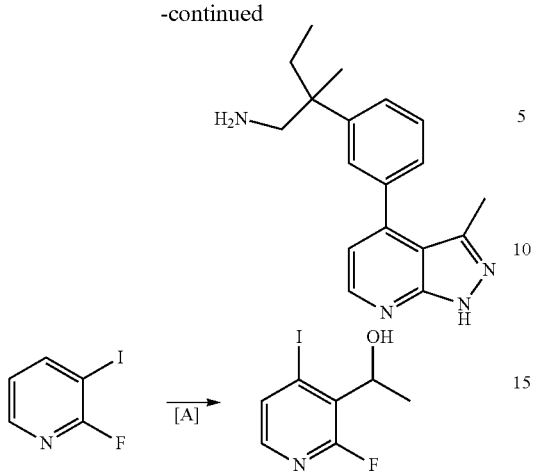

[A] Preparation of 1-(2-fluoro-4-iodopyridin-3-yl)ethanol

Di-1-propylamine (1.623 g, 2.267 mL, 16.04 mmol) was dissolved in dry THF (12 mL) and cooled to −70° C. n-BuLi (6.140 mL of 2.5 M, 15.35 mmol) was added slowly dropwise, keeping the temperature below −60° C., and the resultant mixture was stirred at 0° C. for ~2 minutes and recooled to −70° C. A solution of 2-Fluoro-3-iodopyridine (3.11 g, 13.95 mmol) in dry THF (9 mL) was added slowly dropwise. This solution was stirred at −70° C. for ~1 hr 45 mins, and Acetaldehyde (3.073 g, 3.915 mL, 69.75 mmol) was added slowly dropwise over ~20 minutes. The resultant mixture was stirred at −70° C. for ~1 hour. The reaction was quenched by addition of water (~12 mL) at −70° C. The resulting mixture was partitioned with EtOAc and the aqueous layer was extracted with EtOAc (3×50 mL). The combined organics were dried over Na2SO4, filtered and concentrated under reduced pressure to give an orange/brown oil. The resulting mixture was purified by column chromatography (30% EtOAc in hexanes, ~300 mL silica) to give a light yellow viscous gum (3.3412 g, 90% Yield).

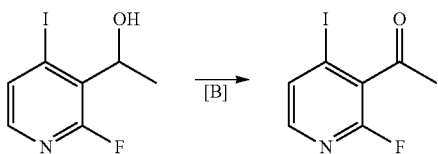

[B]—Preparation of 1-(2-fluoro-4-iodopyridin-3-yl)ethanone 1-(2-fluoro-4-iodopyridin-3-yl)ethanol (3.25 g, 12.17 mmol) was dissolved in dry Toluene (40 mL) and MnO2 (12.45 g, 121.7 mmol) was added in one portion. The resultant suspension was stirred at reflux for 95 minutes. Reaction mixture allowed to cool to RT and filtered through celite, washing copiously with EtOAc. The filtrate was concentrated under reduced pressure to give an orange/brown oil. This material was redissolved in DCM and cooled down onto silica (~30 mL). The resulting solid was purified by column chromatography (15% EtOAc in hexanes, ~300 mL silica) to give a light yellow oil, which solidified on cooling in an ice-bath to give a light yellow solid (1.92 g, 60% Yield).

1H NMR (400.0 MHz, DMSO: 2.57 (3H, s), 7.95 (1H, d), 8.03 (1H, d).

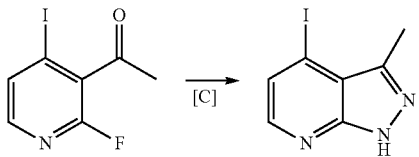

[C]—Preparation of 4-iodo-3-methyl-1H-pyrazolo[3,4-b]pyridine 1-(2-fluoro-4-iodopyridin-3-yl)ethanone (1.9 g, 7.169 mmol) was dissolved in dry THF (8 mL) in a pressure tube and hydrazine (15.77 mL of 1 M, 15.77 mmol) was added slowly dropwise. The resultant yellow, opaque suspension was stirred at 90° C. for ~45 minutes. The reaction was allowed to cool to RT and partitioned between EtOAc and saturated Na2CO3. The aqueous layer was extracteed with EtOAc (3×50 mL) and the combined organics were dried over Na2SO4, filtered and concentrated under reduced pressure to give a light brown solid. This material was triturated with ether, sonicated and filtered. The solid collected was washed with further ether (3×5 mL) and pentane (3×5 mL) to give a brown powder. The resulting solid was purified by column chromatography (60% CH3CN in water, ~200 mL R-P silica) to give an off-white solid. This material was redissolved in EtOAc/MeOH, dried over Na2SO4, filtered and concentrated under reduced pressure to give a light yellow solid. This material was trirurated in pentane using an ultrasonic bath and collected by filtration. The collected solid was washed with pentane (3×5 mL) to give a salmon-pink powder (532.3 mg, 29% Yield).

1H NMR (400.0 MHz, DMSO: 2.61 (3H, s), 7.64 (1H, d), 8.04 (1H, d).

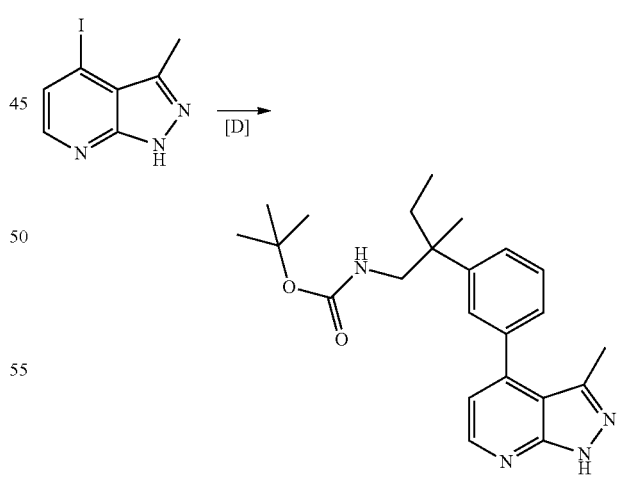

[D]—Preparation of tert-butyl 2-methyl-2-(3-(3-methyl-1H-pyrazolo[3,4-b]pyridin-4-yl)phenyl)butylcarbamate 4-iodo-3-methyl-1H-pyrazolo[3,4-b]pyridine (150 mg, 0.5790 mmol), tert-butyl 2-methyl-2-(3-(4,4,5,5-tetramethyl-1,3,2-dioxaborolan-2-yl)phenyl)butylcarbamate (225.4 mg, 0.5790 mmol), Na2CO3 (868.5 µL of 2 M, 1.737 mmol) and Pd(PPh3)4 (66.91 mg, 0.05790 mmol) were placed in a microwave tube and Dioxane (1.500 mL) was added. The resulting suspension was stirred at 150° C. in the microwave (using a 10 minute ramp and nitrogen cooling) for 45 minutes. The reaction mixture was partitioned between EtOAc and brine. The aqueous layer was extracted with EtOAc (3×20 mL) and the combined organics were dried over Na2SO4, filtered and concentrated under reduced pressure to give a yellow gum. The mixture was purified by column chromatography (75% EtOAc in hexanes, ~75 mL silica) to give a slightly yellow gum (203 mg, 89% Yield).

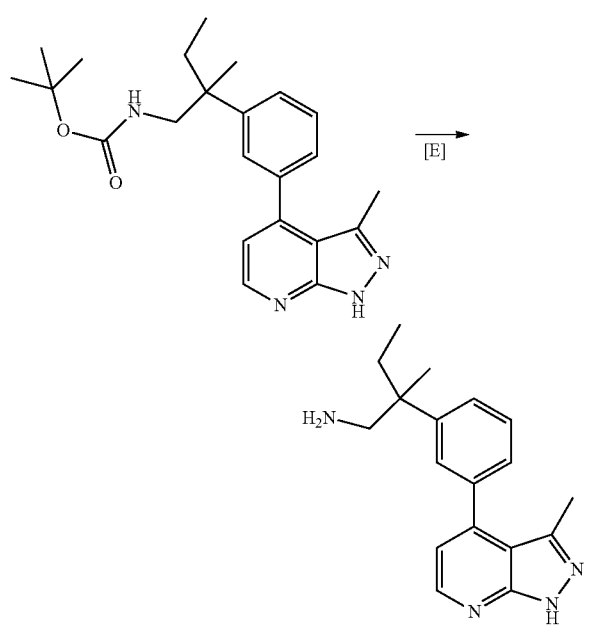

[E]—Preparation of 2-methyl-2-(3-(3-methyl-1H-pyrazolo[3,4-b]pyridin-4-yl)phenyl)butan-1-amine Compound 212 tert-butyl 2-methyl-2-(3-(3-methyl-1H-pyrazolo[3,4-b]pyridin-4-yl)phenyl)butylcarbamate (137 mg, 0.3473 mmol) was dissolved in dry DCM (2 mL) and cooled in an ice-bath. TFA (2 mL,) was added slowly dropwise and the resultant solution was stirred at 0° C. for ~30 minutes and at RT for ~30 minutes. The reaction mixture was concentrated under reduced pressure to give a light brown gum. This material was partitioned between EtOAc and saturated Na2CO3. The aqueous layer was extracted with EtOAc (3×20 mL) and the combined organics were dried over Na2SO4, filtered and concentrated under reduced pressure to give a light yellow gum. This material was redissolved in EtOAc (not fully soluble in DCM) and vacced down onto silica (~10 mL). The resulting solid was purified by column chromatography (9% MeOH in DCM, 1% NH4OH, ~75 mL silica) to give a off-white solid (78.4 mg, 77% Yield).

1H NMR (400.0 MHz, DMSO): 0.64 (t, J=7.4 Hz, 14H), 1.07 (s, 0.5H), 1.26 (s, 4.5H), 1.55 (dd, J=7.4, 13.8 Hz, 1H), 1.76-1.80 (m, 1H), 2.16 (s, 3H), 2.64 (d, J=12.8 Hz, 1H), 2.82 (d, J=12.8 Hz, 1H), 7.04 (d, J=4.8 Hz, 1H), 7.35 (dt, J=7.1, 2.1 Hz, 1H), 7.40 (s, 1H), 7.44-7.51 (m, 2H), 8.49 (d, J=4.7 Hz, 1H) and 13.4 (br s, 1H) ppm.

Table 11 below depicts data for certain exemplary compounds made in general by a similar route to that outlined in Example 10.

TABLE 11

| # | M + 1 (obs) | RT (min) | 1H-NMR |
|---|---|---|---|
| 212 | 295.2 | 2.77 | 1H NMR (400.0 MHz, DMSO) d 0.64 (t, J = 7.4 Hz, 14H), 1.07 (s, 0.5H), 1.26 (s, 4.5H), 1.55 (dd, J = 7.4, 13.8 Hz, 1H), 1.76-1.80 (m, 1H), 2.16 (s, 3H), 2.64 (d, J = 12.8 Hz, 1H), 2.82 (d, J = 12.8 Hz, 1H), 7.04 (d, J = 4.8 Hz, 1H), 7.35 (dt, J = 7.1, 2.1 Hz, 1H), 7.40 (s, 1H), 7.44-7.51 (m, 2H), 8.49 (d, J = 4.7 Hz, 1H) and 13.4 (br s, 1H) ppm. |
| 262 | 311 | 2.19 | 1H NMR (400.0 MHz, DMSO) d 13.45 (s, 1H), 8.50 (d, J = 4.8 Hz, 1H), 7.24-7.21 (m, 1H), 7.09-7.02 (m, 3H), 2.84 (s, 2H), 2.24-2.19 (m, 7H) and 2.02-1.80 (m, 2H) ppm |
| 263 | 325 | 2.27 | 1H NMR (400.0 MHz, DMSO) d 13.45 (s, 1H), 8.50 (d, J = 4.7 Hz, 1H), 7.23-7.20 (m, 1H), 7.08-7.04 (m, 2H), 2.84 (s, 2H), 2.62 (q, J = 7.5 Hz, 2H), 2.23-2.16 (m, 4H), 2.04-1.96 (m, 1H), 1.82-1.77 (m, 1H) and 0.89 (t, J = 7.5 Hz, 3H) ppm |
| 264 | 309.1 | 2.98 | 1H NMR (400.0 MHz, DMSO) d 0.64 (t, J = 7.4 Hz, 3H), 0.81 (t, J = 7.5 Hz, 3H), 1.23-1.29 (m, 3H), 1.55 (dd, J = 7.4, 13.8 Hz, 1H), 1.79 (dd, J = 7.4, 13.8 Hz, 1H), 2.59 (m, 3H), 2.82 (d, J = 12.8 Hz, 1H), 7.03 (d, J = 4.6 Hz, 1H), 7.33-7.35 (m, 1H), 7.38 (s, 1H), 7.44-7.51 (m, 2H), 8.49 (d, J = 4.6 Hz, 1H) and 13.5 (s, 1H) ppm. |
| 265 | 307.1 | 2.87 | 1H NMR (400.0 MHz, DMSO) d 0.72-0.76 (m, 2H), 0.79-0.82 (m, 2H), 0.86-0.91 (m, 3H), 2.38 (d, 3H), 2.58-2.63 (m, 2H), 2.75 (s, 2H), 7.03 (d, 1H), 7.16 (s, 1H), 7.22 (s, 1H), 7.26 (s, 1H), 8.46-8.48 (m, 1H) and 13.38 (bs, 1H, NH) ppm. |
| 266 | 321.1 | 3.09 | 1H NMR (400.0 MHz, DMSO) d 0.60-0.70 (m, 5H), 0.82-0.86 (m, 2H), 1.28 (d, J = 9.3 Hz, 3H), 1.55 (dd, J = 7.4, 13.8 Hz, 1H), 1.63-1.69 (m, 1H), 1.78 (dd, J = 7.4, 13.8 Hz, 1H), |

TABLE 11-continued

| # | M + 1 (obs) | RT (min) | 1H-NMR |
|---|---|---|---|
| | | | 2.65 (d, J = 12.8 Hz, 1H), 2.82 (d, J = 12.8 Hz, 1H), 7.04 (d, J = 4.6 Hz, 1H), 7.42-7.51 (m, 4H), 8.48 (d, J = 4.6 Hz, 1H) and 13.3 (s, 1H) ppm. |
| 267 | 337 | 2.33 | 1H NMR (400.0 MHz, DMSO) d 13.40 (s, 1H), 8.50 (d, J = 4.7 Hz, 1H), 7.32-7.28 (m, 1H), 7.15-7.01 (m, 3H), 2.83 (s, 2H), 2.26-2.15 (m, 4H), 2.03-1.96 (m, 1H), 1.82-1.66 (m, 2H), 0.89-0.85 (m, 2H) and 0.76-0.72 (m, 2H) ppm |
| 268 | 319.2 | 2.92 | 1H NMR (400.0 MHz, DMSO) d 0.74-0.80 (m, 6H), 0.88-0.93 (m, 2H), 1.64-1.72 (m, 1H), 2.39 (s, 3H), 2.75 (s, 2H), 7.06 (d, J = 4.6 Hz, 1H), 7.25 (s, 1H), 7.29 (s, 1H), 7.34 (s, 1H), 8.47 (d, J = 4.7 Hz, 1H) and 13.29 (bs, 1H, NH) ppm. |
| 269 | 265 | 1.96 | 1H NMR (400.0 MHz, DMSO) d 13.34 (brs, 1H), 8.49 (d, J = 4.6 Hz, 1H), 7.63 (d, J = 0.6 Hz, 1H), 7.49-7.46 (m, 3H), 7.06 (d, J = 4.7 Hz, 1H), 3.81 (s, 2H), 1.97 (brs, 2H), 1.67-1.60 (m, 1H), 0.91-0.84 (m, 2H) and 0.76-0.72 (m, 2H) ppm |
| 270 | 253 | 1.85 | 1H NMR (400.0 MHz, DMSO) d 13.45 (brs, 1H), 8.49 (d, J = 4.6 Hz, 1H), 7.66-7.29 (m, 4H), 7.03 (d, J = 4.6 Hz, 1H), 3.81 (s, 2H), 3.24 (s, 2H), 2.60 (q, J = 7.5 Hz, 2H) and 0.88 (t, J = 7.5 Hz, 3H) ppm |

Example 11

Preparation of 2-methyl-2-(3-(3-(trifluoromethyl)-1H-pyrazolo[3,4-b]pyridin-4-yl)phenyl)butan-1-amine (Compound 213)

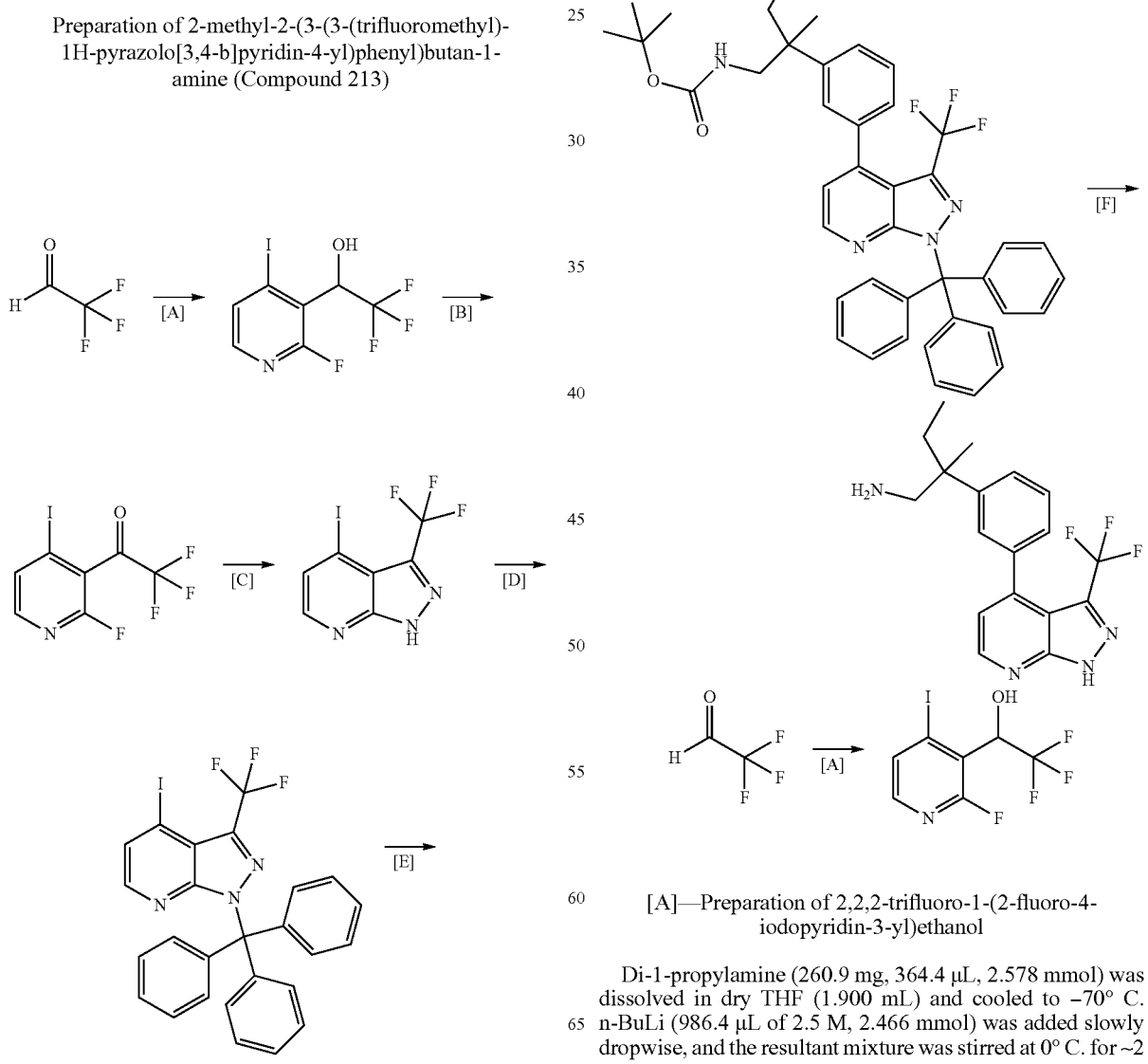

[A]—Preparation of 2,2,2-trifluoro-1-(2-fluoro-4-iodopyridin-3-yl)ethanol

Di-1-propylamine (260.9 mg, 364.4 µL, 2.578 mmol) was dissolved in dry THF (1.900 mL) and cooled to −70° C. n-BuLi (986.4 µL of 2.5 M, 2.466 mmol) was added slowly dropwise, and the resultant mixture was stirred at 0° C. for ~2 minutes and recooled to −70° C. A solution of 2-fluoro-3- iodo-pyridine (500 mg, 2.242 mmol) in dry THF (1.400 mL) was added slowly dropwise and the resultant was stirred at −70° C. for ~2.5 hours. 2,2,2-trifluoroacetaldehyde was added via cannula (bp. is ~−20° C.) and the resultant mixture was stirred at −70° C. for ~1.5 hours. The reaction was quenched at −70° C. by the rapid addition of water (~2 mL) and the resulting mixture was partitioned with EtOAc. The aqueous phase was extracted with EtOAc (3×20 mL) and the combined organics were dried over Na2SO4, filtered and concentrated under reduced pressure to give a mobile light brown oil (581.7 mg). The resulting mixture was purified by column chromatography (5% EtOAc in DCM, ~100 mL silica, loaded in DCM) to give a slightly yellow gum that solidified under high-vacuum to give a light yellow solid (225.2 mg, 31% Yield).

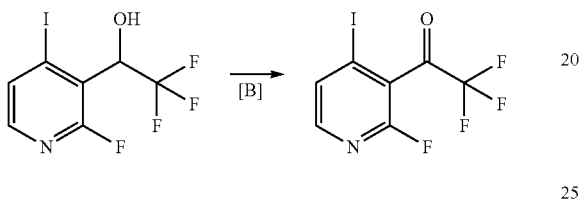

[B]—Preparation of 2,2,2-trifluoro-1-(2-fluoro-4-iodopyridin-3-yl)ethanone 2,2,2-trifluoro-1-(2-fluoro-4-iodo-3-pyridyl)ethanol (216.5 mg, 0.6744 mmol) was dissolved in dry PhMe (5 mL) and MnO2 (689.8 mg, 6.744 mmol) was added in one portion. The resultant suspension was stirred at reflux for ~35 minutes. The reaction mixture was allowed to cool to RT and filtered through celite. The celite was washed copiously with EtOAc and the combined filtrate was concentrated under reduced pressure to give a yellow/orange gum. The resulting mixture was purified by column chromatography (10% EtOAc in hexanes, ~100 mL silica) to give a slightly yellow, mobile oil (106.8 mg, 50% Yield).

1H NMR (400.0 MHz, DMSO: 8.16 (1H, d), 8.24 (1H, d).

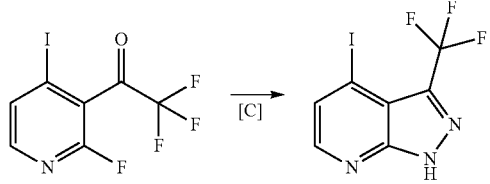

[C]—Preparation of 4-iodo-3-(trifluoromethyl)-1H-pyrazolo[3,4-b]pyridine 2,2,2-trifluoro-1-(2-fluoro-4-iodo-3-pyridyl)ethanone (1.0717 g, 3.360 mmol) was dissolved in dry Dioxane (10 mL) and hydrazine monohydrate (504.6 mg, 490.4 μL, 10.08 mmol) was added in one portion. The resulting mixture was stirred at 90° C. for ~minutes, allowed to cool to RT and partitioned between EtOAc and brine. The aqueous layer was extracted with EtOAc (3×50 mL) and the combined organics were dried over Na2SO4, filtered and concentrated under reduced pressure to give a bright yellow solid. The resulting solid was purified by column chromatography (30% EtOAc in hexanes, ~200 mL silica) to give an off-white solid (801.4 mg, 76% Yield).

1H NMR (400.0 MHz, DMSO: 7.97 (1H, d), 8.27 (1H, d), 14.85 (1H, brs).

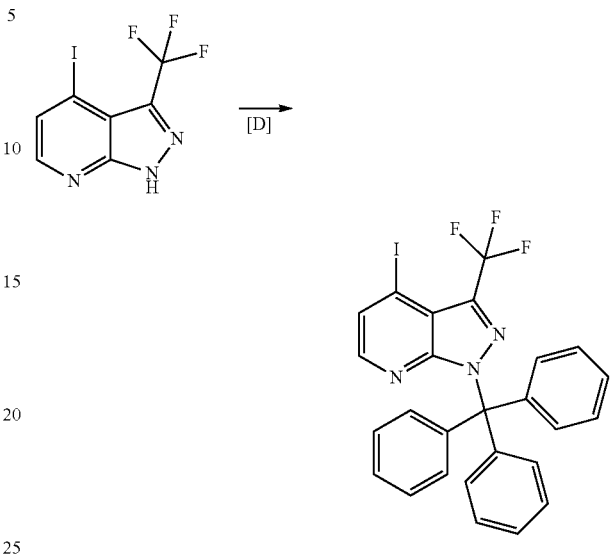

[D]—Preparation of 4-iodo-3-(trifluoromethyl)-1-trityl-1H-pyrazolo[3,4-b]pyridine 4-iodo-3-(trifluoromethyl)-1H-pyrazolo[5,4-b]pyridine (100 mg, 0.3195 mmol) was dissolved in dry DMF (1 mL) and cooled in an ice-bath. Sodium hydride (14.06 mg, 0.3515 mmol) was added in one portion and the resulting mixture was stirred at 0° C. for ~15 minutes. Trityl chloride (93.53 mg, 0.3355 mmol) added in one portion and the resulting light yellow solution was stirred at RT for ~2 hours, by which time it was a light yellow, viscous suspension. This material was concentrated under reduced pressure to remove DMF, to give a cream solid/gum. This material was partitioned between EtOAc and brine. The organic layer was washed with brine (3×2 mL), dried over Na2SO4, filtered and concentrated under reduced pressure to give a cream solid (186.3 mg). The resulting solid was purified by column chromatography (5-10% EtOAc in hexanes, ~75 mL silica) to give a white solid (164.3 mg, 93% Yield).

1H NMR (400.0 MHz, DMSO: 7.21 (6H, m), 7.32 (9H, m), 7.93 (1H, d), 8.00 (1H, d).

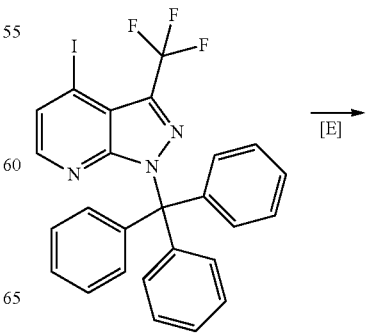

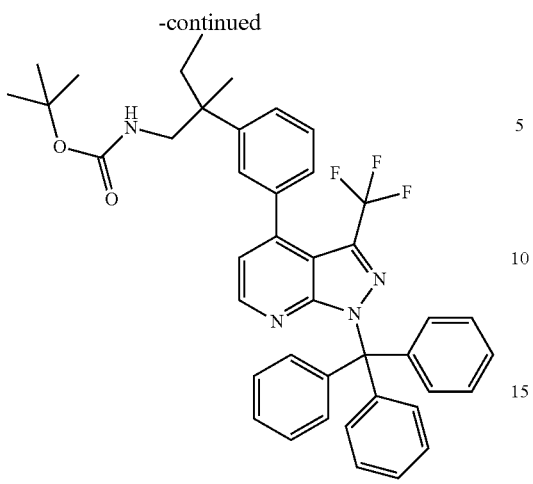

[E]—Preparation of tert-butyl 2-methyl-2-(3-(3-(trifluoromethyl)-1-trityl-1H-pyrazolo[3,4-b]pyridin-4-yl)phenyl)butylcarbamate 4-iodo-3-(trifluoromethyl)-1-trityl-1H-pyrazolo[3,4-b]pyridine (135 mg, 0.2431 mmol) and tert-butyl 2-methyl-2-(3-(4,4,5,5-tetramethyl-1,3,2-dioxaborolan-2-yl)phenyl)butylcarbamate (94.65 mg, 0.2431 mmol) were dissolved in dry Dioxane (1 mL) and Na2CO3 (364.6 µL of 2 M, 0.7293 mmol) was added. The solution was degassed (vacuum/nitrogen cycles×5), Pd[P(tBu)3]2 (12.42 mg, 0.02431 mmol) was added and stirred at 60° C. overnight. The reaction was allowed to cool to RT and partitioned between EtOAc and saturated Na2CO3. The aqueous layer was extracted with further EtOAc (3×10 mL) and the combined organics were dried over Na2SO4, filtered and concentrated under reduced pressure to give a dark purple solid. The resulting solid was purified by column chromatography (15% EtOAc in hexanes, ~75 mL silica) to give a slightly brown gum (164.7 mg, 98% Yield).

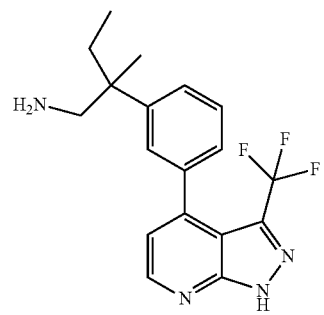

[G]—Preparation of 2-methyl-2-(3-(3-(trifluoromethyl)-1H-pyrazolo[3,4-b]pyridin-4-yl)phenyl)butan-1-amine (Compound 213)

tert-butyl 2-methyl-2-(3-(3-(trifluoromethyl)-1-trityl-1H-pyrazolo[3,4-b]pyridin-4-yl)phenyl)butylcarbamate (148 mg, 0.2142 mmol) was dissolved in dry DCM (2 mL) and cooled in an ice-bath. triethylsilane (99.63 mg, 136.9 µL, 0.8568 mmol) was added followed slowly dropwise by TFA (2 mL,). The resulting mixture was stirred at 0° C. for ~1 hour 50 minutes. The reaction mixture was concentrated under reduced pressure to give a light brown solid/gum. This material was partitioned with ether and brine. The ether layer was washed with 1M HCl (2×10 mL) and the combined aqueous layer was basified with saturated NaHCO3 and extracted with EtOAc (3×10 mL). The combined EtOAc was dried over Na2SO4, filtered and concentrated under reduced pressure to give a colourless gum (56.5 mg). This material was purified by column chromatography (4.5% MeOH/0.5% NH4OH in DCM, ~75 mL silica, loaded in DCM) to give a white powder (15 mg, 20% Yield).

1H NMR (400.0 MHz, DMSO): 0.70 (t, J=7.3 Hz, 3H), 1.31 (s, 3H), 1.60 (dd, J=7.2, 13.8 Hz, 1H), 1.83 (dd, J=7.2, 13.7 Hz, 1H), 2.71 (d, J=12.8 Hz, 1H), 2.87 (d, J=12.7 Hz, 1H), 7.30-7.35 (m, 2H), 7.40 (s, 1H), 7.51-7.55 (m, 2H) and 8.74 (d, J=4.6 Hz, 1H) ppm Table 12 below depicts data for certain exemplary compounds made in general by a similar route to that outlined in Example 11.

TABLE 12

| # | M + 1 (obs) | RT (min) | 1H-NMR |
|---|---|---|---|
| 213 | 349.1 | 3.12 | 1H NMR (400.0 MHz, DMSO) d 0.70 (t, J = 7.3 Hz, 3H), 1.31 (s, 3H), 1.60 (dd, J = 7.2, 13.8 Hz, 1H), 1.83 (dd, J = 7.2, 13.7 Hz, 1H), 2.71 (d, J = 12.8 Hz, 1H), 2.87 (d, J = 12.7 Hz, 1H), |

TABLE 12-continued

| # | M + 1 (obs) | RT (min) | 1H-NMR |
|---|---|---|---|
| | | | 7.30-7.35 (m, 2H), 7.40 (s, 1H), 7.51-7.55 (m, 2H) and 8.74 (d, J = 4.6 Hz, 1H) ppm |
| 214 | 377.1 | 2.21 | 1H NMR (400.0 MHz, DMSO) d 1.79-1.84 (m, 2H), 2.03-2.07 (m, 2H), 2.70 (s, 2H), 3.40 (t, J = 9.1 Hz, 2H), 3.66-3.69 (m, 2H), 7.27-7.31 (m, 2H), 7.38 (s, 1H), 7.49-7.52 (m, 2H) and 8.69 (d, J = 4.5 Hz, 1H) ppm |
| 215 | 361.1 | 3.3 | 1H (DMSO) 1.78-1.86 (1H, m), 2.04-2.11 (1H, m), 2.24-2.37 (4H, m), 2.40 (3H, s), 3.20 (2H, d), 7.12 (1H, s), 7.18 (1H, s), 7.22 (1H, s), 7.28 (1H, d), 7.58 (3H, bs, NH3), 8.72 (1H, d), 14.77 (1H, s, NH). |
| 271 | 377.1 | 3.48 | 1H NMR (400.0 MHz, CDCl3) d 0.76 (t, 3H), 1.30 (t, 3H), 1.34 (s, 3H), 1.58 (dt, 1H), 1.78-1.83 (m, 1H), 2.74-2.77 (m, 3H), 2.99 (d, 1H), 7.14 (s, 1H), 7.19 (s, 1H), 7.23-7.28 (m, 2H) and 8.68 (d, 1H) ppm |
| 272 | 375.1 | 3.5 | 1H (DMSO) 1.21 (3H, t), 1.75-1.82 (1H, m), 1.96-2.05 (1H, m), 2.11-2.27 (4H, m), 2.66 (2H, q), 2.79 (2H, s), 6.96 (1H, s), 7.04 (1H, s), 7.11 (1H, s), 7.22 (1H, d), 8.64 (1H, d). |
| 273 | 329.9 | 3.48 | 1H NMR (400.0 MHz, DMSO) d 1.55-1.58 (m, 2H), 1.78-1.81 (m, 2H), 7.31 (d, J = 4.6 Hz, 1H), 7.40-7.43 (m, 2H), 7.48-7.57 (m, 2H), 8.73 (d, J = 4.6 Hz, 1H) and 14.78 (s, 1H) ppm |
| 274 | 365 | 3.25 | 1H NMR (400.0 MHz, DMSO) d 1.79 (dd, J = 9.3, 19.7 Hz, 1H), 1.94-2.09 (m, 1H), 2.16-2.25 (m, 4H), 2.83 (s, 2H), 7.00 (s, 1H), 7.05 (d, J = 10.0 Hz, 1H), 7.14 (d, J = 9.0 Hz, 1H), 7.29 (d, J = 4.6 Hz, 1H) and 8.69 (d, J = 4.6 Hz, 1H) ppm |
| 275 | 391.06 | 2.98 | 1H NMR (400.0 MHz, DMSO) d 1.76-1.83 (m, 2H), 2.02-2.08 (m, 2H), 2.39 (s, 3H), 2.68 (s, 2H), 3.12-3.42 (masked signal, 4H), 3.64-3.69 (m, 2H), 7.13 (s, 1H), 7.17 (s, 1H), 7.26-7.27 (m, 1H), 7.29 (s, 1H) and 8.68 (d, 1H) ppm |
| 276 | 395.1 | 3 | 1H NMR (400.0 MHz, DMSO) d 1.77-1.84 (m, 2H), 2.06 (d, J = 11.6 Hz, 2H), 2.69 (d, J = 9.9 Hz, 2H), 3.38 (t, J = 9.1 Hz, 2H), 3.67 (dd, J = 3.8, 16.5 Hz, 2H), 7.18-7.22 (m, 2H), 7.30-7.33 (m, 2H) and 8.71 (d, J = 4.6 Hz, 1H) ppm |
| 277 | 367.1 | 3.47 | 1H NMR (400.0 MHz, DMSO) d 0.63 (t, 3H), 1.23 (s, 3H), 1.52 (dd, 1H), 1.75 (dd, 1H), 2.63-2.67 (m, 1H), 2.82 (d, 1H), 7.14-7.18 (m, 2H), 7.25-7.28 (m, 2H) and 8.70 (d, 1H) ppm. |
| 278 | 333.1 | 2.93 | 1H (DMSO) 0.95-1.00 (2H, m), 1.01-1.06 (2H, m), 3.12 (2H, s), 7.30 (1H, d), 7.37-7.42 (1H, m), 7.48 (1H, s), 7.50-7.54 (2H, m), 7.74 (3H, bs, NH3), 8.74 (1H, d), 14.80 (1H, bs, NH). |
| 279 | 343.1 | 3.63 | 1H NMR (400.0 MHz, DMSO) d 1.97-2.07 (m, 1H), 2.24-2.35 (m, 1H), 2.63-2.79 (m, 4H), 7.31 (d, J = 4.6 Hz, 1H), 7.46-7.49 (m, 1H), 7.55-7.63 (m, 3H), 8.72 (d, J = 4.6 Hz, 1H) and 14.78 (bs, 1H, NH) ppm |
| 280 | 347.1 | 3.17 | 1H NMR (400.0 MHz, DMSO) d 1.75-1.83 (m, 1H), 1.97-2.04 (m, 1H), 2.14-2.26 (m, 4H), 2.82 (s, 2H), 7.16 (s, 1H), 7.20-7.28 (m, 3H), 7.43-7.47 (m, 1H) and 8.68 (d, J = 4.6 Hz, 1H) ppm |
| 281 | 335.05 | 3.04 | 1H NMR (400.0 MHz, DMSO) d 0.74 (t, 3H), 1.46-1.57 (m, 1H), 1.74-1.81 (m, 1H), 2.50-2.58 (m, 1H), 2.76-2.86 (m, 2H), 7.23 (d, 1H), 7.27 (s, 1H), 7.32 (t, 2H), 7.45 (t, 1H) and 8.67 (d, 1H) ppm |
| 282 | 347.1 | 3.13 | 1H NMR (400.0 MHz, DMSO) d 0.73-0.82 (m, 4H), 2.35 (s, 3H), 2.77 (s, 2H), 7.12 (s, 1H), 7.18 (s, 1H), 7.22-7.26 (m, 2H) and 8.65 (d, 1H) ppm |
| 284 | 365.1 | 2.8 | 1H NMR (400.0 MHz, DMSO) d 1.70-1.73 (m, 1H), 2.00-2.04 (m, 1H), 2.73-2.77 (m, 3H), 3.12-3.19 (m, 5H), 7.21 (d, 1H), 7.26-7.33 (m, 3H), 7.45 (t, 1H) and 8.65 (d, 1H) ppm |
| 285 | 379.1 | 2.93 | 1H NMR (400.0 MHz, DMSO) d 1.28 (s, 3H), 1.79-1.85 (m, 1H), 1.95-2.02 (m, 1H), 2.67 (d, 1H), 2.79 (d, 1H), 3.01-3.08 (m, 1H), 3.11 (s, 3H), 3.16-3.23 (m, 1H), 7.24 (d, 1H), 7.29 (t, 1H), 7.35 (s, 1H), 7.46-7.48 (m, 2H) and 8.68 (d, 1H) ppm |
| 286 | 379.1 | 2.93 | 1H NMR (400.0 MHz, DMSO) d 1.28 (s, 3H), 1.77-1.85 (m, 1H), 1.96-2.03 (m, 1H), 2.67 (d, 1H), 2.79 (d, 1H), 3.01-3.05 (m, 1H), 3.10 (s, 3H), 3.17-3.23 (m, 1H), 7.24 (d, 1H), 7.28-7.30 (m, 1H), 7.35 (s, 1H), 7.46-7.48 (m, 2H) and 8.68 (d, 1H) ppm |
| 287 | 379.1 | 2.93 | 1H NMR (400.0 MHz, DMSO) d 1.28 (s, 3H), 1.79-1.85 (m, 1H), 1.95-2.02 (m, 1H), 2.68 (d, 1H), 2.80 (d, 1H), 3.01-3.05 (m, 1H), 3.09 (s, 3H), 3.18-3.21 (m, 1H), 7.24-7.30 (m, 2H), 7.35 (s, 1H), 7.46-7.48 (m, 2H) and 8.69 (d, 1H) ppm |
| 288 | 377.05 | 2.99 | (DMSO, 400 MHz) 0.77 (3H, t), 2.02 (2H, q), 3.55 (1H, d), 3.70 (1H, d), 7.30 (1H, d), 7.42-7.44 (2H, m), 7.49-7.58 (2H, m), 7.63 (1H, s), 8.72 (1H, d), 14.75 (1H, br s). |
| 289 | 424 | 4.12 | 1H NMR (400.0 MHz, DMSO) d 14.74 (s, 1H), 8.70 (d, J = 4.6 Hz, 1H), 7.55-7.17 (m, 11H), 4.44 (s, 2H), 3.59 (s, 2H) and 0.90 (s, 4H) ppm |

TABLE 12-continued

| # | M + 1 (obs) | RT (min) | 1H-NMR |
|---|---|---|---|
| 290 | 334 | 3.11 | 1H NMR (400.0 MHz, DMSO) d 14.74 (s, 1H), 8.70 (d, J = 4.7 Hz, 1H), 7.49-7.23 (m, 5H), 4.70 (s, 1H), 3.57 (s, 2H) and 0.95-0.75 (m, 4H) ppm |
| 291 | 348 | 3.31 | 1H NMR (400.0 MHz, DMSO) d 14.75 (s, 1H), 8.70 (d, J = 4.6 Hz, 1H), 7.43 (s, 1H), 7.27-7.18 (m, 4H), 4.82 (m, 1H), 3.52 (d, J = 5.4 Hz, 2H), 2.50-2.24 (m, 4H) and 2.00-1.77 (m, 2H) ppm |
| 292 | 391.11 | 3.12 | (DMSO, 400 MHz) 0.76 (3H, t), 2.01 (2H, q), 2.41 (3H, s), 3.51 (2H, d), 3.68 (2H, d), 7.23 (1H, s), 7.25 (1H, s), 7.30 (1H, d), 7.32 (1H, s), 7.64 (1H, s), 8.72 (1H, d), 14.76 (1H, s). |
| 293 | 367.14 | 2.49 | (DMSO, 400 MHz) 0.71 (3H, t), 1.86-2.08 (2H, m), 2.40 (3H, s), 2.99 (2H, d), 7.20 (1H, s), 7.23 (1H, s), 7.29 (1H, s), 7.30 (1H, d), 8.71 (1H, d). |
| 294 | 293 | 2.12 | 1H NMR (400.0 MHz, DMSO) d 8.67 (d, J = 4.6 Hz, 1H), 7.55-7.41 (m, 3H), 7.32 (d, J = 7.1 Hz, 1H), 7.23 (d, J = 4.6 Hz, 1H), 3.95 (brs, 2H) and 3.82 (s, 2H) ppm |
| 295 | 401.1 | 3.14 | (DMSO, 400 MHz) 1.92 (3H, s), 2.43 (3H, s), 3.69 (1H, d), 3.89 (1H, d), 7.28 (1H, d), 7.33, (1H, s), 7.39 (1H, s), 7.47 (1H, s), 8.00 (1H, s), 8.69 (1H, d), 14.74 (1H, br s). |
| 296 | | | (DMSO, 400 MHz) 0.79 (3H, t), 2.06 (2H, q), 2.40 (3H, s), 3.74 (1H, d), 3.90 (1H, d), 7.12 (br d), 7.21 (1H, s), 7.25 (1H, s), 7.29 (1H, s), 8.58 (1H, d), 10.03 (1H, br s). |
| 297 | 351.07 | 2.38 | 1H nmr (DMSO, 400 MHz) 2.40 (3H, s), 2.85-2.93 (2H, m), 3.20 (3H, s), 4.34-4.37 (1H, m), 7.21 (1H, s), 7.27 (1H, s), 7.28 (1H, s), 7.29 (1H, s), 8.39 (1H, s, formate), 8.70 (1H, d). |
| 298 | 389 | 2.71 | 1H NMR (400.0 MHz, DMSO) d 8.66 (d, J = 4.6 Hz, 1H), 7.47-7.41 (m, 3H), 7.30 (d, J = 6.7 Hz, 1H), 7.19 (d, J = 4.6 Hz, 1H), 5.44 (s, 2H), 3.95 (t, J = 7.2 Hz, 1H) and 1.85-0.71 (m, 13H) ppm |
| 299 | 389 | 2.76 | 1H NMR (400.0 MHz, DMSO) d 8.66 (d, J = 4.6 Hz, 1H), 7.46-7.41 (m, 3H), 7.30 (d, J = 6.4 Hz, 1H), 7.20 (d, J = 4.6 Hz, 1H), 4.97 (brs, 2H), 3.84 (t, J = 6.8 Hz, 1H) and 1.77-0.78 (m, 13H) ppm |
| 300 | 403 | 2.84 | 1H NMR (400.0 MHz, DMSO) d 8.66 (d, J = 4.6 Hz, 1H), 7.45-7.42 (m, 3H), 7.30 (dd, J = 1.6, 5.5 Hz, 1H), 7.20 (d, J = 4.6 Hz, 1H), 4.85 (brs, 2H), 3.81 (t, J = 6.8 Hz, 1H) and 1.70-0.66 (m, 15H) ppm |
| 307 | 347.03 | 2.4 | 1H (400 MHz, DMSO) 1.36-1.47 (1H, m), 1.68-1.76 (3H, m), 1.93-2.09 (2H, m), 2.66 (1H, q), 3.16 (1H, q), 7.19 (1H, d), 7.29 (1H, d), 7.33 (1H, s), 7.38 (1H, t), 7.43 (1H, t), 8.63 (1H, d). |
| 309 | 321 | 2.3 | 1H NMR (400.0 MHz, DMSO) d 8.43 (d, J = 4.6 Hz, 1H), 7.22-7.17 (m, 3H), 7.06 (dd, J = 1.7, 6.5 Hz, 1H), 6.97 (d, J = 4.6 Hz, 1H), 3.54 (t, J = 6.7 Hz, 1H), 3.25 (brs, 2H), 1.40-1.31 (m, 2H) and 0.54 (t, J = 7.4 Hz, 3H) ppm |
| 311 | 408 | 3.22 | 1H NMR (400.0 MHz, DMSO) d 1.63-1.66 (m, 2H), 1.82-1.86 (m, 2H), 3.19 (t, 2H), 7.34 (d, J = 4.5 Hz, 1H), 7.51 (s, 1H), 7.55 (s, 1H), 7.60 (s, 1H) and 8.72 (d, J = 4.6 Hz, 1H) ppm. |
| 312 | 386 | 8.2 | 1H NMR (CD3OD): 1.54-1.58 (2H, m), 1.75-1.79 (2H, m), 1.87-1.94 (2H, m), 2.79-2.88 (2H, m), 3.60-3.63 (2H, m), 7.25-7.31 (3H, m), 7.38 (1H, d), 8.67-8.69 (1H, d). |
| 313 | 370 | 10.02 | |
| 314 | 391.04 | 2.46 | (400 MHz, DMSO) 0.61 (3H, m), 1.21 (1H, br s), 1.59-1.68 (2H, m), 2.35 (3H, s), 3.20-4.01 (5H, m), 7.07-7.09 (2H, m), 7.23 (1H, s), 7.33 (1H, s), 8.56 (1H, s). |
| 315 | 410 | 8.82 | 1H NMR (MeOD) 1.57-1.59 (6H, m), 1.78-1.80 (4H, m), 7.27-7.28 (1H, d), 7.38 (1H, s), 7.45 (1H, s), 7.54-7.55 (1H, d), 8.69-8.70 (1H, d), |
| 316 | 415 | 3.43 | 1H NMR (MeOD): 1.26-1.28 (6H, s), 1.54-1.57 (2H, m), 1.75-1.84 (4H, m), 2.79-2.83 (2H, m), 7.24-7.29 (2H, m), 7.38 (1H, s), 8.67-8.68 (1H, d). |
| 317 | 414 | 7.39 | 1H NMR (MeOD): 1.26 (6H, s), 1.54-1.57 (2H, m), 1.75-1.83 (4H, m), 2.76-2.80 (2H, m), 7.18-7.20 (2H, m), 7.30 (1H, s), 7.38 (1H, s), 8.61-8.62 (1H, d). |
| 318 | 350 | 3.34 | 1H NMR (400.0 MHz, DMSO) d 14.79 (brs, 1H), 8.67 (d, J = 4.6 Hz, 1H), 7.47-7.21 (m, 5H), 3.50 (dd, J = 10.5, 16.5 Hz, 2H), 1.75 (dd, J = 7.4, 13.8 Hz, 1H), 1.59 (dd, J = 7.4, 13.8 Hz, 1H), 1.23 (s, 3H) and 0.62 (t, J = 7.4 Hz, 3H) ppm |
| 324 | 345 | 3.6 | H NMR (400.0 MHz, DMSO) d 14.80 (brs, 1H), 8.72 (d, J = 4.7 Hz, 1H), 7.50 (s, 1H), 7.39 (s, 1H), 7.32-7.29 (m, 2H), 2.42 (s, 3H) and 1.71 (s, 6H) ppm |
| 329 | 386 | 2.9 | 1H NMR (400.0 MHz, DMSO) d 1.51-1.54 (m, 2H), 1.76-1.80 (m, 2H), 3.46 (s, 2H), 6.94 (s, 1H), 7.03 (s, 1H), 7.19 (s, 1H, NH), 7.29 (s, 1H), 7.39 (s, 1H), 7.52 (s, 1H, NH) and 8.52-8.53 (m, 1H) ppm. |

Example 12

Preparation of 1-(3-(3-aminopropyl)-5-(3-(trifluoromethyl)-1H-pyrazolo[3,4-b]pyridin-4-yl)phenyl)cyclopropanecarbonitrile (Compound 283)

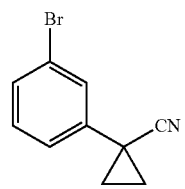 [SMILES: N#CC1(c2cccc(Br)c2)CC1]

Preparation of 1-(3,5-dibromophenyl)cyclopropane-1-carbonitrile

Sodium hydride (1.601 g, 40.02 mmol) was added portionwise over 10 minutes to a solution of 2-(3,5-dibromophenyl)acetonitrile (5.0 g, 18.19 mmol) in DMSO (40 mL) at room temperature. The reaction was stirred at room temperature for 40 mins then cooled in an ice-bath whilst 1,2-dibromoethane (3.588 g, 1.646 mL, 19.10 mmol) was added dropwise. The reaction was then warmed to room temperature and stirred overnight. Water was added (100 mL) and mixture extracted with ethyl acetate/toluene (3×150 mL, 2:1). The organics were combined, washed with 1M HCl, water, and brine then dried over MgSO4, filtered and the solvent removed under reduced pressure. The crude product was purified on silica (Companion, 120 g) eluting with 1-20% EtOAc:Petrol ether to give 1-(3,5-dibromophenyl)cyclopropane-1-carbonitrile as a light yellow solid (4.56 g, 83%).

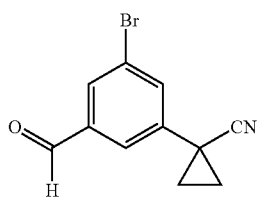 [SMILES: N#CC1(c2cc(Br)cc(C=O)c2)CC1]

Preparation of 1-(3-bromo-5-formyl-phenyl)cyclopropane-1-carbonitrile iPrMgCl.LiCl in THF (5.429 mL of 14% w/v, 5.233 mmol) was placed in an oven-dried 3-necked flask under nitrogen. The flask was cooled to −20° C. and 1-(3,5-dibromophenyl)cyclopropane-1-carbonitrile (1.5 g, 4.984 mmol) was added in one portion. The temperature was maintained between −20 and −10° C. for 90 minutes. DMF (400.7 mg, 424.5 µL, 5.482 mmol) was then added and the reaction allowed to warm to room temperature overnight. NH4Cl (sat. aq. soln.) was added followed by ethyl acetate and water. The mixture was extracted three times with ethyl acetate, the combined organics dried over MgSO4 and the solvent removed under reduced pressure. The crude product was purified on silica (Companion, 24 g) eluting with 2-30% EtOAc:Petrol ether to give 1-(3-bromo-5-formyl-phenyl)cyclopropane-1-carbonitrile as a white solid (1.037 g, 83%).

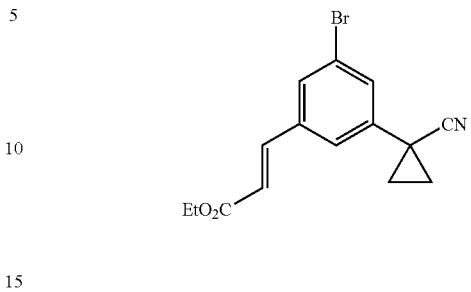

Preparation of (E)-3-[3-bromo-5-(1-cyanocyclopropyl)phenyl]prop-2-enoate

To a suspension of (2-methoxy-2-oxo-ethyl)-triphenylphosphonium bromide (1.502 g, 3.618 mmol) in THF (15 mL) under nitrogen at room temperature was added LHMDS in THF (3.358 mL of 1 M, 3.358 mmol) dropwise. The mixture was stirred for 10 mins then cooled to −25° C. 1-(3-bromo-5-formyl-phenyl)cyclopropane-1-carbonitrile (500 mg, 1.999 mmol) was dissolved in 1 mL of THF and added to the reaction. The reaction was allowed to warm to room temperature over 1 hour. The reaction was quenched with MeOH (2 mL) and then partitioned between ethyl acetate and brine. The aqueous was extracted with ethyl acetate and dried, filtered and concentrated. The crude product was purified on silica (Companion, 24 g) eluting with 1-20% EtOAc:Petrol ether to give methyl (E)-3-[3-bromo-5-(1-cyanocyclopropyl)phenyl]prop-2-enoate as a yellow solid (594 mg, 97%).

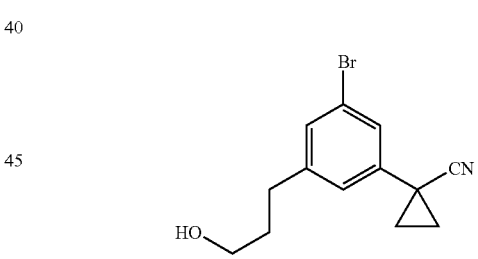

Preparation of 1-[3-bromo-5-(3-hydroxypropyl)phenyl]cyclopropane-1-carbonitrile

To methyl (E)-3-[3-bromo-5-(1-cyanocyclopropyl)phenyl]prop-2-enoate (590 mg, 1.927 mmol) in THF (15 mL) at 0° C. was added lithium borohydride (125.9 mg, 5.781 mmol). The reaction was allowed to warm to room temperature and stirred overnight. HCl (2M, aq. soln.) was added and the reaction stirred for 5 minutes until the fizzing subsided. NaHCO3 (sat. aq. soln.) was added and the mixture extracted three times with ethyl acetate. The combined organics were washed with brine, dried over MgSO4, filtered and the solvent removed under reduced pressure. The crude product was purified on silica (Companion, 40 g) eluting with 10-80%

EtOAc:Petrol ether to give 1-[3-bromo-5-(3-hydroxypropyl)phenyl]cyclopropane-1-carbonitrile as a yellow oil (64 mg, 67%).

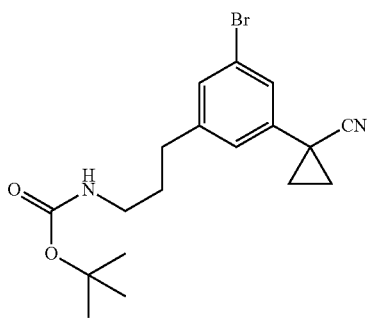 [SMILES: CC(C)(C)OC(=O)NCCCc1cc(Br)cc(C2(C#N)CC2)c1]

Preparation of tert-butyl N-[3-[3-bromo-5-(1-cyano-cyclopropyl)phenyl]propyl]carbamate To a solution of 1-[3-bromo-5-(3-hydroxypropyl)phenyl]cyclopropane-1-carbonitrile (364 mg, 1.299 mmol) and triethylamine (394.3 mg, 543.1 µL, 3.897 mmol) in DCM (6 mL) at 0° C. was added MsCl (223.1 mg, 150.7 µL, 1.948 mmol) dropwise. The reaction mixture was stirred at 0° C. for 30 mins then poured into 5 mL of water. The mixture was extracted three times with ethyl acetate, the combined organics washed with water and brine then dried over MgSO4, filtered and the solvent removed under reduced pressure. This crude mixture was used in the next step.

To a solution of crude mesylate in DMF (3 mL) was added sodium azide (101.4 mg, 1.559 mmol). The mixture was stirred at 80° C. for 1 hour allowed to cool then poured into water. The mixture was extracted three times with ethyl acetate, the combined organics washed with water and brine then dried over MgSO4, filtered and the solvent removed under reduced pressure Do not concentrate completely. The crude was taken to the next step.

To a solution of 1-[3-(3-azidopropyl)-5-bromo-phenyl]cyclopropane-1-carbonitrile (396 mg, 1.298 mmol) in THF (5 mL) and water (0.5 mL) was added PPh3 (347.3 mg, 1.324 mmol) at room temperature. Stir for 24 hours. The reaction was concentrated under reduced pressure and taken directly onto the next step. The residue was re-dissolved in dioxane (12 mL) and water (4 mL) and potassium carbonate (179.4 mg, 1.298 mmol) was added followed by di-tert-butyl dicarbonate (283.3 mg, 1.298 mmol) at room temperature. The reaction was stirred for 1 hour. The dioxane was removed under reduced pressure and the aqueous phase extracted three times with ethyl acetate. The combined organics were washed with water and brine, dried over MgSO4, filtered and the solvent removed under reduced pressure. The crude product was purified on silica (Companion, 24 g) eluting with 2.5-50% EtOAc:Petrol ether to give tert-butyl N-[3-[3-bromo-5-(1-cyanocyclopropyl)phenyl]propyl]carbamate as a colourless oil (315 mg, 64% over 4 steps).

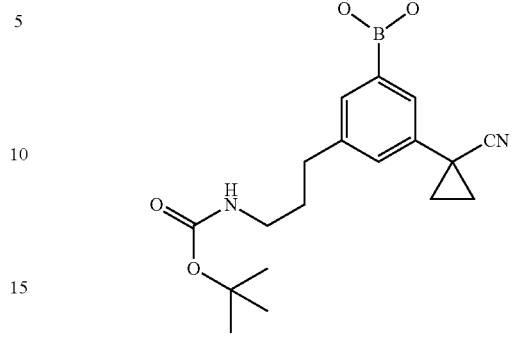

Preparation of tert-butyl N-[3-[3-(1-cyanocyclopropyl)-5-(4,4,5,5-tetramethyl-1,3,2-dioxaborolan-2-yl)phenyl]propyl]carbamate tert-Butyl N-[3-[3-bromo-5-(1-cyanocyclopropyl)phenyl]propyl]carbamate (315 mg, 0.8305 mmol) was dissolved in dioxane (5 mL) and bis(pinacolato)diboron (253.1 mg, 0.9966 mmol) was added followed by potassium acetate (244.6 mg, 2.492 mmol). The reaction mixture was degassed and filled with nitrogen 5 times then Pd(dppf)Cl2.DCM (33.91 mg, 0.04152 mmol) was added. The reaction was refluxed for 4 hours at 90° C. then allowed to cool and was diluted with ethyl acetate. The organics were washed with brine, dried over MgSO4, filtered and the solvent removed under reduced pressure. The crude product was purified on silica (Companion, 24 g) eluting with 2.5-40% EtOAc:Pet.ether to give tert-butyl N-[3-[3-(1-cyanocyclopropyl)-5-(4,4,5,5-tetramethyl-1,3,2-dioxaborolan-2-yl)phenyl]propyl]carbamate as a white foam (250 mg, 71%).

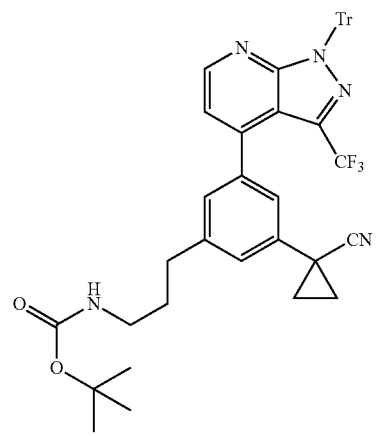

Preparation of tert-butyl 3-(3-(1-cyanocyclopropyl)-5-(3-(trifluoromethyl)-1-trityl-1 H-pyrazolo[3,4-b]pyridin-4-yl)phenyl)propylcarbamate tert-Butyl N-[3-[3-(1-cyanocyclopropyl)-5-(4,4,5,5-tetramethyl-1,3,2-dioxaborolan-2-yl)phenyl]propyl]carbamate (50 mg, 0.1173 mmol) was dissolved in dioxane (2 mL) and 4-iodo-3-(trifluoromethyl)-1-trityl-pyrazolo[5,4-b]pyridine (65.14 mg, 0.1173 mmol) was added followed by sodium carbonate (176.0 μL of 2 M, 0.3519 mmol). The reaction mixture was degassed and filled with nitrogen 5 times then Pd[P(tBu)3]2 (8.994 mg, 0.01760 mmol) was added and the reaction heated at 60° C. overnight. After cooling, water was added and ethyl acetate. The aqueous layer was extracted three times with ethyl acetate, the combined organics were washed with brine, dried over MgSO4, filtered and the solvent removed under reduced pressure. The crude product was purified on silica (Companion, 12 g) eluting with 2.5-50% EtOAc:Petrol ether to give tert-butyl 3-(3-(1-cyanocyclopropyl)-5-(3-(trifluoromethyl)-1-trityl-1H-pyrazolo[3,4-b]pyridin-4-yl)phenyl)propylcarbamate as a viscous oil (72 mg, 84%).

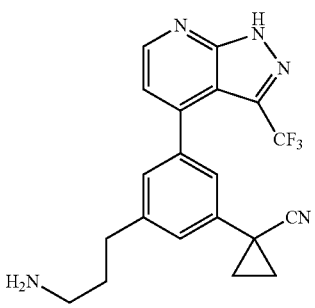 [SMILES: N#CC1(c2cc(CCCN)cc(-c3ccnc4[nH]nc(C(F)(F)F)c34)c2)CC1]

Preparation of 1-(3-(3-aminopropyl)-5-(3-(trifluoromethyl)-1H-pyrazolo[3,4-b]pyridin-4-yl)phenyl)cyclopropanecarbonitrile tert-Butyl 3-(3-(1-cyanocyclopropyl)-5-(3-(trifluoromethyl)-1-trityl-1H-pyrazolo[3,4-b]pyridin-4-yl)phenyl)propylcarbamate (72 mg, 0.09893 mmol) was dissolved in DCM (3 mL) and cooled to 0° C. Triethylsilane (46.01 mg, 63.20 μL, 0.3957 mmol) was added followed by TFA (0.5 mL). The reaction was stirred at 0° C. for 1 hour then the solvent removed under reduced pressure. The crude product was dissolved in DMSO and purified by FractionLynx. The fractions were passed through bicarbonate cartridges to obtain free base and lyophilised to give 1-(3-(3-aminopropyl)-5-(3-(trifluoromethyl)-1H-pyrazolo[3,4-b]pyridin-4-yl)phenyl)cyclopropanecarbonitrile as a white solid (22 mg, 57%).

1H NMR (400.0 MHz, DMSO) d 1.53-1.59 (m, 2H), 1.70-1.79 (m, 4H), 2.60-2.65 (m, 2H), 2.67-2.71 (m, 2H), 7.08-7.17 (m, 2H), 7.20-7.29 (m, 2H) and 8.54-8.58 (m, 1H) ppm.

Table 13 below depicts data for certain exemplary compounds made in general by a similar route to that outlined in Example 12.

TABLE 13

| # | M + 1 (obs) | RT (min) | 1H-NMR |
|---|---|---|---|
| 283 | 386.1 | 2.8 | 1H NMR (400.0 MHz, DMSO) d 1.53-1.59 (m, 2H), 1.70-1.79 (m, 4H), 2.60-2.65 (m, 2H), 2.67-2.71 (m, 2H), 7.08-7.17 (m, 2H), 7.20-7.29 (m, 2H) and 8.54-8.58 (m, 1H) ppm |
| 301 | 318.1 | 2.55 | 1H NMR (400.0 MHz, MeOH) d 1.62-1.65 (m, 2H), 1.82-1.85 (m, 2H), 2.08 (q, 2H), 2.90 (t, 2H), 3.02 (t, 2H), 7.40 (d, 1H), 7.45 (s, 1H), 7.64 (t, 1H), 7.69 (s, 1H), 8.26 (s, 1H) and 8.61 (d, 1H) ppm. |
| 302 | 346.1 | 2.65 | 1H NMR (400.0 MHz, DMSO) d 0.88 (t, J = 7.5 Hz, 3H), 1.58-1.62 (m, 2H), 1.67-1.80 (m, 4H), 2.54-2.61 (m, 4H), 2.67-2.74 (m, 2H), 7.05-7.07 (m, 1H), 7.25 (t, J = 1.6 Hz, 1H), 7.31-7.32 (m, 2H) and 8.50 (d, J = 4.6 Hz, 1H) ppm |
| 303 | 373.1 | 3.15 | 1H NMR (400.0 MHz, DMSO) d 1.54-1.57 (m, 2H), 1.76-1.79 (m, 2H), 2.81 (t, J = 6.9 Hz, 2H), 3.65 (t, J = 6.9 Hz, 2H), 4.71 (bs, 1H, OH), 7.22 (s, 1H), 7.25-7.27 (m, 2H), 7.33 (s, 1H), 8.68 (d, J = 4.7 Hz, 1H) and 14.80 (bs, 1H, NH) ppm. |
| 304 | 372.1 | 2.29 | 1H NMR (400.0 MHz, DMSO) d 1.55-1.58 (m, 2H), 1.75-1.78 (m, 2H), 2.74-2.77 (m, 2H), 2.84-2.87 (m, 2H), 7.21-7.22 (m, 2H), 7.25 (s, 1H), 7.30 (d, J = 1.4 Hz, 1H) and 8.64 (d, J = 4.6 Hz, 1H) ppm |

Example 13

Preparation of (3-(3-(3-(trifluoromethyl)-1H-pyrazolo[3,4-b]pyridin-4-yl)phenyl)oxetan-3-yl)methanamine (Compound 305)

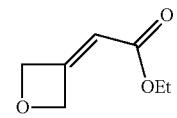

Preparation of ethyl 2-(oxetan-3-ylidene)acetate

To a solution of oxetan-3-one (500 mg, 6.938 mmol) in DCM (15.00 mL) at 0° C. was added ethyl 2-triphenylphosphoranylideneacetate (2.659 g, 7.632 mmol). The solution was allowed to warm to room temperature and stirred for 15 minutes. The reaction mixture was then filtered through a pad of silica (washing with 30% EtOAc:Petrol ether), and the solvent removed under reduced pressure to give ethyl 2-(oxetan-3-ylidene)acetate as a colourless viscous oil (815 mg, 79%).

1H NMR (400 MHz, CDCl3): 1.29 (t, 3H), 4.18 (q, 2H), 5.32-5.34 (m, 2H), 5.52-5.54 (m, 2H), 5.64-5.66 (m, 1H) ppm.

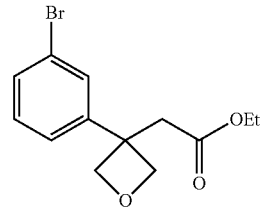 [SMILES: CCOC(=O)CC1(c2cccc(Br)c2)COC1]

Preparation of ethyl 2-[3-(3-bromophenyl)oxetan-3-yl]acetate

To a solution of [Rh(cod)Cl]2 (171.3 mg, 0.3518 mmol) in 30 mL of dioxane was added aqueous KOH (6.097 mL of 1.5 M, 9.145 mmol) followed by ethyl 2-(oxetan-3-ylidene)acetate (1 g, 7.035 mmol) and a solution of (3-bromophenyl)boronic acid (2.119 g, 10.55 mmol) in 10 mL of dioxane. The reaction was stirred for 30 minutes at room temperature then further (3-bromophenyl)boronic acid (706 mg, 0.5 eq) was added and the reaction stirred overnight. Brine was added and the aqueous layer extracted twice with ethyl acetate. The combined organics were washed with brine and then dried, filtered and concentrated under reduced pressure. The crude product was purified on silica (Companion, 80 g) eluting with 1-20% EtOAc:Petrol ether to give ethyl 2-[3-(3-bromophenyl)oxetan-3-yl]acetate as a yellow oil (1.50 g, 71%).

1H NMR (400 MHz, CDCl3): 1.15 (t, 3H), 3.13 (s, 2H), 4.05 (q, 2H), 4.86 (d, 2H), 5.00 (d, 2H), 7.19-7.42 (m, 4H) ppm.

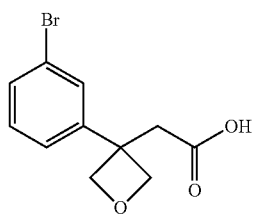 [SMILES: O=C(O)CC1(c2cccc(Br)c2)COC1]

Preparation of 2-[3-(3-bromophenyl)oxetan-3-yl]acetic acid

Ethyl 2-[3-(3-bromophenyl)oxetan-3-yl]acetate (1.5 g, 4.513 mmol) was dissolved in MeOH (25 mL) and cooled to 0° C. NaOH (9.026 mL of 1M, 9.026 mmol) was added and the reaction allowed to warm to rt overnight. The solvent was removed under reduced pressure and the solution neutralised with 2 eq of HCl (1M soln, 9.026 mL) and extracted with ethyl acetate. The combined organics were washed with brine, dried over MgSO4, filtered and the solvent removed under reduced pressure to give 2-[3-(3-bromophenyl)oxetan-3-yl]acetic acid as a viscous yellow oil (1.287 g, 95%).

1H NMR (400 MHz, CDCl3): 3.18 (s, 2H), 4.84 (d, 2H), 4.99 (d, 2H), 7.11-7.14 (m, 1H), 7.23 (t, 1H), 7.34-7.35 (m, 1H), 7.41-7.43 (m, 1H) ppm.

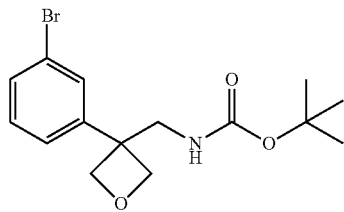 [SMILES: CC(C)(C)OC(=O)NCC1(c2cccc(Br)c2)COC1]

Preparation of tert-butyl N-[[3-(3-bromophenyl)oxetan-3-yl]methyl]carbamate

2-[3-(3-Bromophenyl)oxetan-3-yl]acetic acid (840 mg, 2.789 mmol) was dissolved in tert-butanol (8 mL) and triethylamine (310.5 mg, 427.7 µL, 3.068 mmol) was added followed by diphenylphosphoryl azide (844.3 mg, 661.2 µL, 3.068 mmol). Heat at 80° C. for 4 hours. The reaction was allowed to cool and the solvent removed under reduced pressure. Ethyl acetate was added and the organic layer was washed with 5% citric acid soln, NaHCO3 (sat. aq. soln.) and brine. The organics were dried over MgSO4, filtered and the solvent removed under reduced pressure. The crude product was pre-adsorbed onto silica and purified (Companion, 40 g) eluting with 2.5-50% EtOAc:Petrol ether to give tert-butyl N-[[3-(3-bromophenyl)oxetan-3-yl]methyl]carbamate as a white solid (433 mg, 45%).

1H NMR (400 MHz, CDCl3): 1.43 (s, 9H), 3.68 (d, 2H), 4.72 (bs, 1H, NH), 4.75 (2H), 4.92 (d, 2H), 7.00 (d, 1H), 7.20 (s, 1H), 7.24-7.28 (m, 1H), 7.42-7.45 (m, 1H) ppm.

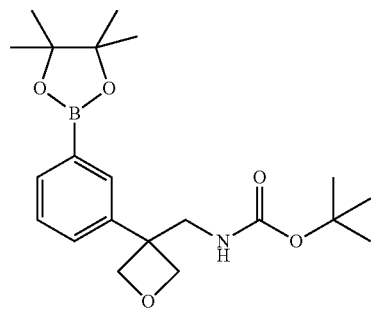 [SMILES: CC(C)(C)OC(=O)NCC1(c2cccc(B3OC(C)(C)C(C)(C)O3)c2)COC1]

Preparation of tert-butyl N-[[3-[3-(4,4,5,5-tetramethyl-1,3,2-dioxaborolan-2-yl)phenyl]oxetan-3-yl]methyl]carbamate tert-Butyl N-[[3-(3-bromophenyl)oxetan-3-yl]methyl]carbamate (151 mg, 0.4412 mmol) was dissolved in dioxane (3 mL) and bis(pinacolato)diboron (168.1 mg, 0.6618 mmol) was added followed by KOAc (129.9 mg, 1.324 mmol). The reaction mixture was degassed and filled with nitrogen 5 times then Pd(dppf)Cl2.DCM (18.02 mg, 0.02206 mmol) was added and the reaction was heated to 90° C. for 4 hours. The reaction was allowed to cool and diluted with ethyl acetate. The organic layer was washed with brine, dried over MgSO4, filtered and the solvent removed under reduced pressure. The crude product was purified on silica (Companion, 12 g) eluting with 2.5% to 50% EtOAc:Pet.ether to give tert-butyl N-[[3-[3-(4,4,5,5-tetramethyl-1,3,2-dioxaborolan-2-yl)phenyl]oxetan-3-yl]methyl]carbamate as a viscous oil (132 mg, 77%).

1H NMR (400 MHz, CDCl3): 1.26 (s, 12H), 1.37 (s, 9H), 3.70 (d, 2H), 4.60 (bs, 1H, NH), 4.77 (d, 2H), 5.00 (d, 2H), 7.15 (d, 1H), 7.40 (t, 1H), 7.47 (s, 1H), 7.73-7.76 (m, 1H) ppm.

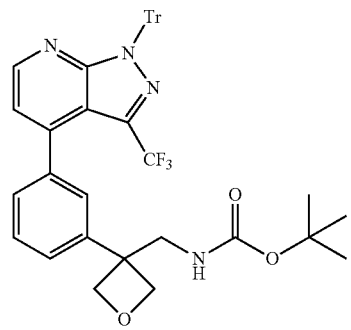

Preparation of tert-butyl N-[[3-[3-[3-(trifluoromethyl)-1-trityl-pyrazolo[3,4-b]pyridin-4-yl]phenyl]oxetan-3-yl]methyl]carbamate tert-Butyl N-[[3-[3-(4,4,5,5-tetramethyl-1,3,2-dioxaborolan-2-yl)phenyl]oxetan-3-yl]methyl]carbamate (65 mg, 0.1670 mmol) was dissolved in dioxane (3 mL) and 4-iodo-3-(trifluoromethyl)-1-trityl-pyrazolo[3,4-b]pyridine (92.74 mg, 0.1670 mmol) was added followed by sodium carbonate (250.5 μL of 2 M, 0.5010 mmol). The reaction was degassed and filled with nitrogen 5 times then Pd[P(tBu)3]2 (12.80 mg, 0.02505 mmol) was added. The reaction was heated at 60° C. overnight. After cooling, water was added followed by ethyl acetate. The aqueous layer was extracted three times with ethyl acetate, the combined organics washed with brine, dried over MgSO4, filtered and the solvent removed under reduced pressure. The crude product was purified on silica (Companion, 12 g) eluting with 2.5-50% EtOAc:Pet.ether to give tert-butyl N-[[3-[3-[3-(trifluoromethyl)-1-trityl-pyrazolo[3,4-b]pyridin-4-yl]phenyl]oxetan-3-yl]methyl]carbamate as a white foam (58 mg, 50%).

1H NMR (400 MHz, CDCl3): 1.34 (s, 9H), 3.75 (d, 2H), 4.60 (bs, 1H, NH), 4.77 (d, 2H), 5.00 (d, 2H), 7.03 (d, 1H), 7.14-7.20 (m, 2H), 7.25-7.31 (m, 15H), 7.38 (d, 1H), 7.49 (t, 1H), 8.31 (d, 1H) ppm.

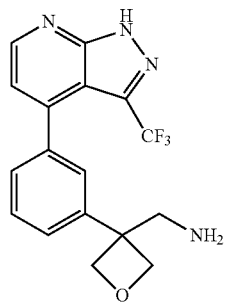 [SMILES: NCC1(c2cccc(-c3ccnc4[nH]nc(C(F)(F)F)c34)c2)COC1]

Preparation of (3-(3-(3-(trifluoromethyl)-1H-pyrazolo[3,4-b]pyridin-4-yl)phenyl)oxetan-3-yl)methanamine tert-Butyl N-[[3-[3-[3-(trifluoromethyl)-1-trityl-pyrazolo[3,4-b]pyridin-4-yl]phenyl]oxetan-3-yl]methyl]carbamate (58 mg, 0.08397 mmol) was dissolved in DCM (2 mL) and cooled to 0° C. Triethylsilane (39.06 mg, 53.65 μL, 0.3359 mmol) was added followed by TFA (0.5 mL). The reaction was stirred at 0° C. for 1 hour then the solvent removed under reduced pressure. The crude product was dissolved in DMSO and purified by FractionLynx. The fractions were passed through bicarbonate cartridges to obtain free base and lyophilised to give (3-(3-(3-(trifluoromethyl)-1H-pyrazolo[3,4-b]pyridin-4-yl)phenyl)oxetan-3-yl)methanamine (7.8 mg, 25%).

1H NMR (400.0 MHz, DMSO) d 3.02 (s, 2H), 4.66 (d, 2H), 4.77 (d, 2H), 7.18 (s, 1H), 7.23-7.29 (m, 2H), 7.35 (d, J=7.6 Hz, 1H), 7.50 (t, 1H) and 8.69 (d, 1H) ppm.

Table 14 below depicts data for certain exemplary compounds made in general by a similar route to that outlined in Example 13.

TABLE 14

| # | M + 1 (obs) | RT (min) | 1H-NMR |
|---|---|---|---|
| 233 | 281 | 2.27 | 1H NMR (400.0 MHz, DMSO) d 3.08 (s, 2H), 3.58 (d, 0.4H), 4.71 (d, 1.6H), 4.79 (d, 0.4H), 4.83 (d, 1.6H), 7.25-7.28 (m, 1H), 7.40 (d, 1H), 7.54-7.60 (m, 2H), 7.73-7.75 (m, 1H), 8.32 (d, |

TABLE 14-continued

| # | M + 1 (obs) | RT (min) | 1H-NMR |
|---|---|---|---|
| | | | 1H), 8.58 (dd, 1H) and 13.81 (bs, 1H, NH) ppm |
| 305 | 349.1 | 2.79 | 1H NMR (400.0 MHz, DMSO) d 3.02 (s, 2H), 4.66 (d, J = 5.9 Hz, 2H), 4.77 (d, J = 5.8 Hz, 2H), 7.18 (s, 1H), 7.23-7.29 (m, 2H), 7.35 (d, J = 7.6 Hz, 1H), 7.50 (t, J = 7.7 Hz, 1H) and 8.69 (d, J = 4.6 Hz, 1H) ppm |
| 306 | 309.1 | 2.55 | 1H NMR (400.0 MHz, DMSO) d 0.87 (t, J = 7.5 Hz, 3H), 2.60 (q, J = 7.5 Hz, 2H), 3.06 (s, 2H), 4.69 (d, J = 5.9 Hz, 2H), 4.79 (d, J = 5.9 Hz, 2H), 7.06 (d, J = 4.6 Hz, 1H), 7.24 (s, 1H), 7.25 (q, J = 2.0 Hz, 1H), 7.42 (dd, J = 1.2, 6.5 Hz, 1H), 7.53 (t, J = 7.9 Hz, 1H), 8.50 (d, J = 4.6 Hz, 1H) and 13.38 (bs, 1H, NH) ppm |

In general, compounds of the invention, including compounds in Table 1, are effective for the inhibition of PKCtheta. Selectivity for inhibition of PKCtheta by the compounds of the invention was tested and the results are shown in the following Example. The data obtained shows values for PKC-theta isoform selectivity by showing Ki potencies for PKC-theta, PKCdelta and PKCalpha.

Example 14

Preparation of 2-methyl-2-(3-(5-methyl-1H-pyrazolo[3,4-b]pyridin-4-yl)phenyl)propan-1-amine (Compound 237)

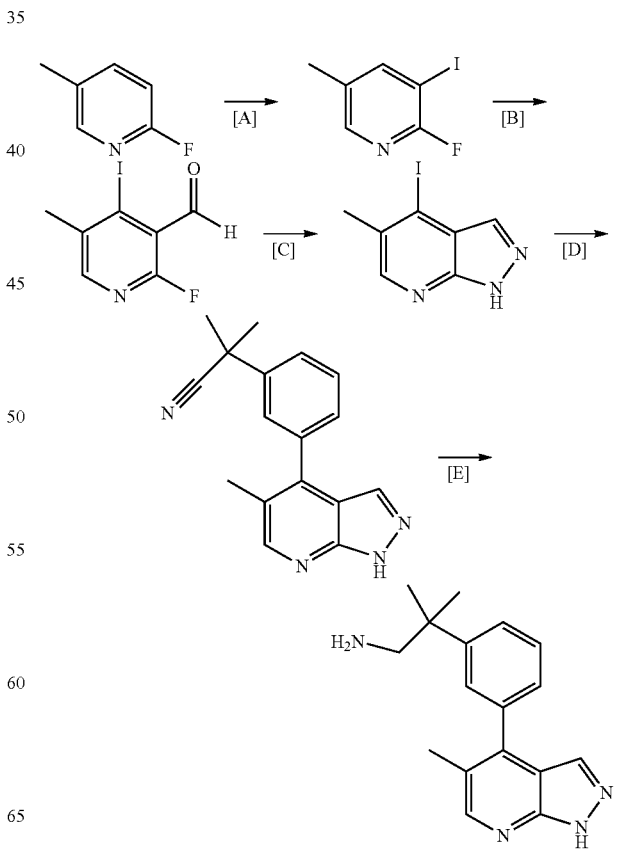

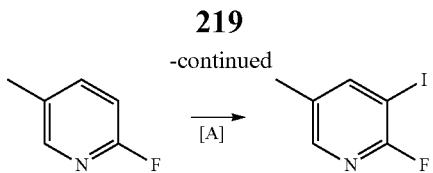

[A]—Preparation of 2-fluoro-3-iodo-5-methylpyridine

Diisopropylamine (910.7 mg, 1.261 mL, 9.000 mmol) was dissolved in dry THF (20 mL) and cooled to −78° C., n-Buli (3.600 mL of 2.5 M, 9.000 mmol) was added slowly dropwise and the resultant mixture was then allowed to warm to −20° C. over 40 min before being cooled back down to −78° C.

A solution of 2-fluoro-5-methyl-pyridine (1.0 g, 9.000 mmol) in dry THF (10 mL) was added dropwise and the solution was stirred at this temp for 2 hours. A solution of iodine (2.284 g, 463.3 µL, 9.000 mmol) in THF (10 mL) was then added and the resultant mixture stirred for a further 1 hour at this temp before being quenched with water. The resulting mixture was partitioned between sodium thiosulfate solution and Et$_2$O, organics separated and washed further with saturated NaCl. The combined organics were dried over Na2SO4, filtered and concentrated under reduced pressure to give a colourless oil. The resulting mixture was purified by column chromatography (30% EtOAc in hexanes, ~200 mL silica) to give a colourless foam (1.409 g, 66% Yield).

1H NMR (400.0 MHz, DMSO) d 1.42 (s, 1H) and 7.07-7.12 (s, 2H) ppm

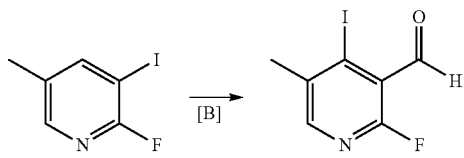

[B]—Preparation of 2-fluoro-4-iodo-5-methylnicotinaldehyde

Diisopropylamine (597.7 mg, 827.8 µL, 5.907 mmol) was dissolved in dry THF (20 mL) and cooled to −78° C., n-Buli (1.607 g, 2.363 mL of 2.5 M, 5.907 mmol) was added slowly dropwise and the resultant mixture was then allowed to warm to −20° C. over 40 min before being cooled back down to −78° C.

A solution of 2-fluoro-3-iodo-5-methyl-pyridine (1.4 g, 5.907 mmol) in dry THF (10 mL) was added dropwise and the solution was stirred at this temp for 2 hours. DMF (431.8 mg, 457.4 µL, 5.907 mmol) was then added and the resultant mixture stirred for a further 3 hours at this temp before being quenched with water. The resulting mixture was diluted with Et$_2$O and the organics separated and washed further with saturated NaCl. The combined organics were dried over Na2SO4, filtered and concentrated under reduced pressure to give an oil. The resulting mixture was purified by column chromatography (30% EtOAc in hexanes, ~200 mL silica) to give the product as a solid (1.565 g, 33% Yield).

1H NMR (400.0 MHz, CDCl3) d 2.43 (s, 3H), 8.07 (s, 1H) and 10.10 (s, 1H) ppm

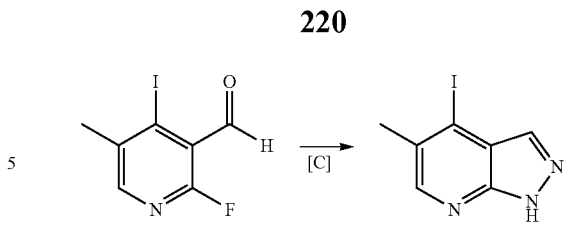

[C]—Preparation of 4-iodo-5-methyl-1H-pyrazolo[3,4-b]pyridine 2-fluoro-4-iodo-5-methyl-pyridine-3-carbaldehyde (510 mg, 1.924 mmol) was dissolved in dry Dioxane (10 mL) and Hydrazine monohydrate (288.9 mg, 280.8 µL, 5.772 mmol) was added in one portion The resultant mixture was stirred at RT for 30 minutes and then allowed to warm to 90° C. This temperature was held for 3.5 hours. The mixture was then concentrated and the resultant residue was partitioned between EtOAc and saturated Na2CO3. The organics were separated and washed with saturated NaCl. The combined organics were dried over Na2SO4, filtered and concentrated under reduced pressure to give a solid which was triturated with DCM and hexanes to give a pale salmon coloured solid (237 mg, 48% Yield).

1H NMR (400.0 MHz, DMSO) d 2.46 (s, 3H), 7.87 (s, 1H) and 13.87 (brs, 1H) ppm; MS (ES$^+$) 260

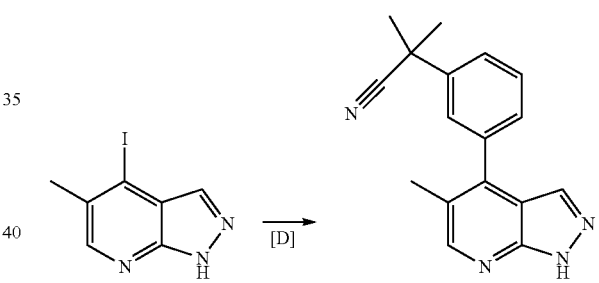

[D]—Preparation of 2-methyl-2-(3-(5-methyl-1H-pyrazolo[3,4-b]pyridin-4-yl)phenyl)propanenitrile Boronate-2-methyl-2-[3-(4,4,5,5-tetramethyl-1,3,2-dioxaborolan-2-yl)phenyl]propanenitrile (200 mg, 0.7376 mmol), iodide-4-iodo-5-methyl-1H-pyrazolo[3,4-b]pyridine (191.1 mg, 0.7376 mmol), Na2CO3 (1.106 mL of 2 M, 2.213 mmol) and Pd(PPh3)4 (85.23 mg, 0.07376 mmol) were placed in a microwave tube and dry Dioxane (5.000 mL) was added. The resulting suspension was stirred at 150° C. in the microwave (using a 10 minute ramp and nitrogen cooling) for 60 minutes. The reaction mixture was partitioned between EtOAc and brine. The aqueous layer was extracted with EtOAc (3×20 mL) and the combined organics were dried over Na2SO4, filtered and concentrated under reduced pressure to give an oil. The mixture was purified by column chromatography (10-100% EtOAc in hexanes, ~100 mL silica, loaded in DCM) to give an oil which was lyophilised from MeCN/H2O to give a solid (217 mg, 57% Yield).

1H NMR (400.0 MHz, DMSO) d 1.83 (s, 614), 2.40 (s, 3H), 7.72-7.40 (m, 4H), 7.87 (s, 1'-1), 8.56 (s, 1H) and 13.69 (s, 1H) ppm; MS (ES$^+$) 277

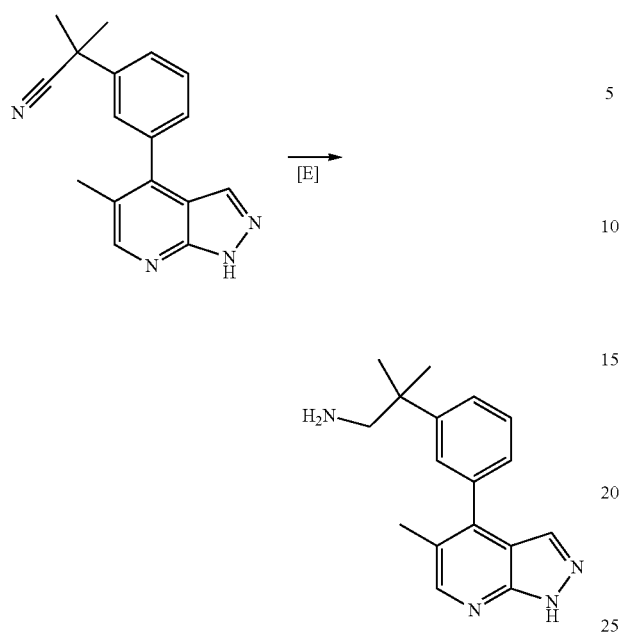

[E]—Preparation of 2-methyl-2-(3-(5-methyl-1H-pyrazolo[3,4-b]pyridin-4-yl)phenyl)propan-1-amine To a cooled solution of 2-methyl-2-(3-(5-methyl-1H-pyrazolo[3,4-b]pyridin-4-yl)phenyl)propanenitrile (108 mg, 0.3908 mmol) at 0° C. in THF (20 ml) was added slowly a solution of lithium aluminium hydride (781.5 μL of 2 M, 1.563 mmol). The reaction mixture was allowed to stir at 0° C. for 2 hours and then allowed to warm to RT and stirred for 16 hours. The mixture was then cooled to 0° C. and quenched with water. EtOAc was added and the mixture passed through a celite pad. The organics were separated, washed with saturated NaCl, dried over Na2SO4, filtered and concentrated under reduced pressure to give a semi solid which was lyophilized from MeCN/H20 (34 mg, Yield=31%).

1H NMR (400.0 MHz, DMSO) d 1.28-1.24 (m, 6H), 2.34 (s, 3H), 3.26-3.14 (m, 2H), 7.37-7.34 (m, 1H), 7.54-7.38 (m, 3H), 7.78 (s, 1H) and 8.43 (d, J=4.0 Hz, 1H) ppm; MS (ES+) 281

TABLE 15

| # | M + 1 (obs) | RT (min) | 1H-NMR |
|---|---|---|---|
| 219 | 277 | 2.89 | 1H NMR (400.0 MHz, DMSO-d6) d 13.69 (s, 1H), 8.56 (s, 1H), 7.87 (s, 1H), 7.72-7.40 (m, 4H), 2.40 (s, 3H) and 1.83 (s, 6H) ppm |
| 237 | 281 | 2.01 | 1H NMR (400.0 MHz, DMSO) d 8.43 (d, J = 4.0 Hz, 1H), 7.78 (s, 1H), 7.54-7.38 (m, 3H), 7.37-7.34 (m, 1H), 3.26-3.14 (m, 2H), 2.34 (s, 3H) and 1.28-1.24 (m, 6H) ppm |

Example 15

Preparation of 2-(3-(1H-pyrazolo[3,4-b]pyridin-4-yl)phenyl)-N,N,2-trimethylbutan-1-amine (Compound 138)

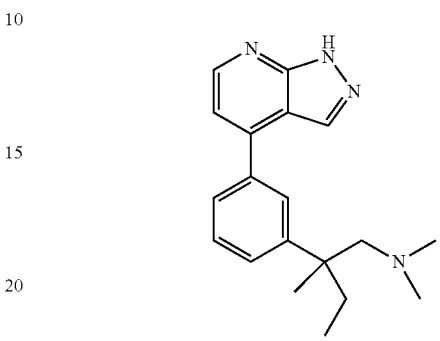

Step 1: 4-iodo-1-trityl-1H-pyrazolo[3,4-b]pyridine 4-iodo-1H-pyrazolo[3,4-b]pyridine (15 g, 61.22 mmol) was dissolved in dimethylformamide (300 mL) and the solution was cooled down in an ice bath to 5° C. Sodium hydride (60%, 2.938 g, 73.46 mmol) was added portionwise and left to stir at this temperature for 2 hours. After this time a solution of trityl chloride (18.77 g, 67.34 mmol) in dimethylformamide (150 mL) was added dropwise over 30 minutes. After an additional 2 hours of stirring, the solvent was removed by evaporation, and the residue was partitioned between ethyl acetate and saturated bicarbonate (2×100 ml). The organic layer was further washed with brine (100 ml), dried over magnesium sulfate and concentrated in vacuo to give a brown oil. This residue was purified on silica gel by flash column chromatography to afford the title compound as a white solid (less polar fraction: 2-regioisomer, 13.71 g, 46% yield; more polar fraction: 3-regioisomer, pale yellow solid, 8.06 g, 27% yield).

$^1$H NMR (DMSO-d$_6$, 400 MHz) δ 7.16-7.31 (15H, m), 7.59 (1H, d), 7.89 (1H, d), and 8.10 (1H, s) ppm; MS (ES+) 488.

Step 2: 4-(4,4,5,5-tetramethyl-1,3,2-dioxaborolan-2-yl)-1-trityl-1H-pyrazolo[3,4-b]pyridine

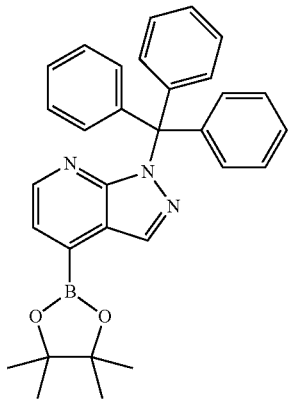 [SMILES: CC1(C)OB(c2ccnc3c2cnn3C(c2ccccc2)(c2ccccc2)c2ccccc2)OC1(C)C]

A mixture of 4-iodo-1-trityl-1H-pyrazolo[3,4-b]pyridine (9.61 g, 19.72 mmol), potassium acetate (5.806 g, 59.16 mmol) and bis(pinacol)diboron (6.008 g, 23.66 mmol) was dissolved in dioxane (100 mL). Nitrogen was bubbled through the reaction mixture for 20 minutes then 1,1'-bis(diphenylphosphino)ferrocene-palladium(II)dichloride dichloromethane complex (805.2 mg, 0.99 mmol) was added in one portion and the reaction mixture was sealed and heated to 120° C. behind a blast shield for 24 hours. The reaction mixture was cooled down to room temperature, filtered through a path of celite and washed with ethyl acetate. The filtrate was concentrated in vacuo and the residue was purified on silica gel by flash column chromatography to afford the title compound as a beige solid (7.08 g, 74% yield).

$^1$H NMR (DMSO-$d_6$, 400 MHz) δ 1.35 (12H, s), 7.19-7.32 (16H, m) and 8.25-8.29 (2H, m) ppm; MS (ES$^+$) 488.

Step 3: 2-(3-bromophenyl)propanenitrile

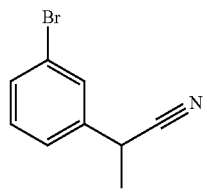

To a solution of 3-bromophenylacetonitrile (12 g, 61.2 mmol) in tetrahydrofuran (150 ml) cooled down to 0° C., was added 60% sodium hydride in mineral oil (2.25 g, 56.3 mmol) portionwise over 10 minutes. The reaction mixture was stirred at 0° C. for 40 minutes. Methyl iodide (5.71 ml, 91.8 mmol) was added dropwise at 0° C. and the reaction mixture was stirred at 0° C. for a further 1 hour. The reaction mixture was diluted with ethyl acetate (250 ml), washed with water and brine. The organic phase was dried over magnesium sulfate, filtered and concentrated in vacuo. The residue was purified on silica gel by flash column chromatography (ISCO Companion, 330 g column, 0-20% EtOAc/Petrol) to afford the title compound as a colourless oil (7.06 g, 55% yield).

$^1$H NMR (DMSO-$d_6$, 400 MHz) δ 1.55 (3H, d), 4.35 (1H, q), 7.37-7.46 (2H, m), 7.56 (1H, d) and 7.63 (1H, t) ppm.

Step 4: 2-(3-bromophenyl)-2-methylbutanenitrile

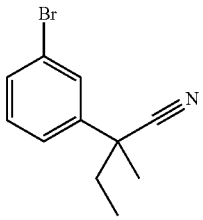

To a solution of 2-(3-bromophenyl)propanenitrile (600 mg, 3.06 mmol) in tetrahydrofuran (15 ml) cooled down to 0° C., was added 60% sodium hydride in mineral oil (184 mg, 4.59 mmol) in one portion. The reaction mixture was stirred at 0° C. for 40 minutes. Ethyl iodide (0.49 ml, 6.12 mmol) was added dropwise at 0° C. and the reaction mixture was stirred at 0° C. for a further 2 hours. The reaction mixture was diluted with ethyl acetate (250 ml), washed with water and brine. The organic phase was dried over magnesium sulfate, filtered and concentrated in vacuo. The residue was purified on silica gel by flash column chromatography (ISCO Companion, 40 g column, 0-10% EtOAc/Petrol) to afford the title compound as a colourless sticky oil (0.526 g, 72% yield).

$^1$H NMR (DMSO-$d_6$, 400 MHz) δ 0.84 (3H, t), 1.67 (3H, s), 1.98 (2H, q), 7.41 (1H, t), 7.51 (1H, m), 7.57 (1H, m) and 7.65 (1H, t) ppm.

Step 5: 2-(3-bromophenyl)-2-methylbutan-1-amine

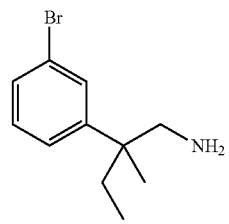

A solution of 2-(3-bromophenyl)-2-methylbutanenitrile (1678.5 mg, 7.049 mmol) in dry THF (28 mL) was cooled in an ice-bath. AlH3:(Me)2EtN complex, 0.5M in PhMe (28.20 mL of 0.5 M, 14.10 mmol) was added slowly dropwise and the resultant solution stirred at 0° C. for 30 mins. The mixture was allowed to warm to RT and stirred for 4.5 hours. The reaction was carefully quenched by dropwise addition of 1:1 THF:water (~30 mL). The resulting suspension was stirred vigorously and filtered through a pad of celite. The collected solid was partitioned between EtOAc and brine and the aqueous layer further extracted with EtOAc (3×50 mL) and the combined organics dried over Na2SO4, filtered and concentrated under reduced pressure to give a light brown oil. The residue was purified on silica gel by flash column chromatography (5% MeOH in DCM, loaded in DCM, ~200 mL silica) to give the product as a yellow oil (1137.8 mg, 67% Yield).

¹H NMR (DMSO-d₆, 400 MHz) δ 0.60 (3H, t), 1.12 (2H, m), 1.49 (1H, m), 1.67 (1H, m), 2.59 (1H, m), 2.75 (1H, m) and 7.25-7.42 (4H, m) ppm; MS (ES⁺) 244

Step 6:
2-(3-bromophenyl)-N,N,2-trimethylbutan-1-amine

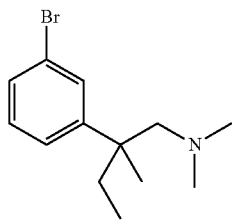

A mixture of 2-(3-bromophenyl)-2-methylbutan-1-amine (200 mg, 0.8259 mmol) and Formic acid (311.7 mg, 255.5 μL, 6.772 mmol) was placed in a 2.5 mL Wheaton vial and treated with Formaldehyde, 37 wt % in water (232.3 mg, 214.5 μL of 37% w/v, 2.643 mmol). The resulting mixture was stirred at RT for 30 minutes and then stirred at 100° C. for 60 minutes. The reaction mixture was partitioned between EtOAc and saturated Na2CO3. The aqueous layer was extracted with EtOAc (3×20 mL) and the combined organics were washed with brine (3×10 mL), dried over Na2SO4, filtered and concentrated under vacuo to give a yellow viscous oil. This was purified on silica gel by flash column chromatography (5% MeOH in DCM, ~75 mL silica) to give a colourless gum which was further purified by column chromatography (MeOH, ~75 mL R-P silica, loaded in MeOH) to give an opaque white oil (68.6 mg, 31% Yield).

¹H NMR (DMSO-d₆, 400 MHz) δ 0.53 (3H, t), 1.21 (3H, m), 1.45 (1H, m), 1.71 (1H, m), 1.92 (6H, m), 2.39 (2H, m) and 7.21-7.41 (4H, m) ppm; MS (ES⁺) 272

Step 7: N,N,2-trimethyl-2-(3-(1-trityl-1H-pyrazolo[3,4-b]pyridin-4-yl)phenyl)butan-1-amine

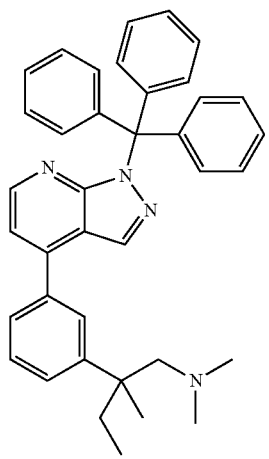 [SMILES: CCC(C)(CN(C)C)c1cccc(-c2ccnc3c2cnn3C(c2ccccc2)(c2ccccc2)c2ccccc2)c1]

A suspension of 2-(3-bromophenyl)-N,N,2-trimethylbutan-1-amine (62 mg, 0.2295 mmol), 1-trityl-4-boronatoazaindazole (111.9 mg, 0.2295 mmol), Na2CO3 (344.2 μL, of 2 M, 0.6885 mmol) in Dioxane (2 mL) was treated with Pd[P(tBu)3]2 (5.867 mg, 0.01148 mmol) and the resultant mixture was stirred at 60° C. for 4 hours. The mixture was allowed to cool to RT and partitioned between EtOAc and brine. The aqueous layer was extracted with EtOAc (3×20 mL) and the combined organics were dried over Na2SO4, filtered and concentrated under vacuo to give an orange/brown gum. This was purified by column chromatography (5% MeOH in DCM, ~75 mL silica) to give a light orange gum (91.4 mg, 72% Yield).

¹H NMR (DMSO-d₆, 400 MHz) δ 0.60 (3H, t), 1.12 (2H, m), 1.41 (3H, m), 1.55 (1H, m), 1.92 (1H, m), 2.01 (6H, m), 7.25 (17H, m), 7.60 (2H, m), 7.71 (1H, m), 7.83 (1H, m) and 8.31 (2H, m) ppm; MS (ES⁺) 551

Step 8: 2-(3-(1H-pyrazolo[3,4-b]pyridin-4-yl)phenyl)-N,N,2-trimethylbutan-1-amine

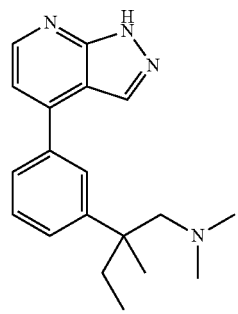 [SMILES: CCC(C)(CN(C)C)c1cccc(-c2ccnc3[nH]ncc23)c1]

N,N,2-trimethyl-2-(3-(1-trityl-1H-pyrazolo[3,4-b]pyridin-4-yl)phenyl)butan-1-amine (89.3 mg, 0.1621 mmol) was dissolved in dry DCM (2 mL) and cooled in an ice-bath. Triethylsilane (75.39 mg, 103.6 μL, 0.6484 mmol) was added followed by TFA (2 mL). The resultant mixture was stirred at 0° C. for 85 minutes and then concentrated under vacuo. The residue was partitioned between EtOAc and 1:1 c.HCl/water. The organic layer was extracted further with 1:1 c.HCl/water (3×20 mL) and the combined aqueous material was cooled in an ice-bath and carefully basified with 5M NaOH. The basic aqueous mixture was extracted with EtOAc (3×20 mL) and the combined organics were washed with brine (3×10 mL), dried over Na2SO4, filtered and concentrated under vacuo to give a yellow gum. This was purified by column chromatography (10% MeOH in DCM, ~75 mL silica) to give a colourless gum which was triturated with pentane to give a white powder (12.3 mg, 24% Yield).

¹H NMR (DMSO-d₆, 400 MHz) δ 0.67 (t, J=7.3 Hz, 3H), 1.35 (s, 3H), 1.57 (dd, J=7.2, 13.8 Hz, 1H), 1.88-1.94 (m, 1H), 2.00 (s, 6H), 7.37 (d, J=4.7 Hz, 1H), 7.53 (t, J=7.6 Hz, 2H), 7.68 (d, J=6.9 Hz, 1H), 7.77 (s, 1H), 8.24 (s, 1H), 8.58 (d, J=4.7 Hz, 1H) and 13.82 (s, 1H) ppm; MS (ES⁺) 309

TABLE 16

| # | M + 1 (obs) | RT (min) | 1H-NMR |
|---|---|---|---|
| 138 | 309.2 | 3.12 | 1H NMR (400.0 MHz, DMSO) d 0.67 (t, J = 7.3 Hz, 3H), 1.35 (s, 3H), 1.57 (dd, J = 7.2, 13.8 Hz, 1H), 1.88-1.94 (m, 1H), 2.00 (s, 6H), 7.37 (d, J = 4.7 Hz, 1H), 7.53 (t, J = 7.6 Hz, 2H), 7.68 (d, J = 6.9 Hz, 1H), 7.77 (s, 1H), 8.24 (s, 1H), 8.58 (d, J = 4.7 Hz, 1H) and 13.82 (s, 1H) ppm |
| 141 | 295.2 | 2.67 | 1H NMR (400.0 MHz, DMSO) d 0.68 (t, J = 7.3 Hz, 3H), 1.34 (s, 3H), 1.63 (dd, J = 7.2, 13.8 Hz, 1H), 1.82 (dd, J = 7.2, 13.9 Hz, 1H), 2.25 (s, 3H), 2.61 (d, J = 11.5 Hz, 1H), 2.79 (d, J = 11.5 Hz, 1H), 7.37 (d, J = 4.7 Hz, 1H), 7.51 (m, 2H), 7.67 (d, J = 7.1 Hz, 1H), 7.77 (s, 1H), 8.26 (s, 1H), 8.58 (d, J = 4.7 Hz, 1H) and 13.81 (s, 1H) ppm |
| 151 | 281.2 | 2.87 | 1H NMR (400.0 MHz, DMSO) d 0.73 (t, J = 7.4 Hz, 3H), 1.36 (s, 3H), 1.63 (dd, J = 7.3, 13.9 Hz, 1H), 1.88 (dd, J = 7.3, 13.9 Hz, 1H), 2.73 (d, J = 12.8 Hz, 1H), 2.90 (d, J = 12.8 Hz, 1H), 7.43 (d, J = 4.8 Hz, 1H), 7.53 (d, J = 7.9 Hz, 1H), 7.60 (t, J = 7.7 Hz, 1H), 7.73 (d, J = 7.5 Hz, 1H), 7.80 (s, 1H), 8.32 (s, 1H) and 8.64 (d, J = 4.7 Hz, 1H) ppm |
| 152 | 281.2 | 2.84 | 1H NMR (400.0 MHz, DMSO) d 0.73 (t, J = 7.4 Hz, 3H), 1.36 (s, 3H), 1.63 (dd, J = 7.3, 13.9 Hz, 1H), 1.88 (dd, J = 7.3, 13.9 Hz, 1H), 2.73 (d, J = 12.8 Hz, 1H), 2.90 (d, J = 12.8 Hz, 1H), 7.43 (d, J = 4.8 Hz, 1H), 7.53 (d, J = 7.9 Hz, 1H), 7.60 (t, J = 7.7 Hz, 1H), 7.73 (d, J = 7.5 Hz, 1H), 7.80 (s, 1H), 8.32 (s, 1H) and 8.64 (d, J = 4.7 Hz, 1H) ppm |
| 310 | 324.05 | 1.92 | 1H nmr: (DMSO, 400 MHz) 1.65 (2H, br s), 2.47 (3H, s), 2.98 (2H, s), 3.56 (1H, d), 3.93 (1H, d), 7.36 (1H, s), 7.38 (1H, d), 7.60 (1H, s), 7.64 (1H, d), 8.29 (1H, s), 8.59 (1H, d), 13.83 (1H, br s). |
| 319 | 319.01 | 2.95 | |
| 323 | 290.03 | 2.72 | (400 MHz, DMSO) ISOMER MIXTURE: 2.40 (3H, s, X), 2.48 (3H, s, Y), 3.71 (2H, s, X), 3.79 (2H, s, Y), 6.01-6.03 (2H, m, X + Y), 7.29 (1H, s, X), 7.35 (1H, s, Y), 7.37 (1H, d, X), 7.39 (1H, d, Y), 7.44 (2H, s, Y), 7.54 (2H, s, Y), 7.70 (1H, s, X), 7.76 (1H, s, Y), 8.32 (1H, s, X), 7.75 (1H, s, Y), 8.34 (1H, s, X), 8.42 (1H, s, Y), 8.58 (1H, d, X), 8.60 (1H, d, Y), 13.79 (1H, br s, X), 13.82 (1H, br s, Y). |
| 325 | 334.37 | 2.73 | (DMSO, 400 MHz) 2.47 (3H, s), 2.81 (2H, d), 3.63 (1H, d), 3.80 (1H, d), 5.12 (1H, d), 5.19 (1H, d), 5.65-5.71 (1H, m), 5.37-5.38 (2H, m), 7.61 (1H, d), 7.63 (1H, s), 7.72 (1H, s, NH), 8.28 (1H, s), 8.59 (1H, d), 13.81 (1H, br s). |
| 326 | 349.05 | 2.9 | (DMSO, 400 MHz) 2.47 (3H, s), 2.76 (3H, s), 2.81 (2H, d), 3.75 (1H, d), 3.84 (1H, d), 5.13 (1H, d), 5.17 (1H, d), 5.62-5.70 (1H, m), 7.73 (1H, d), 7.38 (1H, s), 7.63 (1H, d), 8.29 (1H, s), 8.59 (1H, d), 14.81 (1H, br s). |
| 327 | 385.14 | 2.93 | (DMSO, 400 MHz) 2.45 (3H, s), 3.34 (2H, d), 3.68 (1H, d), 3.86 (1H, d), 7.12-7.27 (5H, m), 7.30 (1H, d), 7.38 (1H, s), 7.52 (1H, s), 7.59 (2H, d), 8.05 (1H, s), 8.57 (1H, d), 13.80 (1H, br s). |
| 330 | 354 | 2.63 | 1H NMR (400.0 MHz, DMSO) d 1.77-1.89 (m, 4H), 2.54-2.61 (m, 2H), 2.78-2.82 (m, 2H), 7.48 (d, J = 4.7 Hz, 1H), 7.64 (s, 1H), 7.82 (s, 1H), 7.87 (s, 1H), 8.28 (s, 1H), 8.31 (s, 1H) and 8.64 (d, J = 4.9 Hz, 1H) ppm |

Example 16

4-methyl-3-(trifluoromethyl)-1-trityl-1H-pyrazolo[3,4-b]pyridine

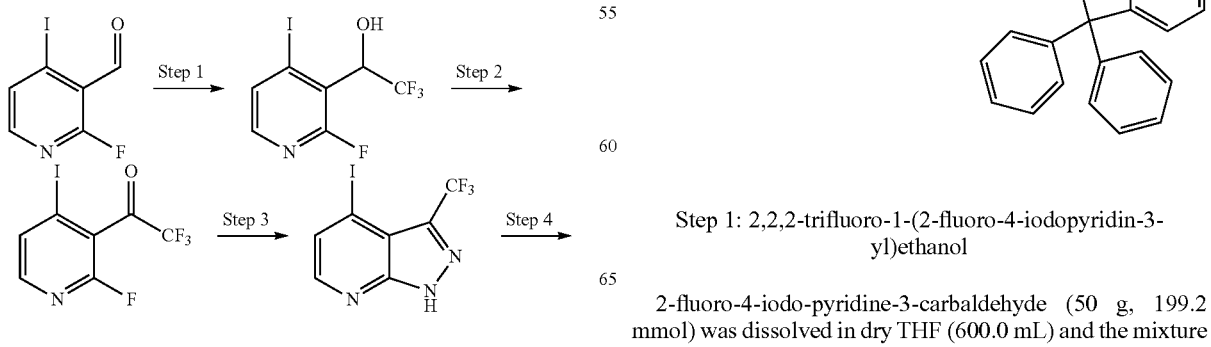

-continued

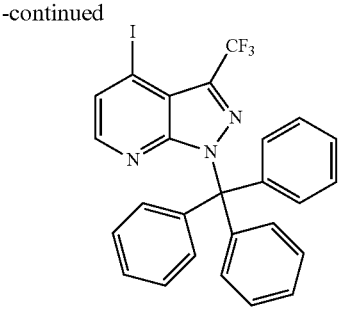

Step 1: 2,2,2-trifluoro-1-(2-fluoro-4-iodopyridin-3-yl)ethanol 2-fluoro-4-iodo-pyridine-3-carbaldehyde (50 g, 199.2 mmol) was dissolved in dry THF (600.0 mL) and the mixture cooled to 3.5° C. Trimethyl-(trifluoromethyl)silane (102.0 g, 106.0 mL, 717.1 mmol) was added and the mixture was stirred for 10 minutes (temp held at 3.6° C.) then tetrabutylammonium fluoride (9.960 mL of 1 M, 9.960 mmol) (in THF) was added dropwise. The temperature increased rapidly to 23.6° C. on adding ca 0.5 ml. The remainder of the solution was added slowly over 10 minutes—the reaction temperature did not increase further. The reaction mixture became dark brown in colour, and was diluted by slow addition of 6M HCl (500 ml) with the ice bath still in place. The temperature increased to a maximum of 27.8° C. The mixture was stirred for 10 minutes and then re-cooled in an ice bath and sodium hydroxide (120 g total) was added partially as solid, then as a concentrated solution in water. The pH of the final mixture was 6-7. The mixture was diluted with EtOAc (500 ml) and the organic layer removed. The aqueous was extracted with EtOAc (2×500 ml) and the combined organics washed with brine (250 ml), dried (MgSO$_4$), filtered and concentrated to a dark brown oil which was purified by filtration through a silica plug eluting with a 15%-30% EtOAc/Hexanes solvent system. The product was collected as a beige solid (45 g, 71% Yield).

1H NMR (400.0 MHz, CDCl$_3$) d 3.47 (m, 1H), 5.34 (m, 1H), 7.60 (m, 1H), 7.72 (m, 1H) ppm; MS (ES$^+$) 322

Step 2: 2,2,2-trifluoro-1-(2-fluoro-4-iodopyridin-3-yl)ethanone 2,2,2-trifluoro-1-(2-fluoro-4-iodo-3-pyridyl)ethanol (45 g, 140.2 mmol) was dissolved in anhydrous toluene (1 L). Manganese (IV) oxide (143.4 g, 1.402 mol) was added portionwise with rapid stirring. The mixture was heated to reflux for 3 hours and then allowed to cool and filtered through a plug of celite. The solid residues were washed with EtOAc and the filtrate was concentrated to a deep red oil which was slurried in petrol and then filtered to give a white solid impurity. The filtrate was concentrated to give the product as a red oil (40 g, 89% Yield).

1H NMR (400.0 MHz, CDCl$_3$) d 7.65 (m, 1H), 7.91 (m, 1H) ppm; MS (ES$^+$) 319

Step 3: 4-methyl-3-(trifluoromethyl)-1H-pyrazolo[3,4-b]pyridine 2,2,2-trifluoro-1-(2-fluoro-4-iodo-3-pyridyl)ethanone (40 g, 125.4 mmol) was dissolved in 1,4-dioxane (300 mL). Hydrazine monohydrate (18.83 g, 18.30 mL, 376.2 mmol) was added dropwise and the mixture heated to 90° C. for 90 minutes. The mixture was cooled and poured into EtOAc (800 ml) and 3:1 sat NaHCO$_3$/brine (500 ml). The organic layer was separated and the aqueous extracted with EtOAc (3×50 ml). The combined organics were washed with brine (100 ml), dried (MgSO$_4$), filtered and concentrated. The residue was slurried in DCM (50 ml) and the resultant white solid was isolated by filtration, washed with DCM and dried (28.7 g, 73% Yield).

1H NMR (400.0 MHz, DMSO) d 7.97 (m, 1H), 8.30 (m, 1H), 14.85 (br s, NH) ppm; MS (ES$^+$) 314

Step 4: 4-methyl-3-(trifluoromethyl)-1-trityl-1H-pyrazolo[3,4-b]pyridine 4-iodo-3-(trifluoromethyl)-1H-pyrazolo[5,4-b]pyridine (28.7 g, 91.69 mmol) was dissolved in dry DMF (300 mL). The mixture was cooled in an ice bath and sodium hydride (4.036 g, 100.9 mmol) was added portionwise over 10 minutes. The mixture was stirred at 0° C. for 30 minutes and then treated with trityl chloride (26.84 g, 96.27 mmol) in one portion. The reaction was allowed to warm to ambient and stirred for 16 hours. The reaction mixture was cooled in an ice bath and water (500 ml) was added slowly. The resultant solid was allowed to stir for 30 minutes and then filtered, washed with water and dried at 50° C. under high vacuum (50.5 g, 99% Yield).

1H NMR (400.0 MHz, DMSO) d 7.15-7.17 (m, 6H), 7.23-7.32 (m, 9H), 7.89 (d, J=4.7 Hz, 1H) and 7.95 (d, J=4.8 Hz, 1H) ppm Example 17

PKC Theta

An assay buffer solution was prepared which consisted of 100 mM HEPES (pH 7.5), 10 mM MgCl$_2$, 25 mM NaCl, 0.1 mM EDTA and 0.01% Brij. An enzyme buffer containing reagents to final assay concentrations of 0.00001% Triton X-100, 200 μg/mL Phosphatidylserine, 20 μg/mL Diacylglycerol, 360 μM NADH, 3 mM phosphoenolpyruvate, 70 μg/mL pyruvate kinase, 24 μg/mL lactate dehydrogenase, 2 mM DTT, 100 μM substrate peptide (ERMRPRKRQGSVR-RRV) and 18 nM PKC theta kinase was prepared in assay buffer. To 60 μL of this enzyme buffer, in a 384 well plate, was added 2 μl of VRT stock solution in DMSO. The mixture was allowed to equilibrate for 10 mins at 30° C. The enzyme reaction was initiated by the addition of 5 μL stock ATP solution prepared in assay buffer to a final assay concentration of 240 μM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 μM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.). Ki values in Tables 2-6 are represented as A<0.05 μA*>0.21 μM, B<0.5 μM, B*>0.7 μM, BB*>0.39 μM, C<2.8 μM, C*>1.2 μM, D*>2.0 μM, D>2.8 μM.

A compounds are: 1, 2, 3, 4, 5, 18, 31, 32, 34, 41, 45, 46, 47, 48, 49, 50, 51, 57, 62, 78, 85, 88, 98, 101, 103, 110, 111, 114, 122, 123, 129, 130, 131, 133, 134, 135, 136, 139, 141, 144, 145, 146, 148, 149, 150, 151, 152, 153, 154, 155, 156, 157, 159, 160, 162, 164, 165, 166, 167, 168, 169, 170, 171, 172, 173, 174, 177, 178, 179, 184, 185, 188, 189, 191, 192, 194, 195, 196, 197, 198, 199, 200, 201, 204, 205, 206, 207, 208, 209, 210, 211, 212, 213, 214, 215, 227, 228, 229, 232, 234, 235, 241, 249, 254, 255, 256, 257, 258, 259, 260, 261, 262, 263, 264, 265, 266, 267, 268, 271, 272, 273, 274, 275, 276, 277, 278, 279, 280, 281, 282, 283, 284, 285, 286, 287, 288, 290, 291, 292, 293, 296, 297, 301, 302, 303, 304, 305, 306, 307, 309, 310, 311, 312, 312, 314, 316, 317, 318, 319, 324, 328, 329, and 330.

A* compounds are: 100.

B compounds are: 6, 8, 10, 11, 13, 14, 17, 19, 20, 21, 22, 23, 24, 25, 28, 30, 36, 38, 39, 40, 42, 44, 52, 54, 55, 59, 61, 63, 64, 65, 66, 67, 68, 70, 73, 74, 79, 80, 86, 87, 89, 90, 91, 92, 93, 94, 95, 97, 99, 102, 104, 105, 106, 107, 108, 109, 113, 120, 121, 125, 126, 127, 128, 132, 137, 138, 140, 142, 143, 147, 158, 161, 163, 175, 176, 181, 182, 183, 186, 190, 193, 216, 218, 220, 224, 225, 231, 233, 236, 238, 240, 242, 243, 245, 246, 247, 248, 250, 251, 294, 308, 321, 323, 325, 326, and 327.

B* compounds are: 112, 115, 116, 117, 118, 119, 124, 180, 219, 221, 222, 226, 239, 244, 252, 253, 269, 270, 289, 295, 298, 320 and 322.

C compounds are: 9, 12, 15, 16, 26, 27, 35, 37, 43, 53, 58, 60, 69, 71, 72, 75, 76, 77, 81, 82, 83, 84, 96, 187, 203, 217, 223, 230, 237 and 315.

D compounds are: 7, 29, 33, 56, and 202:

No Data: 299 and 300.

PKC Delta

An assay buffer solution was prepared which consisted of 100 mM HEPES (pH 7.5), 10 mM MgCl$_2$, 25 mM NaCl, 0.1 mM EDTA and 0.01% Brij. An enzyme buffer containing reagents to final assay concentrations of 0.002% Triton X-100, 200 μg/mL Phosphatidylserine, 20 μg/mL Diacylglycerol, 360 μM NADH, 3 mM phosphoenolpyruvate, 70 μg/mL pyruvate kinase, 24 μg/mL lactate dehydrogenase, 2 mM DTT, 150 μM substrate peptide (ERMRPRKRQGSVRRRV SEQ ID NO. 2) and 46 nM PKC delta kinase was prepared in assay buffer. To 16 μL of this enzyme buffer, in a 384 well plate, was added 1 μL of VRT stock solution in DMSO. The mixture was allowed to equilibrate for 10 mins at 30° C. The enzyme reaction was initiated by the addition of 16 μL stock ATP solution prepared in assay buffer to a final assay concentration of 150 μM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 μM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.).

A compounds are: 41, 51, 129, 135, 148, 151, 155, 185, 204, 205, 212, 213, 234, 255, 258, 260, 261, 264, 266, 277, 281 and 318.

B compounds are: 1, 2, 3, 31, 32, 34, 40, 45, 46, 47, 48, 49, 50, 98, 133, 134, 139, 141, 143, 144, 146, 149, 150, 152, 154, 162, 165, 167, 168, 169, 171, 172, 173, 174, 177, 178, 179, 184, 191, 192, 193, 194, 195, 197, 198, 199, 200, 201, 206, 207, 208, 209, 214, 215, 229, 232, 235, 254, 256, 257, 259, 262, 263, 265, 267, 268, 271, 273, 274, 275, 278, 280, 282, 284, 285, 286, 290, 293, 301, 302, 305, 306, 308, 311, 314, 319 and 330.

C compounds are: 4, 5, 6, 13, 18, 30, 36, 42, 44, 52, 55, 64, 66, 70, 71, 73, 74, 78, 87, 88, 89, 90, 91, 93, 99, 104, 111, 122, 123, 130, 131, 132, 136, 138, 140, 142, 145, 153, 156, 157, 159, 160, 164, 166, 170, 176, 181, 182, 183, 186, 188, 196, 210, 211, 216, 225, 227, 228, 230, 231, 233, 237, 238, 241, 246, 248, 249, 250, 272, 276, 279, 283, 287, 288, 291, 297, 303, 309, 312, 323 and 328.

C* compounds are: 226, 244, 245, 247, 251, 252, 253, 269, 270, 292, 294, 295, 296, 298, 304, 307, 310, 313, 315, 316, 317, 320, 321, 322, 324, 325, 326, 327 and 329.

D compounds are: 7, 8, 10, 11, 17, 19, 21, 22, 39, 54, 57, 59, 62, 67, 69, 72, 75, 76, 77, 79, 80, 84, 85, 86, 92, 94, 95, 96, 97, 100, 101, 137, 147, 202, and 203.

D* compounds are: 102, 103, 105, 106, 107, 108, 109, 110, 112, 113, 114, 115, 116, 117, 118, 119, 120, 121, 124, 125, 126, 127, 128, 158, 161, 163, 175, 180, 187, 190, 217, 218, 219, 220, 221, 222, 223, 224, 236, 239, 240, 242, 243, and 289.

No Data: 9, 12, 14, 15, 16, 20, 23, 24, 25, 26, 27, 28, 29, 33, 35, 37, 38, 43, 53, 56, 58, 60, 61, 63, 65, 68, 81, 82, 83, 189, 299, and 300.

PKC Alpha

An assay buffer solution was prepared which consisted of 100 mM HEPES (pH 7.5), 10 mM MgCl$_2$, 25 mM NaCl, 0.1 mM EDTA, 100 μM CaCl$_2$ and 0.01% Brij. An enzyme buffer containing reagents to final assay concentrations of 0.002% Triton X-100, 100 μg/mL Phosphatidylserine, 20 μg/mL Diacylglycerol, 360 μM NADH, 3 mM phosphoenolpyruvate, 70 μg/mL pyruvate kinase, 24 μg/mL lactate dehydrogenase, 2 mM DTT, 150 μM substrate peptide (RRRRRKGSFKRKA SEQ ID NO. 1) and 4.5 nM PKC alpha kinase was prepared in assay buffer. To 16 μL of this enzyme buffer, in a 384 well plate, was added 1 μL of VRT stock solution in DMSO. The mixture was allowed to equilibrate for 10 mins at 30° C. The enzyme reaction was initiated by the addition of 16 μL stock ATP solution prepared in assay buffer to a final assay concentration of 130 μM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 μM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.).

A compounds are: 135, 185, 204; 212, 213, 255, 256, 258, 261, 263, 264, 266, 274, and 277.

B compounds are: 1, 32, 41, 45, 46, 47, 48, 51, 91, 110, 111, 129, 131, 133, 134, 139, 141, 144, 148, 149, 151, 152, 154, 155, 156, 160, 162, 164, 165, 166, 167, 168, 171, 173, 174, 178, 179, 184, 188, 191, 192, 193, 194, 197, 198, 199, 200, 201, 205, 206, 207, 208, 209, 210, 211, 214, 215, 227, 228, 229, 232, 234, 237, 241, 249, 250, 254, 257, 259, 260, 262, 265, 267, 268, 271, 272, 273, 275, 276, 278, 280, 281, 282, 283, 285, 286, 287, 288, 292, 293, 296, 297, 303, 307, 311, 312, 318, 319, 323, 324, 325 and 330.

BB* compounds are: 100.

C compounds are: 13, 18, 30, 31, 34, 36, 40, 42, 44, 49, 50, 52, 55, 57, 62, 64, 66, 67, 68, 69, 70, 71, 73, 74, 78, 80, 85, 86, 87, 88, 89, 90, 92, 93, 95, 98, 99, 101, 102, 103, 104, 105, 106, 107, 109, 122, 123, 130, 132, 136, 138, 140, 142, 143, 145, 146, 150, 153, 157, 158, 159, 161, 169, 170, 172, 177, 181, 186, 189, 195, 196, 216, 218, 225, 230, 231, 238, 248, 279, 284, 290, 301, 302, 304, 305, 309, 310, 314, 327 and 328.

C* compounds are: 108, 112, 113, 114, 115, 116, 117, 118, 119, 120, 121, 124, 125, 126, 127, 128, 163, 175, 176, 180, 182, 183, 187, 190, 217, 219, 220, 221, 222, 223, 224, 226, 233, 235, 236, 239, 240, 242, 243, 244, 245, 246, 247, 251, 252, 253, 269, 270, 289, 291, 294, 295, 298, 306, 308, 313, 315, 316, 317, 320, 321, 322, 326 and 329.

D compounds are: 11, 17, 19, 21, 22, 39, 54, 59, 72, 75, 76, 77, 79, 84, 94, 96, 97, 137, 147, 202, and 203.

No Data: 2, 3, 4, 5, 6, 7, 8, 9, 10, 12, 14, 15, 16, 20, 23, 24, 25, 26, 27, 28, 29, 33, 35, 37, 38, 43, 53, 56, 58, 60, 61, 63, 65, 81, 82, 83, 299, and 300.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound represented by structural formula IA:

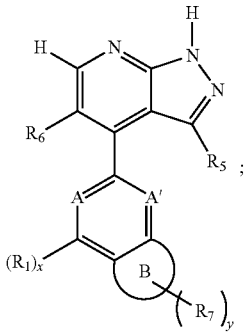

or a pharmaceutically acceptable salt thereof wherein:
A and A' are independently —N— or —C(R$^+$)—;
ring B is five- or six-membered saturated carbocyclic or heterocyclic ring;
$R_1$ is halogen, —CN, —NO$_2$, or -T1-Q1;
T1 is absent or a C1-10 aliphatic wherein one or more methylene units of T1 are optionally and independently replaced by G wherein G is —O—, —S(O)$_p$—, —N(R')—, or —C(O)—; and T1 is optionally and independently substituted with one or more $J_{T1}$;
Q1 is absent or a 3-8 membered saturated, partially saturated, or fully unsaturated monocyclic ring having 0-3 heteroatoms independently selected from the groups consisting of O, N, and S, or an 8-12 membered saturated, partially saturated, or fully unsaturated bicyclic ring having 0-5 heteroatoms independently selected from the group consisting of O, N, and S, wherein Q1 is optionally and independently substituted with one or more $J_{Q1}$; wherein when $R_1$ is T1-Q1, then T1 and Q1 are not both absent;
each $R_5$ and $R_6$ are independently —H, halogen, C1-10 haloaliphatic, or C1-10 aliphatic;
each $R_7$ is independently C1-10 haloaliphatic, C1-10 aliphatic, halogen, —NO$_2$, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R**)$_2$, or two $R_7$ groups together with the carbon to which they are attached form C=O;
each $J_{T1}$ is independently halogen, —OR^, —N(R^)$_2$, or —CN;
each $J_{Q1}$ is independently halogen, C1-10 alkyl, C1-10 haloalkyl, —OR", —N(R")$_2$, —CN, —NO$_2$, —S(O)$_p$R", —S(O)$_p$NR", acyl, carbalkoxyalkyl, or acetoxyalkyl;
each R$^+$ is independently —H, halogen, or C1-10 alkyl optionally and independently substituted with up to five halogen groups;
each R$^{++}$ is independently —H or halogen;
each R' is independently —H or C1-10 alkyl optionally and independently substituted with up to five halogen groups;
each R^ is independently —H, C1-10 alkyl, or aralkyl wherein each R^ is optionally and independently substituted with up to five halogen groups;
each R" is independently —H or C1-10 alkyl optionally and independently substituted with up to five halogen groups;

each R** is independently —H or C1-10 alkyl optionally and independently substituted with up to five halogen groups;
x is 0 or 1;
y is 0, 1 or 2;
each n is independently 0, 1, 2, or 3; and
each p is independently 0, 1, or 2.

2. The compound of claim 1, represented by structural formula IA:

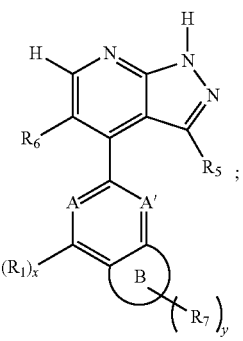

or a pharmaceutically acceptable salt thereof wherein:
A and A' are independently —N— or —C(R$^+$)—;
ring B is five- or six-membered saturated carbocyclic or heterocyclic ring;
$R_1$ is halogen, —CN, —NO$_2$, or -T1-Q1;
T1 is absent or a C1-10 aliphatic wherein up to three methylene units of T1 are optionally and independently replaced by G wherein G is —O—, —S(O)$_p$—, —N(R')—, or —C(O)—; and T1 is optionally and independently substituted with one or more $J_{T1}$;
Q1 is absent or a 3-8 membered saturated, partially saturated, or fully unsaturated monocyclic ring having 0-3 heteroatoms independently selected from the groups consisting of O, N, and S, or an 8-12 membered saturated, partially saturated, or fully unsaturated bicyclic ring having 0-5 heteroatoms independently selected from the group consisting of O, N, and S, wherein Q1 is optionally and independently substituted with one or more $J_{Q1}$; wherein when $R_1$ is T1-Q1, then TI and Q1 are not both absent;
each $R_5$ and $R_6$ are independently —H, halogen, C1-10 haloaliphatic, or C1-10 aliphatic;
each $R_7$ is independently C1-10 haloaliphatic, C1-10 aliphatic, halogen, —NO$_2$, —(CR$^{++}_2$)$_n$CN, —(CR$^{++}_2$)$_n$N(R)$_2$, —(CR$^{++}_2$)$_n$OR, or —(CR$^{++}_2$)$_n$C(O)N(R**)$_2$, or two $R_7$ groups together with the carbon to which they are attached form C=O;
each $J_{T1}$ is independently halogen, —OR^, —N(R^)$_2$, or —CN;
each $J_{Q1}$ is independently halogen, C1-10 alkyl, C1-10 haloalkyl, —OR", —N(R")$_2$, —CN, —NO$_2$, —S(O)$_p$R", —S(O)$_p$NR", acyl, carbalkoxyalkyl, or acetoxyalkyl;
each R$^+$ is independently —H, halogen, or C1-10 alkyl optionally and independently substituted with up to five halogen groups;
each R$^{++}$ is independently —H or halogen;
each R' is independently —H or C1-10 alkyl, optionally and independently substituted with up to five halogen groups;

each R^ is independently —H or C1-10 alkyl, optionally and independently substituted with up to five halogen groups;

each R" is independently —H or C1-10 alkyl, optionally and independently substituted with up to five halogen groups;

each R** is independently —H or C1-10 alkyl, optionally and independently substituted with up to five halogen groups;

x is 0 or 1;

y is 0, 1 or 2;

each n is independently 0, 1, 2, or 3; and each p is independently 0, 1, or 2.

3. The compound of claim 1 or a pharmaceutically acceptable salt thereof wherein:

A is —N— or —C(R⁺)—; and A' is —C(R⁺)—.

4. The compound of claim 1 or a pharmaceutically acceptable salt thereof wherein:

R⁺ is —H.

5. The compound of claim 1 or a pharmaceutically acceptable salt thereof wherein:

$R_1$ is halogen, or -T1-Q1.

6. The compound of claim 1 or a pharmaceutically acceptable salt thereof wherein:

T1 is absent or a C1-10 aliphatic wherein up to three methylene units of T1 are optionally and independently replaced by G wherein G is —O—, —N(R')—, or —C(O)—; and T1 is optionally and independently substituted with one or more $J_{T1}$.

7. The compound of claim 1 or a pharmaceutically acceptable salt thereof wherein:

Q1 is absent or a 3-8 membered saturated, partially saturated, or fully unsaturated monocyclic ring having 0-3 heteroatoms independently selected from the groups consisting of O, N, and S, wherein Q1 is optionally and independently substituted with one or more $J_{Q1}$.

8. The compound of claim 1 or a pharmaceutically acceptable salt thereof wherein:

each $J_{T1}$ is independently —OR^, —N(R^)₂, or —CN.

9. The compound of claim 1 or a pharmaceutically acceptable salt thereof wherein:

each $J_{Q1}$ is independently C1-10 alkyl, —OR", —N(R")₂, or acyl.

10. The compound of claim 1 or a pharmaceutically acceptable salt thereof wherein:

A is —C(R⁺)—.

11. The compound of claim 1 or a pharmaceutically acceptable salt thereof wherein:

$J_{T1}$ is —OR^.

12. The compounds of claim 1 or a pharmaceutically acceptable salt thereof wherein $R_5$ is —H, Cl, C1-4 haloalkyl, or C1-4 alkyl; and $R_6$ is —H or C1-4 alkyl.

13. The compounds of claim 1 or a pharmaceutically acceptable salt thereof wherein $R_5$ is —H, Cl, trifluoromethyl, methyl, ethyl, or cyclopropyl; and $R_6$ is —H.

14. A compound represented by a structural formula selected from the group consisting of:

, or a pharmaceutically acceptable salt thereof.

15. A composition comprising the compound of claim 1 or pharmaceutically acceptable salt thereof, and a pharmaceutically acceptable carrier, adjuvant, or vehicle.

16. A process for preparing a compound of claim 1 comprising:

a) boronation of a compound represented by the following structural formula:

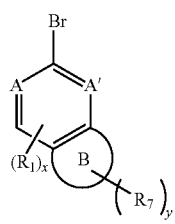

ia in the presence of a boronation agent and a solvent, to give a compound represented by the following structural formula:

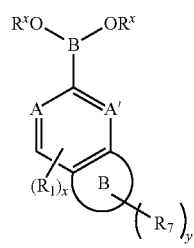

iia wherein:
each $R^x$ is —H or two $R^x$s together form

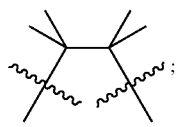 [SMILES: *C(C)(C)C(*)(C)C]

b) cyclization of a compound represented by the following structural formula:

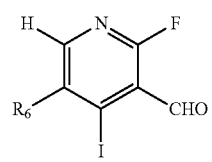

iii in the presence of hydrazine and a solvent to give a compound represented by the following structural formula:

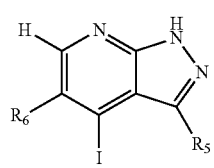

iv c) suzuki coupling of the compound represented by formula iia with a compound represented by formula iv in the presence of a solvent, a catalyst complex and a base to give a compound of claim 1.

17. A process for preparing a compound of claim 1, comprising:
a) cyclization of compound represented by represented by the following structural formula:

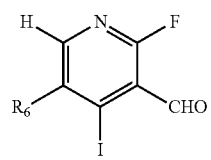

iii in the presence of hydrazine and a solvent to give a compound represented by the following structural formula:

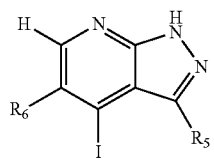

iv b) protection of a compound represented by iv to give a compound represented by the following structural formula:

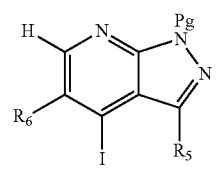

v wherin: Pg represents a protecting group;
c) boronation of a compound represented by formula v in the presence of a boronation agent and a solvent to give a compound represented by represented by the following structural formula:

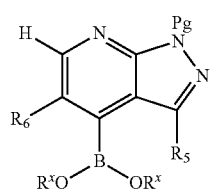

vi wherein:
each $R^x$ is —H or two $R^x$s together form

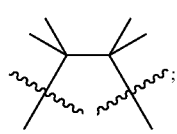 [SMILES: *C(C)(C)C(*)(C)C]

d) suzuki coupling of the compound represented by formula vi with a compound represented the following structural formula:

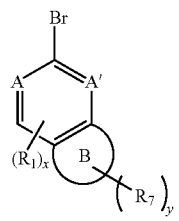

ia in the presence of solvent, a catalyst complex and a base to give a compound represented by structural formula:

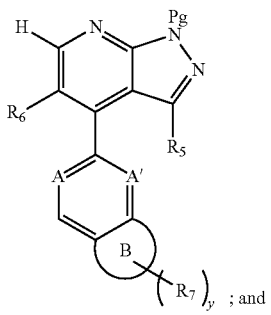

viia

; and e) deprotection of the compound represented by formula viia in the presence of hydrazine to yield a compound of claims 1.

* * * * *